United States Patent
Mondal et al.

(10) Patent No.: US 10,800,843 B2
(45) Date of Patent: Oct. 13, 2020

(54) BETA KLOTHO-BINDING PROTEINS

(71) Applicant: NGM BIOPHARMACEUTICALS, INC., South San Francisco, CA (US)

(72) Inventors: Kalyani Mondal, San Mateo, CA (US); Betty Chan Li, Millbrae, CA (US); Yu Chen, Foster City, CA (US); Taruna Arora, Palo Alto, CA (US); Hugo Matern, San Mateo, CA (US); Wenyan Shen, Redwood City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 62 days.

(21) Appl. No.: 15/748,111

(22) PCT Filed: Jul. 29, 2016

(86) PCT No.: PCT/US2016/044704
§ 371 (c)(1),
(2) Date: Jan. 26, 2018

(87) PCT Pub. No.: WO2017/019957
PCT Pub. Date: Feb. 2, 2017

(65) Prior Publication Data
US 2019/0338046 A1 Nov. 7, 2019

Related U.S. Application Data

(60) Provisional application No. 62/198,664, filed on Jul. 29, 2015.

(51) Int. Cl.
| | | |
|---|---|---|
| C07K 16/18 | (2006.01) | |
| A61K 39/395 | (2006.01) | |
| C07K 16/28 | (2006.01) | |
| A61K 39/00 | (2006.01) | |

(52) U.S. Cl.
CPC ...... *C07K 16/28* (2013.01); *A61K 39/001132* (2018.08); *A61K 2039/505* (2013.01); *C07K 2317/24* (2013.01); *C07K 2317/52* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,579,850 B1 | 6/2003 | Nabeshima |
| 6,635,468 B2 | 10/2003 | Ashkenazi |
| 6,716,626 B1 | 4/2004 | Itoh |
| 6,806,352 B2 | 10/2004 | Desnoyers |
| 6,812,339 B1 | 11/2004 | Venter |
| 6,987,121 B2 | 1/2006 | Kliewer |
| 7,115,415 B2 | 10/2006 | Goddard |
| 7,129,072 B1 | 10/2006 | Schlessinger |
| 7,208,312 B1 | 4/2007 | Desnoyers |
| 7,259,248 B2 | 8/2007 | Itoh |
| 7,288,406 B2 | 10/2007 | Bogin |
| 7,390,879 B2 | 6/2008 | Ashkenazi |
| 7,459,540 B1 | 12/2008 | Thomason |
| 7,491,697 B2 | 2/2009 | Beals |
| 7,537,902 B2 | 5/2009 | Kuro-o |
| 7,576,190 B2 | 8/2009 | Glaesner |
| 7,582,607 B2 | 9/2009 | Frye |
| 7,622,445 B2 | 11/2009 | Frye |
| 7,655,627 B2 | 2/2010 | Frye |
| 7,667,005 B2 | 2/2010 | Nabeshima |
| 7,667,008 B2 | 2/2010 | Thomason |
| 7,705,195 B2 | 4/2010 | French |
| 7,723,297 B2 | 5/2010 | Itoh |
| 7,947,866 B2 | 5/2011 | Sparks |
| 8,012,931 B2 | 9/2011 | Cujec |
| 8,034,770 B2 | 10/2011 | Belouski |
| 8,188,040 B2 | 5/2012 | Belouski |
| 8,324,160 B2 | 12/2012 | Li |
| 8,361,963 B2 | 1/2013 | Belouski |
| 8,372,952 B2 | 2/2013 | Smith |
| 8,383,365 B2 | 2/2013 | Cujec |
| 8,410,051 B2 | 4/2013 | Belouski |
| 8,420,088 B2 | 4/2013 | Glass |
| 8,481,031 B2 | 7/2013 | Glass |
| 8,535,912 B2 | 9/2013 | Sonoda |
| 8,541,369 B2 | 9/2013 | Dickinson |
| 8,580,936 B2 | 11/2013 | Williams |
| 8,618,053 B2 | 12/2013 | Belouski |
| 8,642,546 B2 | 2/2014 | Belouski |
| 8,673,860 B2 | 3/2014 | Schellenberger |
| 8,741,841 B2 | 6/2014 | Darling |
| 8,795,985 B2 | 8/2014 | Belouski |
| 8,802,697 B2 | 8/2014 | Bifulco |
| 8,809,499 B2 | 8/2014 | Fan |

(Continued)

FOREIGN PATENT DOCUMENTS

| | | |
|---|---|---|
| CN | 102858802 A | 1/2013 |
| DE | 10100588 | 7/2002 |

(Continued)

OTHER PUBLICATIONS

Adams et al., "FGF21 requires βklotho to act in vivo," PLoS One, 7(11):e49977 (2012).
Aranha et al., "Bile acid levels are increased in the liver of patients with steatohepatitis," Eur. J. Gastroenterol. Hepatol., 20(6): 519-525 (2008).
Beenken et al, "The FGF family: biology, pathophysiology and therapy," Nat. Rev. Drug Discov., 8:235-253 (2009).
Beuers et al., "Medical treatment of primary sclerosing cholangitis: a role for novel bile acids and other (post-) transcriptional modulators?," Clin. Rev. Allergy Immunol., 36(1):52-61 (2009).

(Continued)

*Primary Examiner* — Christine J Saoud
(74) *Attorney, Agent, or Firm* — Fish & Richardson P.C.

(57) ABSTRACT

The present disclosure provides binding proteins, such as antibodies, that bind beta klotho, including human beta klotho, and methods of their use.

14 Claims, 16 Drawing Sheets

Specification includes a Sequence Listing.

(56) References Cited

U.S. PATENT DOCUMENTS

| | | |
|---|---|---|
| 8,835,385 B2 | 9/2014 | Belouski |
| 8,883,726 B2 | 11/2014 | Dickinson |
| 8,889,426 B2 | 11/2014 | Mohammadi |
| 8,889,621 B2 | 11/2014 | Mohammadi |
| 8,927,492 B2 | 1/2015 | Darling |
| 8,932,589 B2 | 1/2015 | Glass |
| 8,951,966 B2 | 2/2015 | Ling |
| 8,962,557 B2 | 2/2015 | Blaber |
| 8,975,223 B2 | 3/2015 | Vignati |
| 8,993,727 B2 | 3/2015 | Walker |
| 8,999,929 B2 | 4/2015 | Mohammadi |
| 9,006,400 B2 | 4/2015 | Boettcher |
| 9,089,525 B1 | 7/2015 | Ling |
| 9,273,107 B2 | 3/2016 | Ling |
| 9,290,557 B2 | 3/2016 | Ling |
| 9,580,483 B2 | 2/2017 | Ling |
| 9,670,260 B2 | 6/2017 | Ling |
| 9,738,716 B2 | 8/2017 | Mondal |
| 9,751,924 B2 | 9/2017 | Ling |
| 9,878,008 B2 | 1/2018 | Ling |
| 9,878,009 B2 | 1/2018 | Ling |
| 9,889,177 B2 | 2/2018 | Ling |
| 9,889,178 B2 | 2/2018 | Ling |
| 9,895,416 B2 | 2/2018 | Ling |
| 9,925,242 B2 | 3/2018 | Ling |
| 10,093,735 B2 | 10/2018 | Mondal et al. |
| 2002/0012961 A1 | 1/2002 | Botstein |
| 2002/0042367 A1 | 4/2002 | Stewart |
| 2002/0082205 A1 | 6/2002 | Itoh |
| 2002/0151496 A1 | 10/2002 | Bringmann |
| 2002/0155543 A1 | 10/2002 | Adams |
| 2003/0045489 A1 | 3/2003 | Murphy |
| 2003/0065140 A1 | 4/2003 | Vernet |
| 2003/0105302 A1 | 6/2003 | Itoh |
| 2003/0113718 A1 | 6/2003 | Ashkenazi |
| 2003/0119112 A1 | 6/2003 | Baker |
| 2003/0125521 A1 | 7/2003 | Baker |
| 2003/0166051 A1 | 9/2003 | Desnoyers |
| 2003/0170822 A1 | 9/2003 | Itoh |
| 2003/0180890 A1 | 9/2003 | Conklin |
| 2003/0185846 A1 | 10/2003 | Ashkenazi |
| 2003/0220246 A1 | 11/2003 | Conklin |
| 2004/0014658 A1 | 1/2004 | Bogin |
| 2004/0126852 A1 | 7/2004 | Stewart |
| 2004/0146908 A1 | 7/2004 | Adams |
| 2004/0185494 A1 | 9/2004 | Itoh |
| 2005/0026243 A1 | 2/2005 | Stewart |
| 2005/0026832 A1 | 2/2005 | Adams |
| 2005/0107475 A1 | 5/2005 | Jones |
| 2005/0153305 A1 | 7/2005 | Vernet |
| 2005/0181375 A1 | 8/2005 | Aziz |
| 2005/0196842 A1 | 9/2005 | Botstein |
| 2006/0160181 A1 | 7/2006 | Luethy |
| 2006/0172386 A1 | 8/2006 | Itoh |
| 2006/0246540 A1 | 11/2006 | Ashkenazi |
| 2006/0275794 A1 | 12/2006 | Carrino |
| 2006/0281679 A1 | 12/2006 | Itoh |
| 2007/0037165 A1 | 2/2007 | Venter |
| 2007/0042395 A1 | 2/2007 | Botstein |
| 2007/0077626 A1 | 4/2007 | Botstein |
| 2007/0238657 A1 | 10/2007 | Itoh |
| 2007/0253966 A1 | 11/2007 | Glaesner |
| 2008/0057076 A1 | 3/2008 | Bringmann |
| 2008/0124759 A1 | 5/2008 | Conklin |
| 2008/0261236 A1 | 10/2008 | Kuro-o |
| 2009/0081658 A1 | 3/2009 | Belouchi |
| 2009/0098603 A1 | 4/2009 | Botstein |
| 2009/0196876 A1 | 8/2009 | Sparks |
| 2009/0226459 A1 | 9/2009 | Powers |
| 2009/0312265 A1 | 12/2009 | Schmidtchen |
| 2010/0158914 A1 | 6/2010 | Desnoyers |
| 2010/0184665 A1 | 7/2010 | Suzuki |
| 2010/0215657 A1 | 8/2010 | Glass |
| 2010/0239554 A1 | 9/2010 | Schellenberger |
| 2010/0240587 A1 | 9/2010 | Schlein |
| 2010/0323954 A1 | 12/2010 | Li |
| 2010/0330062 A1 | 12/2010 | Koeffler |
| 2011/0015345 A1 | 1/2011 | Pinkstaff |
| 2011/0053787 A1 | 3/2011 | Brulliard |
| 2011/0104152 A1 | 5/2011 | Sonoda |
| 2011/0107439 A1 | 5/2011 | De Wit |
| 2011/0135657 A1 | 6/2011 | Hu |
| 2011/0150903 A1 | 6/2011 | Baurin |
| 2011/0190207 A1 | 8/2011 | Mohammadi |
| 2011/0195077 A1 | 8/2011 | Glass |
| 2011/0195895 A1 | 8/2011 | Walker |
| 2011/0207912 A1 | 8/2011 | Botstein |
| 2011/0306129 A1 | 12/2011 | Nistor |
| 2011/0312881 A1 | 12/2011 | Silverman |
| 2012/0003216 A1 | 1/2012 | Belouski |
| 2012/0064544 A1 | 3/2012 | Econs |
| 2012/0172314 A1 | 7/2012 | Koeffler |
| 2012/0178699 A1 | 7/2012 | Wolf |
| 2012/0288886 A1 | 11/2012 | Mohammadi |
| 2012/0294861 A1 | 11/2012 | Sonoda |
| 2012/0308580 A1 | 12/2012 | Bertoletti |
| 2012/0328616 A1 | 12/2012 | Li |
| 2013/0004492 A1 | 1/2013 | Marshall |
| 2013/0023474 A1 | 1/2013 | Ling |
| 2013/0116171 A1 | 5/2013 | Jonker |
| 2013/0122004 A1 | 5/2013 | Glass |
| 2013/0122020 A1 | 5/2013 | Liu |
| 2013/0129725 A1 | 5/2013 | Fachini |
| 2013/0143796 A1 | 6/2013 | Li |
| 2013/0172275 A1 | 7/2013 | Mohammadi |
| 2013/0183294 A1 | 7/2013 | Pai |
| 2013/0183319 A1 | 7/2013 | Bange |
| 2013/0184211 A1 | 7/2013 | Mohammadi |
| 2013/0231277 A1 | 9/2013 | Mohammadi |
| 2013/0324458 A1 | 12/2013 | Glass |
| 2013/0324701 A1 | 12/2013 | Williams |
| 2013/0331317 A1 | 12/2013 | Mohammadi |
| 2013/0331325 A1 | 12/2013 | Mohammadi |
| 2014/0094406 A1 | 4/2014 | Mohammadi |
| 2014/0148388 A1 | 5/2014 | Sonoda |
| 2014/0155316 A1 | 6/2014 | Mohammadi |
| 2014/0189893 A1 | 7/2014 | Li |
| 2014/0194352 A1 | 7/2014 | Ling |
| 2014/0243260 A1 | 8/2014 | Mohammadi |
| 2014/0243266 A1 | 8/2014 | Ling |
| 2014/0363435 A1 | 12/2014 | Desnoyers |
| 2015/0079065 A1 | 3/2015 | Wolf |
| 2015/0111821 A1 | 4/2015 | Suh |
| 2015/0210764 A1 | 7/2015 | Mondal |
| 2015/0284442 A1 | 10/2015 | Ling |
| 2015/0291677 A1 | 10/2015 | Ling |
| 2016/0045565 A1 | 2/2016 | Ling |
| 2016/0166642 A1 | 6/2016 | Ling |
| 2016/0168215 A1 | 6/2016 | Ling |
| 2016/0168216 A1 | 6/2016 | Ling |
| 2016/0168217 A1 | 6/2016 | Ling |
| 2016/0168218 A1 | 6/2016 | Ling |
| 2016/0168219 A1 | 6/2016 | Ling |
| 2016/0168220 A1 | 6/2016 | Ling |
| 2016/0168221 A1 | 6/2016 | Ling |
| 2016/0168222 A1 | 6/2016 | Ling |
| 2016/0200788 A1 | 7/2016 | Ling |
| 2016/0252497 A1 | 9/2016 | Ling |
| 2017/0182122 A1 | 6/2017 | Ling |
| 2017/0182123 A1 | 6/2017 | Ling |
| 2017/0232067 A1 | 8/2017 | Lindhout |
| 2017/0327551 A1 | 11/2017 | Ling |
| 2018/0100014 A1 | 4/2018 | Mondal et al. |
| 2019/0106490 A1 | 4/2019 | Mondal et al. |

FOREIGN PATENT DOCUMENTS

| | | |
|---|---|---|
| DE | 10100587 | 11/2002 |
| EP | 2163626 A1 | 3/2010 |
| EP | 2510009 B1 | 4/2017 |
| JP | 2001072607 A | 3/2001 |
| JP | 2002112772 A | 4/2002 |
| JP | 2003334088 A | 11/2003 |
| JP | 2006158339 A | 6/2006 |

(56) References Cited

FOREIGN PATENT DOCUMENTS

| | | |
|---|---|---|
| JP | 2006240990 A | 9/2006 |
| JP | 2009039117 A | 2/2009 |
| JP | 2013194049 A | 9/2013 |
| NZ | 602702 | 3/2014 |
| WO | WO 1998/029544 | 7/1998 |
| WO | WO 2000/060085 | 10/2000 |
| WO | WO 2001/018209 A1 | 3/2001 |
| WO | WO 2001/020031 A2 | 3/2001 |
| WO | WO 2001/038529 A1 | 5/2001 |
| WO | WO 2001/049740 A1 | 7/2001 |
| WO | WO 2001/049849 A1 | 7/2001 |
| WO | WO 2001/061007 A2 | 8/2001 |
| WO | WO 2002/036732 A2 | 5/2002 |
| WO | WO 2002/041911 A2 | 5/2002 |
| WO | WO 2002/055693 A2 | 7/2002 |
| WO | WO 2003/080803 A2 | 10/2003 |
| WO | WO 2004/026228 A2 | 4/2004 |
| WO | WO 2004/063355 A2 | 7/2004 |
| WO | WO 2006/004076 A1 | 1/2006 |
| WO | WO 2006/048291 A2 | 5/2006 |
| WO | WO 2006/049854 A2 | 5/2006 |
| WO | WO 2008/021196 A2 | 2/2008 |
| WO | WO 2008/030273 A2 | 3/2008 |
| WO | WO 2008/123625 A1 | 10/2008 |
| WO | WO 2008/135993 A1 | 11/2008 |
| WO | WO 2009/009173 A2 | 1/2009 |
| WO | WO 2009/076478 A2 | 6/2009 |
| WO | WO 2009/090553 A2 | 7/2009 |
| WO | WO 2009/095372 A1 | 8/2009 |
| WO | WO 2009/116861 A2 | 9/2009 |
| WO | WO 2010/004204 A2 | 1/2010 |
| WO | WO 2010/006214 A1 | 1/2010 |
| WO | WO 2010/042747 A2 | 4/2010 |
| WO | WO 2010/065439 A1 | 6/2010 |
| WO | WO 2010/080976 A1 | 7/2010 |
| WO | WO 2010/083051 A2 | 7/2010 |
| WO | WO 2010/129600 A2 | 11/2010 |
| WO | WO 2010/139741 A1 | 12/2010 |
| WO | WO 2010/142665 A1 | 12/2010 |
| WO | WO 2010/148142 A1 | 12/2010 |
| WO | WO 2011/047267 A1 | 4/2011 |
| WO | WO 2011/068893 A1 | 6/2011 |
| WO | WO 2011/071783 A1 | 6/2011 |
| WO | WO 2011/084808 A2 | 7/2011 |
| WO | WO 2011/089203 A1 | 7/2011 |
| WO | WO 2011/092234 A1 | 8/2011 |
| WO | WO 2011/130417 A2 | 10/2011 |
| WO | WO 2011/130729 A2 | 10/2011 |
| WO | WO 2011/154349 A2 | 12/2011 |
| WO | WO 2012/010553 A1 | 1/2012 |
| WO | WO 2012/031603 A2 | 3/2012 |
| WO | WO 2012/062078 A1 | 5/2012 |
| WO | WO 2012/066075 A1 | 5/2012 |
| WO | WO 2012/086809 A1 | 6/2012 |
| WO | WO 2012/138919 A2 | 10/2012 |
| WO | WO 2012/140650 A2 | 10/2012 |
| WO | WO 2012/154263 A1 | 11/2012 |
| WO | WO 2012/158704 A1 | 11/2012 |
| WO | WO 2012/170438 A2 | 12/2012 |
| WO | WO 2012/170704 A2 | 12/2012 |
| WO | WO 2012/177481 A2 | 12/2012 |
| WO | WO 2013/006486 A2 | 1/2013 |
| WO | WO 2013/010780 A1 | 1/2013 |
| WO | WO 2013/027191 A1 | 2/2013 |
| WO | WO 2013/033452 A2 | 3/2013 |
| WO | WO 2013/049234 A2 | 4/2013 |
| WO | WO 2013/109856 A2 | 7/2013 |
| WO | WO 2013/131091 A1 | 9/2013 |
| WO | WO 2013/151671 A1 | 10/2013 |
| WO | WO 2013/173158 A1 | 11/2013 |
| WO | WO 2013/184958 A1 | 12/2013 |
| WO | WO 2013/184960 A2 | 12/2013 |
| WO | WO 2013/184962 A1 | 12/2013 |
| WO | WO 2013/188182 A1 | 12/2013 |
| WO | WO 2014/031420 A1 | 2/2014 |
| WO | WO 2014/037373 A1 | 3/2014 |
| WO | WO 2014/085365 A2 | 6/2014 |
| WO | WO 2014/105939 A1 | 7/2014 |
| WO | WO 2014/130659 A1 | 8/2014 |
| WO | WO 2014/149699 A1 | 9/2014 |
| WO | WO 2014/152090 A1 | 9/2014 |
| WO | WO 2015/065897 A1 | 5/2015 |
| WO | WO 2015/100366 A1 | 7/2015 |
| WO | WO 2015/112886 A2 | 7/2015 |
| WO | WO 2015/183890 A2 | 12/2015 |
| WO | WO 2015/195509 A2 | 12/2015 |
| WO | WO 2016/065106 A1 | 4/2016 |
| WO | WO 2016/073855 A1 | 5/2016 |
| WO | WO 2017/083276 A1 | 5/2017 |
| WO | WO 2018/039557 A1 | 3/2018 |
| WO | WO 2018/044778 A1 | 3/2018 |

OTHER PUBLICATIONS

Bromberg et al., "Stat3 as an oncogene," Cell, 98:295-303 (1999).
Calvisi et al., "Ubiquitous activation of Ras and Jak/Stat pathways in human HCC," Gastroenterol., 130:1117-1128 (2006).
Camilleri et al., "Measurement of Serum 7α-hydroxy-4-cholesten-3-one (or 7αC4), a Surrogate Test for Bile Acid Malabsorption in Health, Ileal Disease and Irritable Bowel Syndrome using Liquid Chromatography-Tandom Mass Spectrometry," Neurogastroenterol, Motil., 21(7):734-e43 (2009).
Casset et al., "A peptide mimetic of an anti-CD4 monoclonal antibody by rational design," Biochem. Biophys. Res. Commun., 307:198-205 (2003).
Chazouilleres, "Primary sclerosing cholangitis and bile acids," Clinics and Research in Hepatology and Gastroenterology, 36:S21-S25 (2012).
Chen et al., "Selection and Analysis of an Optimized Anti-VEGF Antibody: Crystal Structure of an Affinity-matured Fab in Complex with Antigen," J. Mol. Biol., 293:865-881 (1999).
Chen et al., "Soluble FGFR4 extracellular domain inhibits FGF19-induced activation of FGFR4 signaling and prevents nonalcoholic fatty liver disease," Biochem. Biophys. Res. Comm., 409:651-656 (2011).
Chen et al., "Sorafenib overcomes TRAIL resistance of hepatocellular carcinoma cells through the inhibition of STAT3," Clin. Cancer Res., 16:5189-5199 (2010).
Claudel et al., "Role of Nuclear Receptors for Ble Acid Metabolism, Bile Secretion, Cholestasis, and Gallstone Disease," Biochim. Biophys. Acta, 1812:867-878 (2011).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., 169:3076-3084 (2002).
Desnoyers et al., "Targeting FGF19 inhibits tumor growth in colon cancer xenograft and FGF19 transgenic hepatocellular carcinoma models," Oncogene, 27:85-97 (2008).
Ďurovcová et al., "Plasma Concentration of Fibroblast Growth Factors 21 and 19 in Patients with Cushing's Syndrome," Physiol. Res., 59:415-422 (2010).
Foltz et al., "Supplementary Materials for: Treating Diabetes and Obesity with an FGF21-Mimetic Antibody Activating the βKlotho/FGFR1c Receptor Complex," Sci. Transl. Med., 4:162ra153, 1-13 (2012).
Foltz et al., "Treating Diabetes and Obesity with an FGF21-Mimetic Antibody Activating the βKlotho/FGFR1c Receptor Complex," Sci. Transl. Med,. 4(162):1-10 (2012).
French et al., "Targeting FGFR4 Inhibits Hepatocellular Carcinoma in Preclinical Mouse Models," PLoS One, 7(5):e36713, 1-12 (2012).
Fukumoto et al., "FGF23 is a hormone-regulating phosphate metabolism—unique biological characteristics of FGF23," Bone, 40(5):1190-1195 (2007).
Ge et al., "Characterization of a FGF19 Variant with Altered Receptor Specificity Revealed a Central Role for FGFR1c in the Regulation of Glucose Metabolism," PLoS One, 7(3):e33603, 1-9 (2012).

(56) References Cited

OTHER PUBLICATIONS

GenBank EHH53620.1: Beta-klotho (Macaca fascicularis)[online] Nov. 4, 2011 [retrieved Mar. 28, 2015]. Available on the internet: <URL: http://www.ncbi.nlm.nih.gov/protein/355749221?sat=37&satkey=109028311.
Goetz et al., "Molecular insights into the klotho-dependent, endocrine mode of action of fibroblast growth factor 19 subfamily members," Mol. Cell. Biol., 27(9):3417-3428 (2007).
Harmer et al., "The Crystal Structure of Fibroblast Growth Factor (FGF) 19 Reveals Novel Features of the FGF Family and Offers a Structural Basis for Its Unusual Receptor Affinity," Biochemistry, 43:629-640 (2004).
Hasegawa, "The expansion of PROMININ-1-positive epithelial-mesenchymal cells within periportal fibrosis of rotavirusinduced biliary atresia," Hepatol., 58:802A (2013).
He et al., "Hepatocyte IKKbeta/NF-kappaB inhibits tumor promotion and progression by preventing oxidative stress-driven STAT3 activation," Cancer Cell, 17:286-297 (2010).
He et al., "Identification of liver cancer progenitors whose malignant progression depends on autocrine IL-6 signaling," Cell, 155:384-396 (2013).
He et al., "NF-κb and STAT3—key players in liver inflammation and cancer," Cell Res., 21:159-168 (2011).
Hofmann et al., "Chronic diarrhea due to excessive bile acid synthesis and not defective ileal transport: A new syndrome of defective FGF19 release," Clin. Gastroenterol. Hepatol., 7(11):1151-1154 (2009).
Holm et al., "Functional mapping and single chain construction of the anti-cytokeratin 8 monoclonal antibody TS1," Mol. Immunol., 44:1075-1084 (2007).
Holt et al., "Definition of a novel growth factor-dependent signal cascade for the suppression of bile acid biosynthesis," Genes Dev., 17:1581-1591 (2003).
Ikeda et al., "Leptin receptor somatic mutations are frequent in HCV-infected cirrhotic liver and associated with hepatocellular carcinoma," Gastroenterol., 146:222-232 (2014).
Inagaki et al., "Fibroblast Growth Factor 15 Functions as an Enterohepatic Signal to Regulate Bile Acid Homeostasis," Cell Metabolism, 2:217-225 (2005).
Ito et al., "Molecular cloning and expression analyses of mouse betaklotho, which encodes a novel Klotho family protein," Mech. Dev., 98(1-2):115-119 (2000).
Kakumu et al., "Interleukin 6 production by peripheral blood mononuclear cells in patients with chronic hepatitis B virus infection and primary biliary cirrhosis," Gastroenterologia Japonica, 28:18-24 (1993).
Karras et al., "STAT3 regulates the growth and immunoglobulin production of BCL(1) B cell lymphoma through control of cell cycle progression," Cellular Immunol., 202:124-135 (2000).
Kenakin et al., "Signalling bias in new drug discovery: detection, quantification and therapeutic impact," Nat. Rev. Drug Discov., 12:205-216 (2013).
Kir et al., "Roles of FGF19 in Liver Metabolism," Cold Spring Harb. Symp. Quant. Biol., 76:139-144 (2011).
Kumar et al., "Molecular cloning and expression of the Fabs of human autoantibodies in *Escherichia coli*. Determination of the heavy or light chain contribution to the anti-DNA/-cardiolipin activity of the Fab," J. Biol. Chem., 275:35129-35136 (2000).
Kurosu et al., "Regulation of fibroblast growth factor-23 signaling by klotho," J. Biol. Chem., 281(10):6120-6123 (2006).
Kurosu et al., "Supplemental Data for: Tissue-specific Expression fo βKlotho and Fibroblast Growth Factor (FGF) Receptor Isoforms Determines Metabolic Activity of FGF19 and FGF21," J. Biol. Chem., (2007) (available at: http://www.jbc.org/content/suppl/2007/07/11/M704165200.DC1/Kurosu_Suppl_Data.pdf (last visited Jul. 23, 2014).
Kurosu et al., "Tissue-specific Expression fo βKlotho and Fibroblast Growth Factor (FGF) Receptor Isoforms Determines Metabolic Activity of FGF19 and FGF21," J. Biol. Chem., 282(37):26687-26695 (2007).
Lee et al., "Structures of β-klotho reveal a 'zip code'-like mechanism for endocrine FGF signaling," Nature, 553:501-505, Extended Data (2018).
Lin et al., "Liver-specific Activities of FGF19 Require Klotho beta," J. Biol. Chem., 282(37):27277-27284 (2007).
Lin et al., "The STAT3 inhibitor NSC 74859 is effective in hepatocellular cancers with disrupted TGF-beta signaling," Oncogene, 28:961-972 (2009).
Lindor, "Ursodeoxycholic acid for the treatment of primary biliary cirrhosis," New Engl. J Med., 357:1524-1529 (2007).
Ling et al., "Identification of Gut Factors that Mimic the Metabolic Benefits Seen After Gastric Bypass Surgery," American Diabetes Association, 72nd Scientific Sessions, Jun. 8-12, 2012, Philadelphia, PA, http://www.abstactsonline.com.
Ling et al., NGM Biopharmaceuticals, Identification of Gut Factors that Mimic the Metabolic Benefits of Gastric Bypass Surgery, p. 1, Jun. 8-12, 2012 Abstract.
Luo et al., "A nontumorigenic variant of FGF19 treats cholestatic liver diseases," Sci. Transl. Med., 6, 247ra100, 1-11 (2014).
MacCallum et al., "Antibody-antigen Interactions: Contact Analysis and Binding Site Topography," J. Mol.Biol., 262:732-745 (1996).
Mellor, "Targeted inhibition of the FGF19-FGFR4 pathway in hepatocellular carcinoma; translational safety considerations," Liver Int., e1-e9 (2014).
Micanovic et al., "Different roles of N- and C-termini in the functional activity of FGF21," J. Cell. Physiol., 219:227-234 (2009).
Miyata et al., "Involvement of Multiple Elements in FXR-mediated Transcriptional Activation of FGF19," J. Steroid Biochm. Mol. Biol., 132:41-47 (2012).
Moyers et al., "Molecular determinants of FGF-21 activity-synergy and cross-talk with PPARgamma signaling," J. Cell. Physiol., 210(1):1-6 (2007).
NCBI Reference Sequence: NP_783864.1: beta-klotho (*Homo sapiens*) [online] Nov. 2, 2013 [retrieved Mar. 28, 2015]. Available on the internet : URL:http://www.uniprot.org/uniprot/Q86Z14.txt?version=93.
Nicholes et al., "A Mouse Model of Hepatocellular Carcinoma: Ectopic Expression of Fibroblast Growth Factor in Skeletal Muscle of Transgenic Mice," Amer. J. Pathol., 160:2295-2307 (2002).
Ogawa et al., "BetaKlotho is Required for Metabolic Activity of Fibroblast Growth Factor 21," Proc. Natl. Acad. Sci. USA, 104:7432-7437 (2007).
Pai et al., "Antibody-Mediated Inhibition of Fibroblast Growth Factor 19 Results in Increased Bile Acids Synthesis and Ileal Malabsorption of Bile Acids in Cynomolgus Monkeys," Toxicological Sciences, 126(2):446-456 (2012).
Pattni et al., "Fibroblast Growth Factor 19 and 7α-Hydroxy-4-Cholesten-3-one in the Diagnosis of Patients With Possible Bile Acid Diarrhea," Clinical and Translational Gastroenterology, 3:e18 (2012).
Potthoff et al., "Endocrine Fibroblast Growth Factors 15/19 and 21: From Feast to Famine," Genes Dev., 26:312-324 (2012).
Pusl et al., "Intrahepatic cholestasis of pregnancy," Orphanet. J Rare Diseases, 2:26 (2007).
R&D Systems, "Monoclonal Anti-human/mouse Klotho β Antibody," catalog No. MAB3738 (Feb. 6, 2007).
Rose et al., "Molecular Control of Systemic Bile Acid Homeostasis by the Liver Glucocorticoid Receptor," Cell Metabolism, 14:123-130 (2011).
Rossi et al., "Ngm282, a Novel Specific Inhibitor of Cyp7a1-Mediated Bile Acid Synthesis, is Safe and Well Tolerated with Predictable Pharmacokinetics in Healthy Human Subjects," Journal of Hepatology, 60(1): S533 (2014).
Ryan et al., "FXR is a Molecular Target for the Effects of Vertical Sleeve Gastroectomy," Nature, 509(7499):183-188 (2014); epub ahead of print Mar. 26, 2014.
Sawey et al., "Identification of a Therapeutic Strategy Targeting Amplified FGF19 in Liver Cancer by Oncogenomic Screening," Cancer Cell, 19(3):347-358 (2011).
Schaap et al., "High expression of the bile salt-homeostatic hormone fibroblast growth factor 19 in the liver of patients with extrahepatic cholestasis," Hepatol., 49:1228-1235 (2009).

(56) References Cited

OTHER PUBLICATIONS

Schaap, "Role of Fibroblast Growth Factor 19 in the Control of Glucose Homeostasis," Curr. Opin. Clin. Nutr. Metab. Care, 15(4):386-391 (2012).
Smith et al., "FGF21 Can Be Mimicked In Vitro and In Vivo by a Novel Anti-FGFR1c/b-Klotho Bispecific Protein," PLoS One, 8(4):1-11 (2013).
Smith-Gill et al., "Contributions of Immunoglobulin Heavy and Light Chains to Antibody Specificity for Lysozyme and Two Haptens," J. Immunol., 139:4135-4144 (1987).
Song et al., "Light Chain of Natural Antibody Plays a Dominant Role in Protein Antigen Binding," Biochem. Biophys. Res. Comm., 268:390-394 (2000).
Tartaglia et al., "Identification and expression cloning of a leptin receptor, OB-R," Cell, 83:1263-1271 (1995).
Tomlinson et al., "Transgenic Mice Expressing Human Fibroblast Growth Factor-19 Display Increased Metabolic Rate and Decreased Adiposity," Endocrinology, 143(5):1741-1747 (2002).
Urakawa et al., "Klotho converts canonical FGF receptor into a specific receptor for FGF23," Nature, 444(7210):770-774 (2006).
Vajdos et al., "Comprehensive Functional Maps of the Antigen-binding Site of an Anti-ErbB2 Antibody Obtained with Shotgun Scanning Mutagenesis," J. Mol. Biol., 320:415-428 (2002).
Walters et al., "Managing bile acid diarrhoea," Ther. Adv. Gastroenterol., 3(6): 349-357 (2010).
Walters, "A variant of FGF19 for treatment of disorders of cholestasis and bile acid metabolism," Ann. Transl. Med., 3(S1):S7 (2015).
Wang et al., "Leptin in hepatocellular carcinoma," World J. Gastroenterol., 16:5801-5809 (2010).
Wu et al., "FGF19 Regulates Cell Proliferation, Glucose and Bile Acid Metabolism via FGFR4-Dependent and Independent Pathways," PLoS One, 6(3):e17868, 1-11 (2011).
Wu et al., "C-terminal Tail of FGF19 Determines Its Specificity toward Klotho C-receptors," J. Biol. Chem., 283(48):33304-33309 (2008).
Wu et al., "FGF19-induced Hepatocyte Proliferation is Mediated Through FGFR4 Activation," J. Biol. Chem., 285(8):5165-5170 (2010).
Wu et al., "Humanization of a Murine Monoclonal Antibody by Simultaneous Optimization of Framework and CDR Residues," J. Mol. Biol., 294:151-162 (1999).
Wu et al., "Role of FGF19 Induced FGFR4 Activation in the Regulation of Glucose Homeostasis," Aging, 1(12):1023-1027 (2009).
Wu et al., "Selective Activation of FGFR4 by an FGF19 Variant Does Not Improve Glucose Metabolism in ob/ob Mice," Proc. Natl. Acad. Sci. USA, 106(34):14379-14384 (2009).
Wu et al., "Separating Mitogenic and Metabolic Activities of Fibroblast Growth Factor 19 (FGF19)," Proc. Natl. Acad. Sci. USA, 107(32):14158-14163 (2010).
Wu et al., "Therapeutic Utilities of Fibroblast Growth Factor 19," Expert Opin. Ther. Targets, 15(11):1307-1316 (2011).
Xie et al., "FGF-19, A Novel Fibroblast Growth Factor with Unique Specificity for FGFR4," Cytokine, 11(10):729-735 (1999).
Zhang et al., "Adenovirus-adeno-associated virus hybrid for large-scale recombinant adeno-associated virus production," Hum. Gene Ther., 20:922-929 (2009).
Zhang et al., "Fibroblast growth factor 21 analogs for treating metabolic disorders," Front. Endocrinol., 6(168):1-9 (2015).
Zhou et al., "Engineered fibroblast growth factor 19 reduces liver injury and resolves sclerosing cholangitis in Mdr2-deficient mice," Hepatology, 63(3):914-929 (2016).
Zhou et al., "Separating Tumorigenicity from Bile Acid Regulatory Activity for Endocrine Hormone FGF19," Cancer Research, 74(12):3306-3316 (2014).
Fu et al., "Fibroblast growth factor 19 increases metabolic rate and reverses dietary and leptin-deficient diabetes," *Endocrinology*, 145(6):2594-2603 (2004).
Gunawardane et al., "Agonistic Human Antibodies Binding to Lecithin-Cholesterol Acyltransferase Modulate High Density Lipoprotein Metabolism," *J. Biol. Chem.*, 291(6):2799-2811 (2016).
Ito et al., "Impaired negative feedback suppression of bile acid synthesis in mice lacking betaKlotho,"*J. Clin. Invest.*, 115(8):2202-2208 (2005).
Kim et al., "Tethered-variable CL bispecific IgG: an antibody platform for rapid bispecific antibody screening," *Protein Eng. Des. Sel.*, 30(9):627-637 (2017).
Kuro-O; *Endocrine FGFs and Klothos*, Springer-Verlag, New York, chapter 2, pp. 25-40 (2012).
Li et al., "Transgenic expression of cholesterol 7alpha-hydroxylase in the liver prevents high-fat diet-induced obesity and insulin resistance in mice," *Hepatology*, 52(2):678-690 (2010).
PCT International Search Report and Written Opinion in International Appl. No. PCT/US2016/044704, dated Feb. 7, 2017, 14 pages.
PCT International Search Report and Written Opinion in International Appl. No. PCT/US2015/012731, dated Jul. 10, 2015, 13 pages.

VH Domain

```
Kabat    1          10                  22        31----35      40              50--a-------------65
AbM      1          10                  22   26-------35         40             50--a-----58       65
Chothia  1          10                  22   26----32            40                   a--55         65
Contact  1          10                  22        30----35       40                   a----58       65
IMGT     1          10                  23   27-----38  41                       56-----65          74
AHon     1                              23   27         42       47-------                57        76

2J21    EVQLQQSGPELVKPGASVKISCKTS GYTFTEYIMH WVKQSHGKSLEWIG NIDPNTGGTSYNQKFKG
4A2     EVQLQQSGPELVKPGTSVKISCKTS GYTFTEYTMY WVKQSHGKSLEWIG GFNPNYGGASYNQKFKD
3I13    QVQLQQSGPELVKPGASVKISCKTS GYTFTEYTMH WVKQSHGKSLEWIG SFNPDSGGTSYNQKFKG

Kabat    70          80   abc       90       95----100-----102              110
AbM      70          80   abc       90       95----100-----102              110
Chothia  70          80   abc       90       96----100-----101              110
Contact  70          80   abc       90       93----100-----101              110
IMGT     75          89                      105-------------117
AHon                                  106 109              138

2J21    KATLTVDKSSSTAFMELRSLTSEDSAVYYCAR DDGYSTRYWYFDV WGAGTTVTVSS   (SEQ ID NO:103)
4A2     KATLTVDKSSSTAYMELRSLTSEDSAVYYCAR DDGYSTRYWYFDV WGAGTTVTVSS   (SEQ ID NO:104)
3I13    KATLTVDKSSSTAYMELRSLTSEDSAVYYCAR DDGYSTRYWYFDV WGAGTTVTVSS   (SEQ ID NO:105)
```

FIGURE 1A

VL Domain

```
Kabat     1         10         20         24----34       40                    50----56
AbM       1         10         20         24----34       40                    50----56
Chothia   1         10         20         26--32         40                    50---
Contact   1         10         20             30----36   40                    46----55
IMGT      1                                   27---38 41                          56-65 69
                                                                                  |   |
AHon      1                                       42                           58     72
2J21          DIQMTQSPPSLSASVGETVTITC    GASENIYGALN     WYQRKQGKSPQLLIY    GATNLAD
4A2           DIQMTQSPASLSASVGETVTITC    GASENIYGALN     WYQRKQGKSPQLLIY    GATNLAD
3T13          DIQMTQSPASLSASVGETVTITC    GASENIYGALN     WFQRKQGKSPQLLIY    GATNLAD Kabat     60         70         80         89-------97
AbM       60         70         80         89-------97
Chothia   60         70         80            91----96
Contact   60         70         80         89-------96
IMGT      70         89                     105------117
AHon      73         91                     107        138
2J21          GMSSRFSGSGSGRQYSLKISSLHPDDVATYYC  QNVLSTPYT  FGGGTKLEIK   (SEQ ID NO:114)
4A2           GMSSRFSGSGSGRQYSLKISSLHPDDVATYYC  QNVLSTPYT  FGGGTKLEIK   (SEQ ID NO:115)
3T13          GMSSRFSGSGSGRQYSLKISSLHPDDVATYYC  QNVLSTPYT  FGGGTKLEIK   (SEQ ID NO:116)
```

FIGURE 1B

VH Domain

```
Kabat    1            10          22                31---35      40              50---a----60---65
AbM      1            10          22        26-----35            40              50---a----58      65
Chothia  1            10          22        26-----32            40                    a--55       65
Contact  1            10          22             30---35         40              50---a----58      65
IMGT     1            10          23        27-----38   41                                 56---65 74
AHon     1            10          23             27     42                       47                57  76
2J21           EVQLQQSGPELVKPGASVKISCKTS GYTFTEYIMH WVKQSHGKSLEWIG NIDPMTGGTSYNQKFKG
4A2            EVQLQQSGPELVKPGTSVKISCKTS GYTFTEYTMY WVKQSHGKSLEWIG GFNPNYGGASYNQKFKD
3I13           QVQLQQSGPELVKPGASVKISCKTS GYTFTEYTMH WVKQSHGKSLEWIG SFNPDSGGTSYNQKFKG
consensus                                 GYTFTEYx₁Mx₂ (SEQ ID NO:49)  xxxPxxGxSYNQKFKx (SEQ ID NO:50)
                                  where x₁ = T, I and x₂ = H, Y
```

```
Kabat    70           80  abc      90       95---100---102           110
AbM      70           80  abc      90       95---100---102           110
Chothia  70           80  abc      90       96---100---101           110
Contact  70           80  abc      90       93---100---101           110
IMGT     75                89             105-----------117          138
AHon                                         106 109
2J21     KATLTVDKSSTAFMELRSLTSEDSAVYYCAR DDGYSTRYWYFDV WGAGTTVTVSS (SEQ ID NO:103)
4A2      KATLTVDKSSTAYMELRSLTSEDSAVYYCAR DDGYSTRYWYFDV WGAGTTVTVSS (SEQ ID NO:104)
3I13     KATLTVDKSSTAYMELRSLTSEDSAVYYCAR DDGYSTRYWYFDV WGAGTTVTVSS (SEQ ID NO:105)
consensus                                DDGYSTRYWYFDV (SEQ ID NO:51)
```

FIGURE 2A

VL Domain

```
Kabat    1          10          20          24-------34        40              50----56
AbM      1          10          20          24-------34        40              50----56
Chothia  1          10          20          26-----32          40              50---
Contact  1          10          20             30-----36       40              46-----55
IMGT     1                                  27----38           41              56-65  69
                                                                                |    |
AHon               1            23          23                 42              58    72
2J21      DIQMTQSPPSLSASVGETVTITC   GASENIYGALN   WYQRKQGKSPQLLIY   GATNLAD
4A2       DIQMTQSPASLSASVGETVTITC   GASENIYGALN   WYQRKQGKSPQLLIY   GATNLAD
3T13      DIQMTQSPASLSASVGETVTITC   GASENIYGALN   WFQRKQGKSPQLLIY   GATILAD
consensus                           GASENIYGALN (SEQ ID NO:52)    GATx₁LAD (SEQ ID NO:53)
                                                                  where x₁ = N, I
```

```
Kabat     60         70          80          89-----97
AbM       60         70          80          89-----97
Chothia   60         70          80             91----96
Contact   60         70          80          89-----96
IMGT      70         89                      105-----117
AHon      73         91                      107       138
2J21      GMSSRFSGSGSGRQYSLKITSSLHPDDVATYYC   QNVLSTPYT   FGGGTKLEIK (SEQ ID NO:114)
4A2       GMSSRFSGSGSGRQYSLKISSLHPDDVATYYC   QNVLSTPYT   FGGGTKLEIK (SEQ ID NO:115)
3T13      GMSSRFSGSGSGRQYSLKISSLHPDDVATYYC   QNVLSTPYT   FGGGTKLEIK (SEQ ID NO:116)
consensus                                     QNVLSTPYT (SEQ ID NO:54)
```

FIGURE 2B

```
3I13 VH Domain
Kabat    1         10        22        26----31----35  40        50----a----60---65
AbM      1         10        22        26----------35  40        50----a----58    65
Chothia  1         10        22        26----32       40                 a-55    65
Contact  1         10        22        30----------35  40        50----a----58    65
IMGT     1         10        23        27----------38  41        56----------65    74
AHon     1         10        23        27            42                 57        76
m3I13        QVQLQQSGPELVKPGASVKISCKTS GYTFTEYTMH WVKQSHGKSLEWIG SFNPDSGGTSYNQKFKG
HC-007-a     QVQLVQSGAEVKKPGASVKVSCKAS GYTFTEYTMH WVRQAPGQGLEWMG SFNPDSGGTSYNQKFKG
HC-007-b     QVQLQQSGAEVKKPGASVKVSCKAS GYTFTEYTMH WVRQAPGQGLEWMG SFNPDSGGTSYNQKFKG
HC-007-c     QVQLVQSGPEVKKPGASVKVSCKAS GYTFTEYTMH WVRQAPGQGLEWMG SFNPDSGGTSYNQKFKG
HC-007-d     QVQLVQSGAEVKKPGVSVKVSCKAS GYTFTEYTMH WVRQAPGQGLEWMG SFNPDSGGTSYNQKFKG
HC-007-e     QVQLVQSGAEVKKPGASVKVSCKAS GYTFTEYTMH WVRQAHGQGLEWMG SFNPDSGGTSYNQKFKG
HC-007-f     QVQLVQSGAEVKKPGASVKVSCKAS GYTFTEYTMH WVRQAPGKGLEWMG SFNPDSGGTSYNQKFKG
HC-007-g     QVQLVQSGAEVKKPGASVKVSCKAS GYTFTEYTMH WVRQAPGQSLEWMG SFNPDSGGTSYNQKFKG
HC-007-h     QVQLVQSGAEVKKPGASVKVSCKAS GYTFTEYTMH WVRQAPGQGLEWIG SFNPDSGGTSYNQKFKG
HC-007-i     QVQLVQSGAEVKKPGASVKVSCKAS GYTFTEYTMH WVRQAPGQGLEWMG SFNPDSGGTSYNQKFKG
HC-007-j     QVQLVQSGAEVKKPGASVKVSCKAS GYTFTEYTMH WVRQAPGQGLEWMG SFNPDSGGTSYNQKFKG
HC-007-k     QVQLVQSGAEVKKPGASVKVSCKAS GYTFTEYTMH WVRQAPGQGLEWMG SFNPDSGGTSYNQKFKG
HC-007-l     QVQLVQSGAEVKKPGASVKVSCKAS GYTFTEYTMH WVRQAPGQGLEWMG SFNPDSGGTSYNQKFKG
HC-007-m     QVQLVQSGAEVKKPGASVKVSCKAS GYTFTEYTMH WVRQAPGQGLEWMG SFNPDSGGTSYNQKFKG
HC-007-n     QVQLVQSGAEVKKPGASVKVSCKAS GYTFTEYTMH WVRQAPGQGLEWMG SFNPDSGGTSYNQKFKG
HC-007-o     QVQLVQSGAEVKKPGASVKVSCKAS GYTFTEYTMH WVRQAPGQGLEWIG SFNPDSGGTSYNQKFKG
HC-007-p     QVQLVQSGAEVKKPGASVKVSCKAS GYTFTEYTMH WVRQAHKSLEWMG SFNPDSGGTSYNQKFKG
HC-007-q     QVQLVQSGPEVKKPGASVKVSCKAS GYTFTEYTMH WVRQAPGQGLEWMG SFNPDSGGTSYNQKFKG
HC-007-r     QVQLVQSGAEVKKPGASVKVSCKAS GYTFTEYTMH WVRQAHGKSLEWMG SFNPDSGGTSYNQKFKG
HC-007-s     QVQLVQSGAEVKKPGASVKVSCKAS GYTFTEYTMH WVRQAPGKSLEWMG SFNPDSGGTSYNQKFKG
HC-007-t     QVQLVQSGAEVKKPGASVKVSCKAS GYTFTEYTMH WVRQAPGQGLEWIG SFNPDSGGTSYNQKFKG
HC-007-v     QVQLVQSGAEVKKPGASVKVSCKAS GYTFTEYTMH WVRQAPGKSLEWIG SFNPDSGGTSYNQKFKG
HC-007-w     QVQLVQSGAEVKKPGASVKVSCKAS GYTFTEYTMH WVRQAPGKSLEWIG SFNPDSGGTSYNQKFKG
```

FIGURE 3A

| 3I13 VH Domain | | | | | | |
|---|---|---|---|---|---|---|
| Kabat | 70 | 80 abc | 90 | 95--100----102 | 110 | |
| AbM | 70 | 80 abc | 90 | 95--100----102 | 110 | |
| Chothia | 70 | 80 abc | 90 | 96-100---101 | 110 | |
| Contact | 70 | 80 abc | 90 | --100---101 | 110 | |
| IMGT | 75 | 89 | 93------117 | | | |
| Ahon | | | 105------117 | | | |
| | | | 106 109 | 138 | | |
| m3I13 | RATLITVDKSSTAYMELRSLTSEDSAVYYCAR | DDGYSTRYWYFDV | WGAGTTVTVSS | (SEQ ID NO:55) |
| HC-007-a | RVTMTRDTSTSTVYMELSSLRSEDTAVYYCAR | DDGYSTRYWYFDV | WGRGTLVTVSS | (SEQ ID NO:56) |
| HC-007-b | RVTMTRDTSTSTVYMELSSLRSEDTAVYYCAR | DDGYSTRYWYFDV | WGRGTLVTVSS | (SEQ ID NO:57) |
| HC-007-c | RVTMTRDTSTSTVYMELSSLRSEDTAVYYCAR | DDGYSTRYWYFDV | WGRGTLVTVSS | (SEQ ID NO:58) |
| HC-007-d | RVTMTRDTSTSTVYMELSSLRSEDTAVYYCAR | DDGYSTRYWYFDV | WGRGTLVTVSS | (SEQ ID NO:59) |
| HC-007-e | RVTMTRDTSTSTVYMELSSLRSEDTAVYYCAR | DDGYSTRYWYFDV | WGRGTLVTVSS | (SEQ ID NO:60) |
| HC-007-f | RVTMTRDTSTSTVYMELSSLRSEDTAVYYCAR | DDGYSTRYWYFDV | WGRGTLVTVSS | (SEQ ID NO:61) |
| HC-007-g | RVTMTRDTSTSTVYMELSSLRSEDTAVYYCAR | DDGYSTRYWYFDV | WGRGTLVTVSS | (SEQ ID NO:62) |
| HC-007-h | RAIMTRDTSTSTVYMELSSLRSEDTAVYYCAR | DDGYSTRYWYFDV | WGRGTLVTVSS | (SEQ ID NO:63) |
| HC-007-i | RVTMTRDTSTSTVYMELSSLRSEDTAVYYCAR | DDGYSTRYWYFDV | WGRGTLVTVSS | (SEQ ID NO:64) |
| HC-007-j | RVTLTRDTSTSTVYMELSSLRSEDTAVYYCAR | DDGYSTRYWYFDV | WGRGTLVTVSS | (SEQ ID NO:65) |
| HC-007-k | RVTMTRDTSTSTVYMELSSLRSEDTAVYYCAR | DDGYSTRYWYFDV | WGRGTLVTVSS | (SEQ ID NO:66) |
| HC-007-l | RVTMTRDTSTSTVYMELSSLRSEDTAVYYCAR | DDGYSTRYWYFDV | WGRGTLVTVSS | (SEQ ID NO:67) |
| HC-007-m | RVTMTRDTSTSTVYMELSSLRSEDTAVYYCAR | DDGYSTRYWYFDV | WGRGTLVTVSS | (SEQ ID NO:68) |
| HC-007-n | RVTMTVDKSTSTVYMELSSLRSEDTAVYYCAR | DDGYSTRYWYFDV | WGRGTLVTVSS | (SEQ ID NO:69) |
| HC-007-o | RATLTVDKSTSTAYMELSSLRSEDTAVYYCAR | DDGYSTRYWYFDV | WGRGTLVTVSS | (SEQ ID NO:70) |
| HC-007-p | RVTLTRDTSTSTVYMELSSLRSEDTAVYYCAR | DDGYSTRYWYFDV | WGRGTLVTVSS | (SEQ ID NO:71) |
| HC-007-q | RVTLTVDKSTSTVYMELSSLRSEDTAVYYCAR | DDGYSTRYWYFDV | WGRGTLVTVSS | (SEQ ID NO:72) |
| HC-007-r | RVTMTRDTSTSTVYMELRSLRSEDTAVYYCAR | DDGYSTRYWYFDV | WGRGTLVTVSS | (SEQ ID NO:73) |
| HC-007-s | RVTMTRDTSTSTVYMELSSLLTSEDTAVYYCAR | DDGYSTRYWYFDV | WGRGTLVTVSS | (SEQ ID NO:74) |
| HC-007-t | RVTMTVDKSTSTVYMELSSLRSEDTAVYYCAR | DDGYSTRYWYFDV | WGRGTLVTVSS | (SEQ ID NO:75) |
| HC-007-u | RATLTVDKSTSTAYMELSSLRSEDTAVYYCAR | DDGYSTRYWYFDV | WGRGTLVTVSS | (SEQ ID NO:76) |
| HC-007-v | RVTLTVDKSTSTVYMELSSLRSEDTAVYYCAR | DDGYSTRYWYFDV | WGRGTLVTVSS | (SEQ ID NO:77) |
| HC-007-w | RATLTVDKSTSTAYMELSSLRSEDTAVYYCAR | DDGYSTRYWYFDV | WGRGTLVTVSS | (SEQ ID NO:78) |

FIGURE 3A (Continued)

3I13 VL Domain

| | | | | | | |
|---|---|---|---|---|---|---|
| Kabat | 1 | 10 | 20 | 24- -------34 | 40 | 50----56 |
| AbM | 1 | 10 | 20 | 24- -------34 | 40 | 50----56 |
| Chothia | 1 | 10 | 20 | 26----32 | 40 | 50-- |
| Contact | 1 | 10 | 20 | 30----36 | 40 | 46----55 |
| IMGT | 1 | | | 27----38 41 | | 56-65 69 |
| | | | | | | |
| AHon | 1 | | 23 | 42 | | 58 72 |
| m3I13 | DIQMTQSPASLSASVGETVTITC | GASENIYGALN | WFQRKQGKSPQLLIY | GATILAD |
| LC-007-a | DIQMTQSPSSLSASVGDRVTITC | GASENIYGALN | WYQQKPGKAPKLLIY | GATILAD |
| LC-007-b | DIQMTQSPSSLSASVGDRVTITC | GASENIYGALN | WYQQKPGKAPKLLIY | GATILAD |
| LC-007-c | DIQMTQSPSSLSASVGDTVTITC | GASENIYGALN | WYQQKPGKAPKLLIY | GATILAD |
| LC-007-d | DIQMTQSPSSLSASVGDRVTITC | GASENIYGALN | WFQQKPGKAPKLLIY | GATILAD |
| LC-007-e | DIQMTQSPSSLSASVGDRVTITC | GASENIYGALN | WYQQKPGRKPGKAPKLLIY | GATILAD |
| LC-007-f | DIQMTQSPSSLSASVGDRVTITC | GASENIYGALN | WYQQKPGKQKPGKAPKLLIY | GATILAD |
| LC-007-g | DIQMTQSPSSLSASVGDRVTITC | GASENIYGALN | WYQQKPGKNSPKLLIY | GATILAD |
| LC-007-h | DIQMTQSPSSLSASVGDRVTITC | GASENIYGALN | WYQQKPGKAPQLLIY | GATILAD |
| LC-007-i | DIQMTQSPSSLSASVGDRVTITC | GASENIYGALN | WYQQKPGKAPKLLIY | GATILAD |
| LC-007-j | DIQMTQSPSSLSASVGDRVTITC | GASENIYGALN | WYQQKPGKAPKLLIY | GATILAD |
| LC-007-k | DIQMTQSPSSLSASVGDRVTITC | GASENIYGALN | WYQQKPGKAPKLLIY | GATILAD |
| LC-007-l | DIQMTQSPSSLSASVGDRVTITC | GASENIYGALN | WYQQKPGKAPKLLIY | GATILAD |
| LC-007-m | DIQMTQSPSSLSASVGDRVTITC | GASENIYGALN | WYQQKPGKAPKLLIY | GATILAD |
| LC-007-n | DIQMTQSPSSLSASVGDRVTITC | GASENIYGALN | WFQQKPGKAPKLLIY | GATILAD |
| LC-007-o | DIQMTQSPSSLSASVGDRVTITC | GASENIYGALN | WFQQKPGKAPKLLIY | GATILAD |
| LC-007-p | DIQMTQSPSSLSASVGDRVTITC | GASENIYGALN | WYQQKPGKSPKLLIY | GATILAD |

FIGURE 3B

| 2J21 VH Domain | | | | | | | | |
|---|---|---|---|---|---|---|---|---|
| Kabat | 1 | 10 | 22 | 31---35 | 40 | 50--a---- | ----60---65 | |
| AbM | 1 | 10 | 22 | 26-----35 | 40 | 50--a---58 | 65 | |
| Chothia | 1 | 10 | 22 | 26----32 | 40 | a-55 | 65 | |
| Contact | 1 | 10 | 22 | 30----35 | 40 | | 65 | |
| IMGT | 1 | 10 | 23 | 27----38 | 41 | 47------- | ----58 | 74 |
| AHon | 1 | 10 | 23 | 27 | 42 | 56-----65 | 76 | |
| m2J21 | EVQLQQSGPELVKPGASVKISCKTS | GYTFTEYTMH | WVKQSHGKSLEWIG | NIDPMTGGTSYNQKFKG |
| HC-336-a | QVQLVQSGAEVKKPGASVKVSCKAS | GYTFTEYTMH | WVRQAPGQGLEWMG | NIDPMTGGTSYNQKFKG |
| HC-336-b | QVQLVQSGAEVKKPGASVKVSCKAS | GYTFTEYTMH | WVRQAPGQGLEWMG | NIDPMTGGTSYNQKFKG |
| HC-336-c | QVQLVQSGPEVKKPGASVKVSCKAS | GYTFTEYTMH | WVRQAPGQGLEWMG | NIDPMTGGTSYNQKFKG |
| HC-336-d | QVQLVQSGAEVKKPGASVKVSCKAS | GYTFTEYTMH | WVRQAPGQGLEWMG | NIDPMTGGTSYNQKFKG |
| HC-336-e | QVQLVQSGAEVKKPGASVKVSCKAS | GYTFTEYTMH | WVRQAHGQGLEWMG | NIDPMTGGTSYNQKFKG |
| HC-336-f | QVQLVQSGAEVKKPGASVKVSCKAS | GYTFTEYTMH | WVRQAPGKGLEWMG | NIDPMTGGTSYNQKFKG |
| HC-336-g | QVQLVQSGAEVKKPGASVKVSCKAS | GYTFTEYTMH | WVRQAPGQSLEWMG | NIDPMTGGTSYNQKFKG |
| HC-336-h | QVQLVQSGAEVKKPGASVKVSCKAS | GYTFTEYTMH | WVRQAPGQGLEWMG | NIDPMTGGTSYNQKFKG |
| HC-336-i | QVQLVQSGAEVKKPGASVKVSCKAS | GYTFTEYTMH | WVRQAPGQGLEWIG | NIDPMTGGTSYNQKFKG |
| HC-336-j | QVQLVQSGAEVKKPGASVKVSCKAS | GYTFTEYTMH | WVRQAPGQGLEWMG | NIDPMTGGTSYNQKFKG |
| HC-336-k | QVQLVQSGAEVKKPGASVKVSCKAS | GYTFTEYTMH | WVRQAPGQGLEWMG | NIDPMTGGTSYNQKFKG |
| HC-336-l | QVQLVQSGAEVKKPGASVKVSCKAS | GYTFTEYTMH | WVRQAPGQGLEWIG | SFNPDSGGTSYNQKFKG |
| HC-336-m | QVQLVQSGAEVKKPGASVKVSCKAS | GYTFTEYTMH | WVRQAPGQGLEWMG | NIDPMTGGTSYNQKFKG |
| HC-336-n | QVQLVQSGAEVKKPGASVKVSCKAS | GYTFTEYTMH | WVRQAPGQGLEWIG | NIDPMTGGTSYNQKFKG |
| HC-336-o | QVQLVQSGAEVKKPGASVKVSCKAS | GYTFTEYTMH | WVRQAPGQGLEWMG | NIDPMTGGTSYNQKFKG |
| HC-336-p | QVQLVQSGAEVKKPGASVKVSCKAS | GYTFTEYTMH | WVRQAHLKSLEWMG | NIDPMTGGTSYNQKFKG |
| HC-336-q | QVQLVQSGPEVKKPGASVKVSCKAS | GYTFTEYTMH | WVRQAHLKSLEWIG | NIDPMTGGTSYNQKFKG |
| HC-336-r | QVQLVQSGAEVKKPGASVKVSCKAS | GYTFTEYTMH | WVRQAPGKSLEWMG | NIDPMTGGTSYNQKFKG |
| HC-336-s | QVQLQSGAEVKKPGASVKVSCKAS | GYTFTEYTMH | WVRQAPGQGLEWMG | NIDPMTGGTSYNQKFKG |
| HC-336-t | QVQLVQSGAEVKKPGASVKVSCKAS | GYTFTEYTMH | WVRQAPGKSLEWMG | NIDPMTGGTSYNQKFKG |
| HC-336-u | QVQLVQSGAEVKKPGASVKVSCKAS | GYTFTEYTMH | WVRQAPGQGLEWMG | SFNPDSGGTSYNQKFKG |
| HC-336-v | QVQLVQSGAEVKKPGASVKVSCKAS | GYTFTEYTMH | WVRQAPGQGLEWMG | SFNPDSGGTSYNQKFKG |
| HC-336-w | QVQLVQSGAEVKKPGASVKVSCKAS | GYTFTEYTMH | WVRQAPGKSLEWMG | NIDPMTGGTSYNQKFKG |
| HC-336-x | QVQLVQSGAEVKKPGASVKVSCKAS | GYTFTEYTMH | WVRQAPGKSLEWMG | NIDPMTGGTSYNQKFKG |

FIGURE 4A

| 2321 VH Domain | | | | | | |
|---|---|---|---|---|---|---|
| Kabat | 70 | 80 | abc | 90 | 95--100----102 | 110 |
| AbM | 70 | 80 | abc | 90 | 95--100----102 | 110 |
| Chothia | 70 | 80 | abc | 90 | 96--100---101 | 110 |
| Contact | 70 | 80 | abc | 90 | 93-----100---101 | 110 |
| IMGT | 75 | 89 | | | 105-----------117 | |
| AbOn | | | | | 106 109    138 | |
| m2J21 | RATLTVDKSSITAFMELRSLTSEDSAVYYCAR | | | | DDGYSTRYWYFDV | WGAGTTVTVSS (SEQ ID NO:161) |
| HC-336-a | RVTMTRDTSTSTVYMELSSLRSEDTAVYYCAR | | | | DDGYSTRYWYFDV | WGRGTLVTVSS (SEQ ID NO:162) |
| HC-336-b | RVTMTRDTSTSTVYMELSSLRSEDTAVYYCAR | | | | DDGYSTRYWYFDV | WGRGTLVTVSS (SEQ ID NO:164) |
| HC-336-c | RVTMTRDTSTSTVYMELSSLRSEDTAVYYCAR | | | | DDGYSTRYWYFDV | WGRGTLVTVSS (SEQ ID NO:207) |
| HC-336-d | RVTMTRDTSTSTVYMELSSLRSEDTAVYYCAR | | | | DDGYSTRYWYFDV | WGRGTLVTVSS (SEQ ID NO:214) |
| HC-336-e | RVTMTRDTSTSTVYMELSSLRSEDTAVYYCAR | | | | DDGYSTRYWYFDV | WGRGTLVTVSS (SEQ ID NO:216) |
| HC-336-f | RVTMTRDTSTSTVYMELSSLRSEDTAVYYCAR | | | | DDGYSTRYWYFDV | WGRGTLVTVSS (SEQ ID NO:220) |
| HC-336-g | RVTMTRDTSTSTVYMELSSLRSEDTAVYYCAR | | | | DDGYSTRYWYFDV | WGRGTLVTVSS (SEQ ID NO:221) |
| HC-336-h | RAMTRDTSTSTVYMELSSLRSEDTAVYYCAR | | | | DDGYSTRYWYFDV | WGRGTLVTVSS (SEQ ID NO:233) |
| HC-336-i | RVTMTRDTSTSTVYMELSSLRSEDTAVYYCAR | | | | DDGYSTRYWYFDV | WGRGTLVTVSS (SEQ ID NO:234) |
| HC-336-j | RVTMTRDTSTSTVYMELSSLRSEDTAVYYCAR | | | | DDGYSTRYWYFDV | WGRGTLVTVSS (SEQ ID NO:235) |
| HC-336-k | RVTMVTRDKTSTSTVYMELSSLRSEDTAVYYCAR | | | | DDGYSTRYWYFDV | WGRGTLVTVSS (SEQ ID NO:236) |
| HC-336-l | RVTMTRDKTSTSTVYMELSSLRSEDTAVYYCAR | | | | DDGYSTRYWYFDV | WGRGTLVTVSS (SEQ ID NO:237) |
| HC-336-m | RVTMTRDTSTAYMELSSLRSEDTAVYYCAR | | | | DDGYSTRYWYFDV | WGRGTLVTVSS (SEQ ID NO:238) |
| HC-336-n | RVTMVDKSTSTVYMELSSLRSEDTAVYYCAR | | | | DDGYSTRYWYFDV | WGRGTLVTVSS (SEQ ID NO:239) |
| HC-336-o | RATLVDKSTSTAYMELSSLRSEDTAVYYCAR | | | | DDGYSTRYWYFDV | WGRGTLVTVSS (SEQ ID NO:240) |
| HC-336-p | RVTMTRDTSTSTVYMELSSLRSEDTAVYYCAR | | | | DDGYSTRYWYFDV | WGRGTLVTVSS (SEQ ID NO:241) |
| HC-336-q | RVTLVDKTSTSTVYMELSSLRSEDTAVYYCAR | | | | DDGYSTRYWYFDV | WGRGTLVTVSS (SEQ ID NO:242) |
| HC-336-r | RVTLVDKSTSTVYMELSSLRSEDTAVYYCAR | | | | DDGYSTRYWYFDV | WGRGTLVTVSS (SEQ ID NO:243) |
| HC-336-s | RVTMTRDTSTSTVYMELRSLRSEDTAVYYCAR | | | | DDGYSTRYWYFDV | WGRGTLVTVSS (SEQ ID NO:244) |
| HC-336-t | RVTMTRDTSTSTVYMELRSLRSEDTAVYYCAR | | | | DDGYSTRYWYFDV | WGRGTLVTVSS (SEQ ID NO:245) |
| HC-336-u | RVTMTRDTSHVYMELSSLTRSEDTAVYYCAR | | | | DDGYSTRYWYFDV | WGRGTLVTVSS (SEQ ID NO:246) |
| HC-336-v | RVTMTRDTSTSTVYMELSSLRSEDTAVYYCAR | | | | DDGYSTRYWYFDV | WGRGTLVTVSS (SEQ ID NO:247) |
| HC-336-w | RVTMTVDKSTSTAYMELSSLRSEDTAVYYCAR | | | | DDGYSTRYWYFDV | WGRGTLVTVSS (SEQ ID NO:248) |
| HC-336-x | RATLVDKSTSTAYMELSSLRSEDTAVYYCAR | | | | DDGYSTRYWYFDV | WGRGTLVTVSS (SEQ ID NO:249) |

FIGURE 4A (Continued)

```
2J21 VL Domain
Kabat     1           10           20            24-------34          40                   50------56
AbM       1           10           20            24-------34          40                   50------56
Chothia   1           10           20         26-----32               40                   50---
Contact   1           10           20               30-----36         40              46-------55
IMGT      1           10           20         27----38       41                                    56-65  69
                                              42                                          58       72
ABoon     1           23           23
m2J21         DIQMTQSPPSLSASVGETVTITC  GASENIYGALN  WYQRKQGKSPOLLIY  GATNLAD
LC-336-a      DIQMTQSPSSLSASVGDRVTITC  GASENIYGALN  WYQQKPGKAPKLLIY  GATNLAD
LC-336-b      DIQMTQSPSSLSASVGDRVTITC  GASENIYGALN  WYQRKPGKAPKLLIY  GATNLAD
LC-336-c      DIQMTQSPSSLSASVGDRVTITC  GASENIYGALN  WYQQKPGKAPKLLIY  GATNLAD
LC-336-d      DIQMTQSPSSLSASVGDRVTITC  GASENIYGALN  WYQQKQKAPKLLIY   GATNLAD
LC-336-e      DIQMTQSPSSLSASVGDRVTITC  GASENIYGALN  WYQQPGKSPKLLIY   GATNLAD
LC-336-f      DIQMTQSPSSLSASVGDRVTITC  GASENIYGALN  WYQQKPGKAPQLLIY  GATNLAD
LC-336-g      DIQMTQSPSSLSASVGDRVTITC  GASENIYGALN  WYQQKPGKAPKLLIY  GATNLAD
LC-336-h      DIQMTQSPSSLSASVGDRVTITC  GASENIYGALN  WYQQKPGKAPKLLIY  GATNLAD
LC-336-i      DIQMTQSPSSLSASVGDRVTITC  GASENIYGALN  WYQQKPGKAPKLLIY  GATNLAD
LC-336-j      DIQMTQSPSSLSASVGDRVTITC  GASENIYGALN  WYQQKPGKAPKLLIY  GATNLAD
LC-336-k      DIQMTQSPSSLSASVGDRVTITC  GASENIYGALN  WYQQKPGKAPKLLIY  GATNLAD
LC-336-l      DIQMTQSPSSLSASVGDRVTITC  GASENIYGALN  WYQQKPGKAPKLLIY  GATNLAD
LC-336-m      DIQMTQSPSSLSASVGDRVTITC  GASENIYGALN  WYQQKQGKSPKLLIY  GATNLAD
LC-336-n      DIQMTQSPSSLSASVGDRVTITC  GASENIYGALN  WYQQKPGKAPKLLIY  GATNLAD
LC-336-o      DIQMTQSPSSLSASVGDRVTITC  GASENIYGALN  WYQQKQGKSPKLLIY  GATNLAD
LC-336-p      DIQMTQSPSSLSASVGDRVTITC  GASENIYGALN  WYQQKQGRSPKLLIY  GATNLAD
LC-336-q      DIQMTQSPSSLSASVGDTVTITC  GASENIYGALN  WYQQKPGKAPKLLIY  GATNLAD
```

FIGURE 4B

| 4A2 VH Domain | | | | | | | |
|---|---|---|---|---|---|---|---|
| Kabat | 70 | 80 | abc | 90 | 95-100---102 | | 110 |
| AbM | 70 | 80 | abc | 90 | 95-100---102 | | 110 |
| Chothia | 70 | 80 | abc | 90 | 96-100---101 | | 110 |
| Contact | 70 | 80 | abc | 90 | 93------101 | | 110 |
| IMGT | 75 | 89 | | | 105----------117 | | |
| AHon | | | | 106 109 | | 138 | |

| | | | | |
|---|---|---|---|---|
| m4A2 | KATLTVDKSSTAYMELRSLTSEDSAVYYCAR | DDGYSTRYWYFDV | WGAGTTVTVSS | (SEQ ID NO:268) |
| HC-337-a | RVTMTRDTSTSTVYMELSSLRSEDTAVYYCAR | DDGYSTRYWYFDV | WGRGTLVTVSS | (SEQ ID NO:269) |
| HC-337-b | RVTMTRDTSTSTVYMELSSLRSEDTAVYYCAR | DDGYSTRYWYFDV | WGRGTLVTVSS | (SEQ ID NO:270) |
| HC-337-c | RVTMTRDTSTSTVYMELSSLPSEDTAVYYCAR | DDGYSTRYWYFDV | WGRGTLVTVSS | (SEQ ID NO:271) |
| HC-337-d | RVTMTRDTSTSTVYMELSSLRSEDTAVYYCAR | DDGYSTRYWYFDV | WGRGTLVTVSS | (SEQ ID NO:272) |
| HC-337-e | RVTMTRDTSTSTVYMELSSLRSEDTAVYYCAR | DDGYSTRYWYFDV | WGRGTLVTVSS | (SEQ ID NO:273) |
| HC-337-f | RVTMTRDTSTSTVYMELSSLRSEDTAVYYCAR | DDGYSTRYWYFDV | WGRGTLVTVSS | (SEQ ID NO:274) |
| HC-337-g | RVTMTRDTSTSTVYMELSSLRSEDTAVYYCAR | DDGYSTRYWYFDV | WGRGTLVTVSS | (SEQ ID NO:275) |
| HC-337-h | RVTMTRDTSTSTVYMELSSLRSEDTAVYYCAR | DDGYSTRYWYFDV | WGRGTLVTVSS | (SEQ ID NO:276) |
| HC-337-i | RATMTRDTSTSTVYMELSSLRSEDTAVYYCAR | DDGYSTRYWYFDV | WGRGTLVTVSS | (SEQ ID NO:277) |
| HC-337-j | RVTMTRDTSTSTVYMELSSLRSEDTAVYYCAR | DDGYSTRYWYFDV | WGRGTLVTVSS | (SEQ ID NO:278) |
| HC-337-k | RVTMTVDKSTSTVYMELSSLRSEDTAVYYCAR | DDGYSTRYWYFDV | WGRGTLVTVSS | (SEQ ID NO:279) |
| HC-337-l | RVTMTRDTSTSTVYMELSSLRSEDTAVYYCAR | DDGYSTRYWYFDV | WGRGTLVTVSS | (SEQ ID NO:280) |
| HC-337-m | RVTMTRDTSTSTVYMELSSLRSEDTAVYYCAR | DDGYSTRYWYFDV | WGRGTLVTVSS | (SEQ ID NO:281) |
| HC-337-n | RVTMTRDTSTSTVYMELSSLRSEDTAVYYCAR | DDGYSTRYWYFDV | WGRGTLVTVSS | (SEQ ID NO:282) |
| HC-337-o | RATLVVDKSTAYMELSSLRSEDTAVYYCAR | DDGYSTRYWYFDV | WGRGTLVTVSS | (SEQ ID NO:283) |
| HC-337-p | RVTMTRDTSTSTVYMELSSLRSEDTAVYYCAR | DDGYSTRYWYFDV | WGRGTLVTVSS | (SEQ ID NO:284) |
| HC-337-q | RVTLVDTSTSTVYMELRSLRSEDTAVYYCAR | DDGYSTRYWYFDV | WGRGTLVTVSS | (SEQ ID NO:285) |
| HC-337-r | RVTMTVDKSTSTVYMELSSLRSEDTAVYYCAR | DDGYSTRYWYFDV | WGRGTLVTVSS | (SEQ ID NO:288) |
| HC-337-s | RVTMTRDTSTSTVYMELSSLRSEDTAVYYCAR | DDGYSTRYWYFDV | WGRGTLVTVSS | (SEQ ID NO:289) |
| HC-337-t | RVTMTRDTSTSTVYMELSSLTSEDTAVYYCAR | DDGYSTRYWYFDV | WGRGTLVTVSS | (SEQ ID NO:290) |
| HC-337-u | RVTMTVDKSTSTVYMELSSLRSEDTAVYYCAR | DDGYSTRYWYFDV | WGRGTLVTVSS | (SEQ ID NO:291) |
| HC-337-v | RATLVDKSTAYMELSSLRSEDTAVYYCAR | DDGYSTRYWYFDV | WGRGTLVTVSS | (SEQ ID NO:292) |
| HC-337-w | RATLVDKSTAYMELSSLRSEDTAVYYCAR | DDGYSTRYWYFDV | WGRGTLVTVSS | (SEQ ID NO:293) |

FIGURE 5A (Continued)

| 4A2 VL Domain | | | | | | | | |
|---|---|---|---|---|---|---|---|---|
| Kabat | 1 | 10 | 20 | | 24--------34 | 40 | | 50------56 |
| AbM | 1 | 10 | 20 | | 24--------34 | 40 | | 50------56 |
| Chothia | 1 | 10 | 20 | | 26-----32 | 40 | | 50--- |
| Contact | 1 | 10 | 20 | | 30-----36 | 40 | 46--- | ---55 |
| IMGT | 1 | | | 23 | 27---38  41 | | | 56-65  69 |
| | | | | | 42 | | | 58  72 |
| AHon | 1 | | | | | | | |
| m4A2 | DIQMTQSPASLSASVGETVTITC | | | | GASENIYGALN | WYQRKQGNSPQLLIY | | GATNLAD |
| LC-337-a | DIQMTQSPSSLSASVGDRVTITC | | | | GASENIYGALN | WYQQKPGKAPKLLIY | | GATNLAD |
| LC-337-b | DIQMTQSPSSLSASVGDRVTITC | | | | GASENIYGALN | WYQQKPGKAPKLLIY | | GATNLAD |
| LC-337-c | DIQMTQSPSSLSASVGDTVTITC | | | | GASENIYGALN | WYQQKPGKAPKLLIY | | GATNLAD |
| LC-337-d | DIQMTQSPSSLSASVGDRVTITC | | | | GASENIYGALN | WYQRKPGKAPKLLIY | | GATNLAD |
| LC-337-e | DIQMTQSPSSLSASVGDRVTITC | | | | GASENIYGALN | WYQQNQGKAPKLLIY | | GATNLAD |
| LC-337-f | DIQMTQSPSSLSASVGDRVTITC | | | | GASENIYGALN | WYQQKPGKSPKLLIY | | GATNLAD |
| LC-337-g | DIQMTQSPSSLSASVGDRVTITC | | | | GASENIYGALN | WYQQKPGKAPKLLIY | | GATNLAD |
| LC-337-h | DIQMTQSPSSLSASVGDRVTITC | | | | GASENIYGALN | WYQQKPGKAPKLLIY | | GATNLAD |
| LC-337-i | DIQMTQSPSSLSASVGDRVTITC | | | | GASENIYGALN | WYQQKPGKAPKLLIY | | GATNLAD |
| LC-337-j | DIQMTQSPSSLSASVGDRVTITC | | | | GASENIYGALN | WYQQKPGKAFKLLIY | | GATNLAD |
| LC-337-k | DIQMTQSPSSLSASVGDRVTITC | | | | GASENIYGALN | WYQQKPGKAPKLLIY | | GATNLAD |
| LC-337-l | DIQMTQSPSSLSASVGDRVTITC | | | | GASENIYGALN | WYQQKPGKAPKLLIY | | GATNLAD |
| LC-337-m | DIQMTQSPSSLSASVGDTVTITC | | | | GASENIYGALN | WYQQKPGKQSKPLLIY | | GATNLAD |
| LC-337-n | DIQMTQSPSSLSASVGDRVTITC | | | | GASENIYGALN | WYQQKPGKAPKLLIY | | GATNLAD |
| LC-337-o | DIQMTQSPSSLSASVGDRVTITC | | | | GASENIYGALN | WYQQKPGKAPKLLIY | | GATNLAD |
| LC-337-p | DIQMTQSPSSLSASVGDRVTITC | | | | GASENIYGALN | WYQQNQGKSPKLLIY | | GATNLAD |
| LC-337-q | DIQMTQSPSSLSASVGDRVTITC | | | | GASENIYGALN | WYQQNQGKSPKLLIY | | GATNLAD |
| LC-337-r | DIQMTQSPSSLSASVGDRVTITC | | | | GASENIYGALN | WYQQNQGKSPKLLIY | | GATNLAD |

FIGURE 5B

BETA KLOTHO-BINDING PROTEINS

CROSS-REFERENCE TO RELATED APPLICATIONS

This application is a U.S. National Stage Application under 35 U.S.C. § 371 of International Patent Application No. PCT/US2016/044704, filed on Jul. 29, 2016, which claims the benefit of priority to U.S. Provisional Application No. 62/198,664, filed Jul. 29, 2015, the entire contents of which is incorporated by reference.

SEQUENCE LISTING

This application incorporates by reference the Computer Readable Form (CRF) of a Sequence Listing in ASCII text format submitted via EFS-Web. The Sequence Listing text file submitted via EFS-Web, entitled 13370-025-999_SUB_SEQ_LISTING.txt, was created on Nov. 8, 2018, and is 371,304 bytes in size.

FIELD

The present disclosure relates generally to binding proteins, such as antibodies, that bind to beta klotho, including human beta klotho, and methods of their use.

BACKGROUND

Beta klotho, which belongs to the Klotho family, is a single-pass type I membrane protein. Beta klotho has an extracellular domain consisting of two internal repeats which share homology with members of the family 1 glycosidases but lack glucosidase catalytic activity. Beta klotho expression is primarily detected in the liver, pancreas and adipose tissue. Ito and colleagues have reported that beta klotho-deficient (KLB−/−) mice have elevated mRNA levels of CYP7A1 and CY8B1 and exhibit increased synthesis and excretion of bile acid (Ito et al., 2005, J Clin Invest 115: 2202-2208). Beta klotho forms a complex with fibroblast growth factor (FGF) receptors and functions as a co-receptor for FGFs, including FGF19 and FGF21.

Twenty-two members of the human FGF family have been identified and four tyrosine kinase receptors that bind to FGF (FGFR1-FGFR4) have been identified. The interaction between FGF and its receptor results in FGFR dimerization, which enables the cytoplasmic domains of the receptor to transphosphorylate and become activated, which in turn leads to the phosphorylation and activation of downstream signaling molecules.

The high affinity receptor for FGF19 is FGFR4 and the binding of FGF19 to FGFR4 is facilitated by beta klotho. It has been reported that FGF19 transgenic mice have decreased adiposity, increased metabolic rate, reduced liver triglycerides, increased fatty acid oxidation, reduced glucose levels and increased insulin sensitivity (Tomlinson et al., 2002, Endocrinology 143: 1741-1747). In addition, these transgenic mice were reported not to become obese or diabetic on a high-fat diet (Tomlinson et al., 2002, Endocrinology 143: 1741-1747). It has also been reported that FGF19 treatment prevented or reversed diabetes in mice made obese by genetic ablation of brown adipose tissue or the genetic absence of leptin (Fu et al., 2004, Endocrinology 145: 2594-2603).

FGF21 acts through the interaction of FGFRs and beta klotho. FGFR1 is an abundant receptor in white adipose tissue and is most likely the main functional receptor for FGF21 in white adipose tissue. FGF21 expression is detected in the liver, thymus, adipose tissue, and islet beta-cells in the pancreas. It has been reported that the interaction of FGF21 with the beta klotho-FGFR complex stimulates glucose uptake, decreases glucagon secretion, improves insulin sensitivity and glucose clearance, promotes white adipose tissue in response to fasting, increases ketogenesis in liver in response to fasting, reduces plasma triglyceride levels, and increases energy expenditure (Iglesias et al., 2012, European Journal of Endocrinology 167: 301-309).

Since FGF19 and FGF21 require both FGFRs and beta klotho for cell signaling, agents which mimic FGF19 and/or FGF21 may be desirable for their effects or glucose metabolism or lipid metabolism. However, it is not clear what features are required for an agent to confer FGF19-like or FGF21-like cell signaling activity.

SUMMARY

The present disclosure provides proteins that bind to beta klotho, including binding proteins such as antibodies that bind to beta klotho. Such binding proteins including antibodies, may bind to a beta klotho polypeptide, a beta klotho fragment and/or a beta klotho epitope. Such binding proteins, including antibodies, may be agonists (e.g., induce FGF19-like or FGF21-like signaling of a FGF receptor or activate a beta klotho/FGF receptor complex).

The present disclosure also provides binding proteins, including antibodies or fragments thereof, that (i) bind to human beta klotho, (ii) induce FGF19-like signaling and/or FGF21-like signaling, and (iii) do not compete with FGF19 and/or FGF21 for the interaction with beta klotho.

In some embodiments, the anti-beta klotho antibodies are humanized antibodies that bind to a beta klotho polypeptide, a beta klotho fragment, or a beta klotho epitope. In certain embodiments, an anti-beta klotho antibody comprises a VH CDR1, VH CDR2, VH CDR3, VL CDR1, VL CDR2, and/or VL CDR3 of a monoclonal antibody designated 3I13, 2J21 or 4A2 as described herein, (e.g., Tables 1-3) or a humanized variant thereof. In certain embodiments, an anti-beta klotho antibody can further comprise a VH FR1, VH FR2, VH FR3, VH FR4, VL FR1, VL FR2, VL FR3, and/or VL FR4 of a human immunoglobulin amino acid sequence or a variant thereof.

In some embodiments, a binding protein (e.g., an anti-beta klotho antibody) comprises six CDRs or less than six CDRs. In some embodiments, a binding protein (e.g., an anti-beta klotho antibody) comprises one, two, three, four, five, or six CDRs selected from VH CDR1, VH CDR2, VH CDR3, VL CDR1, VL CDR2, and/or VL CDR3. In some embodiments, a binding protein (e.g., an anti-beta klotho antibody) comprises one, two, three, four, five, or six CDRs selected from VH CDR1, VH CDR2, VH CDR3, VL CDR1, VL CDR2, and/or VL CDR3 of a monoclonal antibody designated as 3I13, 2J21 or 4A2 as described herein (e.g., Tables 1-3), or a humanized variant thereof. In some embodiments, a binding protein (e.g., an anti-beta klotho antibody) further comprises a scaffold region or frame work region, including a VH FR1, VH FR2, VH FR3, VH FR4, VL FR1, VL FR2, VL FR3, and/or VL FR4 of a human immunoglobulin amino acid sequence or a variant thereof.

In some embodiments, the antibody is a humanized antibody, a monoclonal antibody, a recombinant antibody, an antigen binding fragment or any combination thereof. In some embodiments, the antibody is a humanized monoclonal antibody, or antigen binding fragment thereof, that binds to a beta klotho polypeptide (e.g., a cell surface-expressed or soluble beta klotho), a beta klotho fragment, or a beta klotho epitope.

The present disclosure also provides binding proteins such as anti-beta klotho antibodies (i) that competitively block (e.g., in a dose-dependent manner) an anti-beta klotho antibody provided herein (e.g., 3I13 with CDRs as described in Table 1) from binding to a beta klotho polypeptide (e.g., a cell surface-expressed or soluble beta klotho), a beta klotho fragment, or a beta klotho epitope and/or (ii) that bind to a beta klotho epitope that is bound by an anti-beta klotho antibody provided herein (e.g., 3I13 with CDRs as described in Table 1). In other embodiments, the binding proteins such as anti-beta klotho antibodies competitively block (e.g., in a dose-dependent manner) monoclonal antibody 3I13 described herein or a humanized variant thereof from binding to a beta klotho polypeptide (e.g., a cell surface-expressed or soluble beta klotho), a beta klotho fragment, or a beta klotho epitope. In other embodiments, the binding proteins such as anti-beta klotho antibodies bind to a beta klotho epitope that is bound (e.g., recognized) by monoclonal antibody 3I13 described herein or a humanized variant thereof.

The present disclosure also provides binding proteins, including antibodies or fragments thereof, that (i) bind to an epitope of human beta klotho and cynomologous monkey beta klotho recognized by an antibody comprising a heavy chain variable region having the amino acid sequence of SEQ ID NO:26 and a light chain variable region having the amino acid sequence of SEQ ID NO:27; or (ii) compete for the binding to human beta klotho with an antibody comprising a heavy chain variable region having the amino acid sequence of SEQ ID NO:26 and a light chain variable region having the amino acid sequence of SEQ ID NO:27. In some embodiments, binding proteins, including antibodies or fragments thereof, are provided herein that bind to a region, including an epitope, of human beta klotho or cyno beta klotho. Such antibodies can, in some embodiments, induce FGF19-like signaling and/or FGF21-like signaling or activate a beta klotho/FGF receptor complex in a cell that expresses human beta klotho and an FGF receptor. Additionally, in some embodiments, the antibody is a monoclonal antibody, for example, a humanized, human or chimeric antibody.

In some embodiments, the binding proteins such as anti-beta klotho antibodies provided herein are combined with, conjugated to, or recombinantly linked to a diagnostic agent, detectable agent or therapeutic agent. In some aspects, the therapeutic agent is a drug, including one or more drugs such as biguanides and sulphonylureas (e.g., metformin tolbutamide, chlorpropamide, acetohexamide, tolazamide, glibenclamide, glyburide, and glipizide), thiazolidinediones (e.g., rosiglitazone, pioglitazone), GLP-1 analogues, PPAR gamma agonists (e.g., pioglitazone and rosiglitazone), dipeptidyl peptidase-4 (DPP-4) inhibitors, (e.g., JANUVIN®, ONGLYZA®) bromocriptine formulations and bile acid sequestrants (e.g., colesevelam), and insulin (e.g., bolus and basal analogs), alpha glucosidase inhibitors (e.g., acarbose, roglibose), metformin (e.g., metformin hydrochloride) with or without a thiazolidinedione (TZD), SGLT-2 inhibitors, appetite suppression or weight loss drugs (e.g., Meridia®/sibutramine, Xenical®/ortistat). In some aspects, the detectable agent is a radioisotope, an enzyme, a fluorescent compound, a bioluminescent compound or a chemiluminescent compound.

In certain embodiments, compositions are provided comprising a binding protein such as an anti-beta klotho antibody described herein. Also provided herein are pharmaceutical compositions comprising a binding protein such as an anti-beta klotho antibody as described herein.

The present disclosure also provides isolated nucleic acid molecules encoding an immunoglobulin heavy chain, an immunoglobulin light chain, VH region, VL region, VH CDR1, VH CDR2, VH CDR3, VL CDR1, VL CDR2, and/or VL CDR3 of binding proteins (e.g., anti-beta klotho antibodies) that bind to a beta klotho polypeptide, a beta klotho polypeptide fragment, or a beta klotho epitope. In some embodiments, the nucleic acid molecule encodes a VH region, VL region, VH CDR1, VH CDR2, VH CDR3, VL CDR1, VL CDR2, and/or VL CDR3 of a monoclonal antibody designated as 3I13, 2J21 or 4A2 as described herein (e.g., Tables 1-3), or a humanized variant thereof. In some embodiments, the nucleic acid molecule further encodes a scaffold region or a framework region, including VH FR1, VH FR2, VH FR3, VH FR4, VL FR1, VL FR2, VL FR3, and/or VL FR4 of a human immunoglobulin amino acid sequence or a variant thereof (e.g., Table 10). Also provided herein are vectors and host cells comprising the nucleic acid molecules encoding an a binding protein such as anti-beta klotho antibody, as well as methods of producing a binding protein such as an anti-beta klotho antibody by culturing the host cells provided herein under conditions that promote the production of a binding protein such as an anti-beta klotho antibody.

The present disclosure also provides methods of treating, preventing or alleviating a disease, disorder or condition (e.g., one or more symptoms) comprising administering a therapeutically effective amount of a binding protein such as an anti-beta klotho antibody provided herein to a subject, including a subject in need thereof, thereby treating, preventing or alleviating the disease, disorder or condition. In some embodiments, the disease, disorder or condition is caused by or otherwise associated with beta klotho, such as those related to FGF19-like and/or FGF21-like signaling in a subject. In certain embodiments, the disease is treatable by lowering blood glucose, insulin or serum lipid levels (e.g., Type 2 diabetes, obesity, dyslipidemia, NASH, cardiovascular disease, metabolic syndrome).

In some embodiments, the disease, disorder or condition is related to glucose metabolism or lipid metabolism. In some embodiments, the disease, disorder or condition is selected from the group of hyperglycemic conditions (e.g., diabetes, such as Type I diabetes, Type 2 diabetes, gestational diabetes, insulin resistance, hyperinsulinemia, glucose intolerance, metabolic syndrome, or obesity).

In some embodiments, the methods of treating, preventing or ameliorating a disease, disorder or condition result in improved glucose metabolism and/or improved lipid metabolism. In some embodiments, the methods of treating, preventing or ameliorating a disease, disorder or condition result in reduced glucose levels (e.g., reduced blood glucose), increased insulin sensitivity, reduced insulin resistance, reduced glycogen, improved glucose tolerance, improved glucose tolerance, improved glucose metabolism, improved homeostasis, improved pancreatic function, reduced triglycerides, reduced cholesterol, reduced IDL, reduced LDL, reduced VLDL, decreased blood pressure, decreased internal thickening of a blood vessel and/or decreased body mass or weight gain.

The present disclosure provides methods of treating a disease, disorder or condition associated with human FGF19 and/or human FGF21, which includes any disease, disorder or condition whose onset in a subject (e.g., a patient) is caused by, at least in part, the induction of FGF19-like and/or FGF21-like signaling, which is initiated in vivo by the formation of a complex comprising FGFR1c, FGFR2c, FGFR3c or FGFR4 and beta klotho and FGF19 or FGF21. The severity of the disease or condition can also be decreased by the induction of FGF19-like and/or FGF21-like signaling. Examples of diseases and conditions that can be treated with the binding proteins such as anti-beta klotho antibodies include type 2 diabetes, obesity, dyslipidemia, NASH, cardiovascular disease, and metabolic syndrome.

As such, the binding proteins such as anti-beta klotho antibodies described herein can be used to treat type 2 diabetes, obesity, dyslipidemia (e.g., hypertriglyceridemia), NASH, cardiovascular disease, and/or metabolic syndrome, as well as any disease, disorder, or condition in which it is desirable to mimic or augment the in vivo effects of FGF19 and/or FGF21, or can be employed as a prophylactic treatment administered, for example, daily, weekly, biweekly, monthly, bimonthly, biannually, etc. to prevent or reduce the frequency and/or severity of symptoms (e.g., elevated plasma glucose levels, elevated triglycerides and cholesterol levels), including, for example, to thereby provide an improved glycemic and/or cardiovascular risk factor profile. The present disclosure provides methods of improving metabolic parameters by administering to a subject binding protein, including an anti-beta klotho antibody or fragment thereof as described herein or a pharmaceutical composition comprising a binding protein, including an anti-beta klotho antibody or fragment thereof described herein, including, for example, wherein the improvement includes a decrease in body weight, body mass index, abdominal circumference, skinfold thickness, glucose, insulin and/or triglycerides.

The present disclosure also provides methods of inducing FGF19-like or FGF21-like signaling of cells having cell surface expression of beta klotho and one or more FGF receptors, such as FGFR1, FGFR2, FGFR3, or FGFR4 comprising contacting the cells with an effective amount of a binding protein (e.g., an antibody) that binds to beta klotho as described herein. In some embodiments, the cell is an adipocyte or hepatocyte. In other embodiments, the cell is a cell transfected with a gene encoding beta klotho and optionally a gene encoding an FGF receptor. Additional methods provided include using an anti-beta klotho antibody as described herein (e.g., with CDRs as described in Table 1), with activity to mediate FGF19-like and/or FGF21 like signaling effects.

The present disclosure also provides methods of modulating an FGF19-like or FGF21-like signaling in a subject comprising administering an effective amount of a binding protein such as an anti-beta klotho antibody as described herein to a subject, including a subject in need thereof. In some embodiments, the modulating comprises FGF19-like activation. In some embodiments, the modulating comprises FGF21-like activation. In some embodiments, the modulating comprises increasing glucose metabolism (e.g., reducing glucose levels such as blood glucose levels).

The present disclosure also provides methods for detecting beta klotho in a sample comprising contacting the sample with a binding protein such as an anti-beta klotho antibody as described herein, that comprises a detectible agent. In certain embodiments, the sample comprises a cell expressing beta klotho on its surface.

The present disclosure also provides kits comprising a binding protein such as an anti-beta klotho antibody that binds to a beta klotho polypeptide, a beta klotho fragment or a beta klotho epitope as described herein (e.g., with CDRs as described in Tables 1-3).

BRIEF DESCRIPTION OF THE FIGURES

FIG. 1A-1B shows sequence alignments of heavy chain variable regions and light chain variable regions of anti-beta klotho antibodies designated 3I13, 2J21 or 4A2. SEQ ID NOS: 103-105 for the heavy chain variable regions and SEQ ID NOS: 114-116 for the light chain variable regions are represented. Boundaries of CDRs are indicated by Kabat, AbM, Chothia, Contact and IMGT numbering.

FIG. 2A shows sequence alignments of heavy chain variable regions of anti-beta klotho antibodies including consensus CDR sequences for antibodies designated 3I13, 2J21 and 4A2. SEQ ID NOS: 103-105 for the heavy chain variable regions are represented. Variable residues are presented by "X." For VH CDR1, the consensus CDR sequence GYTFTEYXMX (SEQ ID NO:49) is represented, and at X at positions 8 and 10 is an independently selected naturally occurring amino acid (e.g., X at position 8 is T or I, and X at position 10 is H or Y). For VH CDR2, the consensus CDR sequence xxxPxxGGxSYNQKFKx (SEQ ID NO:50) is represented, and at X at positions 1, 2, 3, 5, 6, 9 or 17 is an independently selected naturally occurring amino acid (e.g., X at position 1 is N, G, or S; X at position 2 is I or F; X at position 3 is D or N; X at position 5 is D or N; X at position 6 is T, Y, or S; X at position 9 is T or A; and X at position 17 is G or D). For VH CDR3, the consensus CDR sequence DDGYSTRYWYFDV (SEQ ID NO:51) is represented. Boundaries of CDRs are indicated by Kabat, AbM, Chothia, Contact and IMGT numbering.

FIG. 2B shows sequence alignments of light chain variable regions of anti-beta klotho antibodies including consensus CDR sequences for the antibodies designated 3I13, 2J21 and 4A2. SEQ ID NOS: 114-116 for the light chain variable regions are represented. Variable residues are presented by "X." For VL CDR1, the consensus CDR sequence GASENIYGALN (SEQ ID NO:52) is represented. For VL CDR2, the consensus CDR sequence GATXLAD (SEQ ID NO:53) is represented, and X is a naturally occurring amino acid (e.g., X is N or I). For VL CDR3, the consensus CDR sequence QNVLSTPYT (SEQ ID NO:54) is represented. Boundaries of CDRs are indicated by Kabat, AbM, Chothia, Contact and IMGT numbering.

FIG. 3A shows sequence alignments of heavy chain variable region of anti-beta klotho antibody designated 3I13 with humanized sequences. Residues that are bolded indicate exemplary modified residues. SEQ ID NOS:55-78 are represented.

FIG. 4A shows sequence alignments of the heavy chain variable region of anti-beta klotho antibody designated 2J21 with humanized sequences. Residues that are bolded indicate exemplary modified residues. SEQ ID NOS:161, 162, 164, 207, 214, 216, 220, 221 and 233-249 are represented.

DETAILED DESCRIPTION

Figure 3B:
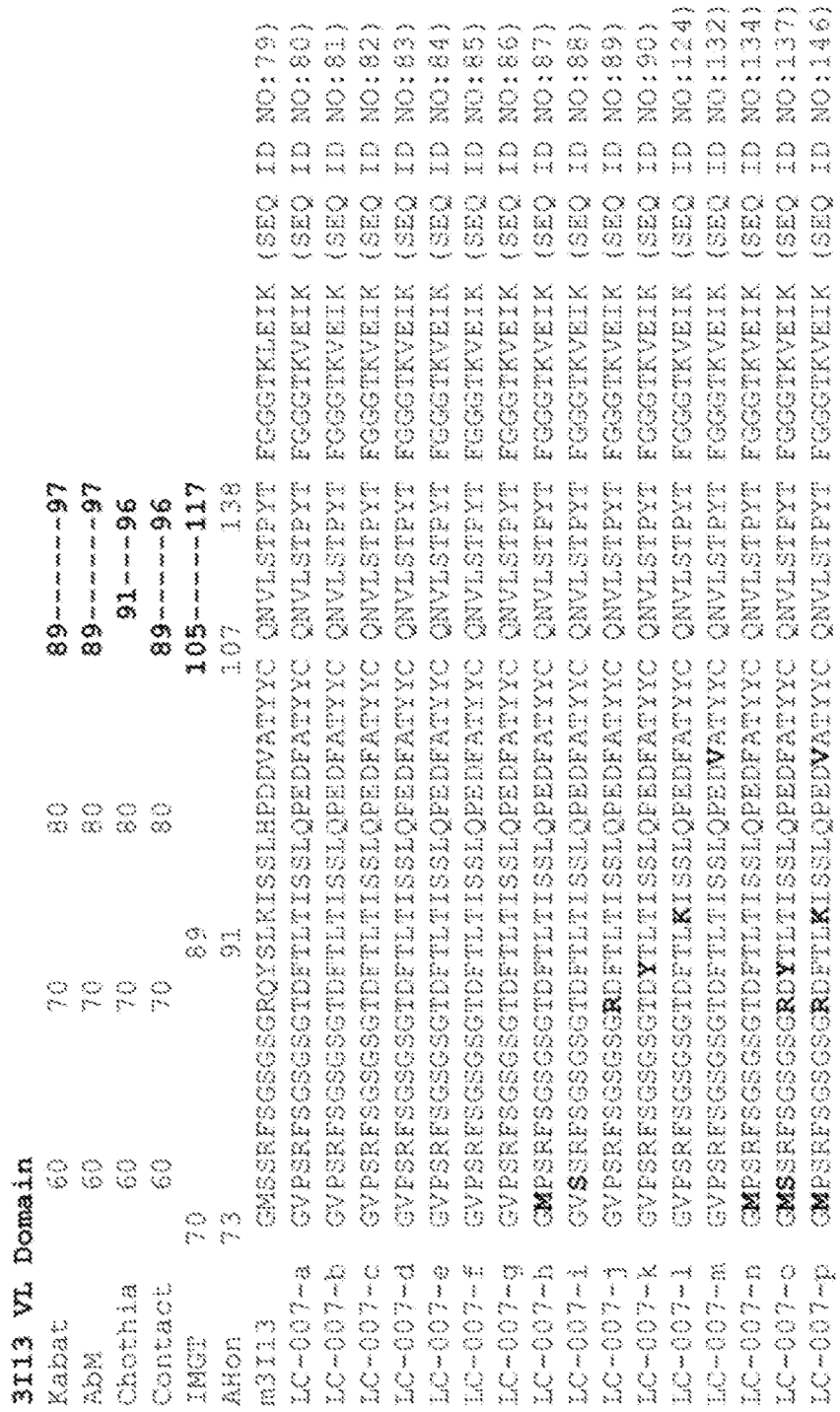
FIG. 3B shows sequence alignments of light chain variable region of anti-beta klotho antibody designated 3I13 with humanized sequences. Residues that are bolded indicate exemplary modified residues. SEQ ID NOS:79-90, 124, 132, 134, 137 and 146 are represented.
Figure 4B:
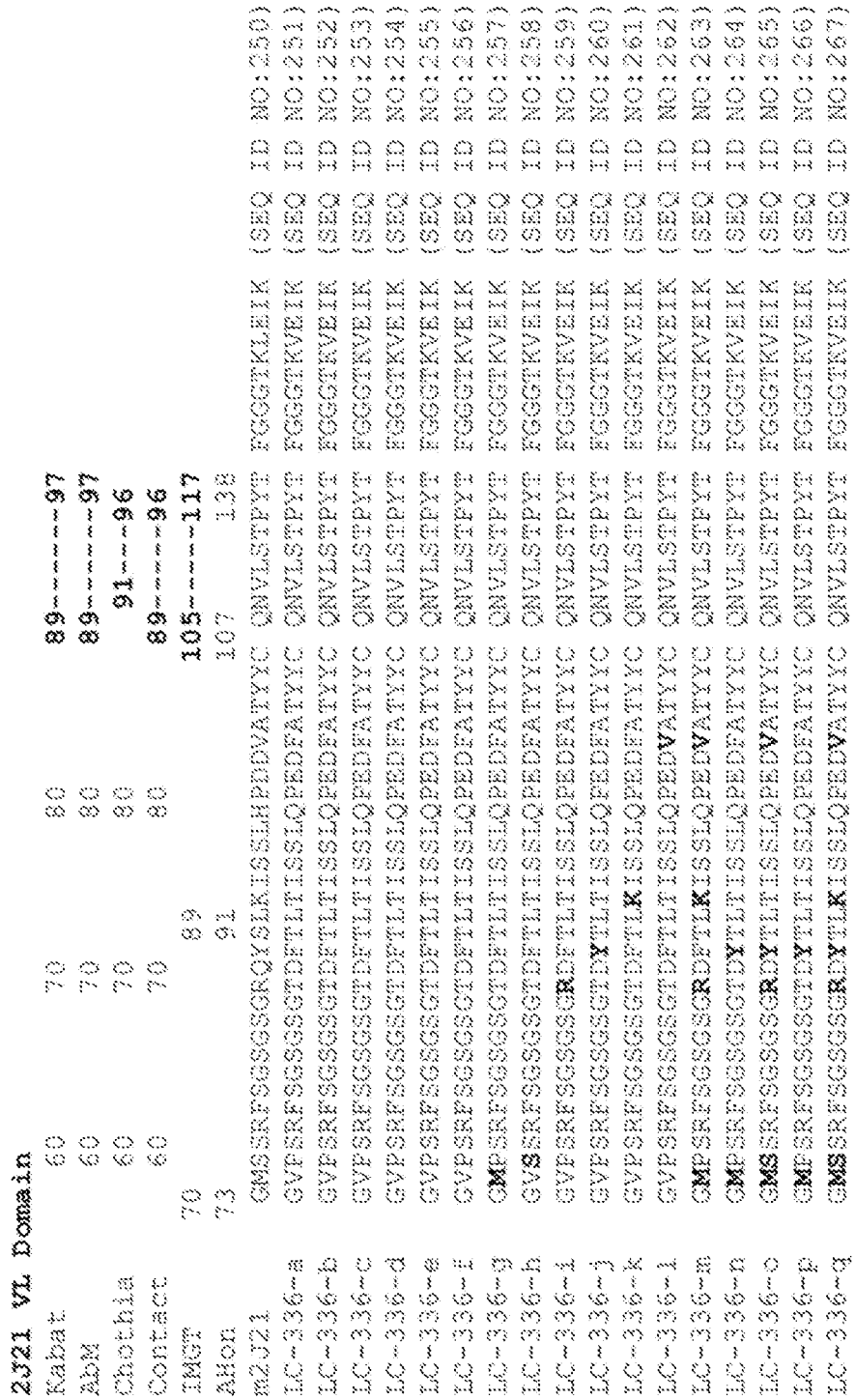
FIG. 4B shows sequence alignments of light chain variable region of anti-beta klotho antibody designated 2J21 with humanized sequences. Residues that are bolded indicate exemplary modified residues. ID NOS:250-267 are represented
Figure 5A:
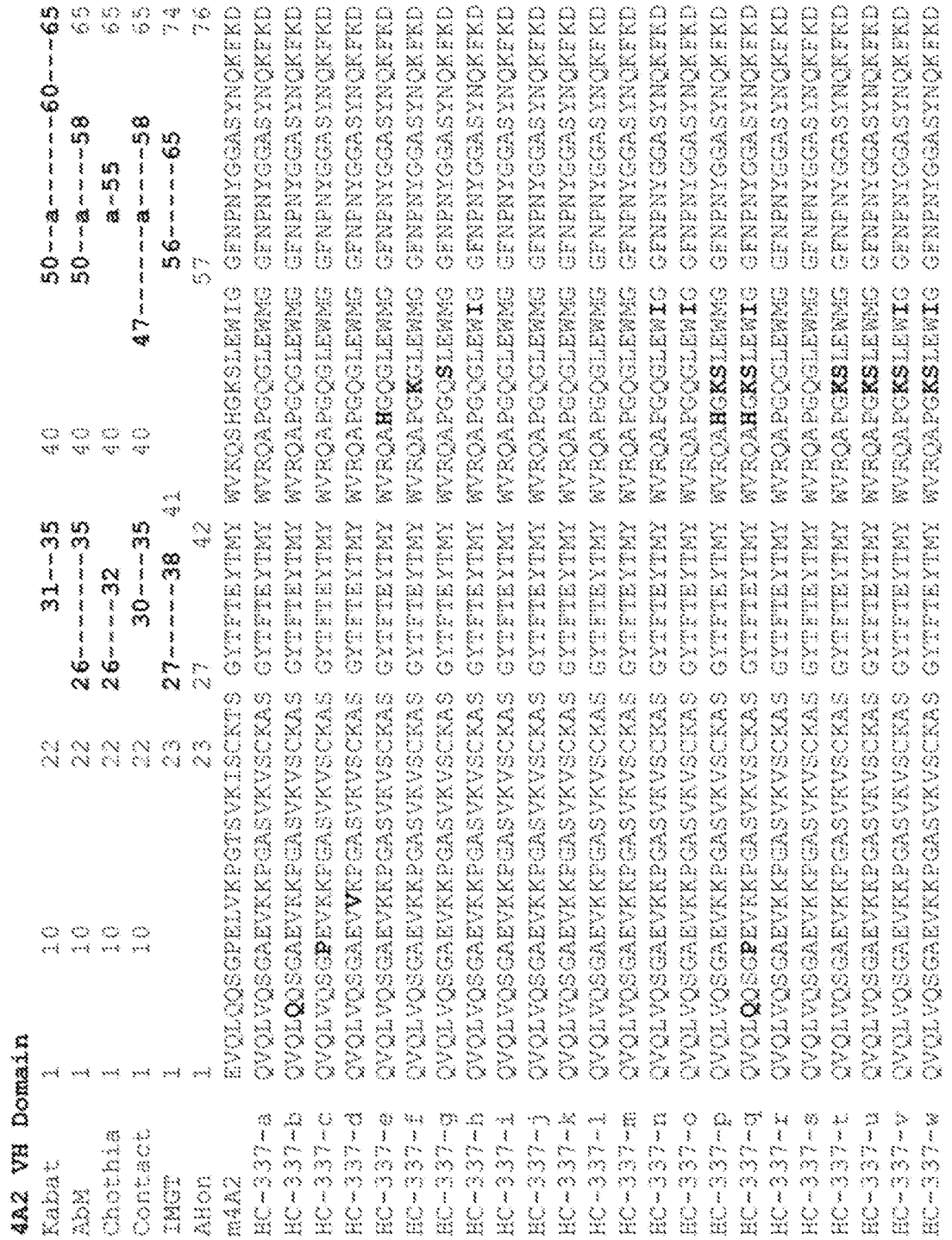
FIG. 5A shows sequence alignments of heavy chain variable region of anti-beta klotho antibody designated 4A2 with humanized sequences. Residues that are bolded indicate exemplary modified residues. SEQ ID NOS:268-285 and 288-293 are represented.
Figure 5B:
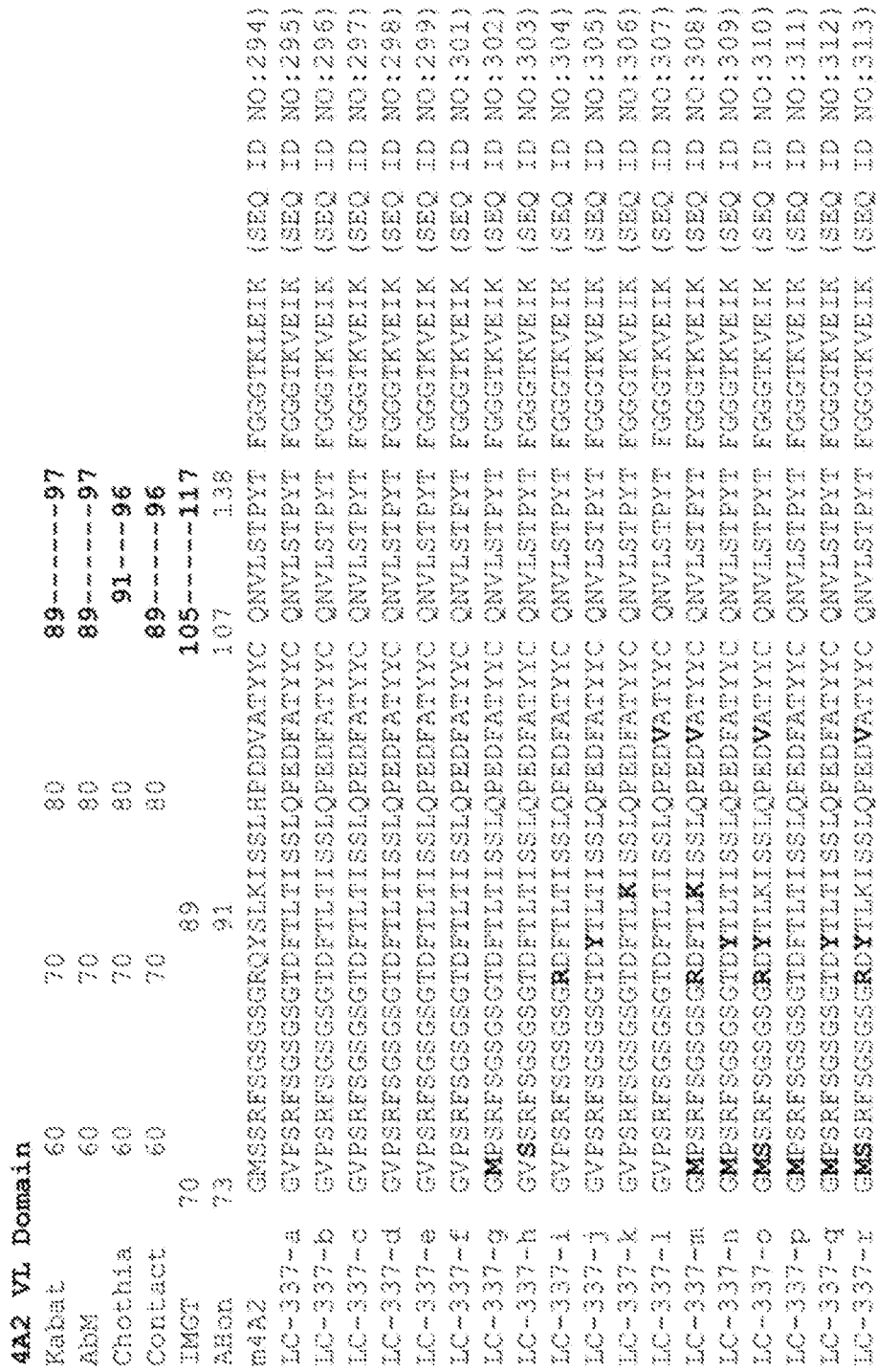
FIG. 5B shows sequence alignments of light chain variable region of anti-beta klotho antibody designated 4A2 with humanized sequences. Residues that are bolded indicate exemplary modified residues. SEQ ID NOS:294-299 and 301-313 are represented.

Binding proteins, such as antibodies that bind beta klotho, including human and/or cyno beta klotho, are provided herein. A unique property of such binding proteins, including antibodies disclosed herein, is their agonistic nature, including the ability to mimic the in vivo effect of FGF19 and/or FGF21 and to induce FGF19-like signaling and/or FGF21-like signaling. More remarkably and specifically, some of the binding proteins such as antibodies to beta klotho disclosed herein (i) bind to human and cyno beta klotho, (ii) do not compete for binding with FGF19 and/or FGF21, and (iii) induce FGF19-like signaling and/or FGF21-like signaling, including, for example, in several in vitro cell-based assays. Such assays may include (1) an ELK-luciferase reporter assay (see, e.g., Example 4); (2) a recombinant FGF19 receptor mediated cell assay for ERK-phosphorylation (see, e.g., Example 4); and (3) a human adipocyte assay for ERK-phosphorylation (see, e.g., Example 5). Binding proteins such as anti-beta klotho antibodies, as described herein, therefore are expected to exhibit activities in vivo that are consistent with the natural biological function of FGF19 and/or FGF21. This property makes the disclosed binding proteins, including anti-beta klotho antibodies, viable therapeutics for the treatment of metabolic diseases (e.g., Type 2 diabetes, obesity, dyslipidemia, NASH, cardiovascular disease, metabolic syndrome) and broadly any disease, disorder, or condition in which it is desirable to mimic or augment the in vivo effects of FGF19 and/or FGF21.

The binding proteins, such as antibodies that bind beta klotho, that are provided herein share the common feature of competing with each other for the binding of beta klotho (see, e.g., Example 3 describing antibodies in the 3I13 epitope bin). This competitive inhibition indicates that each antibody binds to the same region of beta klotho (e.g., the same epitope), thereby asserting similar effects. The anti-beta klotho antibodies provided herein include humanized anti-beta klotho antibodies, including humanized anti-beta klotho antibodies derived from or based on 3I13, 2J21 and/or 4A2 having CDR sequence as described in Tables 1-3 or FIGS. 1-2. Taken together, the results described herein demonstrate that the effects observed for an anti-beta klotho antibody that is derived from or based on 3I13 or an antibody in the 3I13 epitope bin, including an antibody having one or more CDRs described in Tables 1-3 or FIGS. 1-2, can be extrapolated to other anti-beta klotho antibodies, including those described herein, having the same or similar epitope specificity (e.g., the same or similar CDRs). For example, various in vitro activities of antibodies in Examples 4-6, as well as various in vivo effects as described in Example 8 for an exemplary anti-beta klotho antibody, are representative of various activites and effects of anti-beta klotho antibodies as described herein.

In some embodiments of the present disclosure, the binding proteins such as anti-beta klotho antibodies may comprise immunoglobulin variable regions which comprise one or more complementary determining regions (CDRs) as described in Tables 1-3. In such binding proteins (e.g., anti-beta klotho antibodies), the CDRs may be joined with one or more scaffold regions or framework regions, which orient(s) the CDR(s) such that the proper antigen binding properties of the CDR(s) is achieved. Such binding proteins, including anti-beta klotho antibodies as described herein, can facilitate or enhance the interaction between FGFR1c and beta klotho, and can induce FGF19-like and/or FGF21-like signaling.

General Techniques

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y.; Current Protocols in Molecular Biology (F. M. Ausubel, et al. eds., (2003)); Therapeutic Monoclonal Antibodies: From Bench to Clinic, Z. An, ed, Wiley, Hoboken N.J. (2009); Monoclonal Antibodies: Methods and Protocols, M. Albitar, ed., Humana Press, Totawa, N.J. (2010); and Antibody Engineering, 2nd Ed., Vols 1 and 2, Kontermann and Dubel, eds., Springer-Verlag, Heidelberg, 2010.

Terminology

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications and other publications are incorporated by reference in their entirety. In the event that any description of terms set forth conflicts with any document incorporated herein by reference, the description of term set forth below shall control.

The term "beta klotho" or "beta klotho polypeptide" and similar terms refers to a polypeptide ("polypeptide," and "protein" are used interchangeably herein) or any native beta klotho from any vertebrate source, including mammals such as primates (e.g., humans, cynomolgus monkey (cyno)), dogs, and rodents (e.g., mice and rats), unless otherwise indicated, and, in certain embodiments, included related beta klotho polypeptides, including SNP variants thereof. Beta klotho comprises two domains, beta klotho 1 (KLB1) and beta klotho 2 (KLB2). Each beta klotho domain comprises a glycosyl hydrolase 1 region. For example, the KLB1 domain of human beta klotho comprises amino acid residues 1-508 with the glycosyl hydrolase 1 region comprising amino acid residues 77-508, and the KLB2 domain of human beta klotho comprises amino acid residues 509-1044 with the glycosyl hydrolase 1 region comprising amino acid residues 517-967. Antibodies rescribed herein (e.g., 3I13) bind to human beta klotho. The amino acid sequence of human beta klotho is provided below:

(SEQ ID NO: 165)
1   MKPGCAAGSP GNEWIFFSTD EITTRYRNTM SNGGLQRSVI LSALILLRAV

51  TGFSGDGRAI WSKNPNFTPV NESQLFLYDT FPKNFFWGIG TGALQVEGSW

```
101 KKDGKGPSIW DHFIHTHLKN VSSTNGSSDS YIFLEKDLSA LDFIGVSFYQ

151 FSISWPRLFP DGIVTVANAK GLQYYSTLLD ALVLRNIEPI VTLYHWDLPL

201 ALQEKYGGWK NDTIIDIFND YATYCFQMFG DRVKYWITIH NPYLVAWHGY

251 GTGMHAPGEK GNLAAVYTVG HNLIKAHSKV WHNYNTHFRP HQKGWLSITL

301 GSHWIEPNRS ENTMDIFKCQ QSMVSVLGWF ANPIHGDGDY PEGMRKKLFS

351 VLPIFSEAEK HEMRGTADFF AFSFGPNNFK PLNTMAKMGQ NVSLNLREAL

401 NWIKLEYNNP RILIAENGWF TDSRVKTEDT TAIYMMKNFL SQVLQAIRLD

451 EIRVFGYTAW SLLDGFEWQD AYTIRRGLFY VDFNSKQKER KPKSSAHYYK

501 QIIRENGFSL KESTPDVQGQ FPCDFSWGVT ESVLKPESVA SSPQFSDPHL

551 YVWNATGNRL LHRVEGVRLK TRPAQCTDFV NIKKQLEMLA RMKVTHYRFA

601 LDWASVLPTG NLSAVNRQAL RYYRCVVSEG LKLGISAMVT LYYPTHAHLG

651 LPEPLLHADG WLNPSTAEAF QAYAGLCFQE LGDLVKLWIT INEPNRLSDI

701 YNRSGNDTYG AAHNLLVAHA LAWRLYDRQF RPSQRGAVSL SLHADWAEPA

751 NPYADSHWRA AERFLQFEIA WFAEPLFKTG DYPAAMREYI ASKHRRGLSS

801 SALPRLTEAE RRLLKGTVDF CALNHFTTRF VMHEQLAGSR YDSDRDIQFL

851 QDITRLSSPT RLAVIPWGVR KLLRWVRRNY GDMDIYITAS GIDDQALEDD

901 RLRKYYLGKY LQEVLKAYLI DKVRIKGYYA FKLAEEKSKP RFGFFTSDFK

951 AKSSIQFYNK VISSRGFPFE NSSSRCSQTQ ENTECTVCLF LVQKKPLIFL

1001 GCCFFSTLVL LLSIAIFQRQ KRRKFWKAKN LQHIPLKKGK RVVS
```

An encoding nucleic acid sequence of human beta klotho is provided below:

```
                                      (SEQ ID NO: 166)
ATGAAGCCAGGCTGTGCGGCAGGATCTCCAGGGAATGAATGGATTTTCTT

CAGCACTGATGAAATAACCACACGCTATAGGAATACAATGTCCAACGGGG

GATTGCAAAGATCTGTCATCCTGTCAGCACTTATTCTGCTACGAGCTGTT

ACTGGATTCTCTGGAGATGGAAGAGCTATATGGTCTAAAAATCCTAATTT

TACTCCGGTAAATGAAAGTCAGCTGTTTCTCTATGACACTTTCCCTAAAA

ACTTTTTCTGGGGTATTGGACTGGAGCATTGCAAGTGGAAGGGAGTTGG

AAGAAGGATGGAAAAGGACCTTCTATATGGGATCATTTCATCCACACACA

CCTTAAAAATGTCAGCAGCACGAATGGTTCCAGTGACAGTTATATTTTTC

TGGAAAAAGACTTATCAGCCCTGGATTTTATAGGAGTTTCTTTTTATCAA

TTTTCAATTTCCTGGCCAAGGCTTTTCCCCGATGGAATAGTAACAGTTGC

CAACGCAAAAGGTCTGCAGTACTACAGTACTCTTCTGGACGCTCTAGTGC

TTAGAAACATTGAACCTATAGTTACTTTATACCACTGGGATTTGCCTTTG

GCACTACAAGAAAAATATGGGGGGTGGAAAAATGATACCATAATAGATAT

CTTCAATGACTATGCCACATACTGTTTCCAGATGTTTGGGGACCGTGTCA

AATATTGGATTACAATTCACAACCCATATCTAGTGGCTTGGCATGGGTAT

GGGACAGGTATGCATGCCCCTGGAGAGAAGGGAAATTTAGCAGCTGTCTA

CACTGTGGGACACAACTTGATCAAGGCTCACTCGAAAGTTTGGCATAACT

ACAACACACATTTCCGCCCACATCAGAAGGGTTGGTTATCGATCACGTTG

GGATCTCATTGGATCGAGCCAAACCGGTCGGAAAACACGATGGATATATT

CAAATGTCAACAATCCATGGTTTCTGTGCTTGGATGGTTTGCCAACCCTA

TCCATGGGGATGGCGACTATCCAGAGGGGATGAGAAAGAAGTTGTTCTCC

GTTCTACCCATTTTCTCTGAAGCAGAGAAGCATGAGATGAGAGGCACAGC

TGATTTCTTTGCCTTTTCTTTTGGACCCAACAACTTCAAGCCCCTAAACA

CCATGGCTAAAATGGGACAAAATGTTTCACTTAATTTAAGAGAAGCGCTG

AACTGGATTAAACTGGAATACAACAACCCTCGAATCTTGATTGCTGAGAA

TGGCTGGTTCACAGACAGTCGTGTGAAAACAGAAGACACCACGGCCATCT

ACATGATGAAGAATTTCCTCAGCCAGGTGCTTCAAGCAATAAGGTTAGAT

GAAATACGAGTGTTTGGTTATACTGCCTGGTCTCTCCTGGATGGCTTTGA

ATGGCAGGATGCTTACACCATCCGCCGAGGATTATTTTATGTGGATTTTA

ACAGTAAACAGAAAGAGCGGAAACCTAAGTCTTCAGCACACTACTACAAA

CAGATCATACGAGAAAATGGTTTTTCTTTAAAAGAGTCCACGCCAGATGT

GCAGGGCCAGTTTCCCTGTGACTTCTCCTGGGGTGTCACTGAATCTGTTC

TTAAGCCCGAGTCTGTGGCTTCGTCCCCACAGTTCAGCGATCCTCATCTG

TACGTGTGGAACGCCACTGGCAACAGACTGTTGCACCGAGTGGAAGGGGT

GAGGCTGAAAACACGACCCGCTCAATGCACAGATTTTGTAAACATCAAAA

AACAACTTGAGATGTTGGCAAGAATGAAAGTCACCCACTACCGGTTTGCT

CTGGATTGGGCCTCGGTCCTTCCCACTGGCAACCTGTCCGCGGTGAACCG

ACAGGCCCTGAGGTACTACAGGTGCGTGGTCAGTGAGGGGCTGAAGCTTG
```

```
GCATCTCCGCGATGGTCACCCTGTATTATCCGACCCACGCCCACCTAGGC

CTCCCCGAGCCTCTGTTGCATGCCGACGGGTGGCTGAACCCATCGACGGC

CGAGGCCTTCCAGGCCTACGCTGGGCTGTGCTTCCAGGAGCTGGGGACC

TGGTGAAGCTCTGGATCACCATCAACGAGCCTAACCGGCTAAGTGACATC

TACAACCGCTCTGGCAACGACACCTACGGGGCGGCGCACAACCTGCTGGT

GGCCCACGCCCTGGCCTGGCGCCTCTACGACCGGCAGTTCAGGCCCTCAC

AGCGCGGGGCCGTGTCGCTGTCGCTGCACGCGGACTGGGCGGAACCCGCC

AACCCCTATGCTGACTCGCACTGGAGGGCGGCCGAGCGCTTCCTGCAGTT

CGAGATCGCCTGGTTCGCCGAGCCGCTCTTCAAGACCGGGGACTACCCCG

CGGCCATGAGGGAATACATTGCCTCCAAGCACCGACGGGGCTTTCCAGC
```

-continued
```
CGGCTCCGGAAGTACTACCTAGGGAAGTACCTTCAGGAGGTGCTGAAAGC

ATACCTGATTGATAAAGTCAGAATCAAAGGCTATTATGCATTCAAACTGG

CTGAAGAGAAATCTAAACCCAGATTTGGATTCTTCACATCTGATTTTAAA

GCTAAATCCTCAATACAATTTTACAACAAAGTGATCAGCAGCAGGGGCTT

CCCTTTTGAGAACAGTAGTTCTAGATGCAGTCAGACCCAAGAAAATACAG

AGTGCACTGTCTGCTTATTCCTTGTGCAGAAGAAACCACTGATATTCCTG

GGTTGTTGCTTCTTCTCCACCCTGGTTCTACTCTTATCAATTGCCATTTT

TCAAAGGCAGAAGAGAAGAAAGTTTTGGAAAGCAAAAAACTTACAACACA

TACCATTAAAGAAAGGCAAGAGAGTTGTTAGC
```

The amino acid sequence of beta klotho from cynomolgus monkey (cyno), scientific name *Macaca fascicularis*, is provided below:

```
                                                 (SEQ ID NO: 167)
   1 MKPGCAAGSP GNEWIFFSTD EITIRYRNTM SNGGLQRSVI LSALTLLRAV
  51 TGFSGDGRAV WSKNPNFTPV NESQLFLYDT FPKNFFWGVG TGALQVEGSW
 101 KKDGKGPSIW DHFVHTHLKN VSSTNGSSDS YIFLEKDLSA LDFIGVSFYQ
 151 FSISWPRLFP DGIVTVANAK GLQYYNTLLD SLVLRNIEPI VTLYHWDLPL
 201 ALQEKYGGWK NDTIIDIFND YATYCFQTFG DRVKYWITIH NPYLVAWHGY
 251 GTGMHAPGEK GNLAAVYTVG HNLIKAHSKV WHNYNTHFRP HQKGWLSITL
 301 GSHWIEPNRS ENTMDILKCQ QSMVSVLGWF ANPIHGDGDY PEGMKKKLLS
 351 ILPLFSEAEK NEVRGTADFF AFSFGPNNFK PLNTMAKMGQ NVSLNLREAL
 401 NWIKLEYNNP RILIAENGWF TDSHVKTEDT TAIYMMKNFL SQVLQAIRLD
 451 EIRVFGYTAW SLLDGFEWQD AYTIRRGLFY VDFNSKQKER KPKSSAHYYK
 501 QIIRENGFSL KEATPDVQGQ FPCDFSWGVT ESVLKPESVA SSPQFSDPYL
 551 YVWNATGNRL LHRVEGVRLK TRPAQCTDFV NIKKQLEMLA RMKVTHYRFA
 601 LDWASVLPTG NLSAVNRQAL RYYRCVVSEG LKLGISAMVT LYYPTHAHLG
 651 LPEPLLHAGG WLNPSTVEAF QAYAGLCFQE LGDLVKLWIT INEPNRLSDI
 701 YNRSGNDTYG AAHNLLVAHA LAWRLYDRQF RPSQRGAVSL SLHADWAEPA
 751 NPYADSHWRA AERFLQFEIA WFAEPLFKTG DYPAAMREYI ASKHRRGLSS
 801 SALPRLTEAE RRLLKGTVDF CALNHFTTRF VMHEQLAGSR YDSDRDIQFL
 851 QDITRLSSPT RLAVIPWGVR KLLRWVRRNY GDMDIYITAS GIDDQALEDD
 901 RLRKYYLEKY LQEVLKAYLI DKVRIKGYYA FKLAEEKSKP RFGFFTSDFK
 951 AKSSIQFYNK MISSSGFPSE NSSSRCSQTQ KNTECTVCLF LVQKKPLIFL
1001 GCCFFSTLVL LLSITIFHRQ KRRKFWKAKN LQHIPLKKGK RVLS
```

An encoding nucleic acid sequence of cyno beta klotho is provided below:

```
                                                 (SEQ ID NO: 168)
ATGAAGCCTGGATGTGCCGCCGGAAGCCCCGGCAACGAGTGGATCTTCTT

CAGCACCGACGAGATCACCATCCGGTACAGAAACACCATGAGCAACGGCG

GCCTGCAGCGGAGCGTGATCCTGTCTGCTCTGACCCTGCTGAGAGCCGTG

ACCGGCTTCAGCGGAGATGGCAGAGCCGTGTGGTCCAAGAACCCCAACTT
```

-continued
```
TCGGCCCTGCCGCGCCTCACCGAGGCCGAAAGGAGGCTGCTCAAGGGCAC

GGTCGACTTCTGCGCGCTCAACCACTTCACCACTAGGTTCGTGATGCACG

AGCAGCTGGCCGGCAGCCGCTACGACTCGGACAGGGACATCCAGTTTCTG

CAGGACATCACCCGCCTGAGCTCCCCACGCGCCTGGCTGTGATTCCCTG

GGGGGTGCGCAAGCTGCTGCGGTGGGTCCGGAGGAACTACGGCGACATGG

ACATTTACATCACCGCCAGTGGCATCGACGACCAGGCTCTGGAGGATGAC
```

-continued

```
CACCCCCGTGAACGAGAGCCAGCTGTTCCTGTACGATACCTTCCCCAAGA
ACTTCTTCTGGGGCGTGGGCACAGGCGCCCTGCAGGTGGAAGGATCCTGG
AAGAAGGACGGCAAGGGCCCCAGCATCTGGGACCACTTTGTGCACACCCA
CCTGAAGAACGTGTCCAGCACCAACGGCAGCAGCGACAGCTACATCTTTC
TGGAAAAGGACCTGAGCGCCCTGGACTTCATCGGCGTGTCCTTCTACCAG
TTCAGCATCAGCTGGCCCAGACTGTTCCCCGACGGCATCGTGACAGTGGC
CAATGCCAAGGGCCTGCAGTACTACAACACCCTGCTGGACAGCCTGGTGC
TGCGGAACATCGAGCCCATCGTGACCCTGTACCACTGGGACCTGCCACTG
GCTCTGCAGGAGAAATACGGCGGCTGGAAGAACGACACCATCATCGACAT
CTTCAACGACTACGCCACCTACTGCTTCCAGACCTTCGGCGACAGAGTGA
AGTACTGGATCACAATCCACAACCCCTACCTGGTGGCCTGGCACGGCTAT
GGCACCGGAATGCATGCCCCTGGCGAGAAGGGAAATCTGGCCGCCGTGTA
CACCGTGGGCCACAACCTGATCAAGGCCCACAGCAAAGTGTGGCACAACT
ACAATACCCACTTCCGGCCCCACCAGAAGGGCTGGCTGTCTATCACACTG
GGCAGCCACTGGATCGAGCCTAACCGCAGCGAGAACACCATGGACATCCT
GAAGTGCCAGCAGAGCATGGTGTCCGTGCTGGGATGGTTCGCCAACCCCA
TTCACGGCGACGGCGATTACCCCGAGGGCATGAAGAAGAAGCTGCTGAGC
ATCCTGCCCCTGTTCAGCGAGGCCGAGAAGAACGAAGTGCGGGCACCGC
CGATTTCTTCGCCTTTAGCTTCGGCCCCAACAACTTCAAGCCCCTGAATA
CCATGGCCAAGATGGGCCAGAATGTGTCCCTGAACCTGAGAGAGGCCCTG
AACTGGATCAAGCTGGAGTACAACAACCCCGGATCCTGATCGCCGAGAA
CGGCTGGTTCACCGACAGCCACGTGAAAACCGAGGACACCACCGCCATCT
ATATGATGAAGAACTTCCTGAGCCAGGTGCTGCAGGCTATCCGGCTGGAT
GAGATCCGGGTGTTCGGCTACACCGCCTGGTCACTGCTGGACGGCTTCGA
ATGGCAGGACGCCTACACCATCAGACGGGGCCTGTTCTACGTGGACTTCA
ACAGCAAGCAGAAAGAGCGGAAGCCCAAGAGCAGCGCCCACTACTACAAG
CAGATCATCAGAGAGAATGGCTTCAGCCTGAAAGAGGCCACCCCCGACGT
GCAGGGCCAGTTCCCTTGTGATTTCTCTTGGGGCGTGACCGAGAGCGTGC
TGAAGCCTGAAAGCGTGGCCAGCAGCCCCAGTTCAGCGACCCTTACCTG
TACGTGTGGAACGCCACCGGCAACCGGCTGCTGCATAGAGTGGAAGGCGT
GCGGCTGAAAACCAGACCCGCCCAGTGCACCGACTTCGTGAACATCAAGA
AACAGCTGGAAATGCTGGCCCGGATGAAAGTGACCCACTACAGATTCGCC
CTGGACTGGGCCAGCGTGCTGCCTACCGGAAATCTGAGCGCCGTGAACAG
ACAGGCCCTGCGGTACTACAGATGCGTGGTGTCCGAGGGCCTGAAGCTGG
GCATCAGCGCCATGGTCACCCTGTACTACCCTACCCACGCCCACCTGGGA
CTGCCTGAACCTCTGCTGCATGCTGGCGGCTGGCTGAACCCTAGCACCGT
GGAAGCCTTTCAGGCCTACGCCGGGCTGTGCTTCCAGGAACTGGGCGACC
TCGTGAAGCTGTGGATCACCATCAACGAGCCCAACAGACTGAGCGACATC
TACAACAGAAGCGGCAACGACACCTACGGCGCTGCCCACAATCTGCTGGT
GGCTCATGCCCTGGCTTGGCGGCTGTACGACAGACAGTTCCGGCCTTCTC
AGCGGGGAGCCGTGTCTCTGTCTCTGCATGCCGATTGGGCCGAGCCCGCC
AACCCTTACGCCGACTCTCATTGGAGAGCCGCCGAGCGGTTCCTGCAGTT
CGAGATCGCTTGGTTTGCCGAGCCCCTGTTCAAGACCGGCGATTACCCTG
CCGCCATGAGAGAGTATATCGCCAGCAAGCACAGACGGGGCCTGAGCAGC
TCTGCCCTGCCTAGACTGACCGAGGCCGAGCGGAGACTGCTGAAGGGAAC
CGTGGATTTCTGCGCCCTGAACCACTTCACCACCAGATTCGTGATGCACG
AGCAGCTGGCCGGCAGCAGATACGACAGCGACCGGGACATCCAGTTTCTG
CAGGACATCACCCGGCTGAGCAGCCCTACAAGACTGGCCGTGATCCCTTG
GGGAGTGCGGAAGCTGCTGAGATGGGTGCGCAGAAACTACGGCGACATGG
ATATCTACATCACCGCCAGCGGCATCGACGACCAGGCCCTGGAAGATGAC
CGGCTGCGGAAGTACTACCTGGAAAAGTACCTGCAGGAAGTGCTGAAGGC
CTACCTGATCGACAAAGTGCGGATCAAGGGCTACTACGCCTTCAAGCTGG
CCGAGGAAAAGAGCAAGCCCAGATTCGGCTTCTTCACCAGCGACTTCAAG
GCCAAGAGCAGCATCCAGTTCTACAACAAGATGATCAGCAGCAGCGGCTT
CCCCAGCGAGAACAGCAGCTCCAGATGCAGCCAGACCCAGAAAAACACCG
AGTGTACCGTGTGCCTGTTCCTGGTGCAGAAGAAGCCCCTGATCTTCCTG
GGCTGCTGCTTCTTTAGCACCCTGGTGCTGCTGCTGTCCATCACCATCTT
CCACCGGCAGAAGCGGAGAAAGTTCTGGAAGGCCAAAAACCTGCAGCACA
TCCCCCTGAAGAAAGGCAAGCGGGTGCTGAGCTGA
```

The amino acid sequence of beta klotho homolog from mouse, scientific name *Mus musculus*, is provided below:

(SEQ ID NO: 169)

```
  1 MKTGCAAGSP GNEWIFFSSD ERNTRSRKTM SNRALQRSAV LSAFVLLRAV
 51 TGFSGDGKAI WDKKQYVSPV NPSQLFLYDT FPKNFSWGVG TGAFQVEGSW
101 KTDGRGPSIW DRYVYSHLRG VNGTDRSTDS YIFLEKDLLA LDFLGVSFYQ
```

```
151  FSISWPRLFP NGTVAAVNAQ GLRYYRALLD SLVLRNIEPI VTLYHWDLPL

201  TLQEEYGGWK NATMIDLFND YATYCFQTFG DRVKYWITIH NPYLVAWHGF

251  GTGMHAPGEK GNLTAVYTVG HNLIKAHSKV WHNYDKNFRP HQKGWLSITL

301  GSHWIEPNRT DNMEDVINCQ HSMSSVLGWF ANPIHGDGDY PEFMKTGAMI

351  PEFSEAEKEE VRGTADFFAF SFGPNNFRPS NTVVKMGQNV SLNLRQVLNW

401  IKLEYDDPQI LISENGWFTD SYIKTEDTTA IYMMKNFLNQ VLQAIKFDEI

451  RVFGYTAWTL LDGFEWQDAY TTRRGLFYVD FNSEQKERKP KSSAHYYKQI

501  IQDNGFPLKE STPDMKGRFP CDFSWGVTES VLKPEFTVSS PQFTDPHLYV

551  WNVTGNRLLY RVEGVRLKTR PSQCTDYVSI KKRVEMLAKM KVTHYQFALD

601  WTSILPTGNL SKVNRQVLRY YRCVVSEGLK LGVFPMVTLY HPTHSHLGLP

651  LPLLSSGGWL NMNTAKAFQD YAELCFRELG DLVKLWITIN EPNRLSDMYN

701  RTSNDTYRAA HNLMIAHAQV WHLYDRQYRP VQHGAVSLSL HCDWAEPANP

751  FVDSHWKAAE RFLQFEIAWF ADPLFKTGDY PSVMKEYIAS KNQRGLSSSV

801  LPRFTAKESR LVKGTVDFYA LNHFTTRFVI HKQLNTNRSV ADRDVQFLQD

851  ITRLSSPSRL AVTPWGVRKL LAWIRRNYRD RDIYITANGI DDLALEDDQI

901  RKYYLEKYVQ EALKAYLIDK VKIKGYYAFK LTEEKSKPRF GFFTSDFRAK

951  SSVQFYSKLI SSSGLPAENR SPACGQPAED TDCTICSFLV EKKPLIFFGC

1001 CFISTLAVLL SITVFHHQKR RKFQKARNLQ NIPLKKGHSR VFS
```

An encoding nucleic acid sequence of mouse beta klotho is provided below:

```
                                    (SEQ ID NO: 170)
ATGAAGACAGGCTGTGCAGCAGGGTCTCCGGGGAATGAATGGATTTTCTT

CAGCTCTGATGAAAGAAACACACGCTCTAGGAAAACAATGTCCAACAGGG

CACTGCAAAGATCTGCCGTGCTGTCTGCGTTTGTTCTGCTGCGAGCTGTT

ACCGGCTTCTCCGGAGACGGGAAAGCAATATGGGATAAAAAACAGTACGT

GAGTCCGGTAAACCCAAGTCAGCTGTTCCTCTATGACACTTTCCCTAAAA

ACTTTTCCTGGGGCGTTGGGACCGGAGCATTTCAAGTGGAAGGGAGTTGG

AAGACAGATGGAAGAGGACCCTCGATCTGGGATCGGTACGTCTACTCACA

CCTGAGAGGTGTCAACGGCACAGACAGATCCACTGACAGTTACATCTTTC

TGGAAAAAGACTTGTTGGCTCTGGATTTTTTAGGAGTTTCTTTTTATCAG

TTCTCAATCTCCTGGCCACGGTTGTTTCCCAATGGAACAGTAGCAGCAGT

GAATGCGCAAGGTCTCCGGTACTACCGTGCACTTCTGGACTCGCTGGTAC

TTAGGAATATCGAGCCCATTGTTACCTTGTACCATTGGGATTTGCCTCTG

ACGCTCCAGGAAGAATATGGGGGCTGGAAAAATGCAACTATGATAGATCT

CTTCAACGACTATGCCACATACTGCTTCCAGACCTTTGGAGACCGTGTCA

AATATTGGATTACAATTCACAACCCTTACCTTGTTGCTTGGCATGGGTTT

GGCACAGGTATGCATGCACCAGGAGAGAAGGGAAATTTAACAGCTGTCTA

CACTGTGGGACACAACCTGATCAAGGCACATTCGAAAGTGTGGCATAACT

ACGACAAAAACTTCCGCCCTCATCAGAAGGGTTGGCTCTCCATCACCTTG

GGGTCCCATTGGATAGAGCCAAACAGAACAGACAACATGGAGGACGTGAT

CAACTGCCAGCACTCCATGTCCTCTGTGCTTGGATGGTTCGCCAACCCCA

TCCACGGGGACGGCGACTACCCTGAGTTCATGAAGACGGGCGCCATGATC

CCCGAGTTCTCTGAGGCAGAGAAGGAGGAGGTGAGGGGCACGGCTGATTT

CTTTGCCTTTTCCTTCGGGCCCAACAACTTCAGGCCCTCAAACACCGTGG

TGAAAATGGGACAAAATGTATCACTCAACTTAAGGCAGGTGCTGAACTGG

ATTAAACTGGAATACGATGACCCTCAAATCTTGATTTCGGAGAACGGCTG

GTTCACAGATAGCTATATAAAGACAGAGGACACCACGGCCATCTACATGA

TGAAGAATTTCCTAAACCAGGTTCTTCAAGCAATAAAATTTGATGAAATC

CGCGTGTTTGGTTATACGGCCTGGACTCTCCTGGATGGCTTTGAGTGGCA

GGATGCCTATACGACCCGACGAGGGCTGTTTTATGTGGACTTTAACAGTG

AGCAGAAAGAGAGGAAACCCAAGTCCTCGGCTCATTACTACAAGCAGATC

ATACAAGACAACGGCTTCCCTTTGAAAGAGTCCACGCCAGACATGAAGGG

TCGGTTCCCCTGTGATTTCTCTTGGGGAGTCACTGAGTCTGTTCTTAAGC

CCGAGTTTACGGTCTCCTCCCCGCAGTTTACCGATCCTCACCTGTATGTG

TGGAATGTCACTGGCAACAGATTGCTCTACCGAGTGGAAGGGGTAAGGCT

GAAAACAAGACCATCCCAGTGCACAGATTATGTGAGCATCAAAAAACGAG

TTGAAATGTTGGCAAAAATGAAAGTCACCCACTACCAGTTTGCTCTGGAC

TGGACCTCTATCCTTCCCACTGGCAATCTGTCCAAAGTTAACAGACAAGT

GTTAAGGTACTATAGGTGTGTGGTGAGCGAAGGACTGAAGCTGGGCGTCT

TCCCCATGGTGACGTTGTACCACCCAACCCACTCCCATCTCGGCCTCCCC
```

-continued

```
CTGCCACTTCTGAGCAGTGGGGGGTGGCTAAACATGAACACAGCCAAGGC
CTTCCAGGACTACGCTGAGCTGTGCTTCCGGGAGTTGGGGGACTTGGTGA
AGCTCTGGATCACCATCAATGAGCCTAACAGGCTGAGTGACATGTACAAC
CGCACGAGTAATGACACCTACCGTGCAGCCCACAACCTGATGATCGCCCA
TGCCCAGGTCTGGCACCTCTATGATAGGCAGTATAGGCCGGTCCAGCATG
GGGCTGTGTCGCTGTCCTTACATTGCGACTGGGCAGAACCTGCCAACCCC
TTTGTGGATTCACACTGGAAGGCAGCCGAGCGCTTCCTCCAGTTTGAGAT
CGCCTGGTTTGCAGATCCGCTCTTCAAGACTGGCGACTATCCATCGGTTA
TGAAGGAATACATCGCCTCCAAGAACCAGCGAGGGCTGTCTAGCTCAGTC
CTGCCGCGCTTCACCGCGAAGGAGAGCAGGCTGGTGAAGGGTACCGTCGA
CTTCTACGCACTGAACCACTTCACTACGAGGTTCGTGATACACAAGCAGC
TGAACACCAACCGCTCAGTTGCAGACAGGGACGTCCAGTTCCTGCAGGAC
ATCACCCGCCTAAGCTCGCCCAGCCGCCTGGCTGTAACACCCTGGGAGT
GCGCAAGCTCCTTGCGTGGATCCGGAGGAACTACAGAGACAGGGATATCT
ACATCACAGCCAATGGCATCGATGACCTGGCTCTAGAGGATGATCAGATC
CGAAAGTACTACTTGGAGAAGTATGTCCAGGAGGCTCTGAAAGCATATCT
CATTGACAAGGTCAAAATCAAAGGCTACTATGCATTCAAACTGACTGAAG
AGAAATCTAAGCCTAGATTTGGATTTTTCACCTCTGACTTCAGAGCTAAG
TCCTCTGTCCAGTTTTACAGCAAGCTGATCAGCAGCAGTGGCCTCCCCGC
TGAGAACAGAAGTCCTGCGTGTGGTCAGCCTGCGGAAGACACAGACTGCA
CCATTTGCTCATTTCTCGTGGAGAAGAAACCACTCATCTTCTTCGGTTGC
TGCTTCATCTCCACTCTGGCTGTACTGCTATCCATCACCGTTTTTCATCA
TCAAAAGAGAAGAAATTCCAGAAAGCAAGGAACTTACAAAATATACCAT
TGAAGAAAGGCCACAGCAGAGTTTTCAGC
```

The amino acid sequence of beta klotho from rat, scientific name Rattus norvegicus, is provided below:

```
                                      (SEQ ID NO: 171)
MKTGCAAGSPGNEWVFFSSDERSTRSRKTMSNGALQRSAVLSALVLLRAV
TGFSGDGKAIWDKKQYVSPVNPGQLFLYDTFPKNFSWGVGTGAFQVEGSW
KADGRGPSIWDRYVDSHLRGVNSTDRSTDSYVFLEKDLLALDFLGVSFYQ
FSISWPRLFPNGTVAAVNAKGLQYYRALLDSLVLRNIEPIVTLYHWDLPL
TLQEEYGGWKNATMIDLFNDYATYCFQTFGDRVKYWITIHNPYLVAWHGF
GTGMHAPGEKGNLTAVYTVGHNLIKAHSKVWHNYDKNFRPHQKGWLSITL
GSHWIEPNRTENMEDVINCQHSMSSVLGWFANPIHGDGDYPEFMKTSSVI
PEFSEAEKEEVRGTADFFAFSFGPNNFRPSNTVVKMGQNVSLNLRQVLNW
IKLEYDNPRILISENGWFTDSYIKTEDTTAIYMMKNFLNQVLQAIKFDEI
QVFGYTAWTLLDGFEWQDAYTTRRGLFYVDFNSEQKERKPKSSAHYYKQI
IQDNGFPLQESTPDMKGQFPCDFSWGVTESVLKPEFTVSSPQFTDPHLYV
WNVTGNRLLYRVEGVRLKTRPSQCTDYVSIKKRVEMLAKMKVTHYQFALD
WTSILPTGNLSKINRQVLRYYRCVVSEGLKLGISPMVTLYHPTHSHLGLP
MPLLSSGGWLNTNTAKAFQDYAGLCFKELGDLVKLWITINEPNRLSDMYN
RTSNDTYRAAHNLMIAHAQVWHLYDRQYRPVQHGAVSLSLHSDWAEPANP
YVESHWKAAERFLQFEIAWFADPLFKTGDYPLAMKEYIASKKQRGLSSSV
LPRFTLKESRLVKGTIDFYALNHFTTRFVIHKQLNTNCSVADRDVQFLQD
ITRLSSPSRLAVTPWGMRKLLGWIRRNYRDMDIYVTANGIDDLALEDDQI
RKYYLEKYVQEALKAYLIDKVKIKGYYAFKLTEEKSKPRFGFFTSDFKAK
SSVQFYSKLISSSGFSSENRSPACGQPPEDTECAICSFLTQKKPLIFFGC
CFISTLAALLSITIFHHRKRRKFQKARNLQNIPLKKGHSRVFS
```

An encoding nucleic acid sequence of rat beta klotho is provided below:

```
                                      (SEQ ID NO: 172)
ATGAAGACAGGCTGTGCAGCAGGGTCTCCAGGGAATGAATGGGTTTTCTT
CAGCTCTGATGAAAGAAGCACACGCTCTAGGAAAACAATGTCCAACGGAG
CACTGCAAAGATCTGCCGTGCTGTCTGCATTGGTTCTGCTGCGAGCTGTT
ACCGGCTTCTCTGGAGACGGAAAAGCAATATGGGATAAAAAACAATACGT
GAGTCCGGTAAACCCAGGTCAGCTGTTCCTCTATGACACTTTCCCTAAAA
ACTTTTCCTGGGGCGTTGGGACCGGAGCATTTCAAGTGGAAGGGAGTTGG
AAGGCAGATGGAAGAGGACCCTCGATCTGGGACCGTTATGTCGACTCACA
CCTGAGAGGTGTCAACAGCACAGACAGATCCACTGACAGTTATGTCTTTC
TGGAAAAGGACTTGCTGGCTCTGGATTTTTTAGGAGTTTCTTTTTATCAG
TTCTCAATCTCCTGGCCGCGGTTGTTCCCCAACGGAACAGTAGCAGCTGT
GAATGCAAAAGGTCTCCAGTACTACAGAGCACTTCTGGACTCGCTGGTAC
TTAGGAATATCGAACCCATTGTTACCTTATACCATTGGGATTTGCCTTTG
ACGCTACAGGAAGAATATGGGGGCTGGAAAAATGCAACTATGATAGATCT
CTTCAATGACTATGCCACATACTGCTTCCAGACCTTTGGAGACCGTGTCA
AATATTGGATTACAATTCACAACCCTTACCTCGTTGCTTGGCATGGGTTT
GGCACAGGTATGCATGCGCCAGGAGAGAAGGGAAATTTAACAGCTGTCTA
CACTGTGGGACACAACCTGATCAAGGCGCATTCGAAAGTGTGGCATAACT
ACGACAAAAACTTCCGCCCTCATCAGAAGGGTTGGCTCTCCATCACCTTG
GGGTCCCATTGGATAGAACCAAACAGAACAGAAAACATGGAGGACGTGAT
CAACTGCCAGCACTCCATGTCTTCTGTGCTCGGATGGTTTGCCAACCCCA
TCCACGGAGACGGCGACTACCCCGAGTTCATGAAGACGAGCTCCGTAATC
CCTGAGTTCTCTGAGGCAGAGAAGGAGGAGGTGCGGGGCACTGCTGACTT
CTTTGCCTTTTCCTTCGGGCCCAACAATTTCAGGCCCTCGAACACCGTGG
TAAAAATGGGACAAAATGTATCACTCAACTTAAGACAGGTGCTGAACTGG
ATTAAACTAGAATATGACAACCCTCGAATCTTGATTTCGGAGAACGGCTG
GTTCACAGATAGTTATATAAAGACGGAAGATACCACGGCCATCTACATGA
TGAAGAATTTCCTCAACCAGGTTCTTCAAGCAATAAAGTTTGATGAAATA
CAAGTGTTTGGTTATACGGCTTGGACTCTCCTGGATGGCTTTGAGTGGCA
GGATGCCTACACGACCCGACGAGGGCTGTTTTATGTGGACTTTAATAGTG
AGCAGAAAGAGAGGAAACCCAAGTCCTCCGCTCATTACTACAAACAGATT
```

```
ATACAAGACAACGGTTTCCCTTTGCAAGAATCCACACCAGACATGAAGGG

TCAGTTTCCCTGTGACTTCTCCTGGGGAGTCACTGAGTCTGTTCTTAAGC

CGGAGTTTACGGTGTCCTCCCCACAGTTTACTGATCCTCACCTGTATGTG

TGGAATGTCACTGGCAACAGATTGCTATACCGAGTGGAAGGAGTCAGGCT

AAAAACAAGACCGTCCCAATGCACAGATTATGTGAGCATCAAAAAACGAG

TTGAAATGTTGGCCAAAATGAAAGTCACCCACTACCAGTTTGCTCTGGAC

TGGACCTCTATCCTCCCTACCGGAAATCTGTCTAAAATTAATAGACAAGT

GTTGAGGTACTATAGGTGTGTGGTGAGCGAAGGACTGAAGCTGGGCATCT

CCCCTATGGTGACGTTGTACCACCCGACCCACTCCCATCTAGGCCTCCCC

ATGCCACTTCTGAGCAGTGGGGGATGGCTAAACACCAACACAGCCAAGGC

CTTCCAGGACTACGCAGGCCTGTGCTTCAAGGAGCTGGGGGACTTGGTAA

AGCTCTGGATCACCATCAATGAACCCAATAGGCTGAGTGACATGTACAAC

CGCACGAGTAACGACACCTACCGTGCGGCCCACAACCTGATGATCGCCCA

TGCCCAGGTCTGGCACCTCTATGATAGGCAGTATAGGCCGGTCCAGCACG

GGGCTGTGTCGCTGTCCTTACATTCCGACTGGGCAGAACCTGCCAACCCC

TATGTGGAGTCTCACTGGAAGGCAGCCGAGCGCTTCCTCCAGTTTGAGAT

CGCCTGGTTTGCGGATCCACTCTTCAAGACTGGTGACTACCCGCTGGCCA

TGAAGGAATACATCGCCTCCAAGAAGCAGCGAGGGCTGTCTAGCTCAGTC

CTGCCGCGCTTTACCTTGAAGGAGAGCAGGCTGGTGAAGGGGACCATCGA

CTTTTACGCACTGAACCACTTCACTACTAGATTCGTGATACACAAGCAGT

TGAATACCAACTGCTCAGTGGCAGACAGGGACGTCCAGTTCCTGCAGGAC

ATCACCCGCCTGAGCTCGCCCAGTCGCCTAGCCGTAACGCCCTGGGGAAT

GCGCAAGCTCCTTGGGTGGATCCGGAGGAACTACAGAGACATGGATATCT

ACGTCACAGCCAATGGCATTGATGATCTTGCTCTAGAGGACGATCAGATT

AGAAAGTACTACTTGGAGAAGTACGTCCAGGAGGCTCTGAAAGCATATCT

GATTGACAAGGTCAAAATCAAAGGCTACTATGCATTCAAACTGACTGAAG

AGAAATCTAAGCCTAGATTTGGATTTTTCACATCTGACTTCAAAGCTAAA

TCTTCTGTACAGTTTTATAGCAAGCTGATCAGCAGCAGCGGCTTCTCCTC

TGAGAACAGAAGTCCTGCCTGTGGTCAGCCTCCAGAAGACACAGAATGCG

CCATTTGCTCCTTCCTTACACAGAAGAAACCACTCATCTTCTTTGGTTGT

TGCTTCATCTCCACTCTGGCTGCACTGCTATCAATCACTATTTTTCATCA

TCGGAAGAGAAGAAATTCCAGAAAGCAAGGAACTTACAAAATATACCAT

TGAAGAAAGGGCACAGCAGAGTTTTTAGCTAA
```

The amino acid sequence of beta klotho from Hamster, scientific name *Cricetulus griseus*, is provided below:

```
                                        (SEQ ID NO: 173)
MKAGCAAGSPGNEWIFLSSYERNTRSKKTMSNRALQRSVVLSAFVLLRAV

TGLSGDGKAIWDKKQYVSPVNASQLFLYDTFPKNFFWGVGTGAFQVEGNW

QADGRGPSIWDRFIYTHLRDVSITEKSADSYIFLEKDLLALDFLGVSFYQ

FSISWPRLFPNGTVASVNAKGLQYYNKLLDSLILRNIEPVVTLYHWDLPL

ALQEDYGGWKNATMIDLFNDYATYCFQTFGDRVKYWITIHNPYLVAWHGF

ATGMHAPGETGNLTAVYIVGHNLIKAHSKVWHNYDKNFRPHQKGLLSITL

GSHWIEPNKTENMADTISCQHSMAFVLGWFANPIHADGDYPEFMKTLSTM

PVFSEAEKEEVRGTADFFAFSFGPNNFRPSNTVVKMGQNVSLNLRQVLNW

IKLEYDNPRILISENGWFTDSDIKTEDTTAIYMMKHFLNQVLQAIQFDEI

RVFGYTAWSLLDGFEWQYAYTSRRGLFYVDFNSEQKERKPKTSAHYYKQI

IQENGFPLKESTPDMQGQFPCDFSWGVTESVLKPEFMVSSPQFTDPHLYV

WNATGNRLLQRVEGVRLKTKPSHCTDYVSIKKRVEMLAKMKVTHYQFALD

WATILPTGNLSEVNRQVLRYYRCVVSEGLKLGVSPMVTLYHPTHSHLGLP

EPLLNSGGWLNTYTAKAFQDYAGLCFQELGDLVKLWITINEPNRLSDMYN

RTSNDTYRAAHNLMIAHAQVWRLYDRQYRPVQHGAVSLSLHSDWVEPANP

YVDSHWKAAERFLLFEIAWFADPLFKTGDYPLAMKEYIASKNQQGLSRSV

LPRFTPEESRLVKGTIDFYALNHFTTRFVIHKQLNSSRSMADRDVQFLQD

ITRLSSPSRLAVMPWGARKLLGWIQRNYGDMDIYITANGIDDLALENDGI

RKYYLEKYIQEALKAYLIDKVKIKGYYAFKLTEEKSKPRFGFFTSDFKAK

SSVEFYSKLISRSGFPSETSNPACGQPPEDTDCTICSFFTQKKSLIFFGC

CFISTLAVLLSITIFHHRKRRFHKSKNLENIPLKEGHSRVLS
```

An encoding nucleic acid sequence of Hamster beta klotho is provided below:

```
                                        (SEQ ID NO: 174)
ATGTCCAACAGGGCACTGCAAAGATCTGTCGTGCTGTCAGCGTTTGTTCT

GCTGCGAGCTGTTACCGGATTGTCTGGAGACGGGAAAGCGATATGGGATA

AAAAACAGTACGTGAGTCCGGTGAATGCAAGTCAGCTGTTTCTCTATGAC

ACTTTCCCTAAAAACTTTTTCTGGGGTGTTGGAACTGGAGCATTTCAAGT

GGAAGGGAATTGGCAGGCAGACGGAAGAGGACCCTCGATTTGGGATCGTT

TCATCTACACACACCTGAGAGATGTCAGCATCACAGAGAAATCCGCCGAC

AGTTACATTTTTCTGGAAAAAGATTTGTTGGCTCTGGATTTTTTAGGAGT

TTCTTTTTATCAGTTCTCAATCTCCTGGCCACGGTTGTTCCCCAATGGAA

CAGTAGCATCCGTGAATGCAAAAGGTCTCCAATACTACAACAAACTTCTG

GACTCGCTGATACTTAGGAATATTGAGCCCGTTGTTACCTTATACCATTG

GGATTTGCCTTTGGCGCTACAGGAAGACTATGGGGGTTGGAAAAATGCAA

CTATGATAGATCTCTTCAATGACTATGCCACATACTGCTTCCAGACCTTT

GGAGACCGTGTCAAGTATTGGATTACAATTCACAACCCTTACCTGGTTGC

TTGGCATGGGTTTGCCACAGGTATGCATGCGCCAGGAGAGACGGGAAATT

TAACAGCTGTCTACATTGTGGGACACAACCTGATCAAGGCTCATTCGAAA

GTGTGGCATAACTACGACAAAAACTTCCGCCCCCATCAGAAGGGTTTGCT

GTCCATTACCTTGGGGTCCCACTGGATAGAACCAAACAAAACAGAAAACA

TGGCCGATACAATCAGCTGCCAGCACTCTATGGCTTTTGTGCTTGGGTGG

TTTGCCAACCCCATCCATGCAGACGGCGACTACCCTGAGTTCATGAAAAC

ATTGTCCACCATGCCAGTGTTCTCTGAGGCAGAGAAGGAGGAGGTGAGGG

GCACAGCTGACTTCTTTGCCTTTTCCTTTGGGCCCAACAATTTCAGGCCC
```

-continued

```
TCGAACACTGTAGTGAAAATGGGACAAAATGTATCACTCAACTTAAGACA
GGTGCTGAACTGGATTAAATTAGAATATGACAACCCTCGAATCTTGATTT
CGGAGAATGGCTGGTTCACAGATAGTGACATAAAGACAGAGGACACCACA
GCCATCTACATGATGAAGCATTTCCTCAACCAGGTTCTTCAAGCAATACA
GTTTGATGAAATACGAGTGTTTGGTTACACGGCCTGGTCTCTCCTGGATG
GCTTTGAATGGCAGTATGCCTACACGTCTCGCCGAGGACTGTTTTATGTG
GACTTTAATAGTGAACAGAAAGAAAGGAAACCCAAGACCTCGGCACATTA
CTACAAACAGATCATACAAGAAAATGGTTTCCCTTTGAAAGAGTCCACGC
CAGACATGCAGGGTCAGTTTCCCTGTGACTTCTCCTGGGGGGTCACCGAG
TCTGTTCTTAAGCCGGAGTTTATGGTTTCCTCCCCACAGTTTACCGACCC
TCACCTGTATGTGTGGAATGCCACTGGCAACAGATTGCTACAGCGAGTAG
AAGGAGTAAGGCTAAAAACAAAACCATCCCACTGCACAGACTATGTTAGC
ATCAAAAAACGAGTTGAGATGTTGGCCAAAATGAAAGTCACCCACTACCA
GTTTGCTCTGGACTGGGCCACCATCCTTCCCACTGGCAATCTGTCTGAAG
TTAATAGACAAGTACTAAGGTACTATAGGTGTGTGGTGAGCGAAGGACTG
AAGCTGGGCGTCTCTCCCATGGTGACGTTGTACCACCCCACCCACTCCCA
TCTAGGCCTCCCTGAGCCGCTTCTTAACAGTGGGGGATGGCTAAACACTT
ACACCGCCAAGGCCTTCCAGGACTACGCAGGACTGTGCTTCCAGGAACTA
GGGGACTTGGTGAAGCTCTGGATCACCATCAATGAGCCTAATAGGCTGAG
TGACATGTACAACCGCACGAGTAATGACACCTACCGTGCAGCCCATAACC
TGATGATTGCCCATGCCCAGGTCTGGCGTCTCTACGACAGGCAGTATAGG
CCAGTCCAGCATGGAGCTGTGTCGCTGTCCCTACATTCTGACTGGGTGGA
ACCTGCCAACCCCTATGTGGACTCACACTGGAAGGCAGCGGAGCGCTTCC
TCCTGTTTGAGATCGCCTGGTTCGCTGATCCGCTCTTCAAGACTGGCGAC
TATCCACTGGCCATGAAGGAGTACATCGCCTCCAAGAACCAGCAAGGGCT
GTCCCGCTCAGTCCTGCCGCGCTTCACCCCAGAGGAGAGCAGGCTGGTGA
AGGGCACCATCGACTTCTACGCACTGAACCACTTCACTACTAGGTTCGTG
ATACACAAACAGCTCAACAGCAGCCGCTCTATGGCAGACAGGGACGTCCA
GTTCCTGCAGGACATCACCCGCCTGAGCTCGCCCAGCCGCCTGGCTGTTA
TGCCCTGGGGAGCACGCAAGCTGCTTGGGTGGATCCAGAGGAACTATGGG
GACATGGACATCTACATCACAGCCAATGGCATCGATGATCTGGCTCTGGA
GAATGATGGGATCCGAAAGTACTACTTGGAGAAGTACATCCAGGAGGCTC
TGAAAGCATACCTCATTGACAAAGTCAAAATCAAAGGCTATTATGCATTC
AAACTGACTGAAGAGAAATCTAAGCCTAGATTTGGATTTTTCACATCTGA
CTTCAAAGCTAAGTCATCTGTAGAGTTTTATAGCAAGTTGATCAGCAGAA
GTGGCTTCCCCTCTGAGACTAGCAATCCCGCATGTGGTCAGCCTCCAGAA
GACACAGACTGCACCATCTGCTCATTTTTCACTCAGAAGAAATCTCTGAT
CTTCTTTGGTTGTTGCTTCATCTCCACTCTGGCTGTACTGCTGTCAATCA
CCATTTTTCATCATCGAAAGAGAAGATTTCATAAATCAAAGAACTTAGAA
AATATACCATTGAAGGAAGGCCACAGTAGAGTTCTTAGCTAA
```

The amino acid sequence of beta klotho from rabbit, scientific name *Oryctolagus cuniculus*, is provided below:

```
                                               (SEQ ID NO: 175)
MKPGCAAGSPGNEWVSFCTDERNRRCRETMSSGRLRRSVMLSAFILLRAV

TGFPGDGRAVWSQNPNLSPVNESQLFLYDTFPKNFFWGVGTGAFQVEGSW

KKDGKGLSVWDHFIATHLNVSSRDGSSDSYIFLEKDLSALDFLGVSFYQF

SISWPRLFPDGTVAVANAKGLQYYNRLLDSLLLRNIEPVVTLYHWDLPWA

LQEKYGGWKNETLIDLFNDYATYCFQTFGDRVKYWITIHNPYLVAWHGYG

TGLHAPGEKGNVAAVYTVGHNLLKAHSKVWHNYNRNFRPHQKGWLSITLG

SHWIEPNRAESIVDILKCQQSMVSVLGWFANPIHGDGDYPEVMTKKLLSV

LPAFSEAEKNEVRGTADFFAFSFGPNNFKPLNTMAKMGQNVSLNLRQVLN

WIKLEYGNPRILIAENGWFTDSYVQTEDTTAIYMMKNFLNQVLQAIRLDG

VRVFGYTAWSLLDGFEWQDAYNTRRGLFYVDFNSEQRERRPKSSAHYYKQ

VIGENGFTLREATPDLQGQFPCDFSWGVTESVLKPESVASSPQFSDPHLY

VWNATGNRMLHRVEGVRLKTRPAQCTDFITIKKQLEMLARMKVTHFRFAL

DWASVLPTGNLSEVNRQALRYYRCVVTEGLKLNISPMVTLYYPTHAHLGL

PAPLLHSGGWLDPSTAKAFRDYAGLCFRELGDLVKLWITINEPNRLSDVY

NRTSNDTYQAAHNLLIAHALVWHLYDRQYRPSQRGALSLSLHSDWAEPAN

PYVASHWQAAERFLQFEIAWFAEPLFKTGDYPVAMREYIASKTRRGLSSS

VLPRFSDAERRLVKGAADFYALNHFTTRFVMHEQQNGSRYDSDRDVQFLQ

DITRLASPSRLAVMPWGEGKLLRWMRNNYGDLDVYITANGIDDQALQNDQ

LRQYYLEKYVQEALKAYLIDKIKIKGYYAFKLTEEKSKPRFGFFTSDFKA

KSSIQFYNKLITSNGFPSENGGPRCNQTQGNPECTVCLLLLQKKPLIFFS

CCFFCTLVLLSSITIFHRRKRRKFWKAKDLQHIPLKKGHKRVLS
```

An encoding nucleic acid sequence of rabbit beta klotho is provided below:

```
                                               (SEQ ID NO: 176)
TGAAGCCGTGATAAGACGGTCCCGCAGTTCGTGGCAAATGAAGCCAGGCT

GTGCGGCAGGATCTCCAGGGAATGAATGGGTTTCCTTCTGCACCGATGAA

AGAAACAGACGCTGTAGGGAAACGATGTCCAGCGGACGCCTGCGGAGATC

TGTCATGCTGTCAGCCTTCATCCTGCTGCGAGCCGTGACTGGGTTCCCCG

GAGACGGAAGAGCTGTATGGTCGCAAAATCCTAATTTGAGTCCGGTAAAC

GAAAGTCAGCTGTTTCTCTATGACACTTTCCCAAAAAACTTTTTCTGGGG

TGTGGGGACTGGAGCCTTCCAAGTGGAAGGGAGTTGGAAGAAGGATGGGA

AAGGACTCTCTGTATGGGATCATTTCATCGCTACACACCTGAACGTCAGC

AGCCGCGATGGCTCCAGTGACAGCTACATTTTTTTGGAGAAAGACTTATC

GGCGCTGGATTTTTTAGGAGTCTCTTTTTATCAGTTTTCAATTTCCTGGC

CAAGACTGTTCCCGGATGGCACAGTAGCAGTCGCCAATGCAAAAGGTCTC

CAGTACTATAATCGGCTCCTGGACTCTCTGCTACTTAGAAACATTGAACC

TGTAGTCACTTTATACCATTGGGATCTGCCTTGGGCGCTACAAGAAAAAT

ACGGGGGGTGGAAAAACGAGACGTTGATTGATTTATTCAATGACTATGCC

ACCTACTGTTTCCAGACGTTTGGGGACCGTGTCAAATACTGGATCACCAT

TCACAATCCCTATCTGGTGGCTTGGCATGGCTACGGGACAGGTCTGCATG
```

```
CTCCGGGAGAGAAGGGGAATGTGGCAGCTGTCTACACTGTGGGACACAAC
CTGCTTAAGGCTCATTCAAAAGTCTGGCACAACTACAACAGGAATTTCCG
CCCGCATCAGAAAGGCTGGCTGTCGATCACGCTGGGATCCCACTGGATTG
AGCCAAACAGAGCGGAAAGCATCGTGGACATACTCAAGTGCCAGCAGTCC
ATGGTCTCGGTGCTGGGCTGGTTTGCCAACCCGATCCACGGGGACGGGGA
CTACCCAGAGGTGATGACAAAGAAGCTGCTCTCCGTCCTGCCCGCTTTCT
CAGAAGCAGAGAAGAACGAGGTACGAGGCACCGCAGACTTCTTTGCCTTT
TCGTTTGGACCCAACAACTTCAAGCCCTTAAACACCATGGCTAAATGGG
GCAGAATGTGTCACTCAATCTAAGACAGGTGCTGAACTGGATTAAACTGG
AATATGGCAACCCTCGAATCCTGATCGCTGAGAACGGCTGGTTCACAGAC
AGTTACGTGCAAACAGAAGACACCACAGCCATCTACATGATGAAGAATTT
CCTCAACCAGGTTCTTCAAGCAATAAGGTTGGATGGAGTCCGAGTGTTTG
GCTACACTGCCTGGTCTCTCCTGGATGGCTTCGAATGGCAGGACGCTTAC
AACACCCGCCGTGGACTGTTTTATGTGGACTTCAACAGCGAACAGAGAGA
AGAAGGCCCAAGTCCTCGGCGCATTACTATAAACAGGTCATAGGAGAAA
ACGGCTTCACGCTCAGAGAGGCCACCCCGGATCTGCAGGGGCAGTTTCCC
TGTGACTTCTCCTGGGGCGTCACCGAGTCTGTTCTTAAGCCCGAGTCGGT
GGCTTCCTCGCCACAGTTCAGCGACCCTCACCTCTACGTGTGGAACGCCA
CTGGCAACCGAATGCTTCACCGGGTGGAAGGGGTGAGGCTGAAAACACGG
CCCGCTCAGTGCACAGATTTCATCACCATCAAGAAACAACTCGAGATGTT
GGCAAGAATGAAAGTCACCCACTTCCGGTTTGCTCTGGACTGGGCCTCGG
TCCTTCCCACGGGCAACCTGTCCGAGGTGAACCGACAAGCCCTGAGGTAC
TACAGGTGTGTGGTCACCGAGGGGCTGAAGCTCAACATCTCGCCCATGGT
CACCTTGTACTACCCGACCCATGCCCACCTGGGCCTGCCCGCGCCGCTGC
TGCACAGCGGGGGTGGCTGGACCCATCCACGGCCAAGGCCTTCCGCGAC
TACGCAGGGCTGTGCTTCCGGGAGCTGGGGGACCTGGTGAAGCTCTGGAT
CACCATCAACGAGCCCAACCGGCTGAGCGACGTCTACAACCGCACCAGCA
ACGACACCTACCAGGCCGCCCACAACCTGCTGATCGCGCACGCGCTCGTG
TGGCACCTGTACGACCGCCAGTACCGGCCGTCGCAGCGCGGGGCGCTGTC
GCTGTCCCTGCACTCGGACTGGGCCGAGCCCGCCAACCCCTACGTGGCCT
CGCACTGGCAGGCGGCCGAGCGCTTCCTGCAGTTCGAGATTGCGTGGTTC
GCCGAGCCCCTGTTCAAGACCGGGGACTACCCGGTGGCCATGAGGGAGTA
CATCGCCTCCAAGACCCGGCGCGGGCTCTCCAGCTCCGTGCTGCCCCGCT
TCAGCGACGCCGAGCGGCGGCTGGTCAAGGGCGCCGCCGACTTCTACGCC
CTCAACCACTTCACCACCAGGTTCGTGATGCACGAGCAGCAGAACGGCAG
CCGCTACGACTCGGACAGGGACGTGCAGTTCCTGCAGGACATCACCCGCC
TGGCCTCACCCAGCCGCCTGGCCGTGATGCCCTGGGGCGAGGGCAAGCTG
CTGCGGTGGATGCGGAACAACTACGGAGACCTGGACGTCTACATCACGGC
CAATGGCATCGACGACCAGGCCCTGCAGAACGACCAGCTTCGCCAGTACT
ACCTGGAGAAGTACGTCCAGGAGGCTCTGAAAGCATATCTGATAGATAAA
ATAAAAATCAAAGGCTATTATGCATTCAAACTGACTGAAGAAAAATCTAA

ACCCAGGTTTGGATTCTTCACCTCTGATTTCAAAGCCAAGTCTTCAATAC
AGTTTTACAACAAACTAATTACCAGCAACGGCTTCCCGTCTGAGAACGGC
GGTCCTAGATGCAATCAGACTCAAGGAAATCCCGAGTGCACCGTCTGCTT
ACTCCTCCTGCAGAAGAAGCCGCTGATATTCTTTAGCTGCTGCTTCTTCT
GCACCCTGGTTCTACTCTCATCAATTACCATCTTTCACAGACGGAAGAGA
AGAAAATTTTGGAAAGCAAAGGACTTACAACACATACCATTAAAGAAAGG
CCACAAGAGAGTCCTTAGCTAAAGTGAACTTATTTCTCTCTGAAGAGTTT
AGAAATTCACTCCAGTTCCATATGCTGGTAACACAAAAGACATACCCGTA
TTGTACACAGAGTATTTGAGATACTGTGCTAACCAAGGCGATGACAATCA
AAACCTCTGCCATGTGGTTGAATGCATTTTCCCTTAAGCGGTGACAATCA
GCGAACTCAGTTCTTGGTTCTAAAGGAGGCTTCGCACTGCCACTAGGCTA
TGAGTATTACCTGACGCATTGCTTTGTCAAGTTTGATGAGCTGTTTCGCA
TCATTCTCTAGCTTTCTTTAGATACCAATAGCTACTATGGTAAAAGTTGT
TTTTAAAAGTCAAACTCTGTAAGGCTTCACAGCAGATTTAAAACTATTCT
TTACACTGGATCTGTGATTTTGTCACTCGTAGCAAGGTGCTTTCCCCTTT
TGGTCCTAGTGGCTCTCAAATAGAAAGCAAACACATCTTAGGGTAATCTA
CTTATCTATAGCCAATCACAGCACTGACCCACAACTACACAAATCCGTTA
GCTCTTCTCCATAAAACACCTAATTTTGTGATCTTTTAAGTAATCTGAAA
TGTAAAAGTATGACTTCCGTAACCCATCTCATGGAAAGATCGACTAAGGA
GAGCCATACCCAGCTGTGAGGACAATTTAGTCACTAATCTCACCGTACTG
CAACTTCCTCCTTTAGAGCAGGCATTCCTTACCATTTTTGTAAGATGACA
TGATTTAGCATCTAGAACCCCTATCTGCAGTTTCTTTCTATGGCTTACCT
ACATTTCAAGAATATTGAACGGAAAATTTCAGAAAGATTTCCAAGTTTTA
AATTGTGTACTAGCATTAGTGCATGATGAAATCTCATTTTCTTTGCTCCA
TCCTGCACAGGATGTGAAACATCCCTCTGTCCAGCAAGTCCAAGCTACCT
ATATTACTCACTTGATAGTCACCATGGTTATCCAGCTGTTATTACTTGCT
CATACCCAGGTAACCCTTTTTTATTTTAATATAGCTCCAAAGTATAAGAC
TAGTGATGAAAAGGAGGTAAGTCATCAAATATGGAAGGACAGATTAACTC
TGGCACTAAGTGGGAATGCTGCAGGTTTTACAGGAAAACAAAATTCAGTC
AGTGGTTTAAAGCATCCTCTGAGGTACCTGGGGCACAATCTCCACAGATA
AGGGGAAAGAGCACTGACAAAGACTAAACATCCTAAAAAGACGCAATGTT
CTACTTACTGGCCATCAGAATAATGGCCAAAGGACCCTATACTTGCTTGC
TCTCTAGCCAAGTTTCGCTGCACATAGGTGTAGAATGCAGCGACTGACCC
TGGATGCGATTCAGAATGCTGATCTGAGTGAACTAGTTTTTTATACAGCA
CTTTTTAAAGCCTAGAATTCTTCCATCTGAACTTGGGAGTTTTGACTTTT
TTGAAATTAATTGTGCTTAAGATTTATTCAGTGATTCTAAACACTGGAGG
TAGAAAACTGTATACCCATTATGCCTATTAATTTTTCTTGATTAGCCAAC
ATTTAAATAACCACAAAGTGGCCAGTCGTTGTCTTTCCCTTTCAGGAATT
TAAGTCAAAGGATGCTGCTGCCTGCGATGCTGGCACTTCATAGGGGTGAC
AGTTTGTGTCCCTGCGGTTCCACTTCCTATCCAGCTCCCTGCTAATGGCT
```

-continued

```
TGGGAGAGCCCTGCACCCACATGGGAGACCCAAAAGCAGATCCTGCTGCT
TTCAGCCTGCTGCGGCCACTTGGAGTATGAACCAGTGGATGGAAGATCAA
TGTCTCTCCCAACAATTCTTTGAATAAATTTTTTCAAAAGTCAAAATAAA
ATTCTCCAGCTCAAAAAGCTTTAGTAGAAAACGATCCTACATTAAGGCGG
TTGTGATTGTATCCCAAGTGCATCTACGTTACAAACCAAATTGAGTATGC
AATTCAGTATGCTACTAGACTATAAGGAGAAAACAGCCAATTCAAACAAA
ATACCAAAGTCACGTGCAGTTAATTTGCTTTCTGGTTGGCCAAATGTTTT
TTTTCTCTTCTTGCCACCACTGTTTTACATGTACTTTAGAAGAAATTTTG
ACTTTTTGCTTCCTTTGAGAAATCACTATTATCAAAGGCAATTCATAATT
ACAAGTGGTCCATTGTCTTAAGAGCTCAAGATTATAGCCCTTCAAACTTG
CCAAACTCCTCAAATAGTGAAGCTCCTAACGAAGGGTTTACAACATCCTG
TTCCTTAGGGGTTATATTTTTAAGTGACTGTAATTTACCTAACAAATTTA
ATCTGGCTATCTATTGGTAATACATGTAATATTCAGGTTTATCATAAACC
CACTTAAAAACTAAAGGTTAAGTGGAAGTTGCTGCTTTTCAAAGTAACAG
GCTTCTCAGGGGAAAATATCACCTTAGCGTCCACCTGGTACTACATCTCG
TGTATTCACTGTAACCCATCTTTCCGAACATGTCTGATATATATGGAAAC
AACACTAGTGCTTAGCCTCTGGAAATGAGGCCAGGATTTTGTGATTAAAT
GTCTAATTTATTCCAAATAAACTGATTTACGCCAATA
```

The amino acid sequence of beta klotho from dog, scientific name *Canis lupus familiaris*, is provided below:

```
                                        (SEQ ID NO: 177)
MKPGCAAGSPGNEWIFLSTDESNTHYRKTMCNHGLQRSVILSAFILLGAV
PGFSGDGRAIWSKNPHFSPVNESQLFLYDTFPKNFFWGVGTGAFQVEGNW
KTDGKGPSIWDHFIHTHLKNVNSMNSSSDSYIFLEKDLSALDFIGVSFYQ
FSISWPRLFPDGIAAVANAKGLQYYNSLLDALVLRNIEPIVTLYHWDLPL
ALQEKYGGWKNETITDIFNDYATYCFQTFGDRVKYWITIHNPYLVAWHGY
GTGMHAPGEKGNLAAVYTVGHNLIKAHSKVWHNYNTNFRPYQKGLLSITL
GSHWIEPNRSENMMDILKCQQSMVSVLGWFANPIHGNGDYPEVMKKKLLS
TLPLFSEAEKNEVRGTADFFAFSFGPNNFKPQNTMAKMGQNVSLNLREVL
NWIKLEYGNPRILIAENGWFTDSHVKTEDTTAIYMMKNFLNQVLQAIRFD
EIQVFGYTAWSLLDGFEWQDAYSTRRGLFYVDFNSKQKERKPKSSAYYYK
QIIQENGFTFKESTPDVQGQFPCDFSWGVTESVLKPKVVASSPQFSDPHL
YVWNVTGNRLLHRVEGVRLKTRPAQCTDFVSIKRQLEMLARMNVTHYRFA
LDWPSILPTGNLSTVNRQALRYYRCVVSESLKLSISPMVTLYYPTHAHLG
LPSPLLHSGGWLNASTARAFQDYAGLCFQELGDLVKLWITINEPNRLSDV
YSHTSSDTYRAAHNLLIAHALVWHLYDRRYRPAQRGAVSLSLHSDWAEPA
NPYADSHWKAAERFLQFEIAWFAEPLFKTGDYPPAMREYIASKNRQGLSR
STLPRFTDEERRLVKGAADFYALNHFTTRFVMHARQNGSRYDADRDVQFL
QDITCLSSPSRLAVLPWGERKVLRWIQKNYGDVDVYITASGIDDQSLEND
ELRKYYLEKYIQEALKAHLIDKVKVKGYYAFKLTEEKSKPRFGFFTSEFK
AKSSVQLYNKLISNSGFPSENRSPRCSETQRNTECMVCLFLVQKKPLIFF
SCCFFSTLVLLSSITILHKRKRRKIWKAKNLQHIPLKKSKNSLQS
```

An encoding nucleic acid sequence of dog beta klotho is provided below:

```
                                        (SEQ ID NO: 178)
ACAATCACAAGCTTTTACTGAAGCGTTGATAAGACAGGCGAGCAGTTAGT
GGCAAATGAAGCCAGGCTGTGCGGCTGGATCTCCAGGGAATGAATGGATT
TTCCTCAGCACCGATGAAAGCAACACACACTATAGGAAAACAATGTGCAA
CCACGGGCTACAGAGATCTGTCATCCTGTCAGCATTTATTCTCCTAGGAG
CTGTTCCTGGATTCTCTGGAGACGGAAGAGCTATATGGTCTAAAAATCCT
CATTTTAGTCCGGTAAATGAAAGTCAGCTGTTTCTCTATGACACTTTTCC
TAAAAACTTTTTTTGGGGCGTTGGGACTGGAGCATTTCAAGTGGAAGGGA
ATTGGAAGACAGATGGAAAAGGACCCTCTATATGGGATCATTTCATCCAC
ACACACCTTAAAAATGTCAACAGCATGAATAGTTCCAGTGACAGTTACAT
TTTTCTGGAAAAAGACCTATCAGCCCTGGATTTTATCGGAGTTTCTTTTT
ATCAATTTCAATTTCCTGGCCAAGGCTTTTCCCCGATGGAATAGCAGCA
GTTGCCAACGCAAAGGTCTCCAGTACTACAATTCTCTTCTCGATGCTCT
AGTACTTAGGAACATTGAACCTATAGTTACTTTATACCATTGGGATTTGC
CTTTGGCACTACAAGAAAAATATGGGGGGTGGAAAAATGAAACCATAACG
GATATCTTCAATGACTATGCCACCTACTGTTTCCAGACGTTCGGGGATCG
TGTCAAATACTGGATTACAATTCACAATCCATATCTAGTTGCTTGGCATG
GGTATGGGACAGGTATGCACGCGCCTGGAGAGAAGGGAAACTTAGCAGCT
GTCTACACTGTGGGACACAACCTAATCAAGGCTCATTCGAAAGTTTGGCA
TAACTACAACACAAATTTCCGCCCATATCAGAAGGGTTTGTTATCAATCA
CGTTGGGATCCCATTGGATTGAACCAAACAGATCAGAAAACATGATGGAT
ATACTCAAATGTCAACAATCCATGGTTTCAGTGCTCGGGTGGTTTGCCAA
CCCCATCCATGGGAATGGAGACTATCCAGAAGTGATGAAAAAGAAGTTGC
TCTCCACTCTACCCCTTTTCTCTGAAGCAGAGAAGAATGAAGTGAGGGGC
ACAGCTGACTTCTTTGCCTTTTCCTTTGGACCCAACAATTTCAAGCCCCA
GAACACCATGGCTAAAATGGGACAAAATGTGTCACTCAATTTAAGAGAAG
TGCTGAATTGGATTAAACTGGAATATGGCAACCCCCGAATCTTGATTGCT
GAGAATGGCTGGTTCACAGACAGTCATGTGAAAACAGAAGATACCACAGC
CATTTACATGATGAAGAATTTCCTCAACCAGGTTCTTCAAGCAATAAGGT
TTGACGAAATACAAGTGTTTGGCTACACTGCTTGGTCTCTCCTGGATGGC
TTTGAATGGCAGGATGCTTACTCCACTCGCCGAGGATTATTTTATGTGGA
TTTTAATAGTAAACAAAAAGAAAGAAAGCCCAAGTCTTCGGCATATTACT
ATAAACAGATCATACAAGAAAATGGTTTTACTTTCAAAGAGTCCACCCCA
GATGTGCAGGGTCAGTTTCCCTGTGACTTCTCATGGGGTGTCACCGAATC
TGTCCTTAAGCCCAAAGTCGTGGCTTCCTCCCCACAGTTCAGCGACCCTC
ACCTGTACGTGTGGAATGTGACAGGCAACAGACTGTTGCACCGAGTGGAA
```

```
GGGGTGAGGCTGAAGACACGGCCGGCTCAATGCACAGATTTTGTCAGCAT
CAAAAGACAACTTGAGATGTTGGCGAGGATGAACGTCACTCACTACAGGT
TTGCTCTGGACTGGCCCTCCATCCTTCCCACCGGCAACCTGTCCACGGTT
AACCGACAAGCCCTGAGGTACTACAGGTGTGTGGTCAGCGAGTCGCTGAA
GCTCAGCATCTCCCCGATGGTCACGCTGTACTACCCGACCCACGCCCACC
TGGGCCTCCCCTCGCCGCTGCTGCACAGCGGGGCTGGCTGAACGCGTCC
ACCGCCCGCGCCTTCCAGGACTATGCCGGGCTGTGCTTCCAGGAGCTGGG
GGACCTGGTGAAGCTCTGGATCACCATCAATGAGCCCAACCGGCTGAGTG
ACGTCTACAGCCACACCAGCAGCGACACCTACCGGGCAGCGCACAACCTG
CTGATCGCCCACGCCCTGGTGTGGCACCTGTACGACCGGCGGTACCGGCC
GGCGCAGCGCGGGGCCGTGTCGCTGTCCCTGCACTCGGACTGGGCGGAGC
CCGCCAACCCCTACGCCGACTCGCACTGGAAGGCGGCCGAGCGCTTCCTG
CAGTTCGAAATCGCCTGGTTCGCCGAGCCGCTCTTCAAGACCGGGGACTA
CCCGCCGGCCATGAGGGAGTACATCGCCTCCAAGAACAGGCAGGGGCTCT
CGCGCTCCACCCTGCCCCGCTTCACCGACGAGGAGAGGAGGCTGGTCAAG
GGCGCCGCCGACTTCTACGCGCTGAACCACTTCACCACCAGGTTCGTGAT
GCACGCGCGCCAGAACGGCAGCCGCTACGACGCGGACCGCGACGTCCAGT
TCCTGCAGGACATCACCTGCCTGAGCTCCCCCAGCCGCCTGGCCGTCCTG
CCCTGGGGGGAGCGCAAGGTGCTCAGGTGGATCCAGAAGAACTACGGAGA
CGTGGACGTGTACATCACGGCCAGTGGCATCGATGACCAGTCTCTGGAAA
ATGATGAGCTCAGAAAATACTACTTGGAGAAATACATCCAGGAGGCTCTG
AAAGCACACCTAATTGATAAAGTCAAAGTCAAAGGCTATTATGCATTCAA
ACTGACTGAAGAAAAATCTAAACCCAGATTTGGATTCTTCACGTCTGAAT
TCAAAGCTAAATCCTCAGTTCAGCTTTACAACAAACTGATCAGCAACAGT
GGCTTCCCCTTCTGAGAACAGGAGTCCTAGATGCAGTGAGACTCAAAGAA
CACAGAGTGCATGGTCTGCTTATTCTTGTGCAAAAGAAACCACTGATAT
TCTTTAGTTGTTGCTTCTTCTCTACCCTGGTTCTACTTTCATCGATTACC
ATTCTTCATAAGCGAAAGAGAAGAAAAATTTGGAAAGCAAAGAACTTACA
ACATATACCATTAAAGTGAGGCCACAGAAAGTTCTTAGTGAAACTGATCC
TATTTCTGTCTGCATGATAGAAAGTCTAAAAATTCACTCCAGTCCCAAAT
ACTGGTAACATAGAAGACAATTTGAAACACTAGTAGTAACCAAGGTGATG
ACAATCAAGGTCTCTGCTGTGTGGTCCAAATGAATTTTCCATTAGGTGTT
GACATCACTGAATACAGTTTTAGATCTGAAGACTAAGATCTAGAGAGTA
AGCTAGGATTATCTGATACAATGCTTCATTAAGTTTAATAAGCTGTTATC
CATCATTCTTCTCTGGCTTCCTTCTAGAAATACCAATAGCTAATTATAGC
AACTTAGAAAAAGTGCAACTTTTGCTAGACTCCATAGCAGAAATCTAAA
ACTCTTAACACTGGATATTCAGTGATTATTCTATCACTTCTAACAAGGTG
CTTTTCCCCTTTAGAAGATATACAATAGGGTAAATAGTGCTCCTTTATCA
TCCATTCCAGCACTTTTTTTTCCAGCATAGACTCTTAAACACATTGATC
CTAGTTTTTCTCAATAGAAATAAAAAATCATTTAGAAAACATGGAATTTT
GTGAGGTCTCTCCTTGCATTAGATCTGAGTTTTTTTTAAAAAAAGACTT
AACTTCCATAACCCATCTCATGGGAAGATCACAGGACTAAGATTAAGGAG
AGTTAGACCCATCAACTGCCTGAGGAGACAGCACTCAACCTCACAGTACA
GCAAATTCCTTGGGACAAACTGACAGCAATCTTCCGCACTTGGATTGTTG
AGGCAGCACACAAGATCTTAACATACTTAGGAAAGTTAAATATTCTAAAA
AGATGTAAAGTTTTATTTTTATTATCAAGTCTTCAAAGGACCATATTATT
CCATAAGACTTGCTCTCTCCTGAGTTCCACTCTTCTGACACTATGTGTAT
ATGGGGACACTCAAACTGCACCTTGACATTGCAACTTTGGATACAATTCA
GAATGTAAATGTTTGAAGGACTTAAAACTTTCTCCACTGCACCTTTTGAA
GCTGGGATTAAGTAAATACGAACTGGGAGTTTGACTTTTTTGAACTCTGT
GCTTGATTTATTCACTGTATTCTAAATTTTAAGGAAAACCTGAATGTAAA
CCCATTCATACCCTTTCTTTGGGTTAGTAAACATTTAACCACCCATTTC
A.
```

The amino acid sequence of human/mouse beta klotho chimeric protein (human KLB (M1-F508)-mouse KLB (P507-S1043)) is provided below:

(SEQ ID NO: 179)
MKPGCAAGSPGNEWIFFSTDEITTRYRNTMSNGGLQRSVILSALILLRAV
TGFSGDGRAIWSKNPNFTPVNESQLFLYDTFPKNFFWGIGTGALQVEGSW
KKDGKGPSIWDHFIHTHLKNVSSTNGSSDSYIFLEKDLSALDFIGVSFYQ
FSISWPRLFPDGIVTVANAKGLQYYSTLLDALVLRNIEPIVTLYHWDLPL
ALQEKYGGWKNDTIIDIFNDYATYCFQMFGDRVKYWITIHNPYLVAWHGY
GTGMHAPGEKGNLAAVYTVGHNLIKAHSKVWHNYNTHFRPHQKGWLSITL
GSHWIEPNRSENTMDIFKCQQSMVSVLGWFANPIHGDGDYPEGMRKKLFS
VLPIFSEAEKHEMRGTADFFAFSFGPNNFKPLNTMAKMGQNVSLNLREAL
NWIKLEYNNPRILIAENGWFTDSRVKTEDTTAIYMMKNFLSQVLQAIRLD
EIRVFGYTAWSLLDGFEWQDAYTIRRGLFYVDFNSKQKERKPKSSAHYYK
QIIRENGFPLKESTPDMKGRFPCDFSWGVTESVLKPEFTVSSPQFTDPHL
YVWNVTGNRLLYRVEGVRLKTRPSQCTDYVSIKKRVEMLAKMKVTHYQFA
LDWTSILPTGNLSKVNRQVLRYYRCVVSEGLKLGVFPMVTLYHPTHSHLG
LPLPLLSSGGWLNMNTAKAFQDYAELCFRELGDLVKLWITINEPNRLSDM
YNRTSNDTYRAAHNLMIAHAQVWHLYDRQYRPVQHGAVSLSLHCDWAEPA
NPFVDSHWKAAERFLQFEIAWFADPLFKTGDYPSVMKEYIASKNQRGLSS
SVLPRFTAKESRLVKGTVDFYALNHFTTRFVIHKQLNTNRSVADRDVQFL
QDITRLSSPSRLAVTPWGVRKLLAWIRRNYRDRDIYITANGIDDLALEDD
QIRKYYLEKYVQEALKAYLIDKVKIKGYYAFKLTEEKSKPRFGFFTSDFR
AKSSVQFYSKLISSSGLPAENRSPACGQPAEDTDCTICSFLVEKKPLIFF
GCCFISTLAVLLSITVFHHQKRRKFQKARNLQNIPLKKGHSRVFS.

An encoding nucleic acid sequence of human/mouse beta klotho chimeric protein is provided below:

(SEQ ID NO: 180)
ATGAAGCCAGGCTGTGCGGCAGGATCTCCAGGGAATGAATGGATTTTCTT

CAGCACTGATGAAATAACCACACGCTATAGGAATACAATGTCCAACGGGG

GATTGCAAAGATCTGTCATCCTGTCAGCACTTATTCTGCTACGAGCTGTT

ACTGGATTCTCTGGAGATGGAAGAGCTATATGGTCTAAAAATCCTAATTT

TACTCCGGTAAATGAAAGTCAGCTGTTTCTCTATGACACTTTCCCTAAAA

ACTTTTTCTGGGGTATTGGGACTGGAGCATTGCAAGTGGAAGGGAGTTGG

AAGAAGGATGGAAAAGGACCTTCTATATGGGATCATTTCATCCACACACA

CCTTAAAAATGTCAGCAGCACGAATGGTTCCAGTGACAGTTATATTTTTC

TGGAAAAAGACTTATCAGCCCTGGATTTTATAGGAGTTTCTTTTTATCAA

TTTTCAATTTCCTGGCCAAGGCTTTTCCCCGATGGAATAGTAACAGTTGC

CAACGCAAAAGGTCTGCAGTACTACAGTACTCTTCTGGACGCTCTAGTGC

TTAGAAACATTGAACCTATAGTTACTTTATACCACTGGGATTTGCCTTTG

GCACTACAAGAAAAATATGGGGGTGGAAAAATGATACCATAATAGATAT

CTTCAATGACTATGCCACATACTGTTTCCAGATGTTTGGGGACCGTGTCA

AATATTGGATTACAATTCACAACCCATATCTAGTGGCTTGGCATGGGTAT

GGGACAGGTATGCATGCCCCTGGAGAGAAGGGAAATTTAGCAGCTGTCTA

CACTGTGGGACACAACTTGATCAAGGCTCACTCGAAAGTTTGGCATAACT

ACAACACACATTTCCGCCCACATCAGAAGGGTTGGTTATCGATCACGTTG

GGATCTCATTGGATCGAGCCAAACCGGTCGGAAAACACGATGGATATATT

CAAATGTCAACAATCCATGGTTTCTGTGCTTGGATGGTTTGCCAACCCTA

TCCATGGGGATGGCGACTATCCAGAGGGGATGAGAAAGAAGTTGTTCTCC

GTTCTACCCATTTTCTCTGAAGCAGAGAAGCATGAGATGAGAGGCACAGC

TGATTTCTTTGCCTTTTCTTTTGGACCCAACAACTTCAAGCCCCTAAACA

CCATGGCTAAAATGGGACAAAATGTTTCACTTAATTTAAGAGAAGCGCTG

AACTGGATTAAACTGGAATACAACAACCCTCGAATCTTGATTGCTGAGAA

TGGCTGGTTCACAGACAGTCGTGTGAAAACAGAAGACACCACGGCCATCT

ACATGATGAAGAATTTCCTCAGCCAGGTGCTTCAAGCAATAAGGTTAGAT

GAAATACGAGTGTTTGGTTATACTGCCTGGTCTCTCCTGGATGGCTTTGA

ATGGCAGGATGCTTACACCATCCGCCGAGGATTATTTTATGTGGATTTTA

ACAGTAAACAGAAAGAGCGGAAACCTAAGTCTTCAGCACACTACTACAAA

CAGATCATACGAGAAATGGTTTTCCTTTGAAAGAGTCCACGCCAGACAT

GAAGGGTCGGTTCCCCTGTGATTTCTCTTGGGGAGTCACTGAGTCTGTTC

TTAAGCCCGAGTTTACGGTCTCCTCCCCGCAGTTTACCGATCCTCACCTG

TATGTGTGGAATGTCACTGGCAACAGATTGCTCTACCGAGTGGAAGGGGT

AAGGCTGAAAACAAGACCATCCCAGTGCACAGATTATGTGAGCATCAAA

AACGAGTTGAAATGTTGGCAAAAATGAAAGTCACCCACTACCAGTTTGCT

CTGGACTGGACCTCTATCCTTCCCACTGGCAATCTGTCCAAAGTTAACAG

ACAAGTGTTAAGGTACTATAGGTGTGTGGTGAGCGAAGGACTGAAGCTGG

GCGTCTTCCCCATGGTGACGTTGTACCACCCAACCCACTCCCATCTCGGC

CTCCCCCTGCCACTTCTGAGCAGTGGGGGGTGGCTAAACATGAACACAGC

CAAGGCCTTCCAGGACTACGCTGAGCTGTGCTTCCGGGAGTTGGGGGACT

TGGTGAAGCTCTGGATCACCATCAATGAGCCTAACAGGCTGAGTGACATG

TACAACCGCACGAGTAATGACACCTACCGTGCAGCCCACAACCTGATGAT

CGCCCATGCCCAGGTCTGGCACCTCTATGATAGGCAGTATAGGCCGGTCC

AGCATGGGGCTGTGTCGCTGTCCTTACATTGCGACTGGGCAGAACCTGCC

AACCCCTTTGTGGATTCACACTGGAAGGCAGCCGAGCGCTTCCTCCAGTT

TGAGATCGCCTGGTTTGCAGATCCGCTCTTCAAGACTGGCGACTATCCAT

CGGTTATGAAGGAATACATCGCCTCCAAGAACCAGCGAGGGCTGTCTAGC

TCAGTCCTGCCGCGCTTCACCGCGAAGGAGAGCAGGCTGGTGAAGGGTAC

CGTCGACTTCTACGCACTGAACCACTTCACTACGAGGTTCGTGATACACA

AGCAGCTGAACACCAACCGCTCAGTTGCAGACAGGGACGTCCAGTTCCTG

CAGGACATCACCCGCCTAAGCTCGCCCAGCCGCCTGGCTGTAACACCCTG

GGGAGTGCGCAAGCTCCTTGCGTGGATCCGGAGGAACTACAGAGACAGGG

ATATCTACATCACAGCCAATGGCATCGATGACCTGGCTCTAGAGGATGAT

CAGATCCGAAAGTACTACTTGGAGAAGTATGTCCAGGAGGCTCTGAAAGC

ATATCTCATTGACAAGGTCAAAATCAAAGGCTACTATGCATTCAAACTGA

CTGAAGAGAAATCTAAGCCTAGATTTGGATTTTTCACCTCTGACTTCAGA

GCTAAGTCCTCTGTCCAGTTTTACAGCAAGCTGATCAGCAGCAGTGGCCT

CCCCGCTGAGAACAGAAGTCCTGCGTGTGGTCAGCCTGCGGAAGACACAG

ACTGCACCATTTGCTCATTTCTCGTGGAGAAGAAACCACTCATCTTCTTC

GGTTGCTGCTTCATCTCCACTCTGGCTGTACTGCTATCCATCACCGTTTT

TCATCATCAAAAGAGAAGAAAATTCCAGAAAGCAAGGAACTTACAAAATA

TACCATTGAAGAAAGGCCACAGCAGAGTTTTCAGCTGA

The amino acid sequence of mouse/human beta klotho chimeric protein (mouse KLB (M1-F506)-human KLB (S509-S1044)) is provided below:

(SEQ ID NO: 181)
MKTGCAAGSPGNEWIFFSSDERNTRSRKTMSNRALQRSAVLSAFVLLRAV

TGFSGDGKAIWDKKQYVSPVNPSQLFLYDTFPKNFSWGVGTGAFQVEGSW

KTDGRGPSIWDRYVYSHLRGVNGTDRSTDSYIFLEKDLLALDFLGVSFYQ

FSISWPRLFPNGTVAAVNAQGLRYYRALLDSLVLRNIEPIVTLYHWDLPL

TLQEEYGGWKNATMIDLFNDYATYCFQTFGDRVKYWITIHNPYLVAWHGF

GTGMHAPGEKGNLTAVYTVGHNLIKAHSKVWHNYDKNFRPHQKGWLSITL

GSHWIEPNRTDNMEDVINCQHSMSSVLGWFANPIHGDGDYPEFMKTGAMI

PEFSEAEKEEVRGTADFFAFSFGPNNFRPSNTVVKMGQNVSLNLRQVLNW

IKLEYDDPQILISENGWFTDSYIKTEDTTAIYMMKNFLNQVLQAIKFDEI

RVFGYTAWTLLDGFEWQDAYTTRRGLFYVDFNSEQKERKPKSSAHYYKQI

IQDNGFSLKESTPDVQGQFPCDFSWGVTESVLKPESVASSPQFSDPHLYV

WNATGNRLLHRVEGVRLKTRPAQCTDFVNIKKQLEMLARMKVTHYRFALD

```
WASVLPTGNLSAVNRQALRYYRCVVSEGLKLGISAMVTLYYPTHAHLGLP

EPLLHADGWLNPSTAEAFQAYAGLCFQELGDLVKLWITINEPNRLSDIYN

RSGNDTYGAAHNLLVAHALAWRLYDRQFRPSQRGAVSLSLHADWAEPANP

YADSHWRAAERFLQFEIAWFAEPLFKTGDYPAAMREYIASKHRRGLSSSA

LPRLTEAERRLLKGTVDFCALNHFTTRFVMHEQLAGSRYDSDRDIQFLQD

ITRLSSPTRLAVIPWGVRKLLRWVRRNYGDMDIYITASGIDDQALEDDRL

RKYYLGKYLQEVLKAYLIDKVRIKGYYAFKLAEEKSKPRFGFFTSDFKAK

SSIQFYNKVISSRGFPFENSSSRCSQTQENTECTVCLFLVQKKPLIFLGC

CFFFSTLVLLLSIAIFQRQKRRKFWKAKNLQHIPLKKGKRVVS
```

An encoding nucleic acid sequence of mouse/human beta klotho chimeric protein is provided below:

```
                                    (SEQ ID NO: 182)
ATGAAGACAGGCTGTGCAGCAGGGTCTCCGGGGAATGAATGGATTTTCTT

CAGCTCTGATGAAAGAAACACACGCTCTAGGAAAACAATGTCCAACAGGG

CACTGCAAAGATCTGCCGTGCTGTCTGCGTTTGTTCTGCTGCGAGCTGTT

ACCGGCTTCTCCGGAGACGGGAAAGCAATATGGGATAAAAAACAGTACGT

GAGTCCGGTAAACCCAAGTCAGCTGTTCCTCTATGACACTTTCCCTAAAA

ACTTTTCCTGGGGCGTTGGGACCGGAGCATTTCAAGTGGAAGGGAGTTGG

AAGACAGATGGAAGAGGACCCTCGATCTGGGATCGGTACGTCTACTCACA

CCTGAGAGGTGTCAACGGCACAGACAGATCCACTGACAGTTACATCTTTC

TGGAAAAAGACTTGTTGGCTCTGGATTTTTTAGGAGTTTCTTTTTATCAG

TTCTCAATCTCCTGGCCACGGTTGTTTCCCAATGGAACAGTAGCAGCAGT

GAATGCGCAAGGTCTCCGGTACTACCGTGCACTTCTGGACTCGCTGGTAC

TTAGGAATATCGAGCCCATTGTTACCTTGTACCATTGGGATTTGCCTCTG

ACGCTCCAGGAAGAATATGGGGGCTGGAAAAATGCAACTATGATAGATCT

CTTCAACGACTATGCCACATACTGCTTCCAGACCTTTGGAGACCGTGTCA

AATATTGGATTACAATTCACAACCCTTACCTTGTTGCTTGGCATGGGTTT

GGCACAGGTATGCATGCACCAGGAGAGAAGGGAAATTTAACAGCTGTCTA

CACTGTGGGACACAACCTGATCAAGGCACATTCGAAAGTGTGGCATAACT

ACGACAAAAACTTCCGCCCTCATCAGAAGGGTTGGCTCTCCATCACCTTG

GGGTCCCATTGGATAGAGCCAAACAGAACAGACAACATGGAGGACGTGAT

CAACTGCCAGCACTCCATGTCCTCTGTGCTTGGATGGTTCGCCAACCCCA

TCCACGGGACGGCGACTACCCTGAGTTCATGAAGACGGGCGCCATGATC

CCCGAGTTCTCTGAGGCAGAGAAGGAGGAGGTGAGGGGCACGGCTGATTT

CTTTGCCTTTTCCTTCGGGCCCAACAACTTCAGGCCCTCAAACACCGTGG

TGAAAATGGGACAAAATGTATCACTCAACTTAAGGCAGGTGCTGAACTGG

ATTAAACTGGAATACGATGACCCTCAAATCTTGATTTCGGAGAACGGCTG

GTTCACAGATAGCTATATAAAGACAGAGGACACCACGGCCATCTACATGA

TGAAGAATTTCCTAAACCAGGTTCTTCAAGCAATAAAATTTGATGAAATC

CGCGTGTTTGGTTATACGGCCTGGACTCTCCTGGATGGCTTTGAGTGGCA

GGATGCCTATACGACCCGACGAGGGCTGTTTTATGTGGACTTTAACAGTG

AGCAGAAAGAGAGGGAAACCCAAGTCCTCGGCTCATTACTACAAGCAGATC

ATACAAGACAACGGCTTCTCTTTAAAAGAGTCCACGCCAGATGTGCAGGG

CCAGTTTCCCTGTGACTTCTCCTGGGGTGTCACTGAATCTGTTCTTAAGC

CCGAGTCTGTGGCTTCGTCCCCACAGTTCAGCGATCCTCATCTGTACGTG

TGGAACGCCACTGGCAACAGACTGTTGCACCGAGTGGAAGGGGTGAGGCT

GAAAACACGACCCGCTCAATGCACAGATTTTGTAAACATCAAAAAACAAC

TTGAGATGTTGGCAAGAATGAAAGTCACCCACTACCGGTTTGCTCTGGAT

TGGGCCTCGGTCCTTCCCACTGGCAACCTGTCCGCGGTGAACCGACAGGC

CCTGAGGTACTACAGGTGCGTGGTCAGTGAGGGGCTGAAGCTTGGCATCT

CCGCGATGGTCACCCTGTATTATCCGACCCACGCCCACCTAGGCCTCCCC

GAGCCTCTGTTGCATGCCGACGGGTGGCTGAACCCATCGACGGCCGAGGC

CTTCCAGGCCTACGCTGGGCTGTGCTTCCAGGAGCTGGGGGACCTGGTGA

AGCTCTGGATCACCATCAACGAGCCTAACCGGCTAAGTGACATCTACAAC

CGCTCTGGCAACGACACCTACGGGGCGGCGCACAACCTGCTGGTGGCCCA

CGCCCTGGCCTGGCGCCTCTACGACCGGCAGTTCAGGCCCTCACAGCGCG

GGGCCGTGTCGCTGTCGCTGCACGCGGACTGGGCGGAACCCGCCAACCCC

TATGCTGACTCGCACTGGAGGGCGGCCGAGCGCTTCCTGCAGTTCGAGAT

CGCCTGGTTCGCCGAGCCGCTCTTCAAGACCGGGGACTACCCCGCGGCCA

TGAGGGAATACATTGCCTCCAAGCACCGACGGGGCTTTCCAGCTCGGCC

CTGCCGCGCCTCACCGAGGCCGAAAGGAGGCTGCTCAAGGGCACGGTCGA

CTTCTGCGCGCTCAACCACTTCACCACTAGGTTCGTGATGCACGAGCAGC

TGGCCGGCAGCCGCTACGACTCGGACAGGGACATCCAGTTTCTGCAGGAC

ATCACCCGCCTGAGCTCCCCCACGCGCCTGGCTGTGATTCCTGGGGGGT

GCGCAAGCTGCTGCGGTGGGTCCGGAGGAACTACGGCGACATGGACATTT

ACATCACCGCCAGTGGCATCGACGACCAGGCTCTGGAGGATGACCGGCTC

CGGAAGTACTACCTAGGGAAGTACCTTCAGGAGGTGCTGAAAGCATACCT

GATTGATAAAGTCAGAATCAAAGGCTATTATGCATTCAAACTGGCTGAAG

AGAAATCTAAACCCAGATTTGGATTCTTCACATCTGATTTTAAAGCTAAA

TCCTCAATACAATTTTACAACAAAGTGATCAGCAGCAGGGGCTTCCCTTT

TGAGAACAGTAGTTCTAGATGCAGTCAGACCCAAGAAAATACAGAGTGCA

CTGTCTGCTTATTCCTTGTGCAGAAGAAACCACTGATATTCCTGGGTTGT

TGCTTCTTCTCCACCCTGGTTCTACTCTTATCAATTGCCATTTTTCAAAG

GCAGAAGAGAAGAAAGTTTTGGAAAGCAAAAAACTTACAACACATACCAT

TAAAGAAAGGCAAGAGAGTTGTTAGCTAG
```

Related beta klotho polypeptides include allelic variants (e.g., SNP variants); splice variants; fragments; derivatives; substitution, deletion, and insertion variants; fusion polypeptides; and interspecies homologs, preferably, which retain beta klotho activity and/or are sufficient to generate an anti-beta klotho immune response. As those skilled in the art will appreciate, an anti-beta klotho antibody provided herein can bind to a beta klotho polypeptide, a beta klotho polypeptide fragment, a beta klotho antigen, and/or a beta klotho epitope. An epitope may be part of a larger beta klotho antigen, which may be part of a larger beta klotho polypeptide fragment, which, in turn, may be part of a larger beta klotho polypeptide. Beta klotho may exist in a native or denatured form. Beta klotho polypeptides described herein may be isolated from a variety of sources, such as from human tissue types or from another source, or prepared by recombinant or synthetic methods. A beta klotho polypeptide may comprise a polypeptide having the same amino acid sequence as a corresponding beta klotho polypeptide derived from nature. Beta klotho polypeptides encompass truncated or secreted forms of a beta klotho polypeptide (e.g., an extracellular domain sequence), variant forms (e.g., alternatively spliced forms) and allelic variants of the polypeptide. Orthologs to the beta klotho polypeptide are also well known in the art.

The term "beta klotho" encompasses "full-length," unprocessed beta klotho as well as any form of beta klotho that results from processing in the cell. The term also encompasses naturally occurring variants or mutations of beta klotho (e.g., splice variants, allelic variants, SNP variants and isoforms). The beta klotho polypeptides described herein (e.g., human beta klotho) may be isolated from a variety of sources, such as from human tissue types or from another source, or prepared by recombinant or synthetic methods.

The terms "FGF19-like signaling" and "induces FGF19-like signaling," when applied to a binding protein such an antibody that binds to beta klotho of the present disclosure, means that the binding protein (e.g., antibody) mimics, or modulates, an in vitro or an in vivo biological effect induced by the binding of (i) beta klotho; (ii) FGFR1c, FGFR2c, FGFR3c, and FGFR4; or (iii) a complex comprising beta klotho and one of FGFR1c, FGFR2c, FGFR3c, and FGFR4 and induces a biological response that otherwise would result from FGF19 binding to (i) beta klotho; (ii) FGFR1c, FGFR2c, FGFR3c or FGFR4; or (iii) a complex comprising beta klotho and one of FGFR1c, FGFR2c, FGFR3c, and FGFR4 in vivo. In assessing the binding and specificity of anti-beta klotho antibody, for example, an antibody or fragment thereof, that binds to beta klotho (e.g., human beta klotho), an antibody or fragment thereof is deemed to induce a biological response when the response is equal to or greater than 5%, and preferably equal to or greater than 10%, 15%, 20%, 25%, 30%, 35%, 40%, 45%, 50%, 55%, 60%, 65%, 70%, 75%, 80%, 85%, 90% or 95%, of the activity of a wild type FGF19 standard comprising the mature form of SEQ ID NO:187 (e.g., the mature form of human FGF19) and has the following properties: exhibiting an efficacy level of equal to or more than 5% of an FGF19 standard, with an EC50 of equal to or less than 100 nM, e.g., 90 nM, 80 nM, 70 nM, 60 nM, 50 nM, 40 nM, 30 nM, 20 nM or 10 nM in (1) a recombinant FGF19 receptor mediated luciferase-reporter cell assay (see, e.g., Example 4); (2) ERK-phosphorylation in a recombinant FGF19 receptor mediated cell assay (see, e.g., Example 4); or (3) ERK-phosphorylation in human adipocytes (see, e.g., Example 5).

The term "FGF19R" may refer to a multimeric receptor complex that FGF19 is known or suspected to form in vivo. In various embodiments, FGF19R comprises (i) an FGFR, e.g., FGFR1c, FGFR2c, FGFR3c or FGFR4, and (ii) beta klotho.

The terms "FGF21-like signaling" and "induces FGF21-like signaling," when applied to a binding protein such an antibody that binds to beta klotho of the present disclosure, means that the binding protein (e.g., antibody) mimics, or modulates, an in vivo biological effect induced by the binding of (i) beta klotho; (ii) FGFR1c, FGFR2c, FGFR3c, and FGFR4; or (iii) a complex comprising beta klotho and one of FGFR1c, FGFR2c, FGFR3c, and FGFR4 and induces a biological response that otherwise would result from FGF21 binding to (i) beta klotho; (ii) FGFR1c, FGFR2c, FGFR3c or FGFR4; or (iii) a complex comprising beta klotho and one of FGFR1c, FGFR2c, FGFR3c, and FGFR4 in vivo. In assessing the binding and specificity of anti-beta klotho antibody, for example, an antibody or fragment thereof that binds to beta klotho (e.g., human beta klotho), an antibody or fragment thereof is deemed to induce a biological response when the response is equal to or greater than 5%, and preferably equal to or greater than 10%, 15%, 20%, 25%, 30%, 35%, 40%, 45%, 50%, 55%, 60%, 65%, 70%, 75%, 80%, 85%, 90% or 95%, of the activity of a wild type FGF21 standard comprising the mature form of SEQ ID NO:183 or 185 (e.g., the mature form of the human FGF21 sequence) and has the following properties: exhibiting an efficacy level of equal to or more than 5% of an FGF21 standard, with an EC50 of equal to or less than 100 nM, e.g., 90 nM, 80 nM, 70 nM, 60 nM, 50 nM, 40 nM, 30 nM, 20 nM or 10 nM in (1) a recombinant FGF21 receptor mediated luciferase-reporter cell assay (see, e.g., Example 4); (2) ERK-phosphorylation in the recombinant FGF21 receptor mediated cell assay (see, e.g., Example 4); or (3) ERK-phosphorylation in human adipocytes (see, e.g., Example 5).

The term "FGF21R" may refer to a multimeric receptor complex that FGF21 is known or suspected to form in vivo. In various embodiments, FGF21R comprises (i) an FGFR, e.g., FGFR1c, FGFR2c, FGFR3c or FGFR4, and (ii) beta klotho.

The term "binding protein" refers to a protein comprising a portion (e.g., one or more binding regions such as CDRs) that binds to beta klotho, including human and/or cyno beta klotho and, optionally, a scaffold or framework portion (e.g., one or more scaffold or framework regions) that allows the binding portion to adopt a conformation that promotes binding of the binding protein to a beta klotho polypeptide, fragment or epitope. Examples of such binding proteins include antibodies, such as a human antibody, a humanized antibody; a chimeric antibody; a recombinant antibody; a single chain antibody; a diabody; a triabody; a tetrabody; a Fab fragment; a F(ab') 2 fragment; an IgD antibody; an IgE antibody; an IgM antibody; an IgG1 antibody; an IgG2 antibody; an IgG3 antibody; or an IgG4 antibody, and fragments thereof. The binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the binding protein as well as wholly synthetic scaffolds comprising, for example, a biocompatible polymer. See, e.g., Korndorfer et al., 2003, Proteins: Structure, Function, and Bioinformatics, 53(1): 121-129 (2003); Roque et al., Biotechnol. Prog. 20:639-654 (2004). In addition, peptide antibody mimetics ("PAMs") can be used, as well as scaffolds based on antibody mimetics utilizing fibronectin components as a scaffold. In the context of the present disclosure, a binding protein is said to specifically bind or selectively bind to beta klotho, for example, when the dissociation constant ($K_D$) is $\leq 10^{-8}$ M. The binding protein (e.g., antibody) may specifically bind beta klotho with high affinity when the $K_D$ is $\leq 10^{-9}$ M or $K_D$ is $\leq 10^{-10}$ M. In some embodiments, the binding proteins (e.g., antibodies) may bind to beta klotho or a complex comprising FGFR1c and beta klotho, including with a $K_D$ of between about $10^{-7}$ M and about $10^{-12}$ M and in other embodiments, the binding proteins (e.g., antibodies) may bind with a $K_D$ of $1$-$2 \times 10^{-9}$ M.

The term "antibody" and "immunoglobulin" or "Ig" are used interchangeably herein, and is used in the broadest sense and specifically covers, for example, individual anti-beta klotho monoclonal antibodies (including agonist, antagonist, neutralizing antibodies, full length or intact monoclonal antibodies), anti-beta klotho antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain anti-beta klotho antibodies, and fragments of anti-beta klotho antibodies, as described below. An antibody can be human, humanized, chimeric and/or affinity matured as well as an antibody from other species, for example mouse, rabbit etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See, Borrebaeck (ed.) (1995) Antibody Engineering, Second Ed., Oxford University Press.; Kuby (1997) Immunology, Third Ed., W.H. Freeman and Company, New York). In specific embodiments, the specific molecular antigen can be bound by an antibody provided herein includes a beta klotho polypeptide, beta klotho fragment or beta klotho epitope. Antibodies also include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments (e.g., antigens-binding fragments such as beta klotho binding fragments) of any of the above, which refers a portion of an antibody heavy or light chain polypeptide that retains some or all of the binding activity of the antibody from which the fragment was derived. Non-limiting examples of functional fragments (e.g., antigens-binding fragments such as beta klotho binding fragments) include single-chain Fvs (scFv) (e.g., including monospecific, bispecific, etc.), Fab fragments, F(ab') fragments, F(ab)2 fragments, F(ab')2 fragments, disulfide-linked Fvs (sdFv), Fd fragments, Fv fragments, diabody, triabody, tetrabody and minibody. In particular, antibodies provided herein include immunoglobulin molecules and immunologically active portions of immunoglobulin molecules, for example, antigen binding domains or molecules that contain an antigen-binding site that binds to a beta klotho antigen (e.g., one or more complementarity determining regions (CDRs) of an anti-beta klotho antibody). Such antibody fragments can be found described in, for example, Harlow and Lane, Antibodies: A Laboratory Manual, Cold Spring Harbor Laboratory, New York (1989); Myers (ed.), Molec. Biology and Biotechnology: A Comprehensive Desk Reference, New York: VCH Publisher, Inc.; Huston et al., Cell Biophysics, 22:189-224 (1993); PlUckthun and Skerra, Meth. Enzymol., 178:497-515 (1989) and in Day, E. D., Advanced Immunochemistry, Second Ed., Wiley-Liss, Inc., New York, N.Y. (1990). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. Anti-beta klotho antibodies may be agonistic antibodies or antagonistic antibodies. Antibodies provided herein include agonistic antibodies to beta klotho, for example, antibodies that induce FGF19-like signaling and/or FGF21-like signaling. Preferred agonistic antibodies to beta klotho include those that do not compete for the binding of FGF19 and/or FGF21 to an FGF receptor including, for example, FGFR1c, FGFR2c, FGFR3c, or FGFR4c.

The term "fibroblast growth factors" refers to a family of growth factors, including twenty-two members of the human FGF family. The FGF19 subfamily of fibroblast growth factors consists of human FGF21, FGF23 and FGF19 and mouse FGF15. The effects of FGF family members are the result of their heparin-dependent binding to one or more members of the FGF receptor tyrosine kinase (FGFR) family, which includes four members each having a tyrosine kinase domain, FGFR1, FGFR2, FGFR3 and FGFR4, as well as two splice variants each of FGFR1, FGFR2 and FGFR3. These splice variants, which occur in exon 3 of FGFR1, FGFR2 and FGFR3, are designated as "b" and "c" variants (e.g., FGFR1b, FGFR2b, FGFR3c, FGFR1c, FGFR2c and FGFR3c, which are also known as FGFR1(III)b, FGFR2(III)b, FGFR3(III)c, FGFR1(III)c, FGFR2(III)c and FGFR3(III)c, respectively). For example, FGF19 targets and has effects on both adipocytes and hepatocytes. Mice treated with recombinant human FGF19 (rhFGF19), despite being on a high-fat diet, show increased metabolic rates, increased lipid oxidation, a lower respiratory quotient and weight loss. Moreover, such mice showed lower serum levels of leptin, insulin, cholesterol and triglycerides, and normal levels of blood glucose despite the high-fat diet and without appetite diminishment. In addition, obese mice that lacked leptin but included a FGF19 transgene showed weight loss, lowered cholesterol and triglycerides, and did not develop diabetes. In addition, obese, diabetic mice that lack leptin, when injected with rhFGF19, showed reversal of their metabolic characteristics in the form of weight loss and lowered blood glucose. For example, FGF21 is expressed primarily by the liver and has metabolic effects similar to that of FGF19, such as increased metabolism via its effects on adipose tissue, weight loss, lowered blood glucose levels, and resistance to obesity and diabetes. FGF21-transgenic mice were also resistant to diet-induced obesity, and, in diabetic rodent models, FGF21 administration lowered blood glucose and triglyceride levels. FGF19 and FGF21 metabolic effects occur via their binding FGF receptors, including the FGFR1c, FGFR2c and FGFR3c receptors, and required beta klotho for the binding. for the binding. The binding of FGF19 and FGF21 to FGFR1c and FGFR2c are significant. FGF19 has also been shown to have metabolic effects distinct from FGF21, including regulating bile production by the liver via its liver-specific effects, negatively regulating bile production in response to postprandial bile-production, and liver mitogenic effects that are not observed with respect to FGF21. For example, FGF19 transgenic mice develop hepatic adenocarcinoma due to increased proliferation and dysplasia of hepatocytes, and rhFGF19-treated mice exhibit hepatocyte proliferation of hepatocytes. These additional activities of FGF19 appear to be mediated via its binding to FGFR4. FGF19 can bind FGFR4 in both a beta klotho-dependent and beta klotho-independent manner. Although FGF21 has also been shown to bind FGFR4 in a beta klotho-dependent manner, efficient signaling has not previously been observed from the binding of FGF21 to FGFR4.

Binding proteins, such as anti-beta klotho antibodies, as disclosed herein can induce FGF19-like signaling, as described herein. In vivo, the mature form of FGF19 is the active form of the molecule. A nucleic acid sequence encoding full length FGF19 is provided below; the nucleotides encoding the signal sequence are underlined.

(SEQ ID NO: 187)
<u>ATGCGGAGCGGGTGTGTGGTGGTCCACGTATGGATCCTGGCCGGCCTCTG</u>

<u>GCTGGCCGTGGCCGGG</u>CGCCCCCTCGCCTTCTCGGACGCGGGGCCCCACG

TGCACTACGGCTGGGGCGACCCCATCCGCCTGCGGCACCTGTACACCTCC

GGCCCCCACGGGCTCTCCAGCT*GCTT*CCTGCGCATCCGTGCCGACGGCGT

CGTGGACTGCGCGCGGGGCCAGAGCGCGCACAGTTTGCTGGAGATCAAGG

CAGTCGCTCTGCGGACCGTGGCCATCAAGGGCGTGCACAGCGTGCGGTAC

CTCTGCATG*GCGCC*GACGGCAAGATGCAGGGGCTGCTTCAGTACTCGGA

GGAAGACTGTGCTTTCGAGGAGGAGATCCGCCCAGATGGCTACAATGTGT

ACCGATCCGAGAAGCACCGCCTCCCGGTCTCCCTGAGCAGTGCCAAACAG

CGGCAGCTGTACAAGAACAGAGGCTTTCTTCCACTCTCTCATTTCCTGCC

CATGCTGCCCATGGTCCCAGAGGAGCCTGAGGACCTCAGGGGCCACTTGG

AATCTGACATGTTCTCTTCGCCCCTGGAGACCGACAGCATGGACCCATTT

GGGCTTGTCACCGGACT*GGA*

*GGCCGTGAGGAGTCCCAGCTTTGAGAAGTAA*

The amino acid sequence of full length FGF19 is provided; the amino acids that make up the signal sequence are underlined:

(SEQ ID NO: 188)
<u>MRSGCVVVHVWILAGLWLAVAGRPLAFSDAGPH</u>V*HYG*WGDPIRLRHLYTS

GPHGLSSCFLRIRADGVVDCARGQSAHSLLEIKAVA*LRTV*AIKGVH*SVRY*

LCMGADGKMQGLLQYSEEDCAFEEEIRPDGYNVYRSEKHRLPVSLSSAKQ

RQLYKNRGFLPLSHFLPMLPMVPEEPEDLRGHLESDMFSSPLETDSMDPF

GLVTGLEAVRSPSFEK

Binding proteins, such as anti-beta klotho antibodies, as described herein can induce FGF21-like signaling, as described herein. In vivo, the mature form of FGF21 is the active form of the molecule. A nucleic acid sequence encoding a full length FGF21 is provided below; the nucleotides encoding the signal sequence are underlined:

(SEQ ID NO: 184)
<u>ATG GAC TCG GAC GAG ACC GGG TTC GAG CAC TCA GGA</u>

<u>CTG TGG GTT TCT GTG CTG GCT GGT CTT CTG CTG GGA</u>

<u>GCC TGC CAG GCA</u> CAC CCC ATC CCT GAC TCC AGT CCT

CTC CTG CAA TTC GGG GGC CAA GTC CGG CAG CGG TAC

CTC TAC ACA GAT GAT GCC CAG CAG ACA GAA GCC CAC

CTG GAG ATC AGG GAG GAT GGG ACG GTG GGG GGC GCT

GCT GAC CAG AGC CCC GAA AGT CTC CTG CAG CTG AAA

GCC TTG AAG CCG GGA GTT ATT CAA ATC TTG GGA GTC

AAG ACA TCC AGG TTC CTG TGC CAG CGG CCA GAT GGG

GCC CTG TAT GGA TCG CTC CAC TTT GAC CCT GAG GCC

TGC AGC TTC CGG GAG CTG CTT CTT GAG GAC GGA TAC

AAT GTT TAC CAG TCC GAA GCC CAC GGC CTC CCG CTG

CAC CTG CCA GGG AAC AAG TCC CCA CAC CGG GAC CCT

GCA CCC CGA GGA CCA GCT CGC TTC CTG CCA CTA CCA

GGC CTG CCC CCC GCA CCC CCG GAG CCA CCC GGA ATC

CTG GCC CCC CAG CCC CCC GAT GTG GGC TCC TCG GAC

CCT CTG AGC ATG GTG GGA CCT TCC CAG GGC CGA AGC

CCC AGC TAC GCT TCC TGA.

An amino acid sequence of a full length FGF21 is provided below; the amino acids that make up the signal sequence are underlined:

(SEQ ID NO: 183)
<u>M D S D E T G F E H S G L W V S V L A G L L L G A</u>

<u>C Q A</u> H P I P D S S P L L Q F G G Q V R Q R Y L Y

T D D A Q Q T E A H L E I R E D G T V G G A A D

Q S P E S L L Q L K A L K P G V I Q I L G V K T S

R F L C Q R P D G A L Y G S L H F D P E A C S F R

E L L L E D G Y N V Y Q S E A H G L P L H L P G N

K S P H R D P A P R G P A R F L P L P G L P P

A P P E P P G I L A P Q P P D V G S S D P L S

M V G P S Q G R S P S Y A S.

A nucleic acid sequence also encoding a full length FGF21 is provided; the nucleotides encoding the signal sequence are underlined:

(SEQ ID NO: 186)
<u>ATGGACTCGGACGAGACCGGGTTCGAGCACTCAGGACTGTGGGTTTCTGT</u>

<u>GCTGGCTGGTCTTCTGCTGGGAGCCTGCCAGGCA</u>CACCCCATCCCTGACT

CCAGTCCTCTCCTGCAATTCGGGGGCCAAGTCCGGCAGCGGTACCTCTAC

ACAGATGATGCCCAGCAGACAGAAGCCCACCTGGAGATCAGGGAGGATGG

GACGGTGGGGGGCGCTGCTGACCAGAGCCCCGAAAGTCTCCTGCAGCTGA

AAGCCTTGAAGCCGGGAGTTATTCAAATCTTGGGAGTCAAGACATCCAGG

TTCCTGTGCCAGCGGCCAGATGGGGCCCTGTATGGATCGCTCCACTTTGA

CCCTGAGGCCTGCAGCTTCCGGGAGCTGCTTCTTGAGGACGGATACAATG

TTTACCAGTCCGAAGCCCACGGCCTCCCGCTGCACCTGCCAGGGAACAAG

TCCCCACACCGGGACCCTGCACCCCGAGGACCAGCTCGCTTCCTGCCACT

ACCAGGCCTGCCCCCCGCACTCCCGGAGCCACCCGGAATCCTGGCCCCCC

AGCCCCCCGATGTGGGCTCCTCGGACCCTCTGAGCATGGTGGGACCTTCC

CAGGGCCGAAGCCCCAGCTACGCTTCCTGA.

An amino acid sequence also encoding a full length FGF21 is provided; the amino acids that make up the signal sequence are underlined:

(SEQ ID NO: 185)
MDSDETGFEHSGLWVSVLAGLLLGACQAHPIPDSSPLLQFGGQVRQRYLY

TDDAQQTEAHLEIREDGTVGGAADQSPESLLQLKALKPGVIQILGVKTSR

FLCQRPDGALYGSLHFDPEACSFRELLLEDGYNVYQSEAHGLPLHLPGNK

SPHRDPAPRGPARFLPLPGLPPALPEPPGILAPQPPDVGSSDPLSMVGPS

QGRSPSYAS

Binding proteins, such as anti-beta klotho antibodies, as described herein may bind to beta klotho alone or in complex with an FGF receptor, such as FGFR1c. An encoding nucleic acid sequence of human FGFR1c (GenBank Accession Number NM 023110; also designated FGFRαIIIc) is provided below:

(SEQ ID NO: 189)
ATGTGGAGCTGGAAGTGCCTCCTCTTCTGGGCTGTGCTGGTCACAGCCAC

ACTCTGCACCGCTAGGCCGTCCCCGACCTTGCCTGAACAAGCCCAGCCCT

GGGGAGCCCCTGTGGAAGTGGAGTCCTTCCTGGTCCACCCCGGTGACCTG

CTGCAGCTTCGCTGTCGGCTGCGGGACGATGTGCAGAGCATCAACTGGCT

GCGGGACGGGGTGCAGCTGGCGGAAAGCAACCGCACCCGCATCACAGGGG

AGGAGGTGGAGGTGCAGGACTCCGTGCCCGCAGACTCCGGCCTCTATGCT

TGCGTAACCAGCAGCCCCTCGGGCAGTGACACCACCTACTTCTCCGTCAA

TGTTTCAGATGCTCTCCCCTCCTCGGAGGATGATGATGATGATGATGACT

CCTCTTCAGAGGAGAAAGAAACAGATAACACCAAACCAAACCGTATGCCC

GTAGCTCCATATTGGACATCACCGAAAAGATGGAAAAGAAATTGCATGC

AGTGCCGGCTGCCAAGACAGTGAAGTTCAAATGCCCTTCCAGTGGGACAC

CAAACCCAACACTGCGCTGGTTGAAAAATGGCAAAGAATTCAAACCTGAC

CACAGAATTGGAGGCTACAAGGTCCGTTATGCCACCTGGAGCATCATAAT

GGACTCTGTGGTGCCCTCTGACAAGGGCAACTACACCTGCATTGTGGAGA

ATGAGTACGGCAGCATCAACCACACATACCAGCTGGATGTCGTGGAGCGG

TCCCCTCACCGGCCCATCCTGCAAGCAGGGTTGCCCGCCAACAAAACAGT

GGCCCTGGGTAGCAACGTGGAGTTCATGTGTAAGGTGTACAGTGACCCGC

AGCCGCACATCCAGTGGCTAAAGCACATCGAGGTGAATGGGAGCAAGATT

GGCCCAGACAACCTGCCTTATGTCCAGATCTTGAAGACTGCTGGAGTTAA

TACCACCGACAAAGAGATGGAGGTGCTTCACTTAAGAAATGTCTCCTTTG

AGGACGCAGGGGAGTATACGTGCTTGGCGGGTAACTCTATCGGACTCTCC

CATCACTCTGCATGGTTGACCGTTCTGGAAGCCCTGGAAGAGAGGCCGGC

AGTGATGACCTCGCCCCTGTACCTGGAGATCATCATCTATTGCACAGGGG

CCTTCCTCATCTCCTGCATGGTGGGTCGGTCATCGTCTACAAGATGAAG

AGTGGTACCAAGAAGAGTGACTTCCACAGCCAGATGGCTGTGCACAAGCT

GGCCAAGAGCATCCCTCTGCGCAGACAGGTAACAGTGTCTGCTGACTCCA

GTGCATCCATGAACTCTGGGGTTCTTCTGGTTCGGCCATCACGGCTCTCC

TCCAGTGGGACTCCCATGCTAGCAGGGGTCTCTGAGTATGAGCTTCCCGA

AGACCCTCGCTGGGAGCTGCCTCGGGACAGACTGGTCTTAGGCAAACCCC

TGGGGAGAGGGCTGCTTTGGGCAGGTGGTGTTGGCAGAGGCTATCGGGCTG

GACAAGGACAAACCCAACCGTGTGACCAAAGTGGCTGTGAAGATGTTGAA

GTCGGACGCAACAGAGAAAGACTTGTCAGACCTGATCTCAGAAATGGAGA

TGATGAAGATGATCGGGAAGCATAAGAATATCATCAACCTGCTGGGGGCC

TGCACGCAGGATGGTCCCTTGTATGTCATCGTGGAGTATGCCTCCAAGGG

CAACCTGCGGGAGTACCTGCAGGCCCGGAGGCCCCCAGGGCTGGAATACT

GCTACAACCCCAGCCACAACCCAGAGGAGCAGCTCTCCTCCAAGGACCTG

GTGTCCTGCGCCTACCAGGTGGCCCGAGGCATGGAGTATCTGGCCTCCAA

GAAGTGCATACACCGAGACCTGGCAGCCAGGAATGTCCTGGTGACAGAGG

ACAATGTGATGAAGATAGCAGACTTTGGCCTCGCACGGGACATTCACCAC

ATCGACTACTATAAAAAGACAACCAACGGCCGACTGCCTGTGAAGTGGAT

GGCACCCGAGGCATTATTTGACCGGATCTACACCCACCAGAGTGATGTGT

GGTCTTTCGGGGTGCTCCTGTGGGAGATCTTCACTCTGGGCGGCTCCCCA

TACCCCGGTGTGCCTGTGAGGAACTTTTCAAGCTGCTGAAGGAGGGTCA

CCGCATGGACAAGCCCAGTAACTGCACCAACGAGCTGTACATGATGATGC

GGGACTGCTGGCATGCAGTGCCCTCACAGAGACCCACCTTCAAGCAGCTG

GTGGAAGACCTGGACCGCATCGTGGCCTTGACCTCCAACCAGGAGTACCT

GGACCTGTCCATGCCCCTGGACCAGTACTCCCCCAGCTTTCCCGACACCC

GGAGCTCTACGTGCTCCTCAGGGGAGGATTCCGTCTTCTCTCATGAGCCG

CTGCCCGAGGAGCCCTGCCTGCCCCGACACCCAGCCCAGCTTGCCAATGG

CGGACTCAAACGCCGCTGA

The amino acid sequence of human FGFR1c (GenBank Accession Number NP 075598) (also designated FGFRαIIIC) is provided below:

(SEQ ID NO: 190)
MWSWKCLLFWAVLVTATLCTARPSPTLPEQAQPWGAPVEVESFLVHPGDL

LQLRCRLRDDVQSINWLRDGVQLAESNRTRITGEEVEVQDSVPADSGLYA

CVTSSPSGSDTTYFSVNVSDALPSSEDDDDDDDSSSEEKETDNTKPNRMP

VAPYWTSPEKMEKKLHAVPAAKTVKFKCPSSGTPNPTLRWLKNGKEFKPD

HRIGGYKVRYATWSIIMDSVVPSDKGNYTCIVENEYGSINHTYQLDVVER

SPHRPILQAGLPANKTVALGSNVEEMCKVYSDPQPHIQWLKHIEVNGSKI

GPDNLPYVQILKTAGVNTTDKEMEVLHLRNVSFEDAGEYTCLAGNSIGLS

HHSAWLTVLEALEERPAVMTSPLYLEIIIYCTGAFLISCMVGSVIVYKMK

SGTKKSDFHSQMAVHKLAKSIPLRRQVTVSADSSASMNSGVLLVRPSRLS

SSGTPMLAGVSEYELPEDPRWELPRDRLVLGKPLGEGCFGQVVLAEAIGL

DKDKPNRVTKVAVKMLKSDATEKDLSDLISEMEMMKMIGKHKNIINLLGA

CTQDGPLYVIVEYASKGNLREYLQARRPPGLEYCYNPSHNPEEQLSSKDL

VSCAYQVARGMEYLASKKCIHRDLAARNVLVTEDNVMKIADFGLARDIHH

IDYYKKTTNGRLPVKWMAPEALFDRIYTHQSDVWSFGVLLWEIFTLGGSP

-continued

YPGVPVEELFKLLKEGHRMDKPSNCTNELYMNIMRDCWHAVPSQRPTFKQ

LVEDLDRIVALTSNQEYLDLSMPLDQYSPSFPDTRSSTCSSGEDSVFSHE

PLPEEPCLPRHPAQLANGGLKRR

Binding proteins, such as anti-beta klotho antibodies, described herein may bind to beta klotho in complex with the extracellular portion of an FGF receptor such as FGFR1c. An example of an extracellular region of FGFR1c is:

(SEQ ID NO: 191)
MWSWKCLLFWAVLVTATLCTARPSPTLPEQAQPWGAPVEVESFLVHPGDL

LQLRCRLRDDVQSINWLRDGVQLAESNRTRITGEEVEVQDSVPADSGLYA

CVTSSPSGSDTTYFSVNVSDALPSSEDDDDDDDSSSEEKETDNTKPNRMP

VAPYWTSPEKMEKKLHAVPAAKTVKFKCPSSGTPNPTLRWLKNGKEFKPD

HRIGGYKVRYATWSIIMDSVVPSDKGNYTCIVENEYGSINHTYQLDVVER

SPHRPILQAGLPANKTVALGSNVEFMCKVYSDPQPHIQWLKHIEVNGSKI

GPDNLPYVQILKTAGVNTTDKEMEVLHLRNVSFEDAGEYTCLAGNSIGLS

HHSAWLTVLEALEERPAVMTSPLY

An example of an extracellular region of FGFR1c (αIIIc) is:

(SEQ ID NO: 192)
RPSPTLPEQAQPWGAPVEVESFLVHPGDLLQLRCRLRDDVQSINWLRDGV

QLAESNRTRITGEEVEVQDSVPADSGLYACVTSSPSGSDTTYFSVNVSDA

LPSSEDDDDDDDSSSEEKETDNTKPNRMPVAPYWTSPEKMEKKLHAVPAA

KTVKFKCPSSGTPNPTLRWLKNGKEFKPDHRIGGYKVRYATWSIIMDSVV

PSDKGNYTCIVENEYGSINHTYQLDVVERSPHRPILQAGLPANKTVALGS

NVEFMCKVYSDPQPHIQWLKHIEVNGSKIGPDNLPYVQILKTAGVNTTDK

EMEVLHLRNVSFEDAGEYTCLAGNSIGLSHHSAWLTVLEALEERPAVMTS

PLYE

An example of an extracellular region of FGFR1c (βIIIc) is:

(SEQ ID NO: 193)
RPSPTLPEQDALPSSEDDDDDDDSSSEEKETDNTKPNPVAPYWTSPEKME

KKLHAVPAAKTVKFKCPSSGTPNPTLRWLKNGKEFKPDHRIGGYKVRYAT

WSIIMDSVVPSDKGNYTCIVENEYGSINHTYQLDVVERSPHRPILQAGLP

ANKTVALGSNVEFMCKVYSDPQPHIQWLKHIEVNGSKIGPDNLPYVQILK

TAGVNTTDKEMEVLHLRNVSFEDAGEYTCLAGNSIGLSHHSAWLTVLEAL

EERPAVMTSPLYLE.

As described herein, FGFR1c proteins may also include fragments. As used herein, the terms are used interchangeably to mean a receptor, in particular and unless otherwise specified, a human receptor, that upon association with beta klotho and FGF19 or FGF21 induces FGF19-like or FGF21-like signaling activity.

The term FGFR1c also includes post-translational modifications of the FGFR1c amino acid sequence, for example, possible N-linked glycosylation sites. Thus, the antigen binding proteins may bind to or be generated from proteins glycosylated at one or more of the positions.

Binding proteins, such as anti-beta klotho antibodies, as described herein may bind to beta klotho alone or in complex with an FGF receptor, such as FGFR2c. An encoding nucleic acid sequence of human FGFR2c is provided below:

(SEQ ID NO: 194)
ATGGTCAGCTGGGGTCGTTTCATCTGCCTGGTCGTGGTCACCATGGCAAC

CTTGTCCCTGGCCCGGCCCTCCTTCAGTTTAGTTGAGGATACCACATTAG

AGCCAGAAGAGCCACCAACCAAATACCAAATCTCTCAACCAGAAGTGTAC

GTGGCTGCGCCAGGGGAGTCGCTAGAGGTGCGCTGCCTGTTGAAAGATGC

CGCCGTGATCAGTTGGACTAAGGATGGGGTGCACTTGGGGCCCAACAATA

GGACAGTGCTTATTGGGGAGTACTTGCAGATAAAGGGCGCCACGCCTAGA

GACTCCGGCCTCTATGCTTGTACTGCCAGTAGGACTGTAGACAGTGAAAC

TTGGTACTTCATGGTGAATGTCACAGATGCCATCTCATCCGGAGATGATG

AGGATGACACCGATGGTGCGGAAGATTTTGTCAGTGAGAACAGTAACAAC

AAGAGAGCACCATACTGGACCAACACAGAAAAGATGGAAAAGCGGCTCCA

TGCTGTGCCTGCGGCCAACACTGTCAAGTTTCGCTGCCCAGCCGGGGGGA

ACCCAATGCCAACCATGCGGTGGCTGAAAAACGGGAAGGAGTTTAAGCAG

GAGCATCGCATTGGAGGCTACAAGGTACGAAACCAGCACTGGAGCCTCAT

TATGGAAAGTGTGGTCCCATCTGACAAGGGAAATTATACCTGTGTAGTGG

AGAATGAATACGGGTCCATCAATCACACGTACCACCTGGATGTTGTGGAG

CGATCGCCTCACCGGCCCATCCTCCAAGCCGGACTGCCGGCAAATGCCTC

CACAGTGGTCGGAGGAGACGTAGAGTTTGTCTGCAAGGTTTACAGTGATG

CCCAGCCCCACATCCAGTGGATCAAGCACGTGGAAAAGAACGGCAGTAAA

TACGGGCCCGACGGGCTGCCCTACCTCAAGGTTCTCAAGGCCGCCGGTGT

TAACACCACGGACAAAGAGATTGAGGTTCTCTATATTCGGAATGTAACTT

TTGAGGACGCTGGGGAATATACGTGCTTGGCGGGTAATTCTATTGGGATA

TCCTTTCACTCTGCATGGTTGACAGTTCTGCCAGCGCCTGGAAGAGAAAA

GGAGATTACAGCTTCCCCAGACTACCTGGAGATAGCCATTTACTGCATAG

GGGTCTTCTTAATCGCCTGTATGGTGGTAACAGTCATCCTGTGCCGAATG

AAGAACACGACCAAGAAGCCAGACTTCAGCAGCCAGCCGGCTGTGCACAA

GCTGACCAAACGTATCCCCCTGCGGAGACAGGTAACAGTTTCGGCTGAGT

CCAGCTCCTCCATGAACTCCAACACCCCGCTGGTGAGGATAACAACACGC

CTCTCTTCAACGGCAGACACCCCCATGCTGGCAGGGGTCTCCGAGTATGA

ACTTCCAGAGGACCCAAAATGGGAGTTTCCAAGAGATAAGCTGACACTGG

GCAAGCCCCTGGGAGAAGGTTGCTTTGGGCAAGTGGTCATGGCGGAAGCA

GTGGGAATTGACAAAGACAAGCCCAAGGAGGCGGTCACCGTGGCCGTGAA

GATGTTGAAAGATGATGCCACAGAGAAAGACCTTTCTGATCTGGTGTCAG

AGATGGAGATGATGAAGATGATTGGGAAACACAAGAATATCATAAATCTT

CTTGGAGCCTGCACACAGGATGGGCCTCTCTATGTCATAGTTGAGTATGC

CTCTAAAGGCAACCTCCGAGAATACCTCCGAGCCCGGAGGCCACCCGGGA

-continued

```
TGGAGTACTCCTATGACATTAACCGTGTTCCTGAGGAGCAGATGACCTTC

AAGGACTTGGTGTCATGCACCTACCAGCTGGCCAGAGGCATGGAGTACTT

GGCTTCCCAAAAATGTATTCATCGAGATTTAGCAGCCAGAAATGTTTTGG

TAACAGAAAACAATGTGATGAAAATAGCAGACTTTGGACTCGCCAGAGAT

ATCAACAATATAGACTATTACAAAAAGACCACCAATGGGCGGCTTCCAGT

CAAGTGGATGGCTCCAGAAGCCCTGTTTGATAGAGTATACACTCATCAGA

GTGATGTCTGGTCCTTCGGGGTGTTAATGTGGGAGATCTTCACTTTAGGG

GGCTCGCCCTACCCAGGGATTCCCGTGGAGGAACTTTTTAAGCTGCTGAA

GGAAGGACACAGAATGGATAAGCCAGCCAACTGCACCAACGAACTGTACA

TGATGATGAGGGACTGTTGGCATGCAGTGCCCTCCCAGAGACCAACGTTC

AAGCAGTTGGTAGAAGACTTGGATCGAATTCTCACTCTCACAACCAATGA

GGAATACTTGGACCTCAGCCAACCTCTCGAACAGTATTCACCTAGTTACC

CTGACACAAGAAGTTCTTGTTCTTCAGGAGATGATTCTGTTTTTTCTCCA

GACCCCATGCCTTACGAACCATGCCTTCCTCAGTATCCACACATAAACGG

CAGTGTTAAAACATGA
```

The amino acid sequence of human FGFR2c is provided below; the amino acids that make up the signal sequence are underlined:

(SEQ ID NO: 195)
<u>MVSWGRFICLWVTMATLSLA</u>RPSFSLVEDTTLEPEEPPTKYQISQPEVYV

AAPGESLEVRCLLKDAAVISWTKDGVHLGPNNRTVLIGEYLQIKGATPRD

SGLYACTASRTVDSETWYFMVNVTDAISSGDDEDDTDGAEDFVSENSNNK

RAPYWTNTEKMEKRLHAVPAANTVKFRCPAGGNPMPTMRWLKNGKEFKQE

HRIGGYKVRNQHWSLIMESVVPSDKGNYTCVVENEYGSINHTYHLDVVER

SPHRPILQAGLPANASTVVGGDVEFVCKVYSDAQPHIQWIKHVEKNGSKY

GPDGLPYLKVLKAAGVNTTDKEIEVLYIRNVTFEDAGEYTCLAGNSIGIS

FHSAWLTVLPAPGREKEITASPDYLEIAIYCIGVFLIACMVVTVILCRMK

NTTKKPDFSSQPAVHKLTKRIPLRRQVTVSAESSSSMNSNTPLVRITTRL

SSTADTPMLAGVSEYELPEDPKWEFPRDKLTLGKPLGEGCFGQVVMAEAV

GIDKDKPKEAVTVAVKMLKDDATEKDLSDLVSEMEMMKMIGKHKNIINLL

GACTQDGPLYVIVEYASKGNLREYLRARRPPGMEYSYDINRVPEEQMTFK

DLVSCTYQLARGMEYLASQKCIHRDLAARNVLVTENNVMKIADFGLARDI

NNIDYYKKTTNGRLPVKWMAPEALFDRVYTHQSDVWSFGVLMWEIFTLGG

SPYPGIPVEELFKLLKEGHRMDKPANCTNELYMMMRDCWHAVPSQRPTFK

QLVEDLDRILTLTTNEEYLDLSQPLEQYSPSYPDTRSSCSSGDDSVFSPD

PMPYEPCLPQYPHINGSVKT

Binding proteins, such as anti-beta klotho antibodies, as described herein may bind to beta klotho alone or in complex with an FGF receptor, such as FGFR3c. An encoding nucleic acid sequence of human FGFR3c (GenBank Accession Number NP 000133) is provided below:

(SEQ ID NO: 196)
```
ATGGGCGCCCCTGCCTGCGCCCTCGCGCTCTGCGTGGCCGTGGCCATCGT

GGCCGGCGCCTCCTCGGAGTCCTTGGGGACGGAGCAGCGCGTCGTGGGC

GAGCGGCAGAAGTCCCGGGCCCAGAGCCCGGCCAGCAGGAGCAGTTGGTC

TTCGGCAGCGGGGATGCTGTGGAGCTGAGCTGTCCCCCGCCCGGGGGTGG

TCCCATGGGGCCCACTGTCTGGGTCAAGGATGGCACAGGGCTGGTGCCCT

CGGAGCGTGTCCTGGTGGGGCCCCAGCGGCTGCAGGTGCTGAATGCCTCC

CACGAGGACTCCGGGGCCTACAGCTGCCGGCAGCGGCTCACGCAGCGCGT

ACTGTGCCACTTCAGTGTGCGGGTGACAGACGCTCCATCCTCGGGAGATG

ACGAAGACGGGGAGGACGAGGCTGAGGACACAGGTGTGGACACAGGGGCC

CCTTACTGGACACGGCCCGAGCGGATGGACAAGAAGCTGCTGGCCGTGCC

GGCCGCCAACACCGTCCGCTTCCGCTGCCCAGCCGCTGGCAACCCCACTC

CCTCCATCTCCTGGCTGAAGAACGGCAGGGAGTTCCGCGGCGAGCACCGC

ATTGGAGGCATCAAGCTGCGGCATCAGCAGTGGAGCCTGGTCATGGAAAG

CGTGGTGCCCTCGGACCGCGGCAACTACACCTGCGTCGTGGAGAACAAGT

TTGGCAGCATCCGGCAGACGTACACGCTGGACGTGCTGGAGCGCTCCCCG

CACCGGCCCATCCTGCAGGCGGGGCTGCCGGCCAACCAGACGGCGGTGCT

GGGCAGCGACGTGGAGTTCCACTGCAAGGTGTACAGTGACGCACAGCCCC

ACATCCAGTGGCTCAAGCACGTGGAGGTGAATGGCAGCAAGGTGGGCCCG

GACGGCACACCCTACGTTACCGTGCTCAAGACGGCGGGCGCTAACACCAC

CGACAAGGAGCTAGAGGTTCTCTCCTTGCACAACGTCACCTTTGAGGACG

CCGGGGAGTACACCTGCCTGGCGGGCAATTCTATTGGGTTTTCTCATCAC

TCTGCGTGGCTGGTGGTGCTGCCAGCCGAGGAGGAGCTGGTGGAGGCTGA

CGAGGCGGGCAGTGTGTATGCAGGCATCCTCAGCTACGGGGTGGGCTTCT

TCCTGTTCATCCTGGTGGTGGCGGCTGTGACGCTCTGCCGCCTGCGCAGC

CCCCCCAAGAAAGGCCTGGGCTCCCCCACCGTGCACAAGATCTCCCGCTT

CCCGCTCAAGCGACAGGTGTCCCTGGAGTCCAACGCGTCCATGAGCTCCA

ACACACCACTGGTGCGCATCGCAAGGCTGTCCTCAGGGGAGGGCCCCACG

CTGGCCAATGTCTCCGAGCTCGAGCTGCCTGCCGACCCCAAATGGGAGCT

GTCTCGGGCCCGGCTGACCCTGGGCAAGCCCCTTGGGAGGGCTGCTTCG

GCCAGGTGGTCATGGCGGAGGCCATCGGCATTGACAAGGACCGGGCCGCC

AAGCCTGTCACCGTAGCCGTGAAGATGCTGAAAGACGATGCCACTGACAA

GGACCTGTCGGACCTGGTGTCTGAGATGGAGATGATGAAGATGATCGGGA

AACACAAAAACATCATCAACCTGCTGGGCGCCTGCACGCAGGGCGGGCCC

CTGTACGTGCTGGTGGAGTACGCGGCCAAGGGTAACCTGCGGGAGTTTCT

GCGGGCGCGGCGGCCCCCGGGCCTGGACTACTCCTTCGACACCTGCAAGC

CGCCCGAGGAGCAGCTCACCTTCAAGGACCTGGTGTCCTGTGCCTACCAG

GTGGCCCGGGGCATGGAGTACTTGGCCTCCCAGAAGTGCATCCACAGGGA

CCTGGCTGCCCGCAATGTGCTGGTGACCGAGGACAACGTGATGAAGATCG

CAGACTTCGGGCTGGCCCGGGACGTGCACAACCTCGACTACTACAAGAAG

ACAACCAACGGCCGGCTGCCCGTGAAGTGGATGGCGCCTGAGGCCTTGTT
```

```
TGACCGAGTCTACACTCACCAGAGTGACGTCTGGTCCTTTGGGGTCCTGC

TCTGGGAGATCTTCACGCTGGGGGGCTCCCCGTACCCCGGCATCCCTGTG

GAGGAGCTCTTCAAGCTGCTGAAGGAGGGCCACCGCATGGACAAGCCCGC

CAACTGCACACACGACCTGTACATGATCATGCGGGAGTGCTGGCATGCCG

CGCCCTCCCAGAGGCCCACCTTCAAGCAGCTGGTGGAGGACCTGGACCGT

GTCCTTACCGTGACGTCCACCGACGAGTACCTGGACCTGTCGGCGCCTTT

CGAGCAGTACTCCCCGGGTGGCCAGGACACCCCCAGCTCCAGCTCCTCAG

GGGACGACTCCGTGTTTGCCCACGACCTGCTGCCCCCGGCCCCACCCAGC

AGTGGGGGCTCGCGGACGTGA
```

The amino acid sequences of human FGFR3c is provided below; the amino acids that make up the signal sequence are underlined:

```
                                        (SEQ ID NO: 197)
MGAPACALALCVAVAIVAGASSESLGTEQRVVGRAAEVPGPEPGQQEQLV

FGSGDAVELSCPPPGGGPMGPTVWVKDGTGLVPSERVLVGPQRLQVLNAS

HEDSGAYSCRQRLTQRVLCHFSVRVTDAPSSGDDEDGEDEAEDTGVDTGA

PYWTRPERMDKKLLAVPAANTVRFRCPAAGNPTPSISWLKNGREFRGEHR

IGGIKLRHQQWSLVMESVVPSDRGNYTCVVENKFGSIRQTYTLDVLERSP

HRPILQAGLPANQTAVLGSDVEFHCKVYSDAQPHIQWLKHVEVNGSKVGP

DGTPYVTVLKTAGANTTDKELEVLSLHNVTFEDAGEYTCLAGNSIGFSHH

SAWLVVLPAEEELVEADEAGSVYAGILSYGVGFFLFILVVAAVTLCRLRS

PPKKGLGSPTVHKISRFPLKRQVSLESNASMSSNTPLVRIARLSSGEGPT

LANVSELELPADPKWELSRARLTLGKPLGEGCFGQVVMAEAIGIDKDRAA

KPVTVAVKMLKDDATDKDLSDLVSEMEMMKMIGKHKNIINLLGACTQGGP

LYVLVEYAAKGNLREFLRARRPPGLDYSFDTCKPPEEQLTFKDLVSCAYQ

VARGMEYLASQKCIHRDLAARNVLVTEDNVMKIADFGLARDVHNLDYYKK

TTNGRLPVKWMAPEALFDRVYTHQSDVWSFGVLLWEIFTLGGSPYPGIPV

EELFKLLKEGHRMDKPANCTHDLYMIMRECWHAAPSQRPTFKQLVEDLDR

VLTVTSTDEYLDLSAPFEQYSPGGQDTPSSSSSGDDSVFAHDLLPPAPPS

SGGSRT
```

Binding proteins, such as anti-beta klotho antibodies, as described herein may bind to beta klotho alone or in complex with an FGF receptor, such as FGFR4. An encoding nuclic acid sequence of human FGFR4 is provided below:

```
                                        (SEQ ID NO: 198)
ATGCGGCTGCTGCTGGCCCTGTTGGGGGTCCTGCTGAGTGTGCCTGGGCC

TCCAGTCTTGTCCCTGGAGGCCTCTGAGGAAGTGGAGCTTGAGCCCTGCC

TGGCTCCCAGCCTGGAGCAGCAAGAGCAGGAGCTGACAGTAGCCCTTGGG

CAGCCTGTGCGTCTGTGCTGTGGGCGGCTGAGCGTGGTGGCCACTGGTA

CAAGGAGGGCAGTCGCCTGGCACCTGCTGGCCGTGTACGGGGCTGGAGGG

GCCGCCTAGAGATTGCCAGCTTCCTACCTGAGGATGCTGGCCGCTACCTC

TGCCTGGCACGAGGCTCCATGATCGTCCTGCAGAATCTCACCTTGATTAC

AGGTGACTCCTTGACCTCCAGCAACGATGATGAGGACCCCAAGTCCCATA

GGGACCCCTCGAATAGGCACAGTTACCCCCAGCAAGCACCCTACTGGACA

CACCCCCAGCGCATGGAGAAGAAACTGCATGCAGTACCTGCGGGGAACAC

CGTCAAGTTCCGCTGTCCAGCTGCAGGCAACCCCACGCCCACCATCCGCT

GGCTTAAGGATGGACAGGCCTTTCATGGGGAGAACCGCATTGGAGGCATT

CGGCTGCGCCATCAGCACTGGAGTCTCGTGATGGAGAGCGTGGTGCCCTC

GGACCGCGGCACATACACCTGCCTGGTAGAGAACGCTGTGGGCAGCATCC

GCTATAACTACCTGCTAGATGTGCTGGAGCGGTCCCCGCACCGGCCCATC

CTGCAGGCCGGGCTCCCGGCCAACACCACAGCCGTGGTGGGCAGCGACGT

GGAGCTGCTGTGCAAGGTGTACAGCGATGCCCAGCCCCACATCCAGTGGC

TGAAGCACATCGTCATCAACGGCAGCAGCTTCGGAGCCGACGGTTTCCCC

TATGTGCAAGTCCTAAAGACTGCAGACATCAATAGCTCAGAGGTGGAGGT

CCTGTACCTGCGGAACGTGTCAGCCGAGGACGCAGGCGAGTACACCTGCC

TCGCAGGCAATTCCATCGGCCTCTCCTACCAGTCTGCCTGGCTCACGGTG

CTGCCAGAGGAGGACCCCACATGGACCGCAGCAGCGCCCGAGGCCAGGTA

TACGGACATCATCCTGTACGCGTCGGGCTCCCTGGCCTTGGCTGTGCTCC

TGCTGCTGGCCGGGCTGTATCGAGGGCAGGCGCTCCACGGCCGGCACCCC

CGCCCGCCCGCCACTGTGCAGAAGCTCTCCCGCTTCCCTCTGGCCCGACA

GTTCTCCCTGGAGTCAGGCTCTTCCGGCAAGTCAAGCTCATCCCTGGTAC

GAGGCGTGCGTCTCTCCTCCAGCGGCCCCGCCTTGCTCGCCGGCCTCGTG

AGTCTAGATCTACCTCTCGACCCACTATGGGAGTTCCCCGGGACAGGCT

GGTGCTTGGGAAGCCCCTAGGCGAGGGCTGCTTTGGCCAGGTAGTACGTG

CAGAGGCCTTTGGCATGGACCCTGCCCGGCCTGACCAAGCCAGCACTGTG

GCCGTCAAGATGCTCAAAGACAACGCCTCTGACAAGGACCTGGCCGACCT

GGTCTCGGAGATGGAGGTGATGAAGCTGATCGGCCGACACAAGAACATCA

TCAACCTGCTTGGTGTCTGCACCCAGGAAGGGCCCCTGTACGTGATCGTG

GAGTGCGCCGCCAAGGGAAACCTGCGGGAGTTCCTGCGGGCCCGGCGCCC

CCCAGGCCCCGACCTCAGCCCCGACGGTCCTCGGAGCAGTGAGGGGCCGC

TCTCCTTCCCAGTCCTGGTCTCCTGCGCCTACCAGGTGGCCCGAGGCATG

CAGTATCTGGAGTCCCGGAAGTGTATCCACCGGGACCTGGCTGCCCGCAA

TGTGCTGGTGACTGAGGACAATGTGATGAAGATTGCTGACTTTGGCTGG

CCCGCGGCGTCCACCACATTGACTACTATAAGAAAACCAGCAACGGCCGC

CTGCCTGTGAAGTGGATGGCGCCCGAGGCCTTGTTTGACCGGGTGTACAC

ACACCAGAGTGACGTGTGGTCTTTTGGGATCCTGCTATGGGAGATCTTCA

CCCTCGGGGGCTCCCCGTATCCTGGCATCCCGGTGGAGGAGCTGTTCTCG

CTGCTGCGGGAGGGACATCGGATGGAACCGACCCCCACACTGCCCCCAGA

GCTGTACGGGCTGATGCGTGAGTGCTGGCACGCAGCGCCCTCCCAGAGGC

CTACCTTCAAGCAGCTGGTGGAGGCGCTGGACAAGGTCCTGCTGGCCGTC

TCTGAGGAGTACCTCGACCTCCGCCTGACCTTCGGACCCTATTCCCCCTC
```

-continued

```
TGGTGGGGACGCCAGCAGCACCTGCTCCTCCAGCGATTCTGTCTTCAGCC

ACGACCCCTGCCATTGGGATCCAGCTCCTTCCCCTTCGGGTCTGGGGTG

CAGACATGA
```

The amino acid sequence of human FGFR4 (GenBank Accession Number NP_002002.3) is provided below; the amino acids that make up the signal sequence are underlined:

(SEQ ID NO: 199)
MRLLLALLGVLLSVPGPPVLSLEASEEVELEPCLAPSLEQQEQELTVALG

QPVRLCCGRAERGGHWYKEGSRLAPAGRVRGWRGRLEIASFLPEDAGRYL

CLARGSMIVLQNLTLITGDSLTSSNDDEDPKSHRDPSNRHSYPQQAPYWT

HPQRMEKKLHAVPAGNTVKFRCPAAGNPTPTIRWLKDGQAFHGENRIGGI

RLRHQHWSLVMESVVPSDRGTYTCLVENAVGSIRYNYLLDVLERSPHRPI

LQAGLPANTTAVVGSDVELLCKVYSDAQPHIQWLKHIVINGSSFGADGFP

YVQVLKTADINSSEVEVLYLRNVSAEDAGEYTCLAGNSIGLSYQSAWLTV

LPEEDPTWTAAAPEARYTDIILYASGSLALAVLLLLAGLYRGQALHGRHP

RPPATVQKLSRFPLARQFSLESGSSGKSSSSLVRGVRLSSSGPALLAGLV

SLDLPLDPLWEFPRDRLVLGKPLGEGCFGQVVRAEAFGMDPARPDQASTV

AVKMLKDNASDKDLADLVSEMEVMKLIGRHKNIINLLGVCTQEGPLYVIV

ECAAKGNLREFLRARRPPGPDLSPDGPRSSEGPLSFPVLVSCAYQVARGM

QYLESRKCIHRDLAARNVLVTEDNVMKIADFGLARGVHHIDYYKKTSNGR

LPVKWMAPEALFDRVYTHQSDVWSFGILLWEIFTLGGSPYPGIPVEELFS

LLREGHRMDRPPHCPPELYGLMRECWHAAPSQRPTFKQLVEALDKVLLAV

SEEYLDLRLTFGPYSPSGGDASSTCSSSDSVFSHDPLPLGSSSFPFGSGV

QT

An "antigen" is a predetermined antigen to which an antibody can selectively bind. A target antigen may be a polypeptide, carbohydrate, nucleic acid, lipid, hapten or other naturally occurring or synthetic compound. Preferably, the target antigen is a polypeptide.

The term "antigen binding fragment," "antigen binding domain," "antigen binding region," and similar terms refer to that portion of an antibody which comprises the amino acid residues that interact with an antigen and confer on the binding agent its specificity and affinity for the antigen (e.g., the complementarity determining regions (CDRs)).

The terms "binds" or "binding" refer to an interaction (e.g., covalent or non-covalent) between molecules including, for example, to form a complex. A complex can also include the binding of two or more molecules held together by covalent or non-covalent bonds, interactions or forces. Interactions can be, for example, non-covalent interactions including hydrogen bonds, ionic bonds, hydrophobic interactions, and/or van der Waals interactions. The strength of the total non-covalent interactions between a single antigen-binding site on an antibody and a single epitope of a target molecule, such as beta klotho, is the affinity of the antibody or functional fragment for that epitope. The ratio of association (k1) to dissociation (k-1) of an antibody to a monovalent antigen (k1/k-1) is the association constant K, which is a measure of affinity. The value of K varies for different complexes of antibody and antigen and depends on both k1 and k-1. The association constant K for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent beta klotho, come in contact with antibodies containing multiple binding sites, the interaction of antibody with antigen at one site will increase the probability of a reaction at a second site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The terms "antibodies that specifically bind to beta klotho," "antibodies that specifically bind to a beta klotho epitope," and analogous terms are also used interchangeably herein and refer to antibodies that specifically bind to a beta klotho polypeptide, such as a beta klotho antigen, or fragment, or epitope (e.g., human beta klotho such as a human beta klotho polypeptide, antigen or epitope). An antibody that specifically binds to beta klotho, (e.g., human beta klotho) may bind to the extracellular domain or peptide derived from the extracellular domain of beta klotho beta klotho. An antibody that specifically binds to a beta klotho antigen (e.g., human beta klotho) may be cross-reactive with related antigens (e.g., cyno beta klotho). In certain embodiments, an antibody that specifically binds to a beta klotho antigen does not cross-react with other antigens. An antibody that specifically binds to a beta klotho antigen can be identified, for example, by immunoassays, Biacore, or other techniques known to those of skill in the art. An antibody binds specifically to a beta klotho antigen when it binds to a beta klotho antigen with higher affinity than to any cross reactive antigen as determined using experimental techniques, such as radioimmunoassays (RIA) and enzyme linked immunosorbent assays (ELISAs). Typically a specific or selective reaction will be at least twice background signal or noise and may be more than 10 times background. See, e.g., Paul, ed., 1989, *Fundamental Immunology Second Edition*, Raven Press, New York at pages 332 336 for a discussion regarding antibody specificity. An antibody "which binds" an antigen of interest (e.g., a target antigen such as beta klotho) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein, for example, as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-19}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope. In certain embodiments, an antibody that binds to beta klotho has a dissociation constant (Kd) of less than or equal to 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. The lower the $K_D$, the higher the affinity of the anti-beta klotho antibody. In certain embodiments, anti-beta klotho antibody binds to an epitope of beta klotho that is conserved among beta klotho from different species (e.g., between human and cyno beta klotho).

The term "compete" when used in the context of anti-beta klotho antibodies (e.g., agonistic antibodies and binding proteins that bind to (i) beta klotho; or (ii) a complex comprising beta klotho and one of FGFR1c, FGFR2c, FGFR3c, and FGFR4) that bind to or compete for the same epitope or binding site on a target means competition between as determined by an assay in which the antibody (or binding fragment) thereof under study prevents or inhibits the specific binding of a reference molecule (e.g., a reference ligand, or reference antigen binding protein, such as a reference antibody) to a common antigen (e.g., beta klotho or a fragment thereof). Numerous types of competitive binding assays can be used to determine if a test antibody competes with a reference antibody for binding to beta klotho (e.g., human beta klotho). Examples of assays that can be employed include solid phase direct or indirect radioimmunoassay (RIA), solid phase direct or indirect enzyme immunoassay (EIA), sandwich competition assay (see, e.g., Stahli et al., (1983) Methods in Enzymology 9:242-253); solid phase direct biotin-avidin EIA (see, e.g., Kirkland et al., (1986) J. Immunol. 137:3614-3619) solid phase direct labeled assay, solid phase direct labeled sandwich assay (see, e.g., Harlow and Lane, (1988) Antibodies, A Laboratory Manual, Cold Spring Harbor Press); solid phase direct label RIA using 1-125 label (see, e.g., Morel et al., (1988) Molec. Immunol. 25:7-15); solid phase direct biotin-avidin EIA (see, e.g., Cheung, et al., (1990) Virology 176:546-552); and direct labeled RIA (Moldenhauer et al., (1990) Scand. J. Immunol. 32:77-82). Typically, such an assay involves the use of a purified antigen (e.g., beta klotho such as human beta klotho) bound to a solid surface or cells bearing either of an unlabelled test antigen binding protein (e.g., test anti-beta klotho antibody) or a labeled reference antigen binding protein (e.g., reference anti-beta klotho antibody). Competitive inhibition may be measured by determining the amount of label bound to the solid surface or cells in the presence of the test antigen binding protein. Usually the test antigen binding protein is present in excess. Antibodies identified by competition assay (competing antibodies) include antibodies binding to the same epitope as the reference antibody and/or antibodies binding to an adjacent epitope sufficiently proximal to the epitope bound by the reference for antibodies steric hindrance to occur. Additional details regarding methods for determining competitive binding and/or binding to the same epitope are described herein. Usually, when a competing antibodies protein is present in excess, it will inhibit specific binding of a reference antibodies to a common antigen by at least 23%, for example 40%, 45%, 50%, 55%, 60%, 65%, 70% or 75%. In some instance, binding is inhibited by at least 80%, 85%, 90%, 95%, 96% or 97%, 98%, 99% or more.

The term "anti-beta klotho antibody" or "an antibody that binds to beta klotho" includes an antibody that is capable of binding beta klotho with sufficient affinity such that the antibody is useful as a diagnostic and/or therapeutic agent in targeting beta klotho. Preferably, the extent of binding of an anti-beta klotho antibody to an unrelated, non-beta klotho protein is less than about 10% of the binding of the antibody to beta klotho as measured, for example, by fluorescence activated cell sorting (FACS) analysis or an immunoassay such as a radioimmunoassay (RIA). An antibody that "specifically binds to" or is "specific for" beta klotho is Illustrated above. In certain embodiments, an antibody that binds to beta klotho, as described herein has a dissociation constant (Kd) of less than or equal to 10 nM, 9 nM, 8 nM, 7 nM, 6 nM, 5 nM, 4 nM, 0.9 nM, 0.8 nM, 0.7 nM, 0.6 nM, 0.5 nM, 0.4 nM, 0.3 nM, 0.2 nM, or 0.1 nM, and/or is greater than or equal to 0.1 nM. In certain embodiments, anti-beta klotho antibody binds to an epitope of beta klotho that is conserved among beta klotho from different species (e.g., between human and cyno beta klotho).

An "isolated" antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 25%, 20%, 15%, 10%, 5%, or 1% (by dry weight) of heterologous protein (also referred to herein as a "contaminating protein"). In certain embodiments, when the antibody is recombinantly produced, it is substantially free of culture medium, e.g., culture medium represents less than about 20%, 15%, 10%, 5%, or 1% of the volume of the protein preparation. In certain embodiments, when the antibody is produced by chemical synthesis, it is substantially free of chemical precursors or other chemicals, for example, it is separated from chemical precursors or other chemicals which are involved in the synthesis of the protein. Accordingly such preparations of the antibody have less than about 30%, 25%, 20%, 15%, 10%, 5%, or 1% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al. J. Bio. Chem. 193: 265-275, 1951), such as 96%, 97%, 98%, or 99%, by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step. In specific embodiments, antibodies provided herein are isolated.

A 4-chain antibody unit is a heterotetrameric glycoprotein composed of two identical light (L) chains and two identical heavy (H) chains. In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The term "variable region" or "variable domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases forming part of, the β sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, Md., 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. The variability in sequence is concentrated in the CDRs while the less variable portions in the variable region are referred to as framework regions (FR). The CDRs of the light and heavy chains are primarily responsible for the interaction of the antibody with antigen. In specific embodiments, the variable region is a human variable region.

The term "variable region residue numbering as in Kabat" or "amino acid position numbering as in Kabat", and variations thereof, refers to the numbering system used for heavy chain variable regions or light chain variable regions of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc, according to Kabat) after heavy chain FR residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, including, for example, by AbM, Chothia, Contact, IMGT and AHon. Various numbering systems are illustrated in FIGS. 1-5 (e.g., FIGS. 1 and 2).

An "intact" antibody is one comprising an antigen-binding site as well as a light chain constant region CL and at least heavy chain constant regions, CH1, CH2 and CH3. The constant regions may include human constant regions or amino acid sequence variants thereof. Preferably, an intact antibody has one or more effector functions.

"Antibody fragments" comprise a portion of an intact antibody, preferably the antigen binding or variable region of the intact antibody. Examples of antibody fragments include, without limitation, Fab, Fab', F(ab')2, and Fv fragments; diabodies and di-diabodies (see, e.g., Holliger, P. et al., (1993) Proc. Natl. Acad. Sci. 90:6444-8; Lu, D. et al., (2005) J. Biol. Chem. 280:19665-72; Hudson et al., Nat. Med. 9:129-134 (2003); WO 93/11161; and U.S. Pat. Nos. 5,837,242 and 6,492,123); single-chain antibody molecules (see, e.g., U.S. Pat. Nos. 4,946,778; 5,260,203; 5,482,858 and 5,476,786); dual variable domain antibodies (see, e.g., U.S. Pat. No. 7,612,181); single variable domain antibodies (SdAbs) (see, e.g., Woolven et al., Immunogenetics 50: 98-101, 1999; Streltsov et al., Proc Natl Acad Sci USA. 101:12444-12449, 2004); and multispecific antibodies formed from antibody fragments.

A "functional fragment" or "binding fragment" or "antigen binding fragment" of a therapeutic antibody will exhibit at least one if not some or all of the biological functions attributed to the intact antibody, the function comprising at least binding to the target antigen, (e.g., a beta klotho binding fragment or fragment that binds to beta klotho).

The term "fusion protein" as used herein refers to a polypeptide that comprises an amino acid sequence of an antibody and an amino acid sequence of a heterologous polypeptide or protein (e.g., a polypeptide or protein not normally a part of the antibody (e.g., a non-anti-beta klotho antigen binding antibody)). The term "fusion" when used in relation to beta klotho or to an anti-beta klotho antibody refers to the joining of a peptide or polypeptide, or fragment, variant and/or derivative thereof, with a heterologous peptide or polypeptide. In certain embodiments, the fusion protein retains the biological activity of the beta klotho or anti-beta klotho antibody. In certain embodiments, the fusion protein comprises a beta klotho antibody VH region, VL region, VH CDR (one, two or three VH CDRs), and/or VL CDR (one, two or three VL CDRs), wherein the fusion protein binds to a beta klotho epitope, a beta klotho fragment and/or a beta klotho polypeptide.

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region (e.g., CH1, CH2, CH3, CH4). The constant region can be one of five distinct types, (e.g., isotypes) referred to as alpha (α), delta (δ), epsilon (ε), gamma (γ) and mu (μ), based on the amino acid sequence of the heavy chain constant regions. The distinct heavy chains differ in size: α, δ and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG and IgM, respectively, including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "monoclonal antibody" as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell, wherein the antibody binds to only a beta klotho epitope as determined, for example, by ELISA or other antigen-binding or competitive binding assay known in the art. The term "monoclonal" is not limited to any particular method for making the antibody. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York). Exemplary methods of producing monoclonal antibodies are provided in the Examples herein.

The term "native" when used in connection with biological materials such as nucleic acid molecules, polypeptides, host cells, and the like, refers to those which are found in nature and not manipulated, modified, and/or changed (e.g., isolated, purified, selected) by a human being.

The antibodies provided herein can include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA, 81:6851-6855 (1984)).

"Humanized" forms of nonhuman (e.g., murine) antibodies are chimeric antibodies that include human immunoglobulins (e.g., recipient antibody) in which the native CDR residues are replaced by residues from the corresponding CDR of a nonhuman species (e.g., donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., Nature, 321:522-525 (1986); Riechmann et al., Nature, 332:323-329 (1988); and Presta, Curr. Op. Struct. Biol., 2:593-596 (1992); Carter et al., Proc. Natl. Acd. Sci. USA 89:4285-4289 (1992); and U.S. Pat. No. 6,800,738 (issued Oct. 5, 2004), U.S. Pat. No. 6,719,971 (issued Sep. 27, 2005), U.S. Pat. No. 6,639,055 (issued Oct. 28, 2003), U.S. Pat. No. 6,407,213 (issued Jun. 18, 2002), and U.S. Pat. No. 6,054,297 (issued Apr. 25, 2000).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (Hoogenboom and Winter, J. Mol. Biol., 227:381 (1991); Marks et al., J. Mol. Biol., 222:581 (1991) and yeast display libraries (Chao et al., Nature Protocols 1: 755-768 (2006)). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., mice (see, e.g., Jakobovits, A., Curr. Opin. Biotechnol. 1995, 6(5):561-6; Brüggemann and Taussing, Curr. Opin. Biotechnol. 1997, 8(4):455-8; and U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., J. Biol. Chem. 252:6609-6616 (1977); Kabat, Adv. Prot. Chem. 32:1-75 (1978)). CDR region sequences also have been defined structurally by Chothia as those residues that are not part of the conserved β-sheet framework, and thus are able to adapt different conformations (Chothia and Lesk, J. Mol. Biol. 196:901-917 (1987)). Both terminologies are well recognized in the art. CDR region sequences have also been defined by AbM, Contact and IMGT. CDR region sequences are illustrated in FIGS. 1-3. The positions of CDRs within a canonical antibody variable region have been determined by comparison of numerous structures (Al-Lazikani et al., J. Mol. Biol. 273:927-948 (1997); Morea et al., Methods 20:267-279 (2000)). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra (1997)). Such nomenclature is similarly well known to those skilled in the art.

The term "hypervariable region", "HVR", or "HV", when used herein refers to the regions of an antibody variable region that are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (see, e.g., Kabat et al., Sequences of Proteins of Immunological Interest, 5th Ed. Public Health Service, National Institutes of Health, Bethesda, Md. (1991)). Chothia refers instead to the location of the structural loops (see, e.g., Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Martin, in Antibody Engineering, Vol. 2, Chapter 3, Springer Verlag). The "contact" hypervariable regions are based on an analysis of the available complex crystal structures. The residues from each of these hypervariable regions or CDRs are noted below.

Recently, a universal numbering system has been developed and widely adopted, ImMunoGeneTics (IMGT) Information System® (Lafranc et al., Dev. Comp. Immunol. 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Plückthun, J. Mol. Biol. 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra) and is also illustrated in FIGS. 1-3. An Exemplary system, shown herein, combines Kabat and Chothia.

| | Exemplary | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (L1), 46-56 or 50-56 (L2) and 89-97 or 89-96 (L3) in the VL and 26-35 or 26-35A (H1), 50-65 or 49-65 (H2) and 93-102, 94-102, or 95-102 (H3) in the VH. As used herein, the terms "HVR" and "CDR" are used interchangeably.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable region, which contains the antigen binding site. The constant region may contain the CH1, CH2 and CH3 regions of the heavy chain and the CL region of the light chain.

The term "framework" or "FR" residues are those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

An "affinity matured" antibody is one with one or more alterations (e.g., amino acid sequence variations, including changes, additions and/or deletions) in one or more HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. For review, see Hudson and Souriau, Nature Medicine 9:129-134 (2003); Hoogenboom, Nature Biotechnol. 23: 1105-1116 (2005); Quiroz and Sinclair, Revista Ingeneria Biomedia 4: 39-51 (2010).

A "blocking" antibody or an "antagonist" antibody is one which inhibits or reduces biological activity of the antigen it binds. For example, blocking antibodies or antagonist antibodies may substantially or completely inhibit the biological activity of the antigen.

An "agonist antibody" is an antibody that triggers a response, e.g., one that mimics at least one of the functional activities of a polypeptide of interest (e.g., FGF19 or FGF21 as described herein). An agonist antibody includes an antibody that is a ligand mimetic, for example, wherein a ligand binds to a cell surface receptor and the binding induces cell signaling or activities via an intercellular cell signaling pathway and wherein the antibody induces a similar cell signaling or activation.

An "agonist" of beta klotho refers to a molecule that is capable of activating or otherwise increasing one or more of the biological activities of beta klotho, such as in a cell expressing beta klotho and a FGF receptor. In some embodiments, an agonist of beta klotho (e.g., an agonistic antibody as described herein) may, for example, act by activating or otherwise increasing the activation and/or cell signaling pathways of a cell expressing a beta klotho protein and a FGF receptor, thereby increasing a beta klotho-mediated biological activity of the cell relative to the beta klotho-mediated biological activity in the absence of agonist. In some embodiments the antibodies provided herein are agonistic anti-beta klotho antibodies, including antibodies that induce FGF19-like signaling and/or FGF21-like signaling.

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a radiolabeled antigen binding assay (RIA), for example, performed with the Fab version of an antibody of interest and its antigen (Chen, et al., (1999) J. Mol Biol 293:865-881). The $K_D$ or $K_D$ value may also be measured by using surface plasmon resonance assays by Biacore, using, for example, a BIAcore™-2000 or a BIAcore™-3000 BIAcore, Inc., Piscataway, N.J.), or by biolayer interferometry using, for example, the OctetQK384 system (ForteBio, Menlo Park, Calif.). An "on-rate" or "rate of association" or "association rate" or "kon" may can also be determined with the same surface plasmon resonance or biolayer interferometry techniques described above using, for example, a BIAcore™-2000 or a BIAcore™-3000 (BIAcore, Inc., Piscataway, N.J.), or the OctetQK384 sytem (ForteBio, Menlo Park, Calif.).

The phrase "substantially similar" or "substantially the same" denotes a sufficiently high degree of similarity between two numeric values (e.g., one associated with an antibody of the present disclosure and the other associated with a reference antibody) such that one of skill in the art would consider the difference between the two values to be of little or no biological and/or statistical significance within the context of the biological characteristic measured by the values (e.g., $K_D$ values). For example, the difference between the two values may be less than about 50%, less than about 40%, less than about 30%, less than about 20%, less than about 10%, less than about 5%, as a function of the value for the reference antibody.

The phrase "substantially reduced," or "substantially different", as used herein, denotes a sufficiently high degree of difference between two numeric values (e.g., one associated with an antibody of the present disclosure and the other associated with a reference antibody) such that one of skill in the art would consider the difference between the two values to be of statistical significance within the context of the biological characteristic measured by the values. For example, the difference between said two values may be preferably greater than about 10%, greater than about 20%, greater than about 30%, greater than about 40%, greater than about 50% as a function of the value for the reference antibody.

Antibody "effector functions" refer to those biological activities attributable to the Fc region (e.g., a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding region or binding domain (e.g., an antibody variable region or domain) and can be assessed, including using various assays as disclosed herein and/or as known in the art.

A "native sequence Fc region" comprises an amino acid sequence identical to the amino acid sequence of an Fc region found in nature, and not manipulated, modified, and/or changed (e.g., isolated, purified, selected, including or combining with other sequences such as variable region sequences) by a human. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, (e.g., substituting, addition, or deletion) preferably one or more amino acid substitution(s). Preferably, the variant Fc region has at least one amino acid substitution compared to a native sequence Fc region or to the Fc region of a parent polypeptide, for example, from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and more preferably at least about 90% homology therewith, for example, at least about 95% homology therewith. For example, a variant with two amino acid changes to alanine at two positions in the human IgG1 Fc sequence are shown bolded in the amino acid sequence provided below:

```
                                      (SEQ ID NO: 200)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPALAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

Such a variant sequence may be used in humanized heavy chain constructs, including a chimeric construct, such as shown below for 3I13-hIgG1(E233A)(L235A); the amino acids that make up the signal sequence are underlined and the variable region sequence is bolded:

```
                                      (SEQ ID NO: 286)
mdmrvpaqllglllwlrgarcQVQLVQSGAEVKKPGASVKVSCKASGYT

FTEYTMHWVRQAPGQGLEWMGSFNPDSGGTSYNQKFKGRVTMTRDTSTST

VYMELSSLRSEDTAVYYCARDDGYSTRYWYFDVWGRGTLVTVSSASTKGP

SVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKT

HTCPPCPAPALAGGPSVFLFPPKPKDTLMISRTPEVTCWVDVSHEDPEVK

FNWYVDGVEVHNAKTKPREEQYNSTYRVVSVLTVLHQDWLNGKEYKCKVS

NKALPAPIEKTISKAKGQPREPQVYTLPPSREEMTKNQVSLTCLVKGFYP

SDIAVEWESNGQPENNYKTTPPVLDSDGSFFLYSKLTVDKSRWQQGNVFS

CSVMHEALHNHYTQKSLSLSPGK
```

A "light chain constant region" includes kappa and lambda constant regions. An exemplary kappa constant region is provided below:

```
                                      (SEQ ID NO: 300)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```

Such a kappa constant region sequence may be used in humanized light chain constructs including a chimeric construct such as shown below for 3I13; the amino acids that make up the signal sequence are underlined and the variable region sequence is bolded:

```
                                      (SEQ ID NO: 287)
mdmrvpaqllglllwlrgarcDIQMTQSPASLSASVGETVTITCGASEN

IYGALNWFQRKQGKSPQLLIYGATILADGMSSRFSGSGSGRQYSLKISSL

HPDDVATYYCQNVLSTPYTFGGGTKLEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC
```

The term "variant" when used in relation to beta klotho or to an anti-beta klotho antibody may refer to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified beta klotho sequence. For example, a beta klotho variant may result from one or more (such as, for example, about 1 to about 25, about 1 to about 20, about 1 to about 15, about 1 to about 10, or about 1 to about 5) changes to an amino acid sequence of a native beta klotho. Also by way of example, a variant of an anti-beta klotho antibody may result from one or more (such as, for example, about 1 to about 25, about 1 to about 20, about 1 to about 15, about 1 to about 10, or about 1 to about 5) changes to an amino acid sequence of a native or previously unmodified anti-beta klotho antibody. Variants may be naturally occurring, such as allelic or splice variants, or may be artificially constructed. Polypeptide variants may be prepared from the corresponding nucleic acid molecules encoding the variants. In specific embodiments, the beta klotho variant or anti-beta klotho antibody variant at least retains beta klotho or anti-beta klotho antibody functional activity, respectively. In specific embodiments, an anti-beta klotho antibody variant binds beta klotho and/or is antagonistic to beta klotho activity. In specific embodiments, an anti-beta klotho antibody variant binds beta klotho and/or is agonistic to beta klotho activity. In certain embodiments, the variant is encoded by a single nucleotide polymorphism (SNP) variant of a nucleic acid molecule that encodes beta klotho or anti-beta klotho antibody VH or VL regions or subregions, such as one or more CDRs.

The term "vector" refers to a substance that is used to carry or include a nucleic acid sequences, including for example, in order to introduce a nucleic acid sequence into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain or an antibody VH and VL) both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product (e.g. an anti-beta klotho antibody as described herein), and it is further understood that expression levels can be optimized to obtain sufficient expression using methods well known in the art.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is known (see, e.g., Table 3, page 464, Ravetch and Kinet, Annu. Rev. Immunol. 9:457-92 (1991)). To assess ADCC activity of a molecule of interest, an in vitro ADCC assay, (see, e.g., U.S. Pat. No. 5,500,362 or 5,821,337) may be performed. Useful effector cells for such assays include peripheral blood mononuclear cells (PBMC) and Natural Killer (NK) cells. Alternatively, or additionally, ADCC activity of the molecule of interest may be assessed in vivo, for example, in a animal model (see, e.g., Clynes et al. (USA) 95:652-656 (1998)). Antibodies with little or no ADCC activity may be selected for use.

"Fc receptor" or "FcR" describes a receptor that binds to the Fc region of an antibody. The preferred FcR is a native sequence human FcR. Moreover, a preferred FcR is one that binds an IgG antibody (e.g., a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof (see, e.g., review Daëron, Annu. Rev. Immunol. 15:203-234 (1997)). FcRs are known (see, e.g., Ravetch and Kinet, Annu. Rev. Immunol. 9:457-492 (1991); Capel et al., Immunomethods 4:25-34 (1994); and de Haas et al., J. Lab. Clin. Med. 126:330-41 (1995)). Other FcRs, including those to be identified in the future, are encompassed by the term "FcR" herein. The term also includes the neonatal receptor, FcRn, which is responsible for the transfer of maternal IgGs to the fetus (see, e.g., Guyer et al., J. Immunol. 117:587 (1976) and Kim et al., J. Immunol. 24:249 (1994)). Antibody variants with improved or diminished binding to FcRs have been described (see, e.g., in WO 2000/42072; U.S. Pat. Nos. 7,183,387, 7,332,581 and 7,335,742; Shields et al. J. Biol. Chem. 9(2):6591-6604 (2001)).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, (see, e.g., Gazzano-Santoro et al., J. Immunol. Methods 202:163 (1996)), may be performed. Polypeptide variants with altered Fc region amino acid sequences (polypeptides with a variant Fc region) and increased or decreased C1q binding capability have been described, (see, e.g., U.S. Pat. No. 6,194,551, WO 1999/51642, Idusogie et al. J. Immunol. 164: 4178-4184 (2000)). Antibodies with little or no CDC activity may be selected for use.

A beta klotho polypeptide "extracellular domain" or "ECD" refers to a form of the beta klotho polypeptide that is essentially free of (e.g., not comprising) the transmembrane and cytoplasmic domains. For example, a beta klotho polypeptide ECD may have less than 1% of such transmembrane and/or cytoplasmic domains and preferably, may have less than 0.5% of such domains. The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (e.g., an "algorithm"). Methods that can be used to calculate the identity of the aligned nucleic acids or polypeptides include those described in Computational Molecular Biology, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) SIAM J. Applied Math. 48:1073.

In calculating percent identity, the sequences being compared may be aligned in a way that gives the largest match between the sequences. Computer program may be used to determine percent identity is the GCG program package, which includes GAP (Devereux et al., (1984) Nucl. Acid Res. 12:387; Genetics Computer Group, University of Wisconsin, Madison, Wis.). The computer algorithm GAP used to align the two polypeptides or polynucleotides for which the percent sequence identity is to be determined. The sequences may be aligned for optimal matching of their respective amino acid or nucleotide (the "matched span", as determined by the algorithm). A gap opening penalty (which is calculated as 3.times. the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) Atlas of Protein Sequence and Structure 5:345-352 for the PAM 250 comparison matrix; Henikoff et al., (1992) Proc. Natl. Acad. Sci. U.S.A. 89:10915-10919 for the BLOSUM 62 comparison matrix) is also used by the algorithm.

Examplary parameters for determining percent identity for polypeptides or nucleotide sequences using the GAP program are the following: (i) Algorithm: Needleman et al., 1970, J. Mol. Biol. 48:443-453; (ii) Comparison matrix: BLOSUM 62 from Henikoff et al., 1992, supra; (iii) Gap Penalty: 12 (but with no penalty for end gaps) (iv) Gap Length Penalty: 4; and (v) Threshold of Similarity: 0.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (e.g., the GAP program) can be adjusted if so desired to result in an alignment that spans a number of amino acids, for example, at least 50 contiguous amino acids of the target polypeptide.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

A "modification" of an amino acid residue/position refers to a change of a primary amino acid sequence as compared to a starting amino acid sequence, wherein the change results from a sequence alteration involving said amino acid residue/positions. For example, typical modifications include substitution of the residue with another amino acid (e.g., a conservative or non-conservative substitution), insertion of one or more (e.g., generally fewer than 5, 4 or 3) amino acids adjacent to said residue/position, and/or deletion of said residue/position.

An "epitope" is the site on the surface of an antigen molecule to which a single antibody molecule binds, such as a localized region on the surface of an antigen, such as a beta klotho polypeptide, a beta klotho polypeptide fragment or a beta klotho epitope, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. The term, "epitope" specifically includes linear epitopes and conformational epitopes. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a beta klotho epitope is a three-dimensional surface feature of a beta klotho polypeptide. In other embodiments, a beta klotho epitope is linear feature of a beta klotho polypeptide. Generally an antigen has several or many different epitopes and may react with many different antibodies.

An antibody binds "an epitope" or "essentially the same epitope" or "the same epitope" as a reference antibody, when the two antibodies recognize identical, overlapping or adjacent epitopes in a three-dimensional space. The most widely used and rapid methods for determining whether two antibodies bind to identical, overlapping or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies is measured using radioactive, fluorescent or enzyme labels.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three dimensional structure of the protein is in an altered confirmation, such as following activation or binding of another protein or ligand (e.g., the binding of beta klotho to an FCF receptor such as FGRFR1c, FGFR2c, FGFR3c, or FGFR4c.

"Epitope binning" is the process of grouping antibodies based on the epitopes they recognize. More particularly, epitope binning comprises methods and systems for discriminating the epitope recognition properties of different antibodies, using competition assays combined with computational processes for clustering antibodies based on their epitope recognition properties and identifying antibodies having distinct binding specificities.

A "beta klotho-mediated disease" and "beta klotho-mediated disorder" and "beta klotho-mediated condition" are used interchangeably and refer to any disease, disorder or condition that is completely or partially caused by or is the result of beta klotho or the interaction of a beta klotho with an FGF receptor such as FGFR1c, FGFR2c, FGFR3c, or FGFR4 and/or alternatively any disease, disorder, or condition in which it is desirable to mimic or augment the in vivo effects of FGF19 and/or FGF21.

The term "therapeutically effective amount" as used herein refers to the amount of an agent (e.g., an antibody described herein or any other agent described herein) that is sufficient to reduce and/or ameliorate the severity and/or duration of a given disease, disorder or condition, and/or a symptom related thereto. A therapeutically effective amount of a agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody provided herein). A "therapeutically effective amount" of a substance/molecule/agent of the present disclosure (e.g., an anti-beta klotho antibody) may vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects. In certain embodiments, the term "therapeutically effective amount" refers to an amount of an antibody or other agent (e.g., or drug) effective to "treat" a disease, disorder, or condition, in a subject or mammal.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a disease, disorder, or condition, including, for example, diabetes, obesity, dyslipidemia, cardiovascular disease, metabolic syndrome or broadly any disease, disorder, or condition in which it is desirable to mimic or augment the in vivo effects of FGF19 and/or FGF21. In some embodiments, the effective amount is a therapeutically effective amount or a prophylactically effective amount. A "therapeutically effective amount" is an amount sufficient to remedy a disease, disorder, or condition (e.g., Type 2 diabetes, obesity, dyslipidemia, NASH, cardiovascular disease, metabolic syndrome or broadly any disease, disorder, or condition in which it is desirable to mimic or augment the in vivo effects of FGF19 and/or FGF21) or symptoms, particularly a disease, disorder, or condition, or symptoms associated with such a disease, disorder, or condition, or otherwise prevent, hinder, retard or reverse the progression of the disease, disorder, or condition, or any other undesirable symptom associated with such a disease, disorder, or condition, in any way whatsoever. A "prophylactically effective amount" is an amount of a pharmaceutical composition that, when administered to a subject, will have the intended prophylactic effect, e.g., preventing or delaying the onset (or reoccurrence) of diabetes, obesity or dyslipidemia, or reducing the likelihood of the onset (or reoccurrence) of a disease, disorder, or condition or associated symptom(s), including, for example, diabetes, obesity, dyslipidemia, cardiovascular disease, metabolic syndrome or broadly any disease, disorder, or condition in which it is desirable to mimic or augment the in vivo effects of FGF19 and/or FGF21) or associated symptoms. The full therapeutic or prophylactic effect does not necessarily occur by administration of one dose, and may occur only after administration of a series of doses. Thus, a therapeutically or prophylactically effective amount may be administered in one or more administrations.

A "prophylactically effective amount" refers to an amount effective, at dosages and for periods of time necessary, to achieve the desired prophylactic result. Typically, but not necessarily, since a prophylactic dose is used in subjects prior to or at an earlier stage of a disease, disorder, or condition, a prophylactically effective amount may be less than a therapeutically effective amount.

"Chronic" administration refers to administration of the agent(s) in a continuous mode (e.g., for a period of time such as days, weeks, months or years) as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further agents includes simultaneous (e.g., concurrent) and consecutive administration in any order. The term "in combination" in the context of the administration of other therapies (e.g., other agents) includes the use of more than one therapy (e.g., one agent). The use of the term "in combination" does not restrict the order in which therapies are administered to a subject. A first therapy (e.g., agent) can be administered before (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 8 weeks, 8 weeks, 9 weeks, 10 weeks, 11 weeks, or 12 weeks), concurrently, or after (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 7 weeks, 8 weeks, 9 weeks, 10 weeks, 11 weeks, or 12 weeks) the administration of a second therapy (e.g., agent) to a subject which had, has, or is susceptible to a beta klotho-mediated disease.

Any additional therapy (e.g., agent) can be administered in any order with the other additional therapies (e.g., agents). In certain embodiments, the antibodies can be administered in combination with one or more therapies such as agents (e.g., therapies, including agents, that are not the antibodies that are currently administered) to prevent, treat, manage, and/or ameliorate a beta klotho-mediated disease. Non-limiting examples of therapies (e.g., agents) that can be administered in combination with an antibody include, for example, analgesic agents, anesthetic agents, antibiotics, or immunomodulatory agents or any other agent listed in the *U.S. Pharmacopoeia* and/or *Physician's Desk Reference*. Examples of agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, flurprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors. Other agents for combination include steroids such as prednisolone, prednisone, methylprednisolone, betamethasone, dexamethasone, or hydrocortisone. Such a combination may be especially advantageous, since one or more side-effects of the steroid can be reduced or even eliminated by tapering the steroid dose required when treating patients in combination with the present antibodies. Additional examples of agents for combinations include cytokine suppressive anti-inflammatory drug(s) (CSAIDs); antibodies to or antagonists of other human cytokines or growth factors, for example, TNF, LT, IL-1β, IL-2, IL-6, IL-7, IL-8, IL-15, IL-16, IL-18, EMAP-II, GM-CSF, FGF, or PDGF. Combinations of agents may include TNF antagonists like chimeric, humanized or human TNF antibodies, REMICADE, anti-TNF antibody fragments (e.g., CDP870), and soluble p55 or p75 TNF receptors, derivatives thereof, p75TNFRIgG (ENBREL®) or p55TNFR1gG (LENERCEPT®), soluble IL-13 receptor (sIL-13), and also TNFα converting enzyme (TACE) inhibitors; similarly IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination therapy include interferon-β1a (AVONEX); interferon-β1b (BETASERON®); copaxone; hyperbaric oxygen; intravenous immunoglobulin; clabribine; and antibodies to or antagonists of other human cytokines or growth factors (e.g., antibodies to CD40 ligand and CD80).

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. The term "carrier" can also refer to a diluent, adjuvant (e.g., Freund's adjuvant (complete or incomplete)), excipient, or vehicle with which the therapeutic is administered. Such carriers, including pharmaceutical carriers, can be sterile liquids, such as water and oils, including those of petroleum, animal, vegetable or synthetic origin, such as peanut oil, soybean oil, mineral oil, sesame oil and the like. Water is a exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Compositions can take the form of solutions, suspensions, emulsion, tablets, pills, capsules, powders, sustained-release formulations and the like. Oral compositions, including formulations, can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* (1990) Mack Publishing Co., Easton, Pa. Compositions, including pharmaceutical compounds, may contain a prophylactically or therapeutically effective amount of an anti-beta klotho antibody, for example, in isolated or purified form, together with a suitable amount of carrier so as to provide the form for proper administration to the subject (e.g., patient). The formulation should suit the mode of administration.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

The term "pharmaceutical formulation" refers to a preparation which is in such form as to permit the biological activity of the active ingredient (e.g., an anti-beta klotho antibody) to be effective, and which contains no additional components which are unacceptably toxic to a subject to which the formulation would be administered. Such formulation may be sterile.

A "sterile" formulation is aseptic or free from all living microorganisms and their spores.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., Chapter 11 in: *Short Protocols in Molecular Biology*, (2002) 5th Ed., Ausubel et al., eds., John Wiley and Sons, New York).

An "isolated nucleic acid" is a nucleic acid, for example, an RNA, DNA, or a mixed polymer, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides. A cell that produces an anti-beta klotho antibody of the present disclosure may include a parent hybridoma cell, as well as bacterial and eukaryotic host cells into which nucleic acid encoding the antibodies have been introduced. Suitable host cells are disclosed below.

Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "package insert" is used to refer to instructions customarily included in commercial packages of therapeutic products, that contain information about the indications, usage, dosage, administration, contraindications and/or warnings concerning the use of such therapeutic products.

The terms "prevent," "preventing," and "prevention" refer to the total or partial inhibition of the development, recurrence, onset or spread of a beta klotho-mediated disease and/or symptom related thereto, resulting from the administration of a therapy or combination of therapies provided herein (e.g., a combination of prophylactic or therapeutic agents, such as an antibody provided herein).

The term "prophylactic agent" refers to any agent that can totally or partially inhibit the development, recurrence, onset or spread of a beta klotho-mediated disease and/or symptom related thereto in a subject. In certain embodiments, the term "prophylactic agent" refers to an anti-beta klotho antibody as described herein. In certain other embodiments, the term "prophylactic agent" refers to an agent other than an anti-beta klotho antibody as described herein. In certain embodiments, a prophylactic agent is an agent which is known to be useful to or has been or is currently being used to prevent a beta klotho-mediated disease, disorder, or condition, and/or a symptom related thereto or impede the onset, development, progression and/or severity of a beta klotho-mediated disease, disorder, or condition, and/or a symptom related thereto. In specific embodiments, the prophylactic agent is a humanized anti-beta klotho antibody, such as a humanized anti-beta klotho monoclonal antibody.

In certain embodiments, a "prophylactically effective serum titer" is the serum titer in a subject, preferably a human, that totally or partially inhibits the development, recurrence, onset or spread of a beta klotho-mediated disease, disorder, or condition, and/or symptom related thereto in the subject.

In certain embodiments, a "therapeutically effective serum titer" is the serum titer in a subject, preferably a human, that reduces the severity, the duration and/or the symptoms associated with a beta klotho-mediated disease, disorder, or condition, in the subject.

The term "recombinant antibody" refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor, L. D. et al. (1992) Nucl. Acids Res. 20:6287-6295) or antibodies prepared, expressed, created or isolated by any other means that involves splicing of immunoglobulin gene sequences to other DNA sequences. Such recombinant antibodies can have variable and constant regions, including those derived from human germline immunoglobulin sequences (See Kabat, E. A. et al. (1991) *Sequences of Proteins of Immunological Interest*, Fifth Edition, U.S. Department of Health and Human Services, NIH Publication No. 91-3242). In certain embodiments, however, such recombinant antibodies may be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germ line VH and VL sequences, may not naturally exist within the human antibody germ line repertoire in vivo.

The term "serum titer" refers to an average serum titer in a subject from multiple samples (e.g., at one time present or multiple time points) or in a population of least 10, such as at least 20, or at least 40 subjects, up to about 100, 1000 or more.

The term "side effects" encompasses unwanted and/or adverse effects of a therapy (e.g., a prophylactic or therapeutic agent). Unwanted effects are not necessarily adverse. An adverse effect from a therapy (e.g., a prophylactic or therapeutic agent) might be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* (68th ed., 2014).

The terms "subject" and "patient" may be used interchangeably. As used herein, in certain embodiments, a subject is a mammal, such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a beta klotho-mediated disease, disorder or condition. In another embodiment, the subject is a mammal (e.g., a human) at risk of developing a beta klotho-mediated disease, disorder, or condition.

"Substantially all" refers to refers to at least about 60%, at least about 65%, at least about 70%, at least about 75%, at least about 80%, at least about 85%, at least about 90%, at least about 95%, at least about 96%, at least about 97%, at least about 98%, at least about 99%, or about 100%.

The term "therapeutic agent" refers to any agent that can be used in treating, preventing or alleviating a disease, disorder or condition, including in the treatment, prevention or alleviation of one or more symptoms of a beta klotho-mediated disease, disorder, or condition and/or a symptom related thereto. In certain embodiments, a therapeutic agent refers to an anti-beta klotho antibody as described herein. In certain other embodiments, a therapeutic agent refers to an agent other than an antibody provided herein. In certain embodiments, a therapeutic agent is an agent which is known to be useful for, or has been or is currently being used for the treatment, prevention or alleviation of one or more symptoms of a beta klotho-mediated disease, disorder, or condition, or a symptom related thereto.

The combination of therapies (e.g., use of agents, including therapeutic agents) can be more effective than the additive effects of any two or more single therapy (e.g., synergistic). A synergetic effect is unexpected and can not be predicted. For example, a synergistic effect of a combination of therapeutic agents permits the use of lower dosages of one or more of the agents and/or less frequent administration of the agents to a subject with a beta klotho-mediated disease. The ability to utilize lower dosages of therapeutic therapies and/or to administer the therapies less frequently reduces the toxicity associated with the administration of the therapies to a subject without reducing the efficacy of the therapies in the prevention, treatment or alleviation of one or more symptom of a beta klotho-mediated disease. In addition, a synergistic effect can result in improved efficacy of therapies in the prevention, treatment or alleviation of one or more symptom of a beta klotho-mediated disease. Finally, synergistic effect of a combination of therapies (e.g., therapeutic agents) may avoid or reduce adverse or unwanted side effects associated with the use of any single therapy.

The term "therapy" refers to any protocol, method and/or agent that can be used in the prevention, management, treatment and/or amelioration of a beta klotho-mediated disease, disorder, or conditions. In certain embodiments, the terms "therapies" and "therapy" refer to a biological therapy, supportive therapy, and/or other therapies useful in the prevention, management, treatment and/or amelioration of a beta klotho-mediated disease, disorder or condition, known to one of skill in the art such as medical personnel.

The term "detectable probe" refers to a composition that provides a detectable signal. The term includes, without limitation, any fluorophore, chromophore, radiolabel, enzyme, antibody or antibody fragment, and the like, that provide a detectable signal via its activity.

The term "diagnostic agent" refers to a substance administered to a subject that aids in the diagnosis of a disease, disorder, or conditions. Such substances can be used to reveal, pinpoint, and/or define the localization of a disease causing process. In certain embodiments, a diagnostic agent includes a substance that is conjugated to an anti-beta klotho antibody as described herein, that when administered to a subject or contacted to a sample from a subject aids in the diagnosis a beta klotho-mediated disease.

The term "detectable agent" refers to a substance that can be used to ascertain the existence or presence of a desired molecule, such as an anti-beta klotho antibody as described herein, in a sample or subject. A detectable agent can be a substance that is capable of being visualized or a substance that is otherwise able to be determined and/or measured (e.g., by quantitation).

The term "encode" or grammatical equivalents thereof as it is used in reference to nucleic acid molecule refers to a nucleic acid molecule in its native state or when manipulated by methods well known to those skilled in the art that can be transcribed to produce mRNA, which is then translated into a polypeptide and/or a fragment thereof. The antisense strand is the complement of such a nucleic acid molecule, and the encoding sequence can be deduced therefrom.

The term "excipient" refers to an inert substance which is commonly used as a diluent, vehicle, preservative, binder, or stabilizing agent, and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, *Remington's Pharmaceutical Sciences* (1990) Mack Publishing Co., Easton, Pa., which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, beta klotho fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 250, at least 300, at least 350, at least 400, at least 450, at least 500, at least 550, at least 600, at least 650, at least 700, at least 750, at least 800, at least 850, at least 900, or at least 950, contiguous amino acid residues of the amino acid sequence of a beta klotho polypeptide or an antibody that binds to a beta klotho polypeptide. In a specific embodiment, a fragment of a beta klotho polypeptide or an antibody that binds to a beta klotho antigen retains at least 1, at least 2, or at least 3 or more functions of the polypeptide or antibody.

The terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents, such as an antibody provided herein) to "manage" a beta klotho-mediated disease, one or more symptoms thereof, so as to prevent the progression or worsening of the disease.

The terms "about" or "approximately" mean within 20%, within 15%, within 10%, within 9%, within 8%, within 7%, within 6%, within 5%, within 4%, within 3%, within 2%, within or 1% or less of a given value or range.

"Administer" or "administration" refers to the act of injecting or otherwise physically delivering a substance as it exists outside the body (e.g., an anti-beta klotho antibody as described herein) into a patient, such as by mucosal, intradermal, intravenous, intramuscular delivery and/or any other method of physical delivery described herein or known in the art. When a disease, disorder, or condition, or a symptom thereof, is being treated, administration of the substance typically occurs after the onset of the disease, disorder, or condition, or symptoms thereof. When a disease, disorder, or condition or symptoms thereof, are being prevented, administration of the substance typically occurs before the onset of the disease, disorder, or condition, or symptoms thereof.

In the context of a polypeptide, the term "analog" as used herein refers to a polypeptide that possesses a similar or identical function as a beta klotho polypeptide, a fragment of a beta klotho polypeptide, or an anti-beta klotho antibody but does not necessarily comprise a similar or identical amino acid sequence of a beta klotho polypeptide, a fragment of a beta klotho polypeptide, or an anti-beta klotho antibody, or possess a similar or identical structure of a beta klotho polypeptide, a fragment of a beta klotho polypeptide, or an anti-beta klotho antibody. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a beta klotho polypeptide (e.g., SEQ ID NO:165, a fragment of a beta klotho polypeptide, or an anti-beta klotho antibody described herein; (b) a polypeptide encoded by a nucleotide sequence that hybridizes under stringent conditions to a nucleotide sequence encoding a beta klotho polypeptide, a fragment of a beta klotho polypeptide, or an anti-beta klotho antibody (or VH or VL region thereof) described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al. (2001) *Molecular Cloning: A Laboratory Manual*, Cold Spring Harbor Laboratory Press, Cold Spring Harbor, N.Y.; Maniatis et al. (1982) *Molecular Cloning: A Laboratory Manual*, Cold Spring Harbor Press, Cold Spring Harbor, N.Y.); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a beta klotho polypeptide, a fragment of a beta klotho polypeptide, or an anti-beta klotho antibody (or VH or VL region thereof) described herein. A polypeptide with similar structure to a beta klotho polypeptide, a fragment of a beta klotho polypeptide, or an anti-beta klotho antibody described herein refers to a polypeptide that has a similar secondary, tertiary or quaternary structure of a beta klotho polypeptide, a fragment of a beta klotho, or a beta klotho antibody described herein. The structure of a polypeptide can determined by methods known to those skilled in the art, including but not limited to, X-ray crystallography, nuclear magnetic resonance, and crystallographic electron microscopy.

The term "composition" is intended to encompass a product containing the specified ingredients (e.g., an antibody provided herein) in, optionally, the specified amounts, as well as any product which results, directly or indirectly, from combination of the specified ingredients in, optionally, the specified amounts.

In the context of a polypeptide, the term "derivative" as used herein refers to a polypeptide that comprises an amino acid sequence of a beta klotho polypeptide, a fragment of a beta klotho polypeptide, or an antibody that binds to a beta klotho polypeptide which has been altered by the introduction of amino acid residue substitutions, deletions or additions. The term "derivative" as used herein also refers to a beta klotho polypeptide, a fragment of a beta klotho polypeptide, or an antibody that binds to a beta klotho polypeptide which has been chemically modified, e.g., by the covalent attachment of any type of molecule to the polypeptide. For example, but not by way of limitation, a beta klotho polypeptide, a fragment of a beta klotho polypeptide, or a beta klotho antibody may be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a beta klotho polypeptide, a fragment of a beta klotho polypeptide, or a beta klotho antibody may be chemically modified by chemical modifications using techniques known to those of skill in the art, including, but not limited to specific chemical cleavage, acetylation, formulation, metabolic synthesis of tunicamycin, etc. Further, a derivative of a beta klotho polypeptide, a fragment of a beta klotho polypeptide, or a beta klotho antibody may contain one or more non-classical amino acids. A polypeptide derivative possesses a similar or identical function as a beta klotho polypeptide, a fragment of a beta klotho polypeptide, or a beta klotho antibody described herein.

Compositions and Methods of Making the Same

Binding proteins such as antibodies that bind to beta klotho (e.g., human and/or cyno beta klotho) are provided. Antibodies of the present disclosure are useful, for example, for the diagnosis or treatment of diseases, disorders, or conditions associated with expression, of beta klotho. In certain embodiments, antibodies of the present disclosure are useful for the diagnosis or treatment of a diseases, disorder, or condition, such as Type 2 diabetes, obesity, dyslipidemia, NASH, cardiovascular disease, metabolic syndrome or broadly any disease, disorder, or condition in which it is desirable to mimic or augment the in vivo effects of FGF19 and/or FGF21.

Provided herein are antibodies that bind to a beta klotho polypeptide, a beta klotho polypeptide fragment, beta klotho peptide, or a beta klotho epitope. In some embodiments, the anti-beta klotho antibodies bind to the extracellular domain (ECD) of beta klotho. Also provided are antibodies that competitively block an anti-beta klotho antibody provided herein from binding to a beta klotho polypeptide. The anti-beta klotho antibodies provided herein can also be conjugated or recombinantly fused to a diagnostic agent, detectable agent or therapeutic agent. Further provided are compositions comprising an beta klotho antibody.

Also provided herein are isolated nucleic acid molecules encoding an immunoglobulin heavy chain, light chain, VH region, VL region, VH CDR1, VH CDR2, VH CDR3, VL CDR1, VL CDR2, and/or VL CDR3 of anti-beta klotho antibodies that bind to a beta klotho polypeptide, a beta klotho polypeptide fragment, a beta klotho peptide or a beta klotho epitope. Further provided are vectors and host cells comprising nucleic acid molecules encoding anti-beta klotho antibodies that bind to a beta klotho polypeptide, a beta klotho polypeptide fragment, a beta klotho peptide or a beta klotho epitope. Also provided are methods of making antibodies that bind to a beta klotho polypeptide, a beta klotho polypeptide fragment, a beta klotho peptide or a beta klotho epitope.

Methods of using the anti-beta klotho antibodies are provided herein. The methods include treating, preventing or alleviating a disease, disorder or condition, including treating, preventing or alleviating one or more symptoms of a disease, disorder or condition in a subject (e.g., patient). Non limiting examples of diseases, disorders, or conditions include glucose utilization disorders and the sequelae associated therewith, including diabetes mellitus (Type I and Type-2), gestational diabetes, hyperglycemia, insulin resistance, abnormal glucose metabolism, "pre-diabetes" (Impaired Fasting Glucose (IFG) or Impaired Glucose Tolerance (IGT)), or other physiological disorders associated with, or that result from, the hyperglycemic condition, including, for example, histopathological changes such as pancreatic β-cell destruction. For example subjects with a diseases, disorders, or condition, in need of treatment may have a fasting plasma glucose (FPG) level greater than about 100 mg/dl. Other hyperglycemic-related disorders, include kidney damage (e.g., tubule damage or nephropathy), liver degeneration, eye damage (e.g., diabetic retinopathy or cataracts), and diabetic foot disorders. Other of diseases, disorders, or conditions include dyslipidemias and their sequelae such as, for example, atherosclerosis, coronary artery disease, cerebrovascular disorders and the like or other of diseases, disorders, or conditions which may be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), or thromboses, hypercoagulable and prothrombotic states (arterial and venous), hypertension, cardiovascular disease, stroke and heart failure. These diseases, disorders, or conditions include atherosclerosis, chronic inflammatory bowel diseases (e.g., Crohn's disease and ulcerative colitis), asthma, lupus erythematosus, arthritis, or other inflammatory rheumatic disorders. Other diseases, disorders, or conditions include adipose cell tumors, lipomatous carcinomas including, for example, liposarcomas, solid tumors, and neoplasms. Other diseases, disorders, or conditions include neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome. Other diseases, disorders, or conditions include skin and dermatological disorders and/or disorders of wound healing processes, including erythemato-squamous dermatoses. Other diseases, disorders, or conditions include syndrome X, osteoarthritis, and acute respiratory distress syndrome. As used herein, the term "hyperglycemic" or "hyperglycemia," when used in reference to a disease, disorder, or condition of a subject refers to a transient or chronic abnormally high level of glucose present in the blood of a subject. The disease, disorder, or condition may be caused by a delay in glucose metabolism or absorption such that the subject exhibits glucose intolerance or a state of elevated glucose not typically found in normal subjects (e.g., in glucose-intolerant pre-diabetic subjects at risk of developing diabetes, or in diabetic subjects). For example, fasting plasma glucose (FPG) levels for normoglycemia may be less than about 100 mg/dl, for impaired glucose metabolism, between about 100 and 126 mg/dl, and for diabetics greater than about 126 mg/dl. Methods of preventing (e.g., in subjects predisposed to having a particular disorder(s)), relate to delaying, slowing or inhibiting progression of, the onset of, or treating (e.g., ameliorating) obesity or an undesirable body mass (e.g., a greater than normal body mass index, or "BMI" relative to an appropriate matched subject of comparable age, gender, race, etc.). Methods of treating obesity or an undesirable body mass (including the co-morbid conditions of obesity, for example, obstructive sleep apnea, arthritis, cancer (e.g., breast, endometrial, and colon), gallstones or hyperglycemia, include contacting or administering a binding protein such as an anti-beta klotho antibody as described herein in an amount effective to treat obesity or an undesirable body mass. For example, a subject may have a body mass index greater than 25, for example, 25-30, 30-35, 35-40, or greater than 40. Methods of preventing (e.g., in subjects predisposed to having a particular disorder(s)), relate to delaying, slowing or inhibiting the progression of, the onset of, or treating undesirable levels or abnormally elevated serum/plasma LDL, VLDL, triglycerides or cholesterol, all of which, alone or in combination, can lead to, for example, plaque formation, narrowing or blockage of blood vessels, and increased risk of hypertension, stroke and coronary artery disease. Such diseases, disorders, or conditions may be due to, for example, genetic predisposition or diet.

Anti-Beta Klotho Antibodies

In some embodiments, the present disclosure provides anti-beta klotho antibodies that may find use herein as therapeutic agents. Exemplary antibodies include polyclonal, monoclonal, humanized, human, bispecific, and heteroconjugate antibodies, as well as variants thereof having improved affinity or other properties.

In some embodiments, provided herein are antibodies that bind to beta klotho, including a beta klotho polypeptide, a beta klotho polypeptide fragment, a beta klotho peptide or a beta klotho epitope. In some embodiments the anti-beta klotho antibodies are humanized antibodies (e.g., comprising human constant regions) that bind beta klotho, including beta klotho polypeptide, a beta klotho polypeptide fragment, a beta klotho peptide or a beta klotho epitope.

In some embodiments, an anti-beta klotho antibody comprises a VH region, VL region, VH CDR1, VH CDR2, VH CDR3, VL CDR1, VL CDR2, and/or VL CDR3 of any one of the monoclonal antibodies described herein (e.g., 3I13, 2J21, 4A2), such as an amino acid sequence depicted in Tables 1-3. Accordingly, in some embodiments, the isolated antibody or functional fragment thereof provided herein comprises one, two, and/or three heavy chain CDRs and/or one, two, and/or three light chain CDRs from: (a) the antibody designated 3I13; (b) the antibody designated 2J21; (c) the antibody designated 4A2, as shown in Tables 1-3.

The antibody designated 3I13 comprises a VH sequence that is SEQ ID NO:26 and a VL sequence that is SEQ ID NO:27.

The antibody designated 2J21 comprises a VH sequence that is SEQ ID NO:36 and a VL sequence that is SEQ ID NO:37.

The antibody designated 4A2 comprises a VH sequence that is SEQ ID NO:47 and a VL sequence that is SEQ ID NO:48.

TABLE 1

Antibody 3I13 CDR Sequences

| | | Exemplary | IMGT | Kabat | Chothia | Contact | AbM |
|---|---|---|---|---|---|---|---|
| VH CDR Seq. | VH CDR1 | GYTFTEYTMH (SEQ ID NO: 1) | GYTFTEYT (SEQ ID NO: 7) | EYTMH (SEQ ID NO: 12) | GYTFTEY (SEQ ID NO: 14) | TEYTMH (SEQ ID NO: 19) | GYTFTEYTMH (SEQ ID NO: 1) |
| | VH CDR2 | SFNPDSGGTSYNQKFKG (SEQ ID NO: 2) | FNPDSGGT (SEQ ID NO: 8) | SFNPDSGGTSYNQKFKG (SEQ ID NO: 2) | PDSG (SEQ ID NO: 15) | WIGSFNPDSGGTS (SEQ ID NO: 20) | SFNPDSGGTS (SEQ ID NO: 25) |
| | VH CDR3 | DDGYSTRYWYFDV (SEQ ID NO: 3) | ARDDGYSTRYWYFDV (SEQ ID NO: 9) | DDGYSTRYWYFDV (SEQ ID NO: 3) | DGYSTRYWYFD (SEQ ID NO: 16) | ARDDGYSTRYWYFD (SEQ ID NO: 21) | DDGYSTRYWYFDV (SEQ ID NO: 3) |
| VL CDR Seq. | VL CDR1 | GASENIYGALN (SEQ ID NO: 4) | ENIYGA (SEQ ID NO: 10) | GASENIYGALN (SEQ ID NO: 4) | SENIYGA (SEQ ID NO: 17) | YGALNWY (SEQ ID NO: 22) | GASENIYGALN (SEQ ID NO: 4) |
| | VL CDR2 | GATILAD (SEQ ID NO: 5) | GAT (SEQ ID NO: 11) | GATNLAD (SEQ ID NO: 13) | GAT (SEQ ID NO: 11) | LLIYGATNLA (SEQ ID NO: 23) | GATNLAD (SEQ ID NO: 13) |
| | VL CDR3 | QNVLSTPYT (SEQ ID NO: 6) | QNVLSTPYT (SEQ ID NO: 6) | QNVLSTPYT (SEQ ID NO: 6) | VLSTPY (SEQ ID NO: 18) | QNVLSTPY (SEQ ID NO: 24) | QNVLSTPYT (SEQ ID NO: 6) |

VH Sequence:

(SEQ ID NO: 26)

QVQLQQSGPELVKPGASVKISCKTSGYTFTEYTMHWVKQSHGKSLEWIGSFNPDSGGTSYNQKFKGKATLTVDKSSSTAYMELRSLTSEDSAVYYCARDDGYSTRYWYFDVWGAGTTVTSS

VL Sequence:

(SEQ ID NO: 27)

DIQMTQSPASLSASVGETVTITCGASENIYGALNWFQRKQGKSPQLLIYGATILADGMSSRFSGSGSGRQYSLKISSLHPDDVATYYCQNVLSTPYTFGGGTKLEIK

TABLE 2

Antibody 2J21 CDR Sequences

| | | Exemplary | IMGT | Kabat | Chothia | Contact | AbM |
|---|---|---|---|---|---|---|---|
| VH CDR Seq. | VH CDR1 | GYTFTEYIMH (SEQ ID NO: 28) | GYTFTEYI (SEQ ID NO: 30) | EYIMH (SEQ ID NO: 32) | GYTFTEY (SEQ ID NO: 14) | TEYIMH (SEQ ID NO: 96) | GYTFTEYIMH (SEQ ID NO: 28) |
| | VH CDR2 | NIDPNTGGTSYNQKFKG (SEQ ID NO: 29) | IDPNTGGT (SEQ ID NO: 31) | NIDPNTGGTSYNQKFKG (SEQ ID NO: 29) | PNTG (SEQ ID NO: 33) | WIGNIDPNTGGTS (SEQ ID NO: 34) | NIDPNTGGTS (SEQ ID NO: 35) |
| | VH CDR3 | DDGYSTRYWYFDV (SEQ ID NO: 3) | ARDDGYSTRYWYFDV (SEQ ID NO: 9) | DDGYSTRYWYFDV (SEQ ID NO: 3) | DGYSTRYWYFD (SEQ ID NO: 16) | ARDDGYSTRYWYFD (SEQ ID NO: 21) | DDGYSTRYWYFDV (SEQ ID NO: 3) |
| VL CDR Seq. | VL CDR1 | GASENIYGALN (SEQ ID NO: 4) | ENIYGA (SEQ ID NO: 10) | GASENIYGALN (SEQ ID NO: 4) | SENIYGA (SEQ ID NO: 17) | YGALNWY (SEQ ID NO: 22) | GASENIYGALN (SEQ ID NO: 4) |
| | VL CDR2 | GATNLAD (SEQ ID NO: 13) | GAT (SEQ ID NO: 11) | GATNLAD (SEQ ID NO: 13) | GAT (SEQ ID NO: 11) | LLIYGATNLA (SEQ ID NO: 23) | GATNLAD (SEQ ID NO: 13) |
| | VL CDR3 | QNVLSTPYT (SEQ ID NO: 6) | QNVLSTPYT (SEQ ID NO: 6) | QNVLSTPYT (SEQ ID NO: 6) | VLSTPY (SEQ ID NO: 18) | QNVLSTPY (SEQ ID NO: 24) | QNVLSTPYT (SEQ ID NO: 6) |

VH Sequence:

(SEQ ID NO: 36)

EVQLQQSGPELVKPGASVKISCKTSGYTFTEYIMHWVKQSHGKSLEWIGNIDPNTGGTSYNQKFKGKATLTVDKSSITAFMELRSLTSEDSAVYYCARDDGYSTRYWYFDVWGAGTTVTSS

VL Sequence:

(SEQ ID NO: 37)

DIQMTQSPPSLSASVGETVTITCGASENIYGALNWYQRKQGKSPQLLIYGATNLADGMSSRFSGSGSGRQYSLKISSLHPDDVATYYCQNVLSTPYTFGGGTKLEIK

TABLE 3

Antibody 4A2 CDR Sequences

|  |  | Exemplary | IMGT | Kabat | Chothia | Contact | AbM |
|---|---|---|---|---|---|---|---|
| VH CDR Seq. | VH CDR1 | GYTFTEYTMY (SEQ ID NO: 38) | GYTFTEYT (SEQ ID NO: 7) | EYTMY (SEQ ID NO: 41) | GYTFTEY (SEQ ID NO: 14) | TEYTMY (SEQ ID NO: 44) | GYTFTEYTMY (SEQ ID NO: 38) |
|  | VH CDR2 | GFNPNYGGASYNQKFKD (SEQ ID NO: 39) | FNPNYGGA (SEQ ID NO: 40) | GFNPNYGGASYNQKFKD (SEQ ID NO: 42) | PNYG (SEQ ID NO: 43) | WIGGFNPNYGGAS (SEQ ID NO: 45) | GFNPNYGGAS (SEQ ID NO: 46) |
|  | VH CDR3 | DDGYSTRYWYFDV (SEQ ID NO: 3) | ARDDGYSTRYWYFDV (SEQ ID NO: 9) | DDGYSTRYWYFDV (SEQ ID NO: 3) | DGYSTRYWYFD (SEQ ID NO: 16) | ARDDGYSTRYWYFD (SEQ ID NO: 21) | DDGYSTRYWYFDV (SEQ ID NO: 3) |
| VL CDR Seq. | VL CDR1 | GASENIYGALN (SEQ ID NO: 4) | ENIYGA (SEQ ID NO: 10) | GASENIYGALN (SEQ ID NO: 4) | SENIYGA (SEQ ID NO: 17) | YGALNWY (SEQ ID NO: 22) | GASENIYGALN (SEQ ID NO: 4) |
|  | VL CDR2 | GATNLAD (SEQ ID NO: 13) | GAT (SEQ ID NO: 11) | GATNLAD (SEQ ID NO: 13) | GAT (SEQ ID NO: 11) | LLIYGATNLA (SEQ ID NO: 23) | GATNLAD (SEQ ID NO: 13) |
|  | VL CDR3 | QNVLSTPYT (SEQ ID NO: 6) | QNVLSTPYT (SEQ ID NO: 6) | QNVLSTPYT (SEQ ID NO: 6) | VLSTPY (SEQ ID NO: 18) | QNVLSTPY (SEQ ID NO: 24) | QNVLSTPYT (SEQ ID NO: 6) |

VH Sequence:

(SEQ ID NO: 47)

EVQLQQSGPELVKPGTSVKISCKTSGYTFTEYTMYWVKQSHGKSLEWIGGFNPNYGGASYNQKFKDKATLTVDKSSSTAYMELRSLTSEDSAVYYCARDDG
YSTRYWYFDVWGAGTTVTVSS

VL Sequence:

(SEQ ID NO: 48)

DIQMTQSPASLSASVGETVTITCGASENIYGALNWYQRKQGKSPQLLIYGATNLADGMSSRFSGSGSGRQYSLKISSLHPDDVATYYCQNVLSTPYTFGGG
TKLEIK

In some embodiments, the antibodies provided herein comprise a VH region or VH domain In other embodiments, the antibodies provided herein comprise a VL region or VL chain. In some embodiments, the antibodies provided herein have a combination of (i) a VH domain or VH region; and/or (ii) a VL domain or VL region.

In some embodiments, an antibody provided herein comprises or consists of six CDRs, for example, VH CDR1, VH CDR2, VH CDR3, VL CDR1, VL CDR2, and/or VL CDR3 identified in Tables 1-3. In some embodiments, an antibody provided herein can comprise less than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3 identified in Tables 1-3. In some embodiments, the antibody comprises or consists of one, two, three, four, or five CDRs selected from the group consisting of VH CDR1, VH CDR2, VH CDR3, VL CDR1, VL CDR2, and/or VL CDR3 of the murine monoclonal antibody selected from the group consisting of: (a) the antibody designated 3I13; (b) the antibody designated 2J21; (c) the antibody designated; (d) the antibody designated 4A2; described herein. Accordingly, in some embodiments, the antibody comprises or consists of one, two, three four or five CDRs of anyone of the VH CDR1, VH CDR2, VH CDR3, VL CDR1, VL CDR2, and/or VL CDR3 identified in Tables 1-3.

In some embodiments, the antibodies provided herein comprise one or more (e.g., one, two or three) VH CDRs listed in Tables 1-3. In other embodiments, the antibodies provided herein comprise one or more (e.g., one, two or three) VL CDRs listed in Tables 1-3. In yet other embodiments, the antibodies provided herein comprise one or more (e.g., one, two or three) VH CDRs listed in Tables 1-3 and one or more VL CDRs listed in Tables 1-3. Accordingly, in some embodiments, the antibodies comprise a VH CDR1 having the amino acid sequence of any one of SEQ ID NOS:1, 7, 12, 14, 19, 96, 28, 30, 32, 38, 41, and 44. In some embodiments, the antibodies comprise a VH CDR2 having the amino acid sequence of any one of SEQ ID NOS:2, 8, 15, 20, 25, 29, 31, 33, 34, 35, 39, 40, 42, 43, 45, and 46. In some embodiments, the antibodies comprise a VH CDR3 having the amino acid sequence of any one of SEQ ID NOS:3, 9, 16, and 21. In some embodiments, the antibodies comprise a VH CDR1 and/or a VH CDR2 and/or a VH CDR3 independently selected from a VH CDR1, VH CDR2, VH CDR3 as depicted in any one of the amino acid sequences depicted in Table 1-3. In some embodiments, the antibodies comprise a VL CDR1 having the amino acid sequence of any one of SEQ ID NOS:4, 10, 17, and 22. In another embodiment, the antibodies comprise a VL CDR2 having the amino acid sequence of any one of SEQ ID NOS:5, 11, 13, and 23. In some embodiments, the antibodies comprise a VL CDR3 having the amino acid sequence of any one of SEQ ID NOS:6, 18, and 24. In some embodiments, the antibodies comprise a VL CDR1 and/or a VL CDR2 and/or a VL CDR3 independently selected from a VL CDR1, VL CDR2, VL CDR3 as depicted in any one of the amino acid sequences depicted in Tables 1-3.

In some embodiments, the antibodies provided herein comprise a heavy chain variable (VH) region comprising: (1) a VH CDR1 having an amino acid sequence selected from the group consisting of: (i) SEQ ID NO:1, 28, or 38, (ii) SEQ ID NO:7 or 30, (iii) SEQ ID NO:12, 32 or 41, (iv) SEQ ID NO:14 (v) SEQ ID NO:19 96, or 44; (2) a VH CDR2 having an amino acid sequence selected from the group consisting of: (i) SEQ ID NO:2, 29 or 39, (ii) SEQ ID NO:8, 31 or 40, (iii) SEQ ID NO:2, 29 or 42, (iv) SEQ ID NO:15, 33 or 43 (v) SEQ ID NO:20, 34 or 45, (vi) SEQ ID NO: 25, 35 or 46; and (3) a VH CDR3 having an amino acid sequence selected from the group consisting of: (i) SEQ ID NO:3, (ii) SEQ ID NO:9, (iii) SEQ ID NO:16, and (iv) SEQ ID NO:21; and/or a light chain variable (VL) region comprising: (1) a VL CDR1 having an amino acid sequence selected from the group consisting of: (i) SEQ ID NO:4, (ii) SEQ ID NO:10, (iii) SEQ ID NO:17, and (iv) SEQ ID NO:22; (2) a VL CDR2 having an amino acid sequence selected from the group consisting of: (i) SEQ ID NO:5 or 13, (ii) SEQ ID NO:11, (iii) SEQ ID NO:13, (iv) SEQ ID NO:23; and (3) a VL CDR3 having an amino acid sequence selected from the group consisting of: (i) SEQ ID NO:6, (ii) SEQ ID NO:18, and (iii) SEQ ID NO:24.

In some embodiments, the antibodies provided herein comprise a heavy chain variable (VH) region comprising: (1) a VH CDR1 having an amino acid sequence selected from the group consisting of: (i) SEQ ID NO:1, 28 or 38, (ii) SEQ ID NO:7 or 30, (iii) SEQ ID NO:12, 32 or 41, (iv) SEQ ID NO:14, (v) SEQ ID NO:19 96, or 44, and (vi) SEQ ID NO:1, 28 or 38; (2) a VH CDR2 having an amino acid sequence selected from the group consisting of: (i) SEQ ID NO:2, 29 or 39, (ii) SEQ ID NO:8, 31 or 40, (iii) SEQ ID NO:2, 29 or 42, (iv) SEQ ID NO:15, 33 or 43, (v) SEQ ID NO:20, 34 or 45 and (vi) SEQ ID NO:25, 35 or 46; and (3) a VH CDR3 having an amino acid sequence selected from the group consisting of: (i) SEQ ID NO:3, (ii) SEQ ID NO:9, (iii) SEQ ID NO:16, and (iv) SEQ ID NO:21.

In some embodiments, the antibodies provided herein comprise a light chain variable (VL) region comprising: (1) a VL CDR1 having an amino acid sequence selected from the group consisting of: (i) SEQ ID NO:4, (ii) SEQ ID NO:10, (iii) SEQ ID NO:17, and (iv) SEQ ID NO 22; (2) a VL CDR2 having an amino acid sequence selected from the group consisting of: (i) SEQ ID NO:5 or 13, (ii) SEQ ID NO:11, (iii) SEQ ID NO:13, and (iv) SEQ ID NO:23; and (3) a VL CDR3 having an amino acid sequence selected from the group consisting of: (i) SEQ ID NO:6, (ii) SEQ ID NO:18, and (iii) SEQ ID NO:24.

Also provided herein are antibodies comprising one or more VH CDRs and one or more (e.g., one, two or three) VL CDRs listed in Tables 1-3. In particular, provided herein is an antibody comprising a VH CDR1 (SEQ ID NOS:1, 7, 12, 14, 19, 96, 28, 30, 32, 38, 41, and 44) and a VL CDR1 (SEQ ID NOS:4, 10, 17, and 22); a VH CDR1 (SEQ ID NOS:1, 7, 12, 14, 19, 96, 28, 30, 32, 38, 41, and 44) and a VL CDR2 (SEQ ID NOS:5, 1, 13, and 23); a VH CDR1 (SEQ ID NOS:1, 7, 12, 14, 19, 96, 28, 30, 32, 38, 41, and 44) and VL CDR3 (SEQ ID NOS: 6, 18, and 24); a VH CDR2 (SEQ ID NOS:2, 8, 15, 20, 25, 29, 31, 33, 34, 35, 39, 40, 42, 43, 45, and 46) and a VL CDR1 (SEQ ID NOS:4, 10, 17, and 22); a VH CDR2 (SEQ ID NOS:2, 8, 15, 20, 25, 29, 31, 33, 34, 35, 39, 40, 42, 43, 45, and 46) and a VL CDR3 (SEQ ID NOS:6, 18, and 24); a VH CDR3 (SEQ ID NOS:3, 9, 16, and 21) and a VL CDR1 (SEQ ID NOS:4, 10, 17, and 22); a VH CDR3 (SEQ ID NOS:3, 9, 16, and 21) and a VL CDR2 (SEQ ID NOS: 5, 11, 13, and 23); a VH CDR3 (SEQ ID NOS:3, 9, 16, and 21) and a VL CDR3 (SEQ ID NOS: 6, 18, and 24); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46) and a VL CDR1 (SEQ ID NOS: 4, 10, 17, and 22); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46) and a VL CDR3 (SEQ ID NOS: 6, 18, and 24); a VH CDR2 (SEQ ID NOS:2, 8, 15, 20, 25, 29, 31, 33, 34, 35, 39, 40, 42, 43, 45, and 46), a VH CDR3 (SEQ ID NOS: 3, 9, 16, and 21) and a VL CDR1 (SEQ ID NOS: 4, 10, 17, and 22), a VH CDR2 (SEQ ID NOS:2, 8, 15, 20, 25, 29, 31, 33, 34, 35, 39, 40, 42, 43, 45, and 46), a VH CDR3 (SEQ ID NOS: 6, 18, and 24) and a VL CDR2 (SEQ ID NOS:5, 11, 13, and 23); a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21) and a VL CDR3 (SEQ ID NOS:6, 18, and 24); a VH CDR1 (SEQ ID NOS:1, 7, 12, 14, 19, 96, 28, 30, 32, 38, 41, and 44), a VL CDR1 (SEQ ID NOS: 4, 10, 17, and 22) and a VL CDR2 (SEQ ID NOS: 5, 11, 13, and 23); a VH CDR1 (SEQ ID NOS: 1, 7, 12, 14, 19, 96, 28, 30, 32, 38, 41, and 44), a VL CDR1 (SEQ ID NOS: 4, 10, 17, and 22) and a VL CDR3 (SEQ ID NOS: 6, 18, and 24); a VH CDR1 (SEQ ID NOS: 1, 7, 12, 14, 19, 96, 28, 30, 32, 38, 41, and 44), a VL CDR2 (SEQ ID NOS: 5, 11, 13, and 23) and a VL CDR3 (SEQ ID NOS: 6, 18, and 24); a VH CDR2 (SEQ ID NOS: 2, 8, 15, 20, 25, 29, 31, 33, 34, 35, 39, 40, 42, 43, 45, and 46), a VL CDR1 (SEQ ID NOS: 4, 10, 17, and 22) and a VL CDR2 (SEQ ID NOS: 5, 11, 13, and 23); a VH CDR2 (SEQ ID NOS: 2, 8, 15, 20, 25, 29, 31, 33, 34, 35, 39, 40, 42, 43, 45, and 46), a VL CDR2 (SEQ ID NOS: 5, 11, 13, and 23) and a VL CDR3 (SEQ ID NOS: 6, 18, and 24); a VH CDR3 (SEQ ID NOS: 3, 9, 16, and 21), a VL CDR1 (SEQ ID NOS: 4, 10, 17, and 22) and a VL CDR2 (SEQ ID NOS: 5, 11, 13, and 23); a VH CDR3 (SEQ ID NOS: 3, 9, 16, and 21), a VL CDR1 (SEQ ID NOS: 4, 10, 17, and 22) and a VL CDR3 (SEQ ID NOS: 6, 18, and 24); a VH CDR3 (SEQ ID NOS: 3, 9, 16, and 21), a VL CDR2 (SEQ ID NOS: 5, 11, 13, and 23) and a VL CDR3 (SEQ ID NOS: 6, 18, and 24 7); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21) and a VL CDR1 (SEQ ID NOS: 4, 10, 17, and 22); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21) and a VL CDR2 (SEQ ID NOS: 5, 11, 13, and 23); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21), and a VL CDR3 (SEQ ID NOS: 6, 18, and 24); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46), a VL CDR1 (SEQ ID NOS: 4, 10, 17, and 22) and a VL CDR2 (SEQ ID NOS: 5, 11, 13, and 23); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46), a VL CDR1 (SEQ ID NOS: 4, 10, 17, and 22) and a VL CDR3 (SEQ ID NOS: 6, 18, and 24); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46), a VL CDR2 (SEQ ID NOS: 5, 11, 13, and 23) and a VL CDR3 (SEQ ID NOS: 6, 18, and 24); a VH CDR1 (SEQ ID NOS: 1, 7, 12, 14, 19, 96, 28, 30, 32, 38, 41, and 44), a VH CDR3 (SEQ ID NOS: 3, 9, 16, and 21), a VL CDR1 (SEQ ID NOS: 4, 10, 17, and 22) and a VL CDR2 (SEQ ID NOS: 5, 11, 13, and 23); a VH CDR1 (SEQ ID NOS: 1, 7, 12, 14, 19, 96, 28, 30, 32, 38, 41, and 44), a VH CDR3 (SEQ ID NOS: 3, 9, 16, and 21), a VL CDR1 (SEQ ID NOS: 4, 10, 17, and 22) and a VL CDR3 (SEQ ID NOS: 6, 18, and 24); a VH CDR1 (SEQ ID NOS: 1, 7, 12, 14, 19, 96, 28, 30, 32, 38, 41, and 44), a VH CDR3 (SEQ ID NOS:3, 9, 16, and 21), a VL CDR2 (SEQ ID NOS: 5, 11, 13, and 23) and a VL CDR3 (SEQ ID NOS: 6, 18, and 24); a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21), a VL CDR1 (SEQ ID NOS: 4, 10, 17, and 22) and a VL CDR2 (SEQ ID NOS: 5, 11, 13, and 23); a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21), a VL CDR1 (SEQ ID NOS: 4, 10, 17, and 22); a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21), a VL CDR2 (SEQ ID NOS: 5, 11, 13, and 23) and a VL CDR3 (SEQ ID NOS: 6, 18, and 24); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21), a VL CDR1 (SEQ ID NOS: 4, 10, 17, and 22) and a VL CDR2 (SEQ ID NOS: 5, 11, 13, and 23); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21), a VL CDR1 (SEQ ID NOS: 4, 10, 17, and 22) and a VL CDR3 (SEQ ID NOS: 6, 18, and 24); a VH CDR1 (SEQ ID NOS: 1, 7, 12, 14, 19, 96, 28, 30, 32, 38, 41, and 44), a VH CDR2 (SEQ ID NOS: 2, 8, 15, 20, 25, 29, 31, 33, 34, 35, 39, 40, 42, 43, 45, and 46), a VL CDR1 (SEQ ID NOS: 4, 10, 17, and 22), a VL CDR2 (SEQ ID NOS: 5, 11, 13, and 23), and a VL CDR3 (SEQ ID NOS: 6, 18, and 24); a VH CDR1 (SEQ ID NOS: 1, 7, 12, 14, 19, 96, 28, 30, 32, 38, 41, and 44), a VH CDR3 (SEQ ID NOS: 3, 9, 16, and 21), a VL CDR1 (SEQ ID NOS: 4, 10, 17, and 22), a VL CDR2 (SEQ ID NOS: 5, 11, 13, and 23), and a VL CDR3 (SEQ ID NOS: 6, 18, and 24); a VH CDR2 (SEQ ID NOS: 2, 8, 15, 20, 25, 29, 31, 33, 34, 35, 39, 40, 42, 43, 45, and 46), a VH CDR3 (SEQ ID NOS: 3, 9, 16, and 21), a VL CDR1 (SEQ ID NOS: 4, 10, 17, and 22), a VL CDR2 (SEQ ID NOS: 5, 11, 13, and 23) or any combination thereof of the VH CDRs and VL CDRs listed in Tables 1-3.

In yet another aspect, the CDRs disclosed herein include consensus sequences derived from groups of related antibodies (see, e.g., Tables 1-3 and FIGS. 2A-2B). As described herein, a "consensus sequence" refers to amino acid sequences having conserved amino acids common among a number of sequences and variable amino acids that vary within given amino acid sequences. The CDR consensus sequences provided include CDRs corresponding to CDRH1, CDRH2, CDRH3, CDRL1, CDRL2 and/or CDRL3. Consensus sequences of CDRs of anti-beta klotho antibodies are shown in FIGS. 2A-2B.

Accordingly, in certain embodiments, an antibody or fragment thereof described herein comprises: (a) a heavy chain variable (VH) region comprising: (1) a VH CDR1 having an amino acid sequence GYTFTEYXMX (SEQ ID NO:49), wherein X at positions 8 and 10 is an independently selected naturally occurring amino acid; (2) a VH CDR2 having an amino acid sequence xxxPxxGGxSYNQKFKx (SEQ ID NO:50), wherein X at positions 1, 2, 3, 5, 6, 9 or 17 is an independently selected naturally occurring amino acid; and (3) a VH CDR3 having an amino acid sequence DDGYSTRYWYFDV (SEQ ID NO:51); and/or (b) a light chain variable (VL) region comprising: (1) a VL CDR1 having an amino acid sequence GASENIYGALN (SEQ ID NO:52); (2) a VL CDR2 having an amino acid sequence GATXLAD (SEQ ID NO:53), wherein X is a naturally occurring amino acid; and (3) a VL CDR3 having an amino acid sequence QNVLSTPYT (SEQ ID NO:54).

In another embodiment, an antibody or fragment thereof described herein comprises: (a) a heavy chain variable (VH) region comprising: (1) a VH CDR1 having an amino acid sequence GYTFTEYXMX (SEQ ID NO:49), wherein X at position 8 is T or I, and X at position 10 is H or Y; (2) a VH CDR2 having an amino acid sequence xxxPxxGGxSYN-QKFKx (SEQ ID NO:50), wherein X at position 1 is N, G, or S; X at position 2 is I or F; X at position 3 is D or N; X at position 5 is D or N; X at position 6 is T, Y, or S; X at position 9 is T or A; and X at position 17 is G or D; and (3) a VH CDR3 having an amino acid sequence DDGYSTRY-WYFDV (SEQ ID NO:51); and/or (b) a light chain variable (VL) region comprising: (1) a VL CDR1 having an amino acid sequence GASENIYGALN (SEQ ID NO:52); (2) a VL CDR2 having an amino acid sequence GATXLAD (SEQ ID NO:53), wherein X is N or I; and (3) a VL CDR3 having an amino acid sequence QNVLSTPYT (SEQ ID NO:54).

In another embodiment, an antibody or fragment thereof described herein comprises a heavy chain variable (VH) region comprising: (1) a VH CDR1 having an amino acid sequence GYTFTEYXMX (SEQ ID NO:49), wherein X at positions 8 and 10 is an independently selected naturally occurring amino acid; (2) a VH CDR2 having an amino acid sequence xxxPxxGGxSYNQKFKx (SEQ ID NO:50), wherein X at positions 1, 2, 3, 5, 6, 9 or 17 is an independently selected naturally occurring amino acid; and (3) a VH CDR3 having an amino acid sequence DDGYSTRY-WYFDV (SEQ ID NO:51).

In another embodiment, an antibody or fragment thereof described herein comprises a heavy chain variable (VH) region comprising: (1) a VH CDR1 having an amino acid sequence GYTFTEYXMX (SEQ ID NO:49), wherein X at position 8 is T or I, and X at position 10 is H or Y; (2) a VH CDR2 having an amino acid sequence xxxPxxGGxSYN-QKFKx (SEQ ID NO:50), wherein X at position 1 is N, G, or S; X at position 2 is I or F; X at position 3 is D or N; X at position 5 is D or N; X at position 6 is T, Y, or S; X at position 9 is T or A; and X at position 17 is G or D); and (3) a VH CDR3 having an amino acid sequence DDGYSTRY-WYFDV (SEQ ID NO:51).

In another embodiment, an antibody or fragment thereof described herein comprises a light chain variable (VL) region comprising: (1) a VL CDR1 having an amino acid sequence GASENIYGALN (SEQ ID NO:52); (2) a VL CDR2 having an amino acid sequence GATXLAD (SEQ ID NO:53), wherein X is a naturally occurring amino acid and (3) a VL CDR3 having an amino acid sequence QNVLST-PYT (SEQ ID NO:54).

In another embodiment, an antibody or fragment thereof described herein comprises a light chain variable (VL) region comprising: (1) a VL CDR1 having an amino acid sequence GASENIYGALN (SEQ ID NO:52); (2) a VL CDR2 having an amino acid sequence GATXLAD (SEQ ID NO:53), wherein X is N or I; and (3) a VL CDR3 having an amino acid sequence QNVLSTPYT (SEQ ID NO:54).

In another embodiment, an antibody or fragment thereof described herein comprises: (a) a heavy chain variable (VH)

region comprising: (1) a VH CDR1 having an amino acid sequence GYTFTEYXMX (SEQ ID NO:49), wherein X at positions 8 and 10 is an independently selected naturally occurring amino acid; (2) a VH CDR2 having an amino acid sequence xxxPxxGGxSYNQKFKx (SEQ ID NO:50), wherein X at positions 1, 2, 3, 5, 6, 9 or 17 is an independently selected naturally occurring amino acid; and (3) a VH CDR3 having an amino acid sequence DDGYSTRY-WYFDV (SEQ ID NO:51); and (b) a light chain variable (VL) region comprising: (1) a VL CDR1 having an amino acid sequence of SEQ ID NO:4, (2) a VL CDR2 having an amino acid sequence of SEQ ID NO:5, and (3) a VL CDR3 having an amino acid sequence of SEQ ID NO:6.

In another embodiment, an antibody or fragment thereof described herein comprises: (a) a heavy chain variable (VH) region comprising: (1) a VH CDR1 having an amino acid sequence GYTFTEYXMX (SEQ ID NO:49), wherein X at positions 8 and 10 is an independently selected naturally occurring amino acid; (2) a VH CDR2 having an amino acid sequence xxxPxxGGxSYNQKFKx (SEQ ID NO:50), wherein X at positions 1, 2, 3, 5, 6, 9 or 17 is an independently selected naturally occurring amino acid; and (3) a VH CDR3 having an amino acid sequence DDGYSTRY-WYFDV (SEQ ID NO:51); and (b) a light chain variable (VL) region comprising: (1) a VL CDR1 having an amino acid sequence of SEQ ID NO:4, (2) a VL CDR2 having an amino acid sequence of SEQ ID NO:13, and (3) a VL CDR3 having an amino acid sequence of SEQ ID NO:6.

In certain embodiments, an antibody or fragment thereof described herein comprises a VH region that comprises: (1) a VH FR1 having an amino acid sequence selected from the group consisting of SEQ ID NOS: 91, 92, 93, 94, and 95; (2) a VH FR2 having an amino acid sequence selected from the group consisting of SEQ ID NOS: 97, 98, 99, 100, 101, 102, 106, 107, 108, 109, 110, 111, 112, 113, and 217; (3) a VH FR3 having an amino acid sequence selected from the group consisting of SEQ ID NOS: 117, 118, 119, 120, 121, 122, 123, 125, 126, 127, 128, 129, 130, 131, 215, 218, 219, 222, 223, 224, 225, 226, and 227; and/or (4) a VH FR4 having an amino acid of SEQ ID NOS: 133. Accordingly, in some aspects, the humanized antibody comprises a VH region that includes a VH FR1 having an amino acid sequence selected from the group consisting of SEQ ID NOS: 91, 92, 93, 94, and 95. In some aspects, the humanized antibody comprises a VH region that includes a VH FR2 having an amino acid sequence selected from the group consisting of SEQ ID NOS: 97, 98, 99, 100, 101, 102, 106, 107, 108, 109, 110, 111, 112, 113, and 217. In some aspects, the humanized antibody comprises a VH region that includes a VH FR3 having an amino acid sequence selected from the group consisting of SEQ ID NOS: 117, 118, 119, 120, 121, 122, 123, 125, 126, 127, 128, 129, 130, 131, 215, 218, 219, 222, 223, 224, 225, 226, and 227. In some aspects, the humanized antibody comprises a VH region that includes a VH FR4 having an amino acid of SEQ ID NOS: 133.

In certain embodiments, an antibody of fragment thereof described herein comprises a VL region that comprises: (1) a VL FR1 having an amino acid sequence selected from the group consisting of SEQ ID NOS: 135 and 136; (2) a VL FR2 having an amino acid sequence selected from the group consisting of SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213; (3) a VL FR3 having an amino acid sequence selected from the group consisting of SEQ ID NOS: 154, 155, 156, 157, 158, 159, 160, 228, 229, 230, 231, and 232; and/or (4) a VL FR4 having an amino acid of SEQ ID NOS: 163. Accordingly, in some aspects, the humanized antibody comprises a VL region that includes a VL FR1 having an amino acid sequence selected from the group consisting of SEQ ID NOS: 135 and 136. In some aspects, the humanized antibody comprises a VL region that includes a VL FR2 having an amino acid sequence selected from the group consisting of SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213. In some aspects, the humanized antibody comprises a VL region that includes a VL FR3 having an amino acid sequence selected from the group consisting of SEQ ID NOS: 154, 155, 156, 157, 158, 159, 160, 228, 229, 230, 231, and 232. In some aspects, the humanized antibody comprises a VL region that includes a VL FR4 having an amino acid of SEQ ID NOS: 163.

In certain embodiments, an antibody of fragment thereof described herein comprises a VH region and a VL region, wherein the VH region further comprises: (1) a VH FR1 having an amino acid sequence selected from the group consisting of SEQ ID NOS: 91, 92, 93, 94, and 95; (2) a VH FR2 having an amino acid sequence selected from the group consisting of SEQ ID NOS: 97, 98, 99, 100, 101, 102, 106, 107, 108, 109, 110, 111, 112, 113, and 217; (3) a VH FR3 having an amino acid sequence selected from the group consisting of SEQ ID NOS: 117, 118, 119, 120, 121, 122, 123, 125, 126, 127, 128, 129, 130, 131, 215, 218, 219, 222, 223, 224, 225, 226, and 227; and/or (4) a VH FR4 having an amino acid sequence of SEQ ID NOS: 133; and wherein the VL region further comprises: (1) a VL FR1 having an amino acid sequence selected from the group consisting of SEQ ID NOS: 135 and 136; (2) a VL FR2 having an amino acid sequence selected from the group consisting of SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213; (3) a VL FR3 having an amino acid sequence selected from the group consisting of SEQ ID NOS: 154, 155, 156, 157, 158, 159, 160, 228, 229, 230, 231, and 232; and/or (4) a VL FR4 having an amino acid of SEQ ID NO: 163.

Also provided herein are antibodies comprising one or more (e.g., one, two, three or four) VH FRs and one or more (e.g., one, two, three or four) VL FRs listed in Table 10. In particular, provided herein is an antibody comprising a VH FR1 (SEQ ID NOS: 91, 92, 93, 94, and 95) and a VL FR1 (SEQ ID NOS: 135 and 136); a VH FR1 (SEQ ID NOS: 91, 92, 93, 94, and 95) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95) and a VL FR4 (SEQ ID NO: 163);

a VH FR2 (SEQ ID NOS: 97, 98, 99, 100, 101, 102, 106, 107, 108, 109, 110, 111, 112, 113, and 217) and a VL FR1 (SEQ ID NOS: 135 and 136); a VH FR2 (SEQ ID NOS: 97, 98, 99, 100, 101, 102, 106, 107, 108, 109, 110, 111, 112, 113, and 217) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR2 (SEQ ID NOS: 97, 98, 99, 100, 101, 102, 106, 107, 108, 109, 110, 111, 112, 113, and 217) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217) and a VL FR4 (SEQ ID NO: 163);

a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR1 (SEQ ID NOS: 135 and 136); a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR3 (SEQ ID NOS: 154, 155, 156, 157, 158, 159, 160, 228, 229, 230, 231, and 232); a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR4 (SEQ ID NO: 163);

a VH FR4 (SEQ ID NOS:133) and a VH FR1 (SEQ ID NOS: 91, 92, 93, 94, and 95); a VH FR4 (SEQ ID NOS:133) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR4 (SEQ ID NOS:133) and a VL FR3 (SEQ ID NOS: 154, 155, 156, 157, 158, 159, 160, 228, 229, 230, 231, and 232); a VH FR4 (SEQ ID NOS:133) and a VL FR4 (SEQ ID NO: 163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217) and a VL FR1 (SEQ ID NOS: 135 and 136); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217) and a VL FR4 (SEQ ID NO:163);

a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR1 (SEQ ID NOS: 135 and 136), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR4 (SEQ ID NO:163);

a VH FR1 (SEQ ID NOS: 91, 92, 93, 94, and 95), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VL FR1 (SEQ ID NOS: 135 and 136) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VL FR1 (SEQ ID NOS: 135 and 136) and a VL FR4 (SEQ ID NO: 163); a VH FR1 (SEQ ID NOS: 91, 92, 93, 94, and 95), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163);

a VH FR2 (SEQ ID NOS: 97, 98, 99, 100, 101, 102, 106, 107, 108, 109, 110, 111, 112, 113, and 217), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR2 (SEQ ID NOS: 97, 98, 99, 100, 101, 102, 106, 107, 108, 109, 110, 111, 112, 113, and 217), a VL FR1 (SEQ ID NOS: 135 and 136) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VL FR1 (SEQ ID NOS: 135 and 136) and a VL FR4 (SEQ ID NO: 163); a VH FR2 (SEQ ID NOS: 97, 98, 99, 100, 101, 102, 106, 107, 108, 109, 110, 111, 112, 113, and 217), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR2 (SEQ ID NOS: 997, 98, 99, 100, 101, 102, 106, 107, 108, 109, 110, 111, 112, 113, and 217), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163);

a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR3 (SEQ ID NOS: 154, 155, 156, 157, 158, 159, 160, 228, 229, 230, 231, and 232); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR4 (SEQ ID NO: 163); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163);

a VH FR4 (SEQ ID NO: 133), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR4 (SEQ ID NO: 133), a VL FR1 (SEQ ID NOS: 135 and 136) and a VL FR3 (SEQ ID NOS: 154, 155, 156, 157, 158, 159, 160, 228, 229, 230, 231, and 232); a VH FR4 (SEQ ID NO: 133), a VL FR1 (SEQ ID NOS: 135 and 136) and a VL FR4 (SEQ ID NO: 163); a VH FR4 (SEQ ID NO: 133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR4 (SEQ ID NO: 133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR1 (SEQ ID NOS: 135 and 136); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227) and a VL FR4 (SEQ ID NO: 163); a VH FR1 (SEQ ID NOS: 91, 92, 93, 94, and 95), a VH FR1 (SEQ ID NOS: 91, 92, 93, 94, and 95, a VH FR2 (SEQ ID NOS: 97, 98, 99, 100, 101, 102, 106, 107, 108, 109, 110, 111, 112, 113, and 217), a VH FR4 (SEQ ID NO: 133) and a VL FR1 (SEQ ID NOS: 135 and 136); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO: 133) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO: 133) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO: 133) and a VL FR4 (SEQ ID NO: 163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR1 (SEQ ID NOS: 135 and 136); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR4 (SEQ ID NO: 163);

a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR1 (SEQ ID NOS: 135 and 136); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR4 (SEQ ID NO: 163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR1 (SEQ ID NOS: 135 and 136) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR1 (SEQ ID NOS: 135 and 136) and a VL FR4 (SEQ ID NO: 163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR4 (SEQ ID NO: 163); a VH FR1 (SEQ ID NOS: 91, 92, 93, 94, and 95), a VH FR4 (SEQ ID NO: 133), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR4 (SEQ ID NO: 133), a VL FR1 (SEQ ID NOS: 135 and 136) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR4 (SEQ ID NO: 133), a VL FR1 (SEQ ID NOS: 135 and 136) and a VL FR4 (SEQ ID NO: 163);

a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR4 (SEQ ID NO: 163); a VH FR2 (SEQ ID NOS: 97, 98, 99, 100, 101, 102, 106, 107, 108, 109, 110, 111, 112, 113, and 217), a VH FR4 (SEQ ID NO: 133), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR2 (SEQ ID NOS: 97, 98, 99, 100, 101, 102, 106, 107, 108, 109, 110, 111, 112, 113, and 217), a VH FR4 (SEQ ID NO: 133), a VL FR1 (SEQ ID NOS: 135 and 136) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR4 (SEQ ID NO: 133), a VL FR1 (SEQ ID NOS: 135 and 136) and a VL FR4 (SEQ ID NO:163);

a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133), a VL FR1 (SEQ ID NOS: 135 and 136) and a VL FR3 (SEQ ID NOS: 154, 155, 156, 157, 158, 159, 160, 228, 229, 230, 231, and 232); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136) and a VL FR4 (SEQ ID NO: 163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163); a VH FR1 (SEQ ID NOS: 91, 92, 93, 94, and 95), a VH FR4 (SEQ ID NO: 133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR4 (SEQ ID NO: 133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163);

a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163); a VH FR2 (SEQ ID NOS: 97, 98, 99, 100, 101, 102, 106, 107, 108, 109, 110, 111, 112, 113, and 217), a VH FR4 (SEQ ID NO: 133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR4 (SEQ ID NO: 133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR3 (SEQ ID NOS: 154, 155, 156, 157, 158, 159, 160, 228, 229, 230, 231, and 232) and a VL FR4 (SEQ ID NO: 163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR3 (SEQ ID NOS: 154, 155, 156, 157, 158, 159, 160, 228, 229, 230, 231, and 232) and a VL FR4 (SEQ ID NO: 163); a VH FR1 (SEQ ID NOS: 91, 92, 93, 94, and 95), a VH FR4 (SEQ ID NO:133), a VL FR3 (SEQ ID NOS: 154, 155, 156, 157, 158, 159, 160, 228, 229, 230, 231, and 232) and a VL FR4 (SEQ ID NO: 163);

a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR3 (SEQ ID NOS: 154, 155, 156, 157, 158, 159, 160, 228, 229, 230, 231, and 232) and a VL FR4 (SEQ ID NO:163); a VH FR2 (SEQ ID NOS: 97, 98, 99, 100, 101, 102, 106, 107, 108, 109, 110, 111, 112, 113, and 217), a VH FR4 (SEQ ID NO: 133), a VL FR3 (SEQ ID NOS: 154, 155, 156, 157, 158, 159, 160, 228, 229, 230, 231, and 232) and a VL FR4 (SEQ ID NO: 163);

a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163);

a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133), a VL FR3 (SEQ ID NOS: 154, 155, 156, 157, 158, 159, 160, 228, 229, 230, 231, and 232) and a VL FR4 (SEQ ID NO: 163);

a VH FR1 (SEQ ID NOS: 91, 92, 93, 94, and 95), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163); a VH FR1 (SEQ ID NOS: 91, 92, 93, 94, and 95), a VL FR1 (SEQ ID NOS: 135 and 136), a VL FR3 (SEQ ID NOS: 154, 155, 156, 157, 158, 159, 160, 228, 229, 230, 231, and 232) and a VL FR4 (SEQ ID NO: 163);

a VH FR2 (SEQ ID NOS: 97, 98, 99, 100, 101, 102, 106, 107, 108, 109, 110, 111, 112, 113, and 217), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163); a VH FR2 (SEQ ID NOS: 97, 98, 99, 100, 101, 102, 106, 107, 108, 109, 110, 111, 112, 113, and 217), a VL FR1 (SEQ ID NOS: 135 and 136), a VL FR3 (SEQ ID NOS: 154, 155, 156, 157, 158, 159, 160, 228, 229, 230, 231, and 232) and a VL FR4 (SEQ ID NO: 163); a VH FR2 (SEQ ID NOS: 97, 98, 99, 100, 101, 102, 106, 107, 108, 109, 110, 111, 112, 113, and 217), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232) and a VL FR4 (SEQ ID NO: 163);

a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR3 (SEQ ID NOS: 154, 155, 156, 157, 158, 159, 160, 228, 229, 230, 231, and 232) and a VL FR4 (SEQ ID NO: 163); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232) and a VL FR4 (SEQ ID NO:163);

a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR4 (SEQ ID NO: 133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163); a VH FR4 (SEQ ID NO: 133), a VL FR1 (SEQ ID NOS: 135 and 136), a VL FR3 (SEQ ID NOS: 154, 155, 156, 157, 158, 159, 160, 228, 229, 230, 231, and 232) and a VL FR4 (SEQ ID NO:163); a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR1 (SEQ ID NOS: 135 and 136); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133) and a VL FR4 (SEQ ID NO:163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO: 133), a VL FR1 (SEQ ID NOS: 135 and 136) and a VL FR4 (SEQ ID NO: 163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR3 (SEQ ID NOS: 154, 155, 156, 157, 158, 159, 160, 228, 229, 230, 231, and 232) and a VL FR4 (SEQ ID NO:163);

a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136) and a VL FR3 (SEQ ID NOS:

154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136) and a VL FR4 (SEQ ID NO:163); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO: 163); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR3 (SEQ ID NOS: 154, 155, 156, 157, 158, 159, 160, 228, 229, 230, 231, and 232) and a VL FR4 (SEQ ID NO:163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR1 (SEQ ID NOS: 135 and 136), a VL FR3 (SEQ ID NOS: 154, 155, 156, 157, 158, 159, 160, 228, 229, 230, 231, and 232), and a VL FR4 (SEQ ID NO: 163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR4 (SEQ ID NO:163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR3 (SEQ ID NOS: 154, 155, 156, 157, 158, 159, 160, 228, 229, 230, 231, and 232), and a VL FR4 (SEQ ID NO:163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163); a VH FR1 (SEQ ID NOS: 91, 92, 93, 94, and 95), a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR4 (SEQ ID NO:163); a VH FR1 (SEQ ID NOS: 91, 92, 93, 94, and 95), a VH FR4 (SEQ ID NO:133), a VL FR1 (SEQ ID NOS: 135 and 136), a VL FR3 (SEQ ID NOS: 154, 155, 156, 157, 158, 159, 160, 228, 229, 230, 231, and 232), and a VL FR4 (SEQ ID NO:163); a VH FR1 (SEQ ID NOS: 91, 92, 93, 94, and 95), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163);

a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR4 (SEQ ID NO:163); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR3 (SEQ ID NOS: 154, 155, 156, 157, 158, 159, 160, 228, 229, 230, 231, and 232), and a VL FR4 (SEQ ID NO:163); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163);

a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR4 (SEQ ID NO:163); a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136), a VL FR3 (SEQ ID NOS: 154, 155, 156, 157, 158, 159, 160, 228, 229, 230, 231, and 232), and a VL FR4 (SEQ ID NO:163); a VH FR2 (SEQ ID NOS: 97, 98, 99, 100, 101, 102, 106, 107, 108, 109, 110, 111, 112, 113, and 217), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163);

a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR3 (SEQ ID NOS: 154, 155, 156, 157, 158, 159, 160, 228, 229, 230, 231, and 232); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), and a VL FR4 (SEQ ID NO:163); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136), a VL FR3 (SEQ ID NOS: 154, 155, 156, 157, 158, 159, 160, 228, 229, 230, 231, and 232), and a VL FR4 (SEQ ID NO:163); a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163);

a VH FR1 (SEQ ID NOS: 91, 92, 93, 94, and 95), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163);

a VH FR2 (SEQ ID NOS: 97, 98, 99, 100, 101, 102, 106, 107, 108, 109, 110, 111, 112, 113, and 217), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163);

a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163);

a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), a VL FR3 (SEQ ID NOS: 154, 155, 156, 157, 158, 159, 160, 228, 229, 230, 231, and 232), and a VL FR4 (SEQ ID NO:163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), VL FR1 (SEQ ID NOS: 135 and 136) and a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), VL FR1 (SEQ ID NOS: 135 and 136) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), VL FR1 (SEQ ID NOS: 135 and 136) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), VL FR3 (SEQ ID NOS: 154, 155, 156, 157, 158, 159, 160, 228, 229, 230, 231, and 232) and a VL FR4 (SEQ ID NO:163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), VL FR3 (SEQ ID NOS: 154, 155, 156, 157, 158, 159, 160, 228, 229, 230, 231, and 232) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136), VL FR3 (SEQ ID NOS: 154, 155, 156, 157, 158, 159, 160, 228, 229, 230, 231, and 232) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136), VL FR3 (SEQ ID NOS: 154, 155, 156, 157, 158, 159, 160, 228, 229, 230, 231, and 232) and a VL FR4 (SEQ ID NO:163); a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO: 133), a VL FR1 (SEQ ID NOS: 135 and 136), VL FR3 (SEQ ID NOS: 154, 155, 156, 157, 158, 159, 160, 228, 229, 230, 231, and 232) and a VL FR4 (SEQ ID NO: 163); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO: 163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163);

a VH FR1 (SEQ ID NOS: 91, 92, 93, 94, and 95), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163);

a VH FR1 (SEQ ID NOS: 91, 92, 93, 94, and 95), a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO: 163);

a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163); a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163);

a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136), a VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163);

a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR3 (SEQ ID NOS: 154, 155, 156, 157, 158, 159, 160, 228, 229, 230, 231, and 232); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR4 (SEQ ID NO:133), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163); a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (SEQ ID NO:133), a VL FR1 (SEQ ID NOS: 135 and 136), VL FR2 (SEQ ID NOS: 138, 139, 140, 141, 142, 143, 144, 145, 147, 148, 149, 150, 151, 152, 153, 201, 202, 203, 204, 205, 206, 208, 209, 210, 211, 212 and 213), VL FR3 (SEQ ID NOS: 154, 155, 156, 157, 158, 159, 160, 228, 229, 230, 231, and 232) and a VL FR4 (SEQ ID NO:163); a VH FR1 (SEQ ID NOS: 91, 92, 93, 94, and 95), a VH FR2 (SEQ ID NOS: 97, 98, 99, 100, 101, 102, 106, 107, 108, 109, 110, 111, 112, 113, and 217), a VH FR3 (SEQ ID NOS: 117, 118, 119, 120, 121, 122, 123, 125, 126, 127, 128, 129, 130, 131, 215, 218, 219, 222, 223, 224, 225, 226, and 227), a VH FR4 (133), a VL FR1 (135 and 136), a VL FR2 (138, 139, 140, 141, 142, 143, 144, 145, 147, 148, 149, 150, 151, 152, 153, 201, 202, 203, 204, 205, 206, 208, 209, 210, 211, 212 and 213), a VL FR3 (154, 155, 156, 157, 158, 159, 160, 228, 229, 230, 231, and 232), and a VL FR4 (163); or any combination thereof of the VH FRs (SEQ ID NOS: 91, 92, 93, 94, 95, 97, 98, 99, 100, 101, 102, 106, 107, 108, 109, 110, 111, 112, 113, 117, 118, 119, 120, 121, 122, 123, 125, 126, 127, 128, 129, 130, 131, 133, 215, 217, 218, 219, 222, 223, 224, 225, 226, and 227) and VL FRs (SEQ ID NOS: 135 and 136, 138, 139, 140, 141, 142, 143, 144, 145, 147, 148, 149, 150, 151, 152, 153, 154, 155, 156, 157, 158, 159, 160, 163 201, 202, 203, 204, 205, 206, 208, 209, 210, 211, 212, 213, 228, 229, 230, 231, and 232) listed in Table 10.

In yet another aspect, antibodies are provided that compete with one of the exemplified antibodies or functional fragments for binding to (i) beta klotho or (ii) a complex comprising beta klotho and one of FGFR1c, FGFR2c, FGFR3c, and FGFR4. Such antibodies may also bind to the same epitope as one of the herein exemplified antibodies, or an overlapping epitope. Antibodies and fragments that compete with or bind to the same epitope as the exemplified antibodies are expected to show similar functional properties. The exemplified antigen binding proteins and fragments include those with the VH and VL regions, and CDRs provided herein, including those in Tables 1-3. Thus, as a specific example, the antibodies that are provided include those that compete with an antibody comprising: (a) 1, 2, 3, 4, 5 or all 6 of the CDRs listed for an antibody listed in Tables 1-3; (b) a VH and a VL selected from the VH and a VL regions listed for an antibody listed in Tables 1-3, such as for antibody 3I13 (Table 1) or (c) two light chains and two heavy chains comprising a VH and a VL as specified for an antibody listed in Tables 1-3.

1. Polyclonal Antibodies

The antibodies of the present disclosure may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a beta klotho polypeptide or a fusion protein thereof. It may be useful to conjugate the immunizing agent to a protein known to be immunogenic in the mammal being immunized or to immunize the mammal with the protein and one or more adjuvants. Examples of such immunogenic proteins include but are not limited to keyhole limpet hemocyanin, serum albumin, bovine thyroglobulin, and soybean trypsin inhibitor. Examples of adjuvants which may be employed include Ribi, CpG, Poly 1C, Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for beta klotho antibody titer. If desired, the mammal can be boosted until the antibody titer increases or plateaus. Additionally or alternatively, lymphocytes may be obtained from the immunized animal for fusion and the preparation of monoclonal antibodies from hybridoma as described below.

2. Monoclonal Antibodies

The antibodies of the present disclosure may alternatively be monoclonal antibodies. Monoclonal antibodies may be made using the hybridoma method first described by Kohler et al., Nature, 256:495 (1975), or may be made by recombinant DNA methods (see, e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as SP-2 and derivatives, for example, X63-Ag8-653 cells available from the American Type Culture Collection, Manassas, Va., USA and those derived from MOPC-21 and MPC-11 mouse tumors available from the Salk Institute Cell Distribution Center, San Diego, Calif. USA. Human myeloma and mouse-human heteromyeloma cell lines also have been described for the production of human monoclonal antibodies (Kozbor, J., Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., Anal. Biochem., 107: 220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130:151-188 (1992).

In some embodiments, an antibody that binds a beta klotho epitope comprises an amino acid sequence of a VH domain and/or an amino acid sequence of a VL domain encoded by a nucleotide sequence that hybridizes to (1) the complement of a nucleotide sequence encoding any one of the VH and/or VL domain described herein under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In some embodiments, an antibody that binds a beta klotho epitope comprises an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in Tables 1-3 under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In a further embodiment, monoclonal antibodies or antibody fragments can be isolated from antibody phage libraries generated using the techniques described in, for example, *Antibody Phage Display: Methods and Protocols*, P. M. O'Brien and R. Aitken, eds, Humana Press, Totawa N.J., 2002. In principle, synthetic antibody clones are selected by screening phage libraries containing phage that display various fragments of antibody variable region (Fv) fused to phage coat protein. Such phage libraries are screened for against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., *Ann. Rev. Immunol.*, 12: 433-455 (1994).

Repertoires of VH and VL genes can be separately cloned by polymerase chain reaction (PCR) and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, *J. Mol. Biol.*, 227: 381-388 (1992).

Screening of the libraries can be accomplished by various techniques known in the art. For example, beta klotho, (e.g., a beta klotho polypeptide, fragment or epitope) can be used to coat the wells of adsorption plates, expressed on host cells affixed to adsorption plates or used in cell sorting, or conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

Anti-beta klotho antibodies can be obtained by designing a suitable antigen screening procedure to select for the phage clone of interest followed by construction of a full length anti-beta klotho antibody clone using VH and/or VL sequences (e.g., the Fv sequences), or various CDR sequences from VH and VL sequences, from the phage clone of interest and suitable constant region (e.g., Fc) sequences described in Kabat et al., *Sequences of Proteins of Immunological Interest*, Fifth Edition, NIH Publication 91-3242, Bethesda Md. (1991), vols. 1-3.

3. Antibody Fragments

The present disclosure provides antibodies and antibody fragments that bind to beta klotho. In certain circumstances there are advantages of using antibody fragments, rather than whole antibodies. The smaller size of the fragments allows for rapid clearance, and may lead to improved access to cells, tissues or organs. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli* or yeast cells, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., *Bio/Technology* 10:163-167 (1992)). According to another approach, F(ab')2 fragments can be isolated directly from recombinant host cell culture. Fab and F(ab')2 fragment with increased in vivo half-life comprising salvage receptor binding epitope residues are described, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894;

and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. (See, e.g., Antibody Engineering, ed. Borrebaeck, supra). The antibody fragment may also be a "linear antibody", for example, as described, for example, in the references cited above. Such linear antibodies may be monospecific or multi-specific, such as bispecific.

Smaller antibody-derived binding structures are the separate variable domains (V domains) also termed single variable domain antibodies (SdAbs). Certain types of organisms, the camelids and cartilaginous fish, possess high affinity single V-like domains mounted on an Fc equivalent domain structure as part of their immune system. (Woolven et al., *Immunogenetics* 50: 98-101, 1999; Streltsov et al., *Proc Natl Acad Sci USA*. 101:12444-12449, 2004). The V-like domains (called VhH in camelids and V-NAR in sharks) typically display long surface loops, which allow penetration of cavities of target antigens. They also stabilize isolated VH domains by masking hydrophobic surface patches.

These VhH and V-NAR domains have been used to engineer sdAbs. Human V domain variants have been designed using selection from phage libraries and other approaches that have resulted in stable, high binding VL- and VH-derived domains.

Antibodies that bind to beta klotho as provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments, (e.g., beta klotho binding fragments) of any of the above. Non-limiting examples of functional fragments (e.g., fragments that bind to beta klotho) include single-chain Fvs (scFv) (e.g., including monospecific, bispecific, etc.), Fab fragments, F(ab') fragments, F(ab)2 fragements, F(ab')2 fragments, disulfide-linked Fvs (sdFv), Fd fragments, Fv fragments, diabody, triabody, tetrabody and minibody.

Antibodies provided herein include, but are not limited to, immunoglobulin molecules and immunologically active portions of immunoglobulin molecules, for example, molecules that contain an antigen binding site that bind to a beta klotho epitope. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

Variants and derivatives of antibodies include antibody functional fragments that retain the ability to bind to a beta klotho epitope. Exemplary functional fragments include Fab fragments (e.g., an antibody fragment that contains the antigen-binding domain and comprises a light chain and part of a heavy chain bridged by a disulfide bond); Fab' (e.g., an antibody fragment containing a single anti-binding domain comprising an Fab and an additional portion of the heavy chain through the hinge region); F(ab')2 (e.g., two Fab' molecules joined by interchain disulfide bonds in the hinge regions of the heavy chains; the Fab' molecules may be directed toward the same or different epitopes); a bispecific Fab (e.g., a Fab molecule having two antigen binding domains, each of which may be directed to a different epitope); a single chain Fab chain comprising a variable region, also known as, a sFv (e.g., the variable, antigen-binding determinative region of a single light and heavy chain of an antibody linked together by a chain of 10-25 amino acids); a disulfide-linked Fv, or dsFv (e.g., the variable, antigen-binding determinative region of a single light and heavy chain of an antibody linked together by a disulfide bond); a camelized VH (e.g., the variable, antigen-binding determinative region of a single heavy chain of an antibody in which some amino acids at the VH interface are those found in the heavy chain of naturally occurring camel antibodies); a bispecific sFv (e.g., a sFv or a dsFv molecule having two antigen-binding domains, each of which may be directed to a different epitope); a diabody (e.g., a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (e.g., a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody comprises a single-chain Fv ("scFv"). scFvs are antibody fragments comprising the VH and VL domains of an antibody, wherein these domains are present in a single polypeptide chain. The scFv polypeptide may further comprise a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

4. Humanized Antibodies

The present disclosure provides humanized antibodies that bind beta klotho, including human and/or cyno beta klotho. Humanized antibodies of the present disclosure may comprise one or more CDRs as shown in Tables 1-3. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Winter and co-workers (Jones et al. (1986) *Nature* 321: 522-525; Riechmann et al. (1988) *Nature* 332:323-327; Verhoeyen et al. (1988) *Science* 239:1534-1536), by substituting hypervariable region sequences for the corresponding sequences of a human antibody.

In some cases, the humanized antibodies are constructed by CDR grafting, in which the amino acid sequences of the six complementarity determining regions (CDRs) of the parent non-human antibody (e.g., rodent) are grafted onto a human antibody framework. For example, Padlan et al. (*FASEB J*. 9:133-139, 1995) determined that only about one third of the residues in the CDRs actually contact the antigen, and termed these the "specificity determining residues," or SDRs. In the technique of SDR grafting, only the SDR residues are grafted onto the human antibody framework (see, e.g., Kashmiri et al., *Methods* 36: 25-34, 2005).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence which is closest to that of the rodent may be selected as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA*, 89:4285; Presta et al. (1993) *J. Immunol.*, 151:2623. In some cases, the framework is derived from the consensus sequences of the most abundant human subclasses, $V_L 6$ subgroup I ($V_L 6I$) and $V_H$ subgroup III ($V_H III$). In another method, human germline genes are used at the source of the framework regions.

In an alternative paradigm based on comparison of CDRs, called Superhumanization, FR homology is irrelevant. The method consists of comparison of the non-human sequence with the functional human germ line gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., *J. Immunol.* 169: 1119-1125, 2002).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, *Protein Eng.* 13: 819-824, 2000), Modeller (Sali and Blundell, *J. Mol. Biol.* 234: 779-815, 1993), and Swiss PDB Viewer (Guex and Peitsch, *Electrophoresis* 18: 2714-2713, 1997). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes and the differences are scored as HSC. The target sequence is then humanized by maximizing its HSC rather than using a global identity measure to generate multiple diverse humanized variants. (Lazar et al., *Mol. Immunol.* 44: 1986-1998, 2007).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome and yeast display libraries as well as by bacterial colony screening (see, e.g., Hoogenboom, *Nat. Biotechnol.* 23: 1105-1116, 2005; Dufner et al., *Trends Biotechnol.* 24: 523-529, 2006; Feldhaus et al., *Nat. Biotechnol.* 21: 163-70, 2003; Schlapschy et al., *Protein Eng. Des. Sel.* 17: 847-60, 2004).

In the FR library approach, a collection of residue variants are introduced at specific positions in the FR followed by selection of the library to select the FR that best supports the grafted CDR. The residues to be substituted may include some or all of the "Vernier" residues identified as potentially contributing to CDR structure (see, e.g., Foote and Winter, *J. Mol. Biol.* 224: 487-499, 1992), or from the more limited set of target residues identified by Baca et al. (*J. Biol. Chem.* 272: 10678-10684, 1997).

In FR shuffling, whole FRs are combined with the non-human CDRs instead of creating combinatorial libraries of selected residue variants (see, e.g., Dall'Acqua et al., *Methods* 36: 43-60, 2005). The libraries may be screened for binding in a two-step selection process, first humanizing VL, followed by VH. Alternatively, a one-step FR shuffling process may be used. Such a process has been shown to be more efficient than the two-step screening, as the resulting antibodies exhibited improved biochemical and physicochemical properties including enhanced expression, increased affinity and thermal stability (see, e.g., Damschroder et al., *Mol. Immunol.* 44: 3049-60, 2007).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple sub-classes with distinct human V-segment CDRs. Humaneering allows for isolation of antibodies that are 91-96% homologous to human germline gene antibodies. (see, e.g., Alfenito, Cambridge Healthtech Institute's Third Annual PEGS, The Protein Engineering Summit, 2007).

The "human engineering" method involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or are substituted with human residues. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering, 7: 805-814 (1994), U.S. Pat. Nos. 5,766,886, 5,770,196, 5,821,123, and 5,869,619, and PCT Application Publication WO 93/11794.

5. Human Antibodies

Human anti-beta klotho antibodies can be constructed by combining Fv clone variable domain sequence(s) selected from human-derived phage display libraries with known human constant domain sequences(s). Alternatively, human monoclonal anti-beta klotho antibodies of the present disclosure can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is also possible to produce transgenic animals (e.g., mice) that are capable, upon immunization, of producing a full repertoire of human antibodies in the absence of endogenous immunoglobulin production. Transgenic mice that express human antibody repertoires have been used to generate high-affinity human sequence monoclonal antibodies against a wide variety of potential drug targets (see, e.g., Jakobovits, A., *Curr. Opin. Biotechnol.* 1995, 6(5):561-6; Brüggemann and Taussing, *Curr. Opin. Biotechnol.* 1997, 8(4):455-8; U.S. Pat. Nos. 6,075,181 and 6,150,584; and Lonberg et al., *Nature Biotechnol.* 23: 1117-1125, 2005).

Alternatively, the human antibody may be prepared via immortalization of human B lymphocytes producing an antibody directed against a target antigen (e.g., such B lymphocytes may be recovered from an individual or may have been immunized in vitro) (see, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373).

Gene shuffling can also be used to derive human antibodies from non-human, for example, rodent, antibodies, where the human antibody has similar affinities and specificities to the starting non-human antibody. According to this method, which is also called "epitope imprinting" or "guided selection", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/ human chain chimeric scFv or Fab wherein the human chain restores the antigen binding site destroyed upon removal of the corresponding non-human chain in the primary phage display clone, (e.g., the epitope guides (imprints) the choice of the human chain partner). When the process is repeated in order to replace the remaining non-human chain, a human antibody is obtained (see, e.g., PCT WO 93/06213; and Osbourn et al., Methods., 36, 61-68, 2005). Unlike traditional humanization of non-human antibodies by CDR grafting, this technique provides completely human antibodies, which have no FR or CDR residues of non-human origin. Examples of guided selection to humanize mouse antibodies towards cell surface antigens include the folate-binding protein present on ovarian cancer cells (see, e.g., Figini et al., *Cancer Res.*, 58, 991-996, 1998) and CD147, which is highly expressed on hepatocellular carcinoma (see, e.g., Bao et al., *Cancer Biol. Ther.*, 4, 1374-1380, 2005).

A potential disadvantage of the guided selection approach is that shuffling of one antibody chain while keeping the other constant could result in epitope drift. In order to maintain the epitope recognized by the non-human antibody, CDR retention can be applied (see, e.g., Klimka et al., *Br. J. Cancer*, 83, 252-260, 2000; VH CDR2 Beiboer et al., *J. Mol. Biol.*, 296, 833-49, 2000) In this method, the non-human VH CDR3 is commonly retained, as this CDR may be at the center of the antigen-binding site and may be to be the most important region of the antibody for antigen recognition. In some instances, however, VH CDR3 and VL CDR3, as well as VH CDR3, VL CDR3 and VL CFR1, of the non-human antibody may be retained.

6. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for beta klotho and the other is for any other antigen (e.g., an FGF receptor, including FGFR1c, FGFR2c, FGFR3c, FGFR4). In some embodiments, one of the binding specificities is for beta klotho, and the other is for another surface antigen expressed on cells expressing beta klotho and a FGF receptor (e.g., FGFR1c, FGFR2c, FGFR3c, FGFR4). In certain embodiments, bispecific antibodies may bind to two different epitopes of beta klotho. Bispecific antibodies can be prepared as full length antibodies or antibody fragments (e.g., F(ab')$_2$ bispecific antibodies).

Methods for making bispecific antibodies are known in the art, such as, for example, by co-expression of two immunoglobulin heavy chain-light chain pairs, where the two heavy chains have different specificities (see, e.g., Milstein and Cuello, *Nature*, 305: 537 (1983)). For further details of generating bispecific antibodies see, for example, *Bispecific Antibodies*, Kontermann, ed., Springer-Verlag, Hiedelberg (2011).

7. Multivalent Antibodies

A multivalent antibody may be internalized (and/or catabolized) faster than a bivalent antibody by a cell expressing an antigen to which the antibodies bind. The antibodies of the present disclosure can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Fc Engineering

It may be desirable to modify an antibody to beta klotho via Fc engineering, including, with respect to effector function, for example, so as to decrease or remove antigen-dependent cell-mediated cyotoxicity (ADCC) and/or complement dependent cytotoxicity (CDC) of the antibody. This may be achieved by introducing one or more amino acid substitutions in an Fc region of the antibody. For example, substitutions into human IgG1 using IgG2 residues as positions 233-236 and IgG4 residues at positions 327, 330 and 331 were shown to greatly reduce ADCC and CDC (see, e.g., Armour et al., *Eur. J. Immunol.* 29:(8):2613-24 (1999); Shields et al., *J. Biol. Chem.* 276(9): 6591-604 (2001).

To increase the serum half life of the antibody, one may incorporate a salvage receptor binding epitope into the antibody (especially an antibody fragment), for example, as described in U.S. Pat. No. 5,739,277. Term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

9. Alternative Binding Agents

The present disclosure encompasses non-immunoglobulin binding agents that specifically bind to the same epitope as an anti-beta klotho antibody disclosed herein. In some embodiments, a non-immunoglobulin binding agent is identified an agent that displaces or is displaced by an anti-beta klotho antibody of the present disclosure in a competitive binding assay. These alternative binding agents may include, for example, any of the engineered protein scaffolds known in the art. Such scaffolds may comprise one or more CDRs as shown in Tables 1-3. Such scaffolds include, for example, anticalins, which are based upon the lipocalin scaffold, a protein structure characterized by a rigid beta-barrel that supports four hypervariable loops which form the ligand binding site. Novel binding specificities may be engineered by targeted random mutagenesis in the loop regions, in combination with functional display and guided selection (see, e.g., Skerra (2008) *FEBS J.* 275: 2677-2683). Other suitable scaffolds may include, for example, adnectins, or monobodies, based on the tenth extracellular domain of human fibronectin III (see, e.g., Koide and Koide (2007) *Methods Mol. Biol.* 352: 95-109); affibodies, based on the Z domain of staphylococcal protein A (see, e.g., Nygren et al. (2008) *FEBS J.* 275: 2668-2676)); DARPins, based on ankyrin repeat proteins (see, e.g., Stumpp et al. (2008) *Drug. Discov. Today* 13: 695-701); fynomers, based on the SH3 domain of the human Fyn protein kinase Grabulovski et al. (2007) *J. Biol. Chem.* 282: 3196-3204); affitins, based on Sac7d from *Sulfolobus acidolarius* (see, e.g., Krehenbrink et al. (2008) *J. Mol. Biol.* 383: 1058-1068); affilins, based on human y-B-crystallin (see, e.g., Ebersbach et al. (2007) *J. Mol. Biol.* 372: 172-185); avimers, based on the A domains of membrane receptor proteins (see, e.g., Silverman et al. (2005) *Biotechnol.* 23: 1556-1561); cysteine-rich knottin peptides (see, e.g., Kolmar (2008) *FEBS J.* 275: 2684-2690); and engineered Kunitz-type inhibitors (see, e.g., Nixon and Wood (2006) *Curr. Opin. Drug. Discov. Dev.* 9: 261-268) For a review, see, for example, Gebauer and Skerra (2009) *Curr. Opin. Chem. Biol.* 13: 245-255.

Antibody Variants

In some embodiments, amino acid sequence modification(s) of the antibodies that bind to beta klotho or described herein are contemplated. For example, it may be desirable to improve the binding affinity and/or other biological properties of the antibody, including but not limited to specificity, thermostability, expression level, effector functions, glycosylation, reduced immunogenicity or solubility. This, in addition to the anti-beta klotho antibodies described herein, it is contemplated that anti-beta klotho antibody variants can be prepared. For example, anti-beta klotho antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-beta klotho antibody, such as changing the number or position of glycosylation sites or altering the membrane anchoring characteristics.

In some embodiments, antibodies provided herein are chemically modified, for example, by the association with, including covalent attachment of, any type of molecule with the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited, to specific chemical cleavage, acetylation, formulation, metabolic synthesis of tunicamycin, etc. Additionally, the antibody may contain one or more non-classical amino acids.

Variations may be a substitution, deletion or insertion of one or more codons encoding the antibody or polypeptide that results in a change in the amino acid sequence as compared with the native sequence antibody or polypeptide. Amino acid substitutions can be the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In certain embodiments, the substitution, deletion or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a specific embodiment, the substitution is a conservative amino acid substitution made at one or more predicted non-essential amino acid residues. The variation allowed may be determined by systematically making insertions, deletions or substitutions of amino acids in the sequence and testing the resulting variants for activity exhibited by the full-length or mature native sequence.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for antibody-directed enzyme prodrug therapy) or a polypeptide which increases the serum half-life of the antibody.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Alternatively, conservative (e.g., within an amino acid group with similar properties and/or sidechains) substitutions may be made, so as to maintain or not significantly change the properties. Amino acids may be grouped according to similarities in the properties of their side chains (see, e.g., A. L. Lehninger, in Biochemistry, 2nd Ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gin (Q); (3) acidic: Asp (D), Glu (E); and (4) basic: Lys (K), Arg (R), His(H).

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions entail exchanging a member of one of these classes for another class. Such substituted residues also may be introduced into the conservative substitution sites or, into the remaining (non-conserved) sites. Accordingly, in one embodiment, an antibody or fragment thereof that binds to a beta klotho epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a murine monoclonal antibody described herein. In one embodiment, an antibody or fragment thereof that binds to a beta klotho epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in Tables 1-3. In yet another embodiment, an antibody or fragment thereof that binds to a beta klotho epitope comprises a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence depicted in Tables 1-3 and/or a VL CDR amino acid sequence depicted in Tables 1-3. The variations can be made using methods known in the art such as oligonucleotide-mediated (site-directed) mutagenesis, alanine scanning, and PCR mutagenesis. Site-directed mutagenesis (see, e.g., Carter et al., *Nucl. Acids Res.*, 13:4331 (1986); Zoller et al., *Nucl. Acids Res.*, 10:6487 (1987)), cassette mutagenesis (see, e.g., Wells et al., *Gene*, 34:315 (1985)), restriction selection mutagenesis (see, e.g., Wells et al., *Philos. Trans. R. Soc. London SerA*, 317:415 (1986)) or other known techniques can be performed on the cloned DNA to produce the anti-beta klotho antibody variant DNA.

Any cysteine residue not involved in maintaining the proper conformation of the anti-beta klotho antibody also may be substituted, for example, with another amino acid such as alanine or serine, to improve the oxidative stability of the molecule and prevent aberrant crosslinking. Conversely, cysteine bond(s) may be added to the anti-beta klotho antibody to improve its stability (e.g., where the antibody is an antibody fragment such as an Fv fragment).

In some embodiments, an anti-beta klotho antibody molecule of the present disclosure is a "de-immunized" antibody. A "de-immunized" anti-beta klotho antibody is an antibody derived from a humanized or chimeric anti-beta klotho antibody, that has one or more alterations in its amino acid sequence resulting in a reduction of immunogenicity of the antibody, compared to the respective original non-de-immunized antibody. One of the procedures for generating such antibody mutants involves the identification and removal of T-cell epitopes of the antibody molecule. In a first step, the immunogenicity of the antibody molecule can be determined by several methods, for example, by in vitro determination of T-cell epitopes or in silico prediction of such epitopes, as known in the art. Once the critical residues for T-cell epitope function have been identified, mutations can be made to remove immunogenicity and retain antibody activity. For review, see, for example, Jones et al., *Methods in Molecular Biology* 525: 405-423, 2009.

1. In Vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed as Fab, scFv or V domain fragments either on the surface of an organism (e.g., phage, bacteria, yeast or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Preferred affinity matured antibodies will have nanomolar or even picomolar affinities for the target antigen.

Phage display is a widepread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and infected in bacteria to produce phage for further rounds of selection. For review, see, for example, Hoogenboom, *Methods. Mol. Biol.* 178: 1-37, 2002; Bradbury and Marks, *J. Immuno. Methods* 290: 29-49, 2004).

In a yeast display system (see, e.g., Boder et al., *Nat. Biotech.* 15: 553-57, 1997; Chao et al., *Nat. Protocols* 1:755-768, 2006), the antibody may be displayed as single-chain variable fusions (scFv) in which the heavy and light chains are connected by a flexible linker. The scFv is fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the scFv. Expression has been shown to correlate with the stability of the displayed protein, and thus antibodies can be selected for improved stability as well as affinity (see, e.g., Shusta et al., *J. Mol. Biol.* 292: 949-956, 1999). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently 'titrated' while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., US Patent Publication 2003/0186, 374; Blaise et al., *Gene* 342: 211-218, 2004).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reversed transcribed back into cDNA, which can then undergo mutagenesis and be used in the next round of selection (see, e.g., Fukuda et al., *Nucleic Acids Res.* 34, e127, 2006). In mRNA display, a covalent bond between antibody and mRNA is established using puromycin as an adaptor molecule (Wilson et al., *Proc. Natl. Acad. Sci. USA* 98, 3750-3755, 2001).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

Diversity may be introduced into the CDRs or the whole V genes of the antibody libraries in a targeted manner or via random introduction. The former approach includes sequentially targeting all the CDRs of an antibody via a high or low level of mutagenesis or targeting isolated hot spots of somatic hypermutations (see, e.g., Ho, et al., *J. Biol. Chem.* 280: 607-617, 2005) or residues suspected of affecting affinity on experimental basis or structural reasons. Random mutations can be introduced throughout the whole V gene using *E. coli* mutator strains, error-prone replication with DNA polymerases (see, e.g., Hawkins et al., *J. Mol. Biol.* 226: 889-896, 1992) or RNA replicases. Diversity may also be introduced by replacement of regions that are naturally diverse via DNA shuffling or similar techniques (see, e.g., Lu et al., *J. Biol. Chem.* 278: 43496-43507, 2003; U.S. Pat. Nos. 5,565,332; 6,989,250). Alternative techniques target hypervariable loops extending into framework-region residues (see, e.g., Bond et al., *J. Mol. Biol.* 348: 699-709, 2005) employ loop deletions and insertions in CDRs or use hybridization-based diversification (see, e.g., US Patent Publication No. 2004/0005709). Additional methods of generating diversity in CDRs are disclosed, for example, in U.S. Pat. No. 7,985,840.

Screening of the libraries can be accomplished by various techniques known in the art. For example, beta klotho can be immobilized onto solid supports, columns, pins or cellulose/poly(vinylidene fluoride) membranes/other filters, expressed on host cells affixed to adsorption plates or used in cell sorting, or conjugated to biotin for capture with streptavidin-coated beads, or used in any other method for panning display libraries.

For review of in vitro affinity maturation methods, see, e.g., Hoogenboom, *Nature Biotechnology* 23: 1105-1116, 2005 and Quiroz and Sinclair, Revista Ingeneria Biomedia 4: 39-51, 2010 and references therein.

2. Modifications of Anti-Beta Klotho Antibodies

Covalent modifications of anti-beta klotho antibodies are included within the scope of the present disclosure. Covalent modifications include reacting targeted amino acid residues of an anti-beta klotho antibody with an organic derivatizing agent that is capable of reacting with selected side chains or the N- or C-terminal residues of the anti-beta klotho antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see, e.g., T. E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Other types of covalent modification of the anti-beta klotho antibody included within the scope of this present disclosure include altering the native glycosylation pattern of the antibody or polypeptide (see, e.g., Beck et al., *Curr. Pharm. Biotechnol.* 9: 482-501, 2008; Walsh, *Drug Discov. Today* 15: 773-780, 2010), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192 or 4,179,337.

An anti-beta klotho antibody of the present disclosure may also be modified to form chimeric molecules comprising an anti-beta klotho antibody fused to another, heterologous polypeptide or amino acid sequence, for example, an epitope tag (see, e.g., Terpe, *Appl. Microbiol. Biotechnol.* 60: 523-533, 2003) or the Fc region of an IgG molecule (see, e.g., Aruffo, "Immunoglobulin fusion proteins" in Antibody Fusion Proteins, S. M. Chamow and A. Ashkenazi, eds., Wiley-Liss, New York, 1999, pp. 221-242).

Also provided herein are fusion proteins comprising an antibody provided herein that binds to a beta klotho antigen and a heterologous polypeptide. In some embodiments, the heterologous polypeptide to which the antibody is fused is useful for targeting the antibody to cells having cell surface-expressed beta klotho.

Also provided herein are panels of antibodies that bind to a beta klotho antigen. In specific embodiments, panels of antibodies have different association rate constants different dissociation rate constants, different affinities for beta klotho antigen, and/or different specificities for a beta klotho antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96 well or 384 well plates, such as for assays such as ELISAs.

Preparation of Anti-Beta Klotho Antibodies

Anti-beta klotho antibodies may be produced by culturing cells transformed or transfected with a vector containing anti-beta klotho antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression and purification are further described, in Plückthun et al., (1996) in *Antibody Engineering: Producing antibodies in Escherichia coli: From PCR to fermentation* (McCafferty, J., Hoogenboom, H. R., and Chiswell, D. J., eds), 1 Ed., pp. 203-252, IRL Press, Oxford; Kwong, K. & Rader, C., *E. coli* expression and purification of Fab antibody fragments, Current protocols in protein science editorial board John E Coligan et al., Chapter 6, Unit 6.10 (2009); Tachibana and Takekoshi, "Production of Antibody Fab Fragments in *Escherischia coli*," in *Antibody Expression and Production*, M. Al-Rubeai, Ed., Springer, New York, 2011; *Therapeutic Monoclonal Antibodies: From Bench to Clinic* (ed Z. An), John Wiley & Sons, Inc., Hoboken, N.J., USA.

It is, of course, contemplated that alternative methods, which are well known in the art, may be employed to prepare anti-beta klotho antibodies. For instance, the appropriate amino acid sequence, or portions thereof, may be produced by direct peptide synthesis using solid-phase techniques (see, e.g., Stewart et al., *Solid-Phase Peptide Synthesis*, W.H. Freeman Co., San Francisco, Calif. (1969); Merrifield, *J. Am. Chem. Soc.,* 85:2149-2154 (1963)). In vitro protein synthesis may be performed using manual techniques or by automation. Various portions of the anti-beta klotho antibody may be chemically synthesized separately and combined using chemical or enzymatic methods to produce the desired anti-beta klotho antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

Immunoconjugates

The present disclosure also provides conjugates comprising any one of the anti-beta klotho antibodies of the present disclosure covalently bound, including by a synthetic linker, to one or more non-antibody agents.

A variety of radioactive isotopes are available for the production of radioconjugated antibodies. Examples include $At^{211}$, I4, I4, Y4, Re4, Re4, Sm4, Bi4, P4, Pb4 and radioactive isotopes of Lu. When the conjugate is used for detection, it may comprise a radioactive atom for scintigraphic studies, for example tc4 or I4, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron. The radioisotopes may be incorporated in the conjugate in known ways as described, e.g., in Reilly, "The radiochemistry of monoclonal antibodies and peptides," in Monoclonal Antibody and Peptide-Targeted Radiotherapy of Cancer, R. M. Reilly, ed., Wiley, Hoboken N.J., 2010.

In some embodiments, antibodies provided herein are conjugated or recombinantly fused to a diagnostic, detectable or therapeutic agent or any other molecule. The conjugated or recombinantly fused antibodies can be useful, for example, for monitoring or prognosing the onset, development, progression and/or severity of a beta klotho-mediated disease as part of a clinical testing procedure, such as determining the efficacy of a particular therapy.

Such diagnosis and detection can accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; chemiluminescent material, such as but not limited to, an acridinium based compound or a HALOTAG; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

Also provided herein are antibodies that are conjugated or recombinantly fused to a therapeutic moiety (or one or more therapeutic moieties), as well as uses thereof. The antibody may be conjugated or recombinantly fused to a therapeutic moiety, including a cytotoxin such as a cytostatic or cytocidal agent, a therapeutic agent or a radioactive metal ion such as alpha-emitters. A cytotoxin or cytotoxic agent includes any agent that is detrimental to cells.

Further, an antibody provided herein may be conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, e.g., International Publication No. WO 97/33899), AIM II (see, e.g., International Publication No. WO 97/34911), Fas Ligand (see, e.g., Takahashi et al., 1994, J. Immunol., 6:1567-1574), and VEGF (see, e.g., International Publication No. WO 99/23105), an anti-angiogenic agent, including, for example angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

Also provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90 or about 100 amino acids) to generate fusion proteins, as well as uses thereof. In particular, provided herein are fusion proteins comprising an antigen-binding fragment of an antibody provided herein (e.g., a Fab fragment, Fd fragment, Fv fragment, F(ab)2 fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses beta klotho or an beta klotho receptor. For example, an antibody that binds to a cell surface receptor expressed by a particular cell type (e.g., an immune cell) may be fused or conjugated to a modified antibody provided herein.

In addition, an antibody provided herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7, 10-tetraazacyclododecane-N,N',N",N'"-tetraacetic acid (DOTA) which can be attached to the antibody via a linker molecule. Such linker molecules are commonly known in the art and described, for example, in Denardo et al., 1998, *Clin Cancer Res.* 4(10):2483-90; Peterson et al., 1999, *Bioconjug. Chem.* 10(4):553-7; and Zimmerman et al., 1999, *Nucl. Med. Biol.* 26(8):943-50.

Moreover, antibodies provided herein can be fused to marker or "tag" sequences, such as a peptide to facilitate purification. In specific embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-824, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating therapeutic moieties (including polypeptides) to antibodies are well known, (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of anti-beta klotho antibodies as provided herein, including, for example, antibodies with higher affinities and lower dissociation rates (see, e.g., U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313). Antibodies, or the encoded antibodies, may be altered by being subjected to random mutagenesis by error-prone PCR, random nucleotide insertion or other methods prior to recombination. A polynucleotide encoding an antibody provided herein may be recombined with one or more components, motifs, sections, parts, domains, fragments, etc. of one or more heterologous molecules.

An antibody provided herein can also be conjugated to a second antibody to form an antibody heteroconjugate as described, for example, in U.S. Pat. No. 4,676,980.

The therapeutic moiety or drug conjugated or recombinantly fused to an antibody provided herein that binds to beta klotho (e.g., a beta klotho polypeptide, fragment, epitope) should be chosen to achieve the desired prophylactic or therapeutic effect(s). In certain embodiments, the antibody is a modified antibody. A clinician or other medical personnel may consider, for example, the following when deciding on which therapeutic moiety or drug to conjugate or recombinantly fuse to an antibody provided herein: the nature of the disease, the severity of the disease, and the condition of the subject.

Antibodies that bind to beta klotho as provided herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The linker may be a "cleavable linker" facilitating release of the conjugated agent in the cell, but non-cleavable linkers are also contemplated herein. Linkers for use in the conjugates of the present disclosure include without limitation acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers (see, e.g., Chari et al., *Cancer Research* 52:127-131 (1992); U.S. Pat. No. 5,208, 020), thioether linkers, or hydrophilic linkers designed to evade multidrug transporter-mediated resistance (see, e.g., Kovtun et al., *Cancer Res.* 70: 2528-2537, 2010).

Conjugates of the antibody and agent may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate). The present disclosure further contemplates that conjugates of antibodies and agents may be prepared using any suitable methods as disclosed in the art, (see, e.g., in Bioconjugate Techniques, 2nd Ed., G. T. Hermanson, ed., Elsevier, San Francisco, 2008).

Conventional conjugation strategies for antibodies and agents have been based on random conjugation chemistries involving the ε-amino group of Lys residues or the thiol group of Cys residues, which results in heterogenous conjugates. Recently developed techniques allow site-specific conjugation to antibodies, resulting in homogeneous loading and avoiding conjugate subpopulations with altered antigen-binding or pharmacokinetics. These include engineering of "thiomabs" comprising cysteine substitutions at positions on the heavy and light chains that provide reactive thiol groups and do not disrupt immunoglobulin folding and assembly or alter antigen binding (see, e.g., Junutula et al., *J. Immunol. Meth.* 332: 41-52 (2008); Junutula et al., *Nat. Biotechnol.* 26: 925-932, 2008). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., *Proc. Natl. Acad. Sci. USA* 105: 12451-12456 (2008); Hofer et al., *Biochemistry* 48(50): 12047-12057, 2009).

Pharmaceutical Formulations

Anti-beta klotho antibodies of the present disclosure may be administered by any route appropriate to the disease, disorder or condition to be treated. The antibody will typically be administered parenterally, for example, infusion, subcutaneous, intramuscular, intravenous, intradermal, intrathecal and epidural. The antibody dose will vary, including depending on the nature and/or severity of the disease or disorder as well as the condition of the subject, may include doses between 1 mg and 100 mg. Doses may also include those between 1 mg/kg and 15 mg/kg. In some embodiments, the dose is between about 5 mg/kg and about 7.5 mg/kg. In some embodiments, the dose is about 5 mg/kg. In some embodiments, the dose is about 7.5 mg/kg. Flat doses selected from the group consisting of: (a) 375-400 mg every two weeks and (b) 550-600 mg every three weeks. In some embodiments, the flat dose is 375-400 mg every two weeks. In some embodiments, the flat dose is 550-600 mg every three weeks. In some embodiments the flat dose is 400 mg every two weeks. In some embodiments the flat dose is 600 mg every three weeks. In some embodiments of sequential dosing, a first dose and a second dose are each between 1 mg/kg and 15 mg/kg with the second dose following the first does by between 1 and 4 weeks. In some embodiments, the first dose and the second dose are each between 5 mg/kg and 7.5 mg/kg and the second dose follows the first dose by between 2 and 3 weeks. In some embodiments, the first dose and the second dose are each 5 mg/kg and the second dose follows the first dose by 2 weeks. In some embodiments, the first dose and the second dose are each 7.5 mg/kg and the second dose follows the first dose by 3 weeks.

For treating diseases, disorders or conditions, the antibody in some embodiments is administered via intravenous infusion. The dosage administered via infusion is in the range of about 1 µg/m$^2$ to about 10,000 µg/m$^2$ per dose, generally one dose per week for a total of one, two, three or four doses. Alternatively, the dosage range is of about 1 µg/m$^2$ to about 1000 µg/m$^2$, about 1 µg/m$^2$ to about 800 µg/m$^2$, about 1 µg/m$^2$ to about 600 µg/m$^2$, about 1 µg/m$^2$ to about 400 µg/m$^2$; alternatively, about 10 µg/m$^2$ to about 500 µg/m$^2$, about 10 µg/m$^2$ to about 300 µg/m$^2$, about 10 µg/m$^2$ to about 200 µg/m$^2$, and about 1 µg/m$^2$ to about 200 µg/m$^2$. The dose may be administered once per day, once per week, multiple times per week, but less than once per day, multiple times per month but less than once per day, multiple times per month but less than once per week, once per month or intermittently to relieve or alleviate symptoms of the disease, disorder, or condition. Administration may continue at any of the disclosed intervals until amelioration of the disease, disorder or condition, or amelioration of symptoms of the disease, disorder or condition being treated. Administration may continue after remission or relief of symptoms is achieved where such remission or relief is prolonged by such continued administration.

In one aspect, the present disclosure further provides pharmaceutical formulations comprising at least one anti-beta klotho antibody of the present disclosure. In some embodiments, a pharmaceutical formulation comprises 1) an anti-beta klotho antibody, and 2) a pharmaceutically acceptable carrier. In some embodiments, a pharmaceutical formulation comprises 1) an anti-beta klotho antibody and/or an immunoconjugate thereof, and optionally, 2) at least one additional therapeutic agent.

Pharmaceutical formulations comprising an antibody is prepared for storage by mixing the antibody having the desired degree of purity with optional physiologically acceptable carriers, excipients or stabilizers (see, e.g., Remington's Pharmaceutical Sciences 16th edition, Osol, A. Ed. (1980)) in the form of aqueous solutions or lyophilized or other dried formulations. The formulations herein may also contain more than one active compound as necessary for the particular disease, disorder or condition (e.g., a particular indication) being treated, preferably those with complementary activities that do not adversely affect each other. For example, in addition to an anti-beta klotho antibody, it may be desirable to include in the one formulation, an additional antibody, e.g., a second anti-beta klotho antibody which binds a different epitope on the beta klotho polypeptide, or an antibody to some other target. Alternatively, or additionally, the composition may further comprise another agent, including, for example, a chemotherapeutic agent, cytotoxic agent, cytokine, growth inhibitory agent, anti-hormonal agent, and/or cardioprotectant. In some embodiments the formulation includes an alkylating agent (e.g., chlorambucil, bendamustine hydrochloride or cyclophosphamide) a nucleoside analog (e.g., fludurabine, pentostatin, cladribine or cytarabine) a corticosteroid (e.g., prednisone, prednisolone or methylprednisolone), an immunomodulatory agent (e.g., lenalidomide), an antibiotic (e.g., doxorubicin, daunorubicin idarubicin or mitoxentrone), a synthetic flavon (e.g., flavopiridol), a Bcl2 antagonist, (e.g., oblimersen or ABT- 263), a hypomethylating agent (e.g., azacytidine or decitabine), an FLT3 inhibitor (e.g., midostaurin, sorafenib and AC220). Such molecules are suitably present in combination in amounts that are effective for the purpose intended.

The antibodies of the present disclosure may be formulated in any suitable form for delivery to a target cell/tissue, for example, as microcapsules or macroemulsions (Remington's *Pharmaceutical Sciences,* 16th edition, Osol, A. Ed. (1980); Park et al., *Molecules* 10: 146-161 (2005); Malik et al., *Curr. Drug. Deliv.* 4: 141-151 (2007)); as sustained release formulations (Putney and Burke, *Nature Biotechnol.* 16: 153-157, (1998)); encapsulation-free controlled release formulations using, for example, poly(lactic-co-glycolic acid) (PLGA) nanoparticles (Pakulska et al., *Sci. Adv.,* 2(5):e1600519 (2016)) or in liposomes (Maclean et al., *Int. J. Oncol.* 11: 235-332 (1997); Kontermann, *Curr. Opin. Mol. Ther.* 8: 39-45 (2006)).

An antibody provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed, for example, in Remington's Pharmaceutical Sciences (1990) Mack Publishing Co., Easton, Pa.

Various delivery systems are known and can be used to administer a prophylactic or therapeutic agent (e.g., an antibody that binds to beta klotho as described herein), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. In another embodiment, a prophylactic or therapeutic agent, or a composition provided herein can be delivered in a controlled release or sustained release system. In one embodiment, a pump may be used to achieve controlled or sustained release (see, e.g., Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibody that binds to beta klotho as described herein) or a composition of the invention (see, e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105; Pakulska et al., *Sci. Adv.,* 2(5):e1600519 (2016); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable.

In yet another embodiment, a controlled or sustained release system can be placed in proximity of the therapeutic target, for example, the nasal passages or lungs, thus requiring only a fraction of the systemic dose (see, e.g., Goodson, in Medical Applications of Controlled Release, supra, vol. 2, pp. 115-138 (1984)). Controlled release systems are discussed, for example, by Langer (1990, Science 249:1527-1533). Any technique known to one of skill in the art can be used to produce sustained release formulations comprising one or more antibodies that bind to beta klotho as described herein. (See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Intl. Symp. Control. Rel. Bioact. Mater. 24:853-854, and Lam et al., 1997, "Microencapsulation of Recombinant Humanized Monoclonal Antibody for Local Delivery," Proc. Intl. Symp. Control Rel. Bioact. Mater. 24:759-760).

Additional delivery systems can be used to administer a prophylactic or therapeutic agent (e.g., an antibody that binds to beta klotho as described herein) including, but not limited to, injectable drug delivery devices. Injectable drug delivery devices for anti-beta klotho antibodies include, for example, hand-held devices or wearable devices. Hand-held devices useful for anti-beta klotho antibodies include autoinjectors, such as the FLEXIQ-DV (Elcam Medical) or PRO-JECT (Aptar Pharma) autoinjectors. Wearable devices useful for anti-beta klotho antibodies include, for example, on-body drug delivery systems, such as the NEULASTA drug delivery kit (Amgen). Injectable drug delivery devices for anti-beta klotho antibodies can contain the antibody as a prophyactic or therapeutic agent, for example, in prefilled syringes, cartridges or vials. Injectable drug delivery devices (e.g., autoinjectors) and/or their containers (e.g., syringes, cartridges or vials) for anti-beta klotho antibodies can be disposable. Exemplary injectable devices useful for anti-beta klotho antibodies are described in WO2014/081780.

In some embodiments, additional drug delivery systems can be used to administer a prophylactic or therapeutic agent (e.g., an antibody that binds to beta klotho as described herein) including, but not limited to, osmotic pumps. Different types of osmotic pump systems for anti-beta klotho antibodies can be used, including, for example, single compartment systems, dual compartment systems, and multiple compartment systems. Exemplary osmotic pump systems useful for anti-beta klotho antibodies are described, for example, in Herrlich et al. (2012) Advanced Drug Delivery Reviews 64, 1617-1627. In some embodiments, the osmotic pump for anti-beta klotho antibodies can include implantable drug-dispensing osmotic pumps such as the DUROS pump.

Therapeutic Methods

An anti-beta klotho antibody of the present disclosure may be used in, for example, in vitro, ex vivo, and in vivo therapeutic methods. In one aspect, the present disclosure provides methods for treating or preventing a disease, disorder, or condition, either in vivo or in vitro, the method comprising exposing a cell to an anti-beta klotho antibody.

In one aspect, an antibody of the present disclosure is used to treat or prevent a disease, disorder, or condition, including, for example, Type 2 diabetes, obesity, dyslipidemia, NASH, cardiovascular disease, metabolic syndrome or broadly any disease, disorder, or condition in which it is desirable to mimic or augment the in vivo effects of FGF19 and/or FGF21.

In one aspect, methods are provided for treating a disease, disorder or condition comprising administering to an individual an effective amount of an anti-beta klotho antibody or fragment thereof. In certain embodiments, a method for treating a disease, disorder, or condition comprises administering to an individual an effective amount of a pharmaceutical formulation comprising an anti-beta klotho antibody and, optionally, at least one additional therapeutic agent, such as those described herein.

An anti-beta klotho antibody or fragment thereof can be administered to a human for therapeutic purposes. Moreover, an anti-beta klotho antibody or fragment thereof can be administered to a non-human mammal expressing beta klotho with which the antibody cross-reacts (e.g., a primate, pig, rat, or mouse) for veterinary purposes or as an animal model of human disease. Regarding the latter, such animal models may be useful for evaluating the therapeutic efficacy of antibodies of the present disclosure (e.g., testing of dosages and time courses of administration).

Antibodies of the present disclosure can be used either alone or in combination with other compositions in a therapy. For example, an anti-beta klotho antibody of the present disclosure may be co-administered with at least one additional therapeutic agent and/or adjuvant. In some embodiments, the additional compound is a therapeutic antibody other than an anti-beta klotho antibody.

Such combination therapies noted above encompass combined administration (where two or more therapeutic agents are included in the same or separate formulations), and separate administration, in which case, administration of an anti-beta klotho antibody or fragment thereof of the present disclosure can occur prior to, simultaneously, and/or following, administration of the additional therapeutic agent and/or adjuvant. Antibodies of the present disclosure can also be used in combination with additional therapeutic regimens including, without limitation, those described herein.

An anti-beta klotho antibody of the present disclosure (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody or conjugate is suitably administered by pulse infusion, particularly with declining doses of the antibody or fragment thereof. Dosing can be by any suitable route, for example, by injections, such as intravenous or subcutaneous injections, depending in part on whether the administration is brief or chronic.

Antibodies of the present disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The anti-beta klotho antibody need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a disease, disorder, or condition, the appropriate dosage of an anti-beta klotho antibody of the present disclosure (when used alone or in combination with one or more other additional therapeutic agents, such as agents described herein) will depend on the type of disease, disorder, or condition, to be treated, the type of antibody, the severity and course of the disease, disorder, or condition, whether the antibody is administered for preventive or therapeutic purposes, previous therapy, the patient's clinical history and response to the antibody, and the discretion of the attending physician. The anti-beta klotho antibody is suitably administered to the patient at one time or over a series of treatments. Depending on the type and severity of the disease, about 1 μg/kg to 100 mg/kg (e.g., 0.1 mg/kg-20 mg/kg, 1 mg/kg-15 mg/kg, etc.) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. Exemplary dosages of the antibody may be in the range from about 0.05 mg/kg to about 10.0 mg/kg. Thus, one or more doses of about 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, or 10.0 mg/kg (or any combination thereof) of antibody may be administered to the patient. Such doses may be administered intermittently, e.g., every week or every three weeks (e.g., such that the patient receives from about two to about twenty, or e.g., about six doses of the antibody). An initial higher loading dose, followed by one or more lower doses may be administered. An exemplary dosing regimen comprises administering an initial loading dose, followed by a maintenance dose (e.g., weekly) of the antibody. The initial loading dose may be greater than the maintenance dose. However, other dosage regimens may be useful. The progress of this therapy is easily monitored by conventional techniques and assays.

Diagnostic Methods and Methods of Detection

In one aspect, anti-beta klotho antibodies and fragments thereof of the present disclosure are useful for detecting the presence of beta klotho in a biological sample. Such anti-beta klotho antibodies may include those that bind to human and/or cyno beta klotho, but do not induce FGF19-like signaling and/or FGF21-like signaling activity. The term "detecting" as used herein encompasses quantitative or qualitative detection. In certain embodiments, a biological sample comprises a cell or tissue.

In one aspect, the present disclosure provides a method of detecting the presence of beta klotho in a biological sample. In certain embodiments, the method comprises contacting the biological sample with an anti-beta klotho antibody under conditions permissive for binding of the anti-beta klotho antibody to beta klotho, and detecting whether a complex is formed between the anti-beta klotho antibody and beta klotho.

In one aspect, the present disclosure provides a method of diagnosing a disorder associated with expression of beta klotho. In certain embodiments, the method comprises contacting a test cell with an anti-beta klotho antibody; determining the level of expression (either quantitatively or qualitatively) of beta klotho by the test cell by detecting binding of the anti-beta klotho antibody to beta klotho; and comparing the level of expression of beta klotho by the test cell with the level of expression of beta klotho by a control cell (e.g., a normal cell of the same tissue origin as the test cell or a cell that expresses beta klotho at levels comparable to such a normal cell), wherein a higher level of expression of beta klotho by the test cell as compared to the control cell indicates the presence of a disorder associated with increased expression of beta klotho. In certain embodiments, the test cell is obtained from an individual suspected of having a disease, disorder or condition associated with expression of beta klotho and/or a disease, disorder or condition in which it is desirable to mimic or augment the in vivo effects of FGF19 and/or FGF21. In certain embodiments, the disease, disorder or condition is, for example, Type 2 diabetes, obesity, dyslipidemia, NASH, cardiovascular disease or metabolic syndrome. Such exemplary diseases, disorders or conditions may be diagnosed using an anti-beta klotho antibody of the present disclosure.

In certain embodiments, a method of diagnosis or detection, such as those described above, comprises detecting binding of an anti-beta klotho antibody to beta klotho expressed on the surface of a cell or in a membrane preparation obtained from a cell expressing beta klotho on its surface. In certain embodiments, the method comprises contacting a cell with an anti-beta klotho antibody under conditions permissive for binding of the anti-beta klotho antibody to beta klotho, and detecting whether a complex is formed between the anti-beta klotho antibody and beta klotho on the cell surface. An exemplary assay for detecting binding of an anti-beta klotho antibody to beta klotho expressed beta klotho on the surface of a cell is a "FACS" assay.

Certain other methods can be used to detect binding of anti-beta klotho antibodies to beta klotho. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-beta klotho antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, for example, through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, for example, firefly luciferase and bacterial luciferase (see, e.g., U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, anti-beta klotho antibodies are immobilized on an insoluble matrix. Immobilization entails separating the anti-beta klotho antibody from any beta klotho that remains free in solution. This conventionally is accomplished by either insolubilizing the anti-beta klotho antibody before the assay procedure, as by adsorption to a water-insoluble matrix or surface (see, e.g., Bennich et al., U.S. Pat. No. 3,720,760), or by covalent coupling (for example, using glutaraldehyde cross-linking), or by insolubilizing the anti-beta klotho antibody after formation of a complex between the anti-beta klotho antibody and beta klotho, for example, by immunoprecipitation.

Any of the above embodiments of diagnosis or detection may be carried out using an immunoconjugate of the present disclosure in place of or in addition to an anti-beta klotho antibody.

Assays

Anti-beta klotho antibodies of the present disclosure may be characterized for their physical/chemical properties and/or biological activities by various assays known in the art.

1. Activity Assays

In one aspect, assays are provided for identifying anti-beta klotho antibodies thereof having biological activity. Biological activity may include, for example, assays which measure effects on glucose and/or lipid metabolism. For example, a blood glucose assay may be used. Blood glucose (e.g., in mouse tail snip or in a human blood sample) may be measured using ACCU-CHEK Active test strips read by ACCU-CHEK Active meter (Roche Diagnostics, Indianapolis, Ind.) following manufacturer's instruction. In addition, for example, a lipid profile assay may be used. Whole blood (e.g., from mouse tail snips or from a human blood sample) may be collected into plain capillary tubes (BD Clay Adams SurePrep, Becton Dickenson and Co. Sparks, Md.). Serum and blood cells can be separated by spinning the tubes in an Autocrit Ultra 3 (Becton Dickinson and Co. Sparks, Md.). Serum samples can be assayed for lipid profile (triglyceride, total cholesterol, HDL, and non-HDL) using Integra 400 Clinical Analyzer (Roche Diagnostics, Indianapolis, Ind.) following the manufacturer's instructions.

2. Binding Assays and Other Assays

In one aspect, an anti-beta klotho antibody is tested for its antigen binding activity. For example, in certain embodiments, an anti-beta klotho antibody is tested for its ability to bind to exogenous or endogenous beta klotho expressed on the surface of a cell. A FACS assay may be used for such testing.

A panel of monoclonal antibodies raised against beta klotho may be grouped based upon the epitopes they recognize, a process known as epitope binning. Epitope binning is typically carried out using competition assays, which evaluate an antibody's ability to bind to an antigen in the presence of another antibody. In an exemplary competition assay, immobilized beta klotho is incubated in a solution comprising a first labeled antibody that binds to beta klotho and a second unlabeled antibody that is being tested for its ability to compete with the first antibody for binding to beta klotho. The second antibody may be present in a hybridoma supernatant. As a control, immobilized beta klotho is incubated in a solution comprising the first labeled antibody but not the second unlabeled antibody. After incubation under conditions permissive for binding of the first antibody to beta klotho, excess unbound antibody is removed, and the amount of label associated with immobilized beta klotho is measured. If the amount of label associated with immobilized beta klotho is substantially reduced in the test sample relative to the control sample, then that indicates that the second antibody is competing with the first antibody for binding to beta klotho. In certain embodiments, immobilized beta klotho is present on the surface of a cell or in a membrane preparation obtained from a cell expressing beta klotho on its surface.

High-throughput methods of epitope binning are also known in the art (see, e.g., Jia et al., *J. Immunol. Methods* 2004, 288(1-2):91-98, describing a method of multiplexed competitive antibody binning for the characterization of monoclonal antibodies; and Miller et al., *J. Immunol. Methods* 2011, 365(1-2):118-25, describing epitope binning of murine monoclonal antibodies by a multiplexed pairing assay).

3. Epitope Mapping

Epitope mapping is the process of identifying the binding sites, or epitopes, of an antibody on its target protein antigen (e.g., epitopes of an anti-beta klotho antibody on beta klotho). Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

A variety of methods are known in the art for mapping antibody epitopes on target protein antigens. These include mutagenesis methods, peptide scanning methods, display methods, methods involving and mass spectroscopy, and structural determination.

The site directed mutagenesis method involves targeted site-directed mutagenesis where critical amino acids are identified by systematically introducing substitutions along the protein sequence and then determining the effects of each substitution on antibody binding. This may be done by "alanine scanning mutagenesis," as described, for example, by Cunningham and Wells (1989) Science 244: 1081-1085, or some other form of point mutagenesis of amino acid residues in human beta klotho. Mutagenesis studies, however, may also reveal amino acid residues that are crucial to the overall three-dimensional structure of beta klotho but that are not directly involved in antibody-antigen contacts, and thus other methods may be necessary to confirm a functional epitope determined using this method.

Shotgun mutagenesis mapping utilizes a comprehensive plasmid-mutation library for the target gene, with each clone in the library bearing a unique amino acid mutation and the entire library covering every amino acid in the target protein. The clones that constitute the mutation library are individually arranged in microplates, expressed within living mammalian cells, and tested for immunoreactivity with antibodies of interest. Amino acids critical for antibody epitopes are identified by a loss of reactivity and are then mapped onto a protein structure to visualize epitopes. By automating the analysis, new epitope maps can be derived within days to weeks. Because it uses the native structure of proteins within mammalian cells, the technique allows both linear and conformational epitope structures to be mapped on complex proteins. (See, e.g., Paes et al., *J. Am. Chem. Soc.* 131(20): 6952-6954 (2009); Banik and Doranz, *Genetic Engineering and Biotechnology News* 3(2): 25-28 (2010)).

The epitope bound by an anti-beta klotho antibody may also be determined using peptide scanning methods. In peptide scanning, libraries of short peptide sequences from overlapping segments of the target protein, beta klotho, are tested for their ability to bind antibodies of interest. The peptides are synthesized and screened for binding, e.g., using ELISA or BIACORE, or on a chip, by any of the multiple methods for solid-phase screening (see, e.g., Reineke et al., *Curr. Opin. Biotechnol.* 12: 59-64, 2001) as in the "pepscan" methodology (see, e.g., WO 84/03564; WO 93/09872). Such peptide screening methods may not be capable of detecting some discontinuous functional epitopes, i.e. functional epitopes that involve amino acid residues that are not contiguous along the primary sequence of the beta klotho polypeptide chain.

A recently developed technology termed CLIPS (chemical linkage of peptides onto scaffolds) may be used to map conformational epitopes. The loose ends of the peptides are affixed onto synthetic scaffolds, so that the scaffolded peptide may be able to adopt the same spatial structure as the corresponding sequence in the intact protein. CLIPS technology is used to fix linear peptides into cyclic structures ('single-loop' format), and to bring together different parts of a protein binding site ('double-loop', 'triple-loop', etc. format), so as to create conformational epitopes that may be assayed for antibody binding (see, e.g., U.S. Pat. No. 7,972, 993).

The epitopes bound by anti-beta klotho antibodies of the present disclosure may also be mapped using display techniques, including, for example, phage display, microbial display, and ribosome/mRNA display as described above. In these methods, libraries of peptide fragments are displayed on the surface of the phage or cell. Epitopes are then mapped by screening mAbs against these fragments using selective binding assays. A number of computational tools have been developed which allow the prediction of conformational epitopes based upon linear affinity-selected peptides obtained using phage display (see, e.g., Mayrose et al., *Bioinformatics* 23: 3244-3246, 2007). Methods are also available for the detection of conformational epitopes by phage display. Microbial display systems may also be used to express properly folded antigenic fragments on the cell surface for identification of conformational epitopes (see, e.g., Cochran et al., *J. Immunol. Meth.* 287: 147-158, 2004; Rockberg et al., *Nature Methods* 5: 1039-1045, 2008).

Methods involving proteolysis and mass spectroscopy may also be used to determine antibody epitopes (see, e.g., Baerga-Ortiz et al., *Protein Sci.* 2002 June; 11(6): 1300-1308). In limited proteolysis, the antigen is cleaved by different proteases, in the presence and in the absence of the antibody, and the fragments are identified by mass spectrometry. The epitope is the region of the antigen that becomes protected from proteolysis upon binding of the antibody (see, e.g., Suckau et al., *Proc. Natl. Acad. Sci. USA* 87:9848-9852, 1990). Additional proteolysis based methods include, for example, selective chemical modification (see, e.g., Fiedler et al., *Bioconjugate Chemistry* 1998, 9(2): 236-234, 1998), epitope excision (see, e.g., Van de Water et al., *Clin. Immunol. Immunopathol.* 1997, 85(3): 229-235, 1997), and the recently developed method of hydrogen-deuterium (H/D) exchange (see, e.g., Flanagan, N., *Genetic Engineering and Biotechnology News* 3(2): 25-28, 2010).

The epitope bound by anti-beta klotho antibodies of the present disclosure may also be determined by structural methods, such as X-ray crystal structure determination (see, e.g., WO 2005/044853), molecular modeling and nuclear magnetic resonance (NMR) spectroscopy, including NMR determination of the H-D exchange rates of labile amide hydrogens when free and when bound in a complex with an antibody of interest (see, e.g., Zinn-Justin et al. (1992) *Biochemistry* 31:11335-11347; Zinn-Justin et al. (1993) *Biochemistry* 32:6884-6891).

Additional antibodies binding to the same epitope as an anti-beta klotho antibody of the present disclosure may be obtained, for example, by screening of antibodies raised against beta klotho for binding to the epitope, by immunization of an animal with a peptide comprising a fragment of human beta klotho comprising the epitope sequence, or by selection of antibodies using phage display for binding to the epitope sequence. Antibodies that bind to the same functional epitope might be expected to exhibit similar biological activities, such as blocking a biological activity of beta klotho, and such activities can be confirmed by functional assays of the antibodies.

Additional Activity Assays

In one embodiment, an anti-beta klotho antibody of the present disclosure is an antagonist antibody that inhibits a biological activity of beta klotho. The anti-beta klotho antibodies of the present disclosure may be assayed to determine if they inhibit a biological activity of beta klotho.

In one aspect, purified anti-beta klotho antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In one embodiment, the present disclosure contemplates an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. An in vitro assay to assess ADCC activity of a molecule of interest is described, for example, in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, for example, in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, for example, as described in Gazzano-Santoro et al., *J. Immunol. Methods* 202:163 (1996), may be performed. FcRn binding and in vivo clearance/half life determinations can also be performed using methods known in the art.

Although the foregoing present disclosure has been described in some detail by way of illustration and example for purposes of clarity of understanding, the descriptions and examples should not be construed as limiting the scope of the present disclosure. The disclosures of all patent and scientific literatures cited herein are expressly incorporated in their entirety by reference.

EXAMPLES

The following are examples of methods and compositions of the present disclosure.

Example 1: Generation of Antibodies to Beta Klotho

Antibodies to beta klotho were generated, for example, by immunizations of mice (i) with cells expressing human beta klotho (HuKLB) and FGF receptor 1c (FGFR1c or R1c) and (ii) with HuKLB and cynomologous beta klotho (cyno KLB) protein.

For example, beta klotho expressing cells were prepared as follows. 293EXPI (Invitrogen) cells were transiently co-transfected with nucleic acid sequences encoding a variant of FGFR1c with a mutation at amino acid position 623 (see, e.g., SEQ ID NO:190 but with a mutation D623N) and HuKLB (SEQ ID NO:165). Cells were analyzed for expression of R1c and HuKLB by the respective specific antibodies by FACS. Cells were washed 2 times in PBS, pelleted by centrifugation and frozen in individual vials at $6 \times 10^7$ cells for immunization. 129/B6 animals were immunized with $1 \times 10^7$ cells with adjuvants (Ribi, CpG, and PolyIC). Animals were boosted every 2 weeks for the duration necessary to induce a suitable titer. Animals were boosted with HuKLB and CyKLB protein after 4 boosts with R1c and HuKLB overexpressing-293EXPI cells. Titers were determined by ELISA and FACS. Single cell suspensions of lymphocytes were obtained from spleen and draining lymph nodes of animals with suitable titers. Cells were fused with SP2/0 myeloma cells at a ratio of 1:2 by electrofusion. Fused cells were plated at $2.5 \times 10^6$ cells per plate in 70 μL into twenty-four×384-well plates in the presence of HAT selection. After 7 days, 50 μL of supernatant were removed and replaced with fresh HAT containing media. After 10-14 days of culture, supernatants were collected and subjected to screening by FACS using R1c and HuKLB overexpressing-293EXPI cells or by Biacore using HuKLB protein to confirm binding. Positive clones were further selected and subjected to subcloning.

In a first campaign of immunizations and fusions, at least 25-30 384 well plates were screened for binding to HuKLB (e.g., HuKLB protein and/or cells expressing HuKLB). In a second campaign for immunizations and fusions, a similar number of plates were screened as described for the first campaign. Thousands of clones were screened and hundreds of clones were selected for additional study, including in assays for binding, affinity and epitope specificity as described in Examples 2 and 3. Hundreds of hybridoma supernatants were also tested in functional assays as described, in Examples 4 and 5, including for agonist activity similar to FGF receptor ligands FGF19 and/or FGF21 (e.g., FGF19-like and/or FGF21-like signaling activity).

Example 2: Screening and Selection of Antibodies to Beta Klotho

Antibodies to beta klotho were generated from hybridomas, for example, such as described in Example 1. Hybridoma supernatants were screened for binding to beta klotho (e.g., human and/or cyno beta klotho) in FACS-based and/or Biacore-based assays.

For example, after 2 weeks of culture, hybridoma supernatants were screened for monoclonal antibodies binding to human beta klotho by a FACS based binding screen. Briefly, hybridoma supernatants were co-incubated with human beta klotho over-expressing cells for 30 minutes at 4° C. After washing with PBS/1% BSA/0.1% azide, human beta klotho over-expressing cells were co-incubated with labeled anti-mouse Fc (Jackson Immunoresearch) for 30 minutes at 4° C. After washing with PBS/1% BSA/0.1% azide, cells were acquired on flow cytometer (FACS Calibur) and analyzed by cytometric analytical software (FlowJo). A binding antibody is one that shows a shift from cells incubated with labeled anti-mouse Fc only.

For example, after 2 weeks of culture, hybridoma supernatants were screened for monoclonal antibodies binding to human beta klotho by a Biacore based binding screen. Briefly, anti-mouse Fc antibody (Sigma-Aldrich, St. Louis, Mo.) was immobilized on all four flow cells of a CM5 chip using amine coupling reagents (GE Healthcare LifeSciences, Piscataway, N.J.). Hybridoma supernatants were diluted three fold with PBS-P buffer (PBS containing 0.005% P20) and injected for 30 seconds on flow cells 2, 3 and 4 to capture the antibody (flow cell 1 was used as a reference). This was followed by a short injection of human beta klotho (25 nM, R&D Systems, Minneapolis, Minn.) for 60 seconds at a flow rate of 30 µL/min to test for binding to captured antibody on each flow cell.

From two immunization and fusion campaigns as described in Example 1, fifty-sixty 384 well plates of hybridoma supernatants were assayed for binding by FACS and/or Biacore. From these assays, approximately of 250 antibodies were identified as binders to human beta klotho. These antibodies were purified and subsequently tested for their binding affinity to human beta klotho and cyno beta klotho by Biacore and for their functional activity by reporter assays as described in Example 3.

In additional Biacore-based binding/screening assays, the binding affinity of antibodies to human and cyno beta klotho were measured. For example, antibodies were rank ordered based on their binding affinity to human beta klotho and cyno beta klotho by low resolution $K_D$ measurement by Biacore. Briefly, anti-mouse Fc antibody (Sigma-Aldrich, St. Louis, Mo.) was immobilized on all four flow cells of a CM5 chip using amine coupling reagents (GE Healthcare LifeSciences, Piscataway, N.J.). Purified antibodies were captured (~100 RUs) on flow cells 2, 3 and 4 using flow cell 1 as a reference. This was followed by injection of human or cyno beta klotho (25 nM in PBS-P buffer) at a flow rate of 70 µL/min and monitoring the binding kinetics at 25° C.

Binding affinity measurements were also made in additional Biacore based assays. For example, equilibrium dissociation constant ($K_D$) measurements were carried out with purified antibodies to evaluate their binding to human beta klotho and cyno beta klotho. As mentioned above, anti-mouse Fc antibody (Sigma-Aldrich, St. Louis, Mo.) was immobilized on all four flow cells of a CM5 chip using amine coupling reagents (GE Healthcare LifeSciences, Piscataway, N.J.). Purified antibodies were captured (~100 RUs) on flow cells 2, 3 and 4 using flow cell 1 as a reference. This was followed by injection of different concentrations of human or cyno beta klotho (1.56 nM to 25 nM, two-fold dilutions in PBS-P buffer) at a flow rate of 70 µL/min and the binding kinetics were evaluated at 25° C.

Representative results are reported as $K_D$ (nM) values as shown in Table 4 below.

TABLE 4

| | Affinity $K_D$ (nM) | |
|---|---|---|
| | HuKLB | Cyno KLB |
| 3I13 | 0.4 | 1.9 |
| 1N18 | 1.4 | 4.5 |
| 4A2 | 0.92 | 3.2 |
| 2J21 | 4.8 | 12.2 |

Example 3: Screening and Selection of Antibodies to Beta Klotho

Antibodies that were selected for binding to beta klotho, for example, such as described in Example 2, were evaluated in competition binding assays and epitope binning experiments.

For example, for competition binding assays by FACS analysis, antibody standards were prepared that were conjugated to a fluorochrome using either A488 or A647 antibody labeling kit (Invitrogen) following manufacturer's instructions. A dose titration of the conjugated antibody standard was evaluated using HuKLB overexpressing cells. The plateau of the maximal signal of antibody binding is EC=100 and the background signal is EC=0. Competition by FACS against the fluorochrome labeled antibody was performed by pre-incubating HuKLB overexpressing cells with hybridoma supernatants for 15 minutes at room temperature. Without washing, an EC=10 concentration of A488 or A647 labelled antibody standard was added. EC=10 for an individual antibody was determined by 10% of signal using the maximum signal as (100%) and background signal as (0%). After 30 minutes at 4° C., cells are washed and analyzed by FACS. In these assays, a competing antibody is one that shows signal comparable to the competition by 3I13. A non-competing antibody (e.g., 9E19) is one that shows signal equal to labelled antibody alone. A partial competing antibody is one sample that show signal between labelled antibody alone and background. Antibodies that show complete competition against the same standard antibody are considered to be in the same bin.

In exemplary competition binding experiments by FACS, antibody 3I13 or 9E19 was used as an antibody standard for a positive control (competing antibody) or a negative control (labeled antibody alone), respectively. Representative results are shown in Table 5 below reported as mean fluorescence intensity (MFI). For these experiments, signal comparable to labeled antibody alone is a non-competing antibody, while signal comparable to the competition by 3I13 is a competing antibody.

TABLE 5

| | Mean Florescence Intensity (MFI) | |
|---|---|---|
| Antibody | 3I13 - Alexa488 | 9E19 - Alexa647 |
| 3I13 | 8.1 | 27.8 |
| 4A2 | 9.1 | 28.5 |
| 2J21 | 10.2 | 25.7 |
| Negative Control | 21.1 | 21.9 |
| Positive Control | 7.9 | 14.7 |

Additionally or alternatively, to evaluate the binding sites of the antibodies on human beta klotho, competition experiments are set up on the Biacore. For example, two antibodies are immobilized on two flow cells of a CM5 chip. Human beta klotho-antibody complexes were prepared with different antibodies (e.g., antibody concentration is titrated from 0.1-50 nM while keeping beta klotho concentration constant at 5 nM) in a 96-well micro plate and injected on the antibody surfaces. The measured signal (Response Unit, RU) is plotted against the solution antibody concentration [nM]. If the antibody in solution recognizes the same epitope as the antibody immobilized on the chip surface, then a decrease in RU is observed with increase in concentration of antibody in solution (demonstrating competition for the binding site on beta klotho). However, if the antibody in solution recognizes a distinct epitope relative to the immobilized antibody, an increase in RU is observed. In the latter scenario, the antibody-klotho complex may bind to the immobilized antibody surface leading to the observed increase in signal.

In exemplary competition binding experiments as described above, antibody 3I13 competed with itself for binding to HuKLB and additional antibodies 4A2 and 2J21 competed with 3I13 (see e.g., Table 5). These antibodies were designated as members of the 3I13 epitope bin. The sequences for these epitope-related antibodies are aligned and shown in FIGS. 1 and 2. FIG. 2 also shows conserved amino acid sequences for the CDRs of these related antibodies.

Example 4: Functional Assays

Antibodies to beta klotho generated, for example, such as described in Example 1, were tested for their functional activity in cell-based reporter assays.

For example, ELK1-luciferase reporter assays, which measure FGFR1c/beta klotho signaling, were performed using transiently transfected HEK293, or HEK293T cells (ATCC). The transfecting plasmids consisted of two reporter plasmids Gal4-Elk1 and 5×UAS-Luc (Agilent Technologies PathDetect Elk1 trans-reporting system Cat #219005), and plasmids encoding human beta klotho (GeneCopoeia Cat # EX-E1104-M02) or cynomolgus monkey beta klotho (cyno beta klotho) and human FGFR1c (GeneCopoeia Cat # EX-A0260-M02). In these assays, activation of recombinantly expressed FGFR1c/beta klotho receptor complex in the cells induces intracellular signaling transduction, which leads to ERK and then Elk1 phosphorylation. Once Gal4-Elk1 is phosphorylated, Gal4-Elk1 binds to the 5×UAS promoter region and turns on luciferase reporter gene transcription. The activity of luciferase is then measured in luciferase enzymatic assays.

For these experiments, the above mentioned four plasmids (e.g., 2 reporter plasmids, beta klotho, R1c) were transfected into newly harvested cells in suspension using FuGene6 or Fugene HD transfection reagent (Promega). Cell density and transfection reagent amount were optimized for each cell type and each Fugene batch. Beta klotho and FGFR1c DNA ratio in transfection was optimized for each cell line and varied between 6:1 to 27:1. Transfected cells were seeded into 96-well (30,000 cells/100 µL/well), or 384-well plate (7500 cells/25 µL/well) in normal growth medium. After overnight incubation at 37° C., a variety of antibodies to beta klotho were added, including a control antibody (e.g., a known anti-beta klotho antibody). After 6 hrs of 37° C. incubation with the antibodies, an equal volume of Bright-Glo reagent (Promega) was added and luminescence signal was read using Enspire reader (Perkin Elmer).

Representative results using human beta klotho and cyno beta klotho, transfected into HEK 293 and HEK 293 T cells, are reported as EC50 values as shown in Table 6 and Table 7, respectively, below.

TABLE 6

| mAb | Experiment - A<br>HEK293 huKLB/R1c<br>reporter assay EC50<br>(pM) | Experiment - B<br>HEK293 huKLB/R1c<br>reporter assay EC50<br>(pM) |
| --- | --- | --- |
| Control | 27.9 | 377.6 |
| 3I13 | 332.8 | 1985 |

TABLE 7

| mAb | HEK293 cynoKLB/R1c<br>reporter assay EC50<br>(pM) |
| --- | --- |
| Control | 178.4 |
| 3I13 | 437.8 |

Example 5: Additional Functional Assays

Antibodies to beta klotho generated, for example, as described in Example 1, were tested for their functional activity in a cell-based assay, such as an adipocyte assay, which measures endogenous FGFR1c/beta klotho signaling. FGF19 or FGF21 stimulate ERK phosphorylation, increase glucose uptake and lipolyses in cultured adipocytes. Adipocytes are considered physiologically relevant for demonstrating the functional activity of receptor ligands or agonist antibodies which mimic the function of ligands (e.g., signaling of the receptor by the ligands).

For example, frozen human preadipocytes (Lonza Cat # PT-5005) were thawed on day 1, differentiated on day 3 and maintained in differentiation medium for about two weeks before the experiment (e.g., then starved on day 17, and assayed on day 18). The seeding medium was 1:1 DMEM/F12K+10% FBS. Seeding cell density was 25,000 cells/100 µL/well in 96-well plate. On day 3, medium was replaced with human adipocytes differentiation medium (Cell Applications Inc). From then on, fresh differentiation medium was added onto cells every 2-3 days. On day 17 (the day before the assay), the cells were rinsed two times and left with DMEM/0.1% BSA (Sigma cat # A3803 essential fatty acids free BSA) overnight. The next day, fresh DMEM/0.1% BSA medium was added for 1 hour before the cells were treated with test anti-beta klotho antibodies (e.g., 0.1 µg/m L, 1.0 µg/m L, 10 µg/m L), for 15 minutes at 37° C. Cis-bio Cellul'erk assay kit (Cat #64ERKPEH) was used to assay for ERK phosphorylation level following the manufacturer's protocol. For an exemplary antibody, 3I13, as shown in Table 8 below, positive results were obtained at the highest concentration of antibody used in an adipocyte assay, whereas 4A2 and 2J21 antibodies were not positive at comparable concentration.

TABLE 8

| mAb | hAdip pERK assay |
|---|---|
| Control (FGF 19) | +++ |
| 3I13 | ++ |

Example 6: Ligand Competition

Ligand (FGF19 or FGF21) competition assays were conducted to evaluate whether antibody-human beta klotho interaction influences the binding of beta klotho to its natural ligand, FGF19 or FGF21.

For example, Biacore-based competition assays were set up in which FGF19 (e.g., SEQ ID NO: 188) or FGF21 (e.g., SEQ ID NO: 183) was immobilized on a flow cell (Fc2) of a CM5 chip (using Fc1 as a reference surface). Human beta klotho-antibody complexes were prepared with an exemplary antibody of the present disclosure, such as 3I13 (e.g., VH SEQ ID NO: 26 and VL SEQ ID NO: 27). For example, 3I13 at 200 nM and 5 nM beta klotho were injected on the FGF 21 surface. The signal (Response Unit, RU) was measured. If the antibody in solution recognized the same epitope as FGF19 ligand or FGF21 ligand immobilized on the chip surface, then a decrease in RU was observed with increase in concentration of antibody in solution, demonstrating competition with FGF19 ligand or FGF21 ligand for the binding site on beta klotho. However, if the antibody in solution recognized a distinct epitope relative to the immobilized FGF19 ligand or FGF21 ligand, an increase in RU was observed. In the latter scenario, the antibody-klotho complex could bind to the immobilized FGF19 ligand surface or immobilized FGF21 ligand surface leading to the observed increase in signal. In an exemplary experiment with FGF21, 3I13 did not compete with the FGF21 ligand for binding to beta klotho as indicated by an increase in RU (e.g., 110%).

Example 7: Humanization

Humanized anti-beta klotho antibodies were generated, including from antibodies selected as described in Examples 1-6.

A number of anti-beta klotho antibodies were selected for sequencing and their VH and VL regions, including their CDRs, are shown in Tables 1-3 and in FIGS. 1 and 2. An exemplary anti-beta klotho antibody, 3I13, was selected for humanization. A variety of methods of humanization may be utilized. For some of the humanized antibodies, the method for humanization was empirical and may be based in part on structural information related to immunoglobulin variable regions including molecular models and requirements of antibody structural stability (see, e.g., Ewert et al., 2004, Methods 34:184-199; Honegger, 2008, Handb. Exp. Pharmacol. 181:47-68; Kügler et al., 2009, Protein Eng. Des. Sel. 22: 135-147). The method may be also based in part on considerations of antigen contact residues and/or framework stability residues. For example, consideration of typical antigen contact residues depends on the size of the antigen particularly residues outside CDRs which can contact the antigen, upper core, central core and lower core divisions, VH:VL interface residues, conserved Pro/Gly (positive phi angles) and VH subtype correlated residues match (see, e.g., Ewert et al., supra; Honegger, supra; Kügler et al., supra).

For example, human germline sequences were identified with significant similarity to murine 3I13 VH and VL sequences. Suitable human framework acceptors for VH, included, for example, IgHv1-46, IgHv1-2, IgHv1-69 or IgHv1-18. Suitable acceptor sequences for VL, included, for example, IgHv1-5, IgHv1-16, IgHv1-12 or IgHv1-39. Consideration of sequence similarities, biophysical properties and potential immunogenicity, lead to the empirical selection of IgHv1-46 and IgHv1-39 human framework sequences. Next, framework 4 sequences were identified with a similar approach. Initially, sequences for mouse 3I13 VH and VL were searched against human immunoglobulin sequences at Im Muno Gene Tics (IMGT) and IgHJ2-1 as well as IgKJ4-1 were selected as suitable human donor sequences. The CDR sequences of murine 3I13 were then transferred (e.g., grafted) to the corresponding positions of IgHv1-46 and IgKv1-39 and J-region residues corresponding to framework four were added. The resulting protein sequence was back translated into a DNA sequence, codon optimized for expression in mammalian cells and synthesized (GeneArt/Life Technologies). Subsequently, the synthesized DNA fragment was closed using In-Fusion (Clontech) into pTT5 vector (NRC Biotechnology Research Institute) to create the hIgGK signal peptide-humanized 3I13vH-hIgG1 constant region and hIgGK signal peptide-humanized 3I13 VK-hIgGK constant region expression constructs (HC-008-a and LC-008-a respectively). Next, individual residues in the framework regions were empirical selected and back-mutated to mouse residues using Quick-Change site directed mutagenesis (Agilent). To elucidate which back mutations (if any) are beneficial for binding affinities of humanized 3I13 to beta klotho, various mutated heavy chain (e.g., VH) sequences are expressed with chimeric 3I13 light chain and vice versa (mutated light chain sequences are expressed with chimeric 3I13 heavy chain). Several humanized heavy chain sequences, including the fully humanized sequences with zero back mutations, may show similar binding affinities compared to the fully mouse antibody. In contrast, some humanized light chain variants may show reduced binding. After analysis as described in Examples 2-3 (e.g., binding affinities and cell-based assay results), humanized 3I13 VH and VL sequences are selected.

The amino acid sequences of the resulting humanized VH (HC-007-a to HC-007-w) and VL (LC-007-a to LC-007-r) sequences are shown with 3I13 VH and VL sequences in FIG. 3A-3B. For example, using the various humanization methods described in this Example, a number of amino acid residues of 3I13 VH and VL were substituted for the corresponding human residue to obtain humanized sequences as shown, for example, in FIG. 3A-3B, as well as for 2J21 VH and VL (e.g., FIGS. 4A-4B) and for 4A2 VH and VL (e.g., FIG. 5A-5B). Exemplary humanized 3I13 antibodies include those comprising VH sequences such as HC-007-n and HC-007-o and VL sequences such as LC-007-n and LC-007-o (e.g., HC-007-n and LC-007-n, HC-007-o and LC-007-o).

Humanized beta klotho antibodies may be prepared using any of the CDR sequences as disclosed in Tables 1-3, including, for example, those shown in Table 9 in combination with suitable framework sequences such as any of the framework sequences in Table 10.

TABLE 9

Exemplary CDR Sequences for Humanized Anti-Beta Klotho Antibodies

```
VH CDR1
SEQ ID NO: 1 GYTFTEYTMH
SEQ ID NO: 28 GYTFTEYIMH
SEQ ID NO: 38 GYTFTEYTMY

VH CDR2
SEQ ID NO: 2 SFNPDSGGTSYNQKFKG
SEQ ID NO: 29 NIDPNTGGTSYNQKFKG
SEQ ID NO: 39 GFNPNYGGASYNQKFKD

VH CDR3
SEQ ID NO: 3 DDGYSTRYWYFDV

VL CDR1
SEQ ID NO: 4 GASENIYGALN

VL CDR2
SEQ ID NO: 5 GATILAD

VL CDR3
SEQ ID NO: 6 QNVLSTPYT
```

TABLE 10

Exemplary Framework Sequences for Humanized Anti-Beta Klotho Antibodies

```
VH
Framework 1 (FR1)
SEQ ID NO: 91 QVQLVQSGAEVKKPGASVKVSCKAS
SEQ ID NO: 92 QVQLQQSGAEVKKPGASVKVSCKAS
SEQ ID NO: 93 QVQLVQSGPEVKKPGASVKVSCKAS
SEQ ID NO: 94 QVQLVQSGAEVVKPGASVKVSCKAS
SEQ ID NO: 95 QVQLQQSGPEVKKPGASVKVSCKAS Framework 2 (FR2)
SEQ ID NO: 97 WVRQAPGQGLE
SEQ ID NO: 98 WVRQAHGQGLE
SEQ ID NO: 99 WVRQAPGKGLE
SEQ ID NO: 100 WVRQAPGQSLE
SEQ ID NO: 101 WVRQAPGKSLE
SEQ ID NO: 102 WVRQAHGKSLE
SEQ ID NO: 106 WVRQAPGQGLEWMG
SEQ ID NO: 107 WVRQAHGQGLEWMG
SEQ ID NO: 108 WVRQAPGKGLEWMG
SEQ ID NO: 109 WVRQAPGQSLEWMG
SEQ ID NO: 110 WVRQAPGQGLEWIG
SEQ ID NO: 111 WVRQAPGKSLEWMG
SEQ ID NO: 112 WVRQAHGKSLEWMG
SEQ ID NO: 113 WVRQAHGKSLEWIG
SEQ ID NO: 217 WVRQAPGKSLEWIG Framework 3 (FR3)
SEQ ID NO: 117 RVTMTRDTSTSTVYMELSSLRSEDTAVYYC
SEQ ID NO: 118 RVTLTRDTSTSTVYMELSSLRSEDTAVYYC
SEQ ID NO: 119 RVTMTVDTSTSTVYMELSSLRSEDTAVYYC
SEQ ID NO: 120 RVTMTRDKSTSTVYMELSSLRSEDTAVYYC
SEQ ID NO: 121 RVTMTRDTSTSTVYMELRSSLRSEDTAVYYC
SEQ ID NO: 122 RVTMTRDTSTSTVYMELSSLTSEDTAVYYC
SEQ ID NO: 123 RVTLTVDTSTSTVYMELRSSLRSEDTAVYYC
SEQ ID NO: 125 RVTMTRDTSTSTVYMELSSLRSEDTAVYYCAR
SEQ ID NO: 126 RVTLTRDTSTSTVYMELSSLRSEDTAVYYCAR
SEQ ID NO: 127 RVTMTVDTSTSTVYMELSSLRSEDTAVYYCAR
SEQ ID NO: 128 RVTMTRDKSTSTVYMELSSLRSEDTAVYYCAR
SEQ ID NO: 129 RVTMTRDTSTSTVYMELRSSLRSEDTAVYYCAR
SEQ ID NO: 130 RVTMTRDTSTSTVYMELSSLTSEDTAVYYCAR
SEQ ID NO: 131 RVTLTVDTSTSTVYMELRSSLRSEDTAVYYCAR
SEQ ID NO: 215 RVTMTRDTSTITVYMELSSLRSEDTAVYYCAR
SEQ ID NO: 218 RATMTRDTSTSTVYMELSSLRSEDTAVYYC
SEQ ID NO: 219 RATMTRDTSTSTVYMELSSLRSEDTAVYYCAR
SEQ ID NO: 222 RVTMTRDTSTSTAYMELSSLRSEDTAVYYC
SEQ ID NO: 223 RVTMTRDTSTSTAYMELSSLRSEDTAVYYCAR
SEQ ID NO: 224 RVTMTVDKSTSTVYMELSSLRSEDTAVYYC
SEQ ID NO: 225 RVTMTVDKSTSTVYMELSSLRSEDTAVYYCAR
SEQ ID NO: 226 RATLTVDKSTSTAYMELSSLRSEDTAVYYC
SEQ ID NO: 227 RATLTVDKSTSTAYMELSSLRSEDTAVYYCAR Framework 4 (FR4)
SEQ ID NO: 133 WGRGTLVTVSS VL
Framework 1 (FR1)
SEQ ID NO: 135 DIQMTQSPSSLSASVGDRVTITC
SEQ ID NO: 136 DIQMTQSPSSLSASVGDTVTITC Framework 2 (FR2)
SEQ ID NO: 138 WYQQKPGKAPK
SEQ ID NO: 139 WFQQKPGKAPK
SEQ ID NO: 140 WYQRKPGKAPK
SEQ ID NO: 141 WYQQKPGKAPK
SEQ ID NO: 142 WYQQKPGKSPK
SEQ ID NO: 143 WYQQKPGKAPQ
SEQ ID NO: 144 WYQQKQGKSPK
SEQ ID NO: 145 WYQQKQGKSPQ
SEQ ID NO: 147 WFQQKPGKAPKLLIY
SEQ ID NO: 148 WYQRKPGKAPKLLIY
SEQ ID NO: 149 WYQQKQGKAPKLLIY
SEQ ID NO: 150 WYQQKPGKSPKLLIY
SEQ ID NO: 151 WYQQKPGKAPQLLIY
SEQ ID NO: 152 WYQQKQGKSPKLLIY
SEQ ID NO: 153 WYQQKQGKSPQLLVY
SEQ ID NO: 201 QQKPGKAPK
SEQ ID NO: 202 QRKPGKAPK
SEQ ID NO: 203 QQKQGKAPK
SEQ ID NO: 204 QQKPGKSPK
SEQ ID NO: 205 QQKPGKAPQ
SEQ ID NO: 206 QQKQGKSPK
SEQ ID NO: 208 QQKPGKAPKLLIY
SEQ ID NO: 209 QRKPGKAPKLLIY
SEQ ID NO: 210 QQKQGKAPKLLIY
SEQ ID NO: 211 QQKPGKSPKLLIY
SEQ ID NO: 212 QQKPGKAPQLLIY
SEQ ID NO: 213 QQKQGKSPKLLIY Framework 3 (FR3)
SEQ ID NO: 154 GVPSRFSGSGSGTDFTLTISSLQPEDFATYYC
SEQ ID NO: 155 GMPSRFSGSGSGTDFTLTISSLQPEDFATYYC
SEQ ID NO: 156 GVSSRFSGSGSGTDFTLTISSLQPEDFATYYC
SEQ ID NO: 157 GVPSRFSGSGSGRDFTLTISSLQPEDFATYYC
SEQ ID NO: 158 GVPSRFSGSGSGTDFTLKISSLQPEDFATYYC
SEQ ID NO: 159 GVPSRFSGSGSGTDFTLTISSLQPEDVATYYC
SEQ ID NO: 160 GMPSRFSGSGSGRDFTLKISSLQPEDVATYYC
SEQ ID NO: 228 GVPSRFSGSGSGTDYTLTISSLQPEDFATYYC
SEQ ID NO: 229 GMPSRFSGSGSGTDYTLTISSLQPEDFATYYC
SEQ ID NO: 230 GVSSRFSGSGSGRDYTLTISSLQPEDVATYYC
SEQ ID NO: 231 GMSSRFSGSGSGRDYTLKISSLQPEDVATYYC
SEQ ID NO: 232 GMSSRFSGSGSGRDYTLTISSLQPEDFATYYC Framework 4 (FR4)
SEQ ID NO: 163 FGGGTKLEIK
```

For example, a humanized anti-beta klotho antibody may comprise a heavy chain variable region (VH) comprising: FR1 (e.g., SEQ ID NO: 91, 92, 93, 94, and 95); CDR1 (e.g., SEQ ID NO:1, 7, 12, 14, 19, 96, 28, 30, 32, 38, 41, or 44); FR2 (e.g., SEQ ID NO: 97, 98, 99, 100, 101, 102, 106, 107, 108, 109, 110, 111, 112, 113, and 217); CDR2 (e.g., SEQ ID NO:2, 8, 15, 20, 25, 29, 31, 33, 34, 35, 39, 40, 42, 43, 45, or 46); FR3 (e.g., SEQ ID NO: 117, 118, 119, 120, 121, 122, 123, 125, 126, 127, 128, 129, 130, 131, 215, 218, 219, 222, 223, 224, 225, 226, and 227); CDR3 (e.g., SEQ ID NO:3, 9, 16, or 21); and/or FR4 (e.g., SEQ ID NO:133); and/or a light chain variable region (VL) comprising: FR1 (e.g., SEQ ID NO: 135 and 136); CDR1 (e.g., SEQ ID NO:4, 10, 17 or 22); FR2 (e.g., SEQ ID NO: 138, 139, 140, 141, 142, 143, 144, 145, 147, 148, 149, 150, 151, 152, 153, 201, 202, 203, 204, 205, 206, 208, 209, 210, 211, 212 and 213); CDR2 (e.g., SEQ ID NO:5, 11, 13 or 23); FR3 (e.g., SEQ ID NO: 154, 155, 156, 157, 158, 159, 160, 228, 229, 230, 231, and 232); CDR3 (e.g., SEQ ID NO:6, 18 or 24); and/or FR4 (e.g., SEQ ID NO:163).

As described in this Example, humanized anti-beta klotho antibodies were empirically designed and may be expressed as beta klotho binding proteins, including humanized variants of the VH region and of the VL region of antibody 3I13, 2J21, and 4A2. The sequences of exemplary humanized VH and VL regions are shown in FIGS. 3, 4, and 5, respectively.

Example 8: Animal Studies

Effects of anti-beta klotho antibodies are evaluated in animal studies. Animal studies may include studies with cynomolgus monkeys.

For example, in obese cynomolgus monkey studies, an exemplary anti-beta klotho antibody that binds to human beta klotho and cyno beta klotho (e.g., antibody 3I13 or humanized variant thereof), as well as an antibody comprising one or more of the CDRs of 3I13 as shown in Table 1 or alternatively, an antibody comprising one or more of the CDRs of an antibody or humanized variant thereof shown in Tables 2 or 3 that compete for the binding of 3I13 to human beta klotho as described in Example 3, is administered. Effects on a variety of metabolic parameters may be measured. Exemplary parameters include food intake, body weight, body mass index (BMI), abdominal circumference (AC), skin fold thickness (SFT), oral glucose tolerance test (OGTT), fasting and/or fed (e.g., postprandial) blood (e.g., serum) glucose levels, insulin levels, and/or triglyceride levels.

For example, twenty spontaneous obese cynomolgus monkeys with body mass index equal to or above 40 may be selected and randomized into vehicle (n=10) and antibody treatment (n=10) groups. Animals may receive subcutaneous injection of either vehicle or anti-beta klotho antibody on days 1 and 14. Food intake for each meal may be recorded and body weight measured once a week. Blood samples may be taken once a week for 7 weeks for the measurements of plasma (alternatively, serum) glucose, insulin, lipids and parameters of interest. On days 14, 28 and 49, an oral glucose tolerance test may be conducted.

Exemplary treatment effects may include reduced food intake, decreased body weight, decreased BMI, AC and/or SFT, improved glucose tolerance, decreased insulin levels, decreased fasting and/or fed (e.g., postprandial) plasma (alternatively, serum) glucose levels, insulin levels, and/or reduced triglyceride levels. These effects indicate improved metabolic parameters with treatment with anti-beta klotho antibodies.

The embodiments of the present disclosure described above are intended to be merely exemplary, and those skilled in the art will recognize, or be able to ascertain using no more than routine experimentation, numerous equivalents to the specific procedures described herein. All such equivalents are considered to be within the scope of the present disclosure and are covered by the following claims. Furthermore, as used in this specification and claims, the singular forms "a," "an" and "the" include plural forms unless the content clearly dictates otherwise. Thus, for example, reference to "an antibody" may include a mixture of two or more such antibodies, and the like. Additionally, ordinarily skilled artisans will recognize that operational sequences must be set forth in some specific order for the purpose of explanation and claiming, but the present disclosure contemplates various changes beyond such specific order.

The contents of all references described herein are hereby incorporated by reference.

Other embodiments are within the following claims.

What is claimed:

1. An antibody or fragment thereof that binds human beta-klotho, which comprises
a heavy chain variable region comprising a heavy chain variable region CDR1 comprising the amino acid sequence of SEQ ID NO:1, a heavy chain variable region CDR2 comprising the amino acid sequence of SEQ ID NO:2, a heavy chain variable region CDR3 comprising the amino acid sequence of SEQ ID NO:3, and a light chain variable region comprising a light chain variable region CDR1 comprising the amino acid sequence of SEQ ID NO:4, a light chain variable region CDR2 comprising the amino acid sequence of SEQ ID NO:5, and a light chain variable region CDR3 comprising the amino acid sequence of SEQ ID NO:6.

2. The antibody or fragment thereof of claim 1, wherein the heavy chain variable region has at least 90% sequence identity to the amino acid sequence of SEQ ID NO:26 and the light chain variable region has at least 90% sequence identity to the amino acid sequence of SEQ ID NO:27.

3. The antibody or fragment thereof of claim 1, which is a monoclonal antibody.

4. The antibody or fragment thereof of claim 1, which is a humanized antibody.

5. The antibody or fragment thereof of claim 1, wherein the fragment is a Fab, Fab', F(ab')$_2$, Fv, scFv, (scFv)$_2$, single chain antibody, dual variable region antibody, or linear antibody.

6. A pharmaceutical composition which comprises the antibody or fragment thereof of claim 1 and a pharmaceutically acceptable carrier.

7. A method of activating a beta-klotho/FGF receptor complex in a cell, wherein the method comprises contacting the cell with the antibody or fragment thereof of claim 1.

8. The antibody or fragment thereof of claim 1, wherein the heavy chain variable region has at least 95% sequence identity to the amino acid sequence of SEQ ID NO:26 and the light chain variable region has at least 95% sequence identity to the amino acid sequence of SEQ ID NO:27.

9. The antibody or fragment thereof of claim 1, wherein the heavy chain variable region comprises the amino acid sequence as set forth in SEQ ID NO:26 and the light chain variable region comprises the amino acid sequence as set forth in SEQ ID NO:27.

10. The antibody or fragment thereof of claim 1, wherein the heavy chain variable region comprises one of the amino acid sequences set forth in SEQ ID NOs:56-78.

11. The antibody or fragment thereof of claim 1, wherein the light chain variable region comprises one of the amino acid sequences set forth in SEQ ID NOs:80-90, 124, 132, 134, 137, or 146.

12. The antibody or fragment thereof of claim 1, wherein the heavy chain variable region comprises one of the amino acid sequences set forth in SEQ ID NOs:56-78 and the light chain variable region comprises one of the amino acid sequences set forth in SEQ ID NOs:80-90, 124, 132, 134, 137, or 146.

13. The antibody or fragment thereof of claim 1, wherein the heavy chain variable region comprises the amino acid sequence set forth in SEQ ID NO:69 and the light chain variable region comprises the amino acid sequence set forth in SEQ ID NO:134.

14. The antibody or fragment thereof of claim 1, wherein the heavy chain variable region comprises the amino acid sequence set forth in SEQ ID NO:70 and the light chain variable region comprises the amino acid sequence set forth in SEQ ID NO:137.

* * * * *

SEQUENCE LISTING

```
<160> NUMBER OF SEQ ID NOS: 313

<210> SEQ ID NO 1
<211> LENGTH: 10
<212> TYPE: PRT
<213> ORGANISM: Artificial Sequence
<220> FEATURE:
<223> OTHER INFORMATION: Antibody 3I13 VH CDR1 - Exemplary

<400> SEQUENCE: 1

Gly Tyr Thr Phe Thr Glu Tyr Thr Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Antibody 3I13 VH CDR2 - Exemplary

<400> SEQUENCE: 2

Ser Phe Asn Pro Asp Ser Gly Gly Thr Ser Tyr Asn Gln Lys Phe Lys
1               5                   10                  15

Gly

<210> SEQ ID NO 3
<211> LENGTH: 13
```

```
<212> TYPE: PRT
<213> ORGANISM: Artificial Sequence
<220> FEATURE:
<223> OTHER INFORMATION: Antibody 3I13 VH CDR3 - Exemplary

<400> SEQUENCE: 3

Asp Asp Gly Tyr Ser Thr Arg Tyr Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Antibody 3I13 VL CDR1 - Exemplary

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Antibody 3I13 VL CDR2 - Exemplary

<400> SEQUENCE: 5

Gly Ala Thr Ile Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Antibody 3I13 VL CDR3 - Exemplary

<400> SEQUENCE: 6

Gln Asn Val Leu Ser Thr Pro Tyr Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Antibody 3I13 VH CDR1 - IMGT

<400> SEQUENCE: 7

Gly Tyr Thr Phe Thr Glu Tyr Thr
1               5

<210> SEQ ID NO 8
<211> LENGTH: 8
<212> TYPE: PRT
<213> ORGANISM: Artificial Sequence
<220> FEATURE:
<223> OTHER INFORMATION: Antibody 3I13 VH CDR2 - IMGT

<400> SEQUENCE: 8

Phe Asn Pro Asp Ser Gly Gly Thr
1               5

<210> SEQ ID NO 9
<211> LENGTH: 15
<212> TYPE: PRT
```

```
<213> ORGANISM: Artificial Sequence
<220> FEATURE:
<223> OTHER INFORMATION: Antibody 3I13 VH CDR3 - IMGT

<400> SEQUENCE: 9

Ala Arg Asp Asp Gly Tyr Ser Thr Arg Tyr Trp Tyr Phe Asp Val
1               5                   10                  15

<210> SEQ ID NO 10
<211> LENGTH: 6
<212> TYPE: PRT
<213> ORGANISM: Artificial Sequence
<220> FEATURE:
<223> OTHER INFORMATION: Antibody 3I13 VL CDR1 - IMGT

<400> SEQUENCE: 10

Glu Asn Ile Tyr Gly Ala
1               5

<210> SEQ ID NO 11
<211> LENGTH: 3
<212> TYPE: PRT
<213> ORGANISM: Artificial Sequence
<220> FEATURE:
<223> OTHER INFORMATION: Antibody 3I13 VL CDR2 - IMGT

<400> SEQUENCE: 11

Gly Ala Thr
1

<210> SEQ ID NO 12
<211> LENGTH: 5
<212> TYPE: PRT
<213> ORGANISM: Artificial Sequence
<220> FEATURE:
<223> OTHER INFORMATION: Antibody 3I13 VH CDR1 - Kabat

<400> SEQUENCE: 12

Glu Tyr Thr Met His
1               5

<210> SEQ ID NO 13
<211> LENGTH: 7
<212> TYPE: PRT
<213> ORGANISM: Artificial Sequence
<220> FEATURE:
<223> OTHER INFORMATION: Antibody 3I13 VL CDR2 - Kabat

<400> SEQUENCE: 13

Gly Ala Thr Asn Leu Ala Asp
1               5

<210> SEQ ID NO 14
<211> LENGTH: 7
<212> TYPE: PRT
<213> ORGANISM: Artificial Sequence
<220> FEATURE:
<223> OTHER INFORMATION: Antibody 3I13 VH CDR1 - Chothia

<400> SEQUENCE: 14

Gly Tyr Thr Phe Thr Glu Tyr
1               5

<210> SEQ ID NO 15
<211> LENGTH: 4
<212> TYPE: PRT
<213> ORGANISM: Artificial Sequence
```

-continued

```
<220> FEATURE:
<223> OTHER INFORMATION: Antibody 3I13 VH CDR2 - Chothia

<400> SEQUENCE: 15

Pro Asp Ser Gly
1

<210> SEQ ID NO 16
<211> LENGTH: 11
<212> TYPE: PRT
<213> ORGANISM: Artificial Sequence
<220> FEATURE:
<223> OTHER INFORMATION: Antibody 3I13 VH CDR3 - Chothia

<400> SEQUENCE: 16

Asp Gly Tyr Ser Thr Arg Tyr Trp Tyr Phe Asp
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Antibody 3I13 VL CDR1 - Chothia

<400> SEQUENCE: 17

Ser Glu Asn Ile Tyr Gly Ala
1               5

<210> SEQ ID NO 18
<211> LENGTH: 6
<212> TYPE: PRT
<213> ORGANISM: Artificial Sequence
<220> FEATURE:
<223> OTHER INFORMATION: Antibody 3I13 VL CDR3 - Chothia

<400> SEQUENCE: 18

Val Leu Ser Thr Pro Tyr
1               5

<210> SEQ ID NO 19
<211> LENGTH: 6
<212> TYPE: PRT
<213> ORGANISM: Artificial Sequence
<220> FEATURE:
<223> OTHER INFORMATION: Antibody 3I13 VH CDR1 - Contact

<400> SEQUENCE: 19

Thr Glu Tyr Thr Met His
1               5

<210> SEQ ID NO 20
<211> LENGTH: 13
<212> TYPE: PRT
<213> ORGANISM: Artificial Sequence
<220> FEATURE:
<223> OTHER INFORMATION: Antibody 3I13 VH CDR2 - Contact

<400> SEQUENCE: 20

Trp Ile Gly Ser Phe Asn Pro Asp Ser Gly Gly Thr Ser
1               5                   10

<210> SEQ ID NO 21
<211> LENGTH: 14
<212> TYPE: PRT
<213> ORGANISM: Artificial Sequence
<220> FEATURE:
```

```
<223> OTHER INFORMATION: Antibody 3I13 VH CDR3 - Contact

<400> SEQUENCE: 21

Ala Arg Asp Asp Gly Tyr Ser Thr Arg Tyr Trp Tyr Phe Asp
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Antibody 3I13 VL CDR1 - Contact

<400> SEQUENCE: 22

Tyr Gly Ala Leu Asn Trp Tyr
1               5

<210> SEQ ID NO 23
<211> LENGTH: 10
<212> TYPE: PRT
<213> ORGANISM: Artificial Sequence
<220> FEATURE:
<223> OTHER INFORMATION: Antibody 3I13 VL CDR2 - Contact

<400> SEQUENCE: 23

Leu Leu Ile Tyr Gly Ala Thr Asn Leu Ala
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Antibody 3I13 VL CDR3 - Contact

<400> SEQUENCE: 24

Gln Asn Val Leu Ser Thr Pro Tyr
1               5

<210> SEQ ID NO 25
<211> LENGTH: 10
<212> TYPE: PRT
<213> ORGANISM: Artificial Sequence
<220> FEATURE:
<223> OTHER INFORMATION: Antibody 3I13 VH CDR2 - AbM

<400> SEQUENCE: 25

Ser Phe Asn Pro Asp Ser Gly Gly Thr Ser
1               5                   10

<210> SEQ ID NO 26
<211> LENGTH: 122
<212> TYPE: PRT
<213> ORGANISM: Artificial Sequence
<220> FEATURE:
<223> OTHER INFORMATION: Antibody 3I13 VH sequence

<400> SEQUENCE: 26

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Ser Phe Asn Pro Asp Ser Gly Gly Thr Ser Tyr Asn Gln Lys Phe
```

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Ala Gly Thr Thr Val Thr Val Ser Ser
        115                 120

<210> SEQ ID NO 27
<211> LENGTH: 107
<212> TYPE: PRT
<213> ORGANISM: Artificial Sequence
<220> FEATURE:
<223> OTHER INFORMATION: Antibody 3I13 VL sequence

<400> SEQUENCE: 27

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Phe Gln Arg Lys Gln Gly Lys Ser Pro Gln Leu Leu Ile
        35                  40                  45

Tyr Gly Ala Thr Ile Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Tyr
                85                  90                  95

Thr Phe Gly Gly Gly Thr Lys Leu Glu Ile Lys
            100                 105

<210> SEQ ID NO 28
<211> LENGTH: 10
<212> TYPE: PRT
<213> ORGANISM: Artificial Sequence
<220> FEATURE:
<223> OTHER INFORMATION: Antibody 2J21 VH CDR1 - Exemplary

<400> SEQUENCE: 28

Gly Tyr Thr Phe Thr Glu Tyr Ile Met Tyr
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Antibody 2J21 VH CDR2 - Exemplary

<400> SEQUENCE: 29

Asn Ile Asp Pro Asn Thr Gly Gly Thr Ser Tyr Asn Gln Lys Phe Lys
1               5                   10                  15

Gly

<210> SEQ ID NO 30
<211> LENGTH: 8
<212> TYPE: PRT
<213> ORGANISM: Artificial Sequence
<220> FEATURE:

```
<223> OTHER INFORMATION: Antibody 2J21 VH CDR1 - IMGT

<400> SEQUENCE: 30

Gly Tyr Thr Phe Thr Glu Tyr Ile
1               5

<210> SEQ ID NO 31
<211> LENGTH: 8
<212> TYPE: PRT
<213> ORGANISM: Artificial Sequence
<220> FEATURE:
<223> OTHER INFORMATION: Antibody 2J21 VH CDR2 - IMGT

<400> SEQUENCE: 31

Ile Asp Pro Asn Thr Gly Gly Thr
1               5

<210> SEQ ID NO 32
<211> LENGTH: 5
<212> TYPE: PRT
<213> ORGANISM: Artificial Sequence
<220> FEATURE:
<223> OTHER INFORMATION: Antibody 2J21 VH CDR1 - Kabat

<400> SEQUENCE: 32

Glu Tyr Ile Met His
1               5

<210> SEQ ID NO 33
<211> LENGTH: 4
<212> TYPE: PRT
<213> ORGANISM: Artificial Sequence
<220> FEATURE:
<223> OTHER INFORMATION: Antibody 2J21 VH CDR2 - Chothia

<400> SEQUENCE: 33

Pro Asn Thr Gly
1

<210> SEQ ID NO 34
<211> LENGTH: 13
<212> TYPE: PRT
<213> ORGANISM: Artificial Sequence
<220> FEATURE:
<223> OTHER INFORMATION: Antibody 2J21 VH CDR2 - AbM

<400> SEQUENCE: 34

Trp Ile Gly Asn Ile Asp Pro Asn Thr Gly Gly Thr Ser
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Antibody 2J21 VH CDR2 - Kabat

<400> SEQUENCE: 35

Asn Ile Asp Pro Asn Thr Gly Gly Thr Ser
1               5                   10

<210> SEQ ID NO 36
<211> LENGTH: 122
<212> TYPE: PRT
<213> ORGANISM: Artificial Sequence
<220> FEATURE:
<223> OTHER INFORMATION: Antibody 2J21 VH sequence
```

<400> SEQUENCE: 36

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Ile Met His Trp Val Lys Gln Ser His Gly Lys Ser Leu Glu Trp Ile
        35                  40                  45

Gly Asn Ile Asp Pro Asn Thr Gly Gly Thr Ser Tyr Asn Gln Lys Phe
    50                  55                  60

Lys Gly Lys Ala Thr Leu Thr Val Asp Lys Ser Ser Ile Thr Ala Phe
65                  70                  75                  80

Met Glu Leu Arg Ser Leu Thr Ser Glu Asp Ser Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Ala Gly Thr Thr Val Thr Val Ser Ser
            115                 120

<210> SEQ ID NO 37
<211> LENGTH: 107
<212> TYPE: PRT
<213> ORGANISM: Artificial Sequence
<220> FEATURE:
<223> OTHER INFORMATION: Antibody 2J21 VL sequence

<400> SEQUENCE: 37

Asp Ile Gln Met Thr Gln Ser Pro Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Tyr
                85                  90                  95

Thr Phe Gly Gly Gly Thr Lys Leu Glu Ile Lys
            100                 105

<210> SEQ ID NO 38
<211> LENGTH: 10
<212> TYPE: PRT
<213> ORGANISM: Artificial Sequence
<220> FEATURE:
<223> OTHER INFORMATION: Antibody 4A2 VH CDR1 - Exemplary

<400> SEQUENCE: 38

Gly Tyr Thr Phe Thr Glu Tyr Thr Met Tyr
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Antibody 4A2 VH CDR2 - Exemplary

```
<400> SEQUENCE: 39

Gly Phe Asn Pro Asn Tyr Gly Gly Ala Ser Tyr Asn Gln Lys Phe Lys
1               5                   10                  15

Asp

<210> SEQ ID NO 40
<211> LENGTH: 8
<212> TYPE: PRT
<213> ORGANISM: Artificial Sequence
<220> FEATURE:
<223> OTHER INFORMATION: Antibody 4A2 VH CDR2 - IMGT

<400> SEQUENCE: 40

Phe Asn Pro Asn Tyr Gly Gly Ala
1               5

<210> SEQ ID NO 41
<211> LENGTH: 5
<212> TYPE: PRT
<213> ORGANISM: Artificial Sequence
<220> FEATURE:
<223> OTHER INFORMATION: Antibody 4A2 VH CDR1 - Kabat

<400> SEQUENCE: 41

Glu Tyr Thr Met Tyr
1               5

<210> SEQ ID NO 42
<211> LENGTH: 17
<212> TYPE: PRT
<213> ORGANISM: Artificial Sequence
<220> FEATURE:
<223> OTHER INFORMATION: Antibody 4A2 VH CDR2 - Kabat

<400> SEQUENCE: 42

Gly Phe Asn Pro Asn Tyr Gly Gly Ala Ser Tyr Asn Gln Lys Phe Lys
1               5                   10                  15

Asp

<210> SEQ ID NO 43
<211> LENGTH: 4
<212> TYPE: PRT
<213> ORGANISM: Artificial Sequence
<220> FEATURE:
<223> OTHER INFORMATION: Antibody 4A2 VH CDR2 - Chothia

<400> SEQUENCE: 43

Pro Asn Tyr Gly
1

<210> SEQ ID NO 44
<211> LENGTH: 6
<212> TYPE: PRT
<213> ORGANISM: Artificial Sequence
<220> FEATURE:
<223> OTHER INFORMATION: Antibody 4A2 VH CDR1 - Contact

<400> SEQUENCE: 44

Thr Glu Tyr Thr Met Tyr
1               5

<210> SEQ ID NO 45
<211> LENGTH: 13
<212> TYPE: PRT
<213> ORGANISM: Artificial Sequence
```

```
<220> FEATURE:
<223> OTHER INFORMATION: Antibody 4A2 VH CDR2 - Contact

<400> SEQUENCE: 45

Trp Ile Gly Gly Phe Asn Pro Asn Tyr Gly Gly Ala Ser
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Antibody 4A2 VH CDR2 - AbM

<400> SEQUENCE: 46

Gly Phe Asn Pro Asn Tyr Gly Gly Ala Ser
1               5                   10

<210> SEQ ID NO 47
<211> LENGTH: 122
<212> TYPE: PRT
<213> ORGANISM: Artificial Sequence
<220> FEATURE:
<223> OTHER INFORMATION: Antibody 4A2 VH sequence

<400> SEQUENCE: 47

Glu Val Gln Leu Gln Gln Ser Gly Pro Glu Leu Val Lys Pro Gly Thr
1               5                   10                  15

Ser Val Lys Ile Ser Cys Lys Thr Ser Gly Tyr Thr Phe Thr Glu Tyr
            20                  25                  30

Thr Met Tyr Trp Val Lys Gln Ser His Gly Lys Ser Leu Glu Trp Ile
        35                  40                  45

Gly Gly Phe Asn Pro Asn Tyr Gly Gly Ala Ser Tyr Asn Gln Lys Phe
    50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Ala Gly Thr Thr Val Thr Val Ser Ser
        115                 120

<210> SEQ ID NO 48
<211> LENGTH: 107
<212> TYPE: PRT
<213> ORGANISM: Artificial Sequence
<220> FEATURE:
<223> OTHER INFORMATION: Antibody 4A2 VL sequence

<400> SEQUENCE: 48

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80
```

```
Asp Asp Val Ala Thr Tyr Tyr Cys Gln Asn Val Leu Ser Thr Pro Tyr
                85                  90                  95

Thr Phe Gly Gly Gly Thr Lys Leu Glu Ile Lys
            100                 105

<210> SEQ ID NO 49
<211> LENGTH: 10
<212> TYPE: PRT
<213> ORGANISM: Artificial Sequence
<220> FEATURE:
<223> OTHER INFORMATION: consensus CDR1 of VH domain
<220> FEATURE:
<221> NAME/KEY: VARIANT
<222> LOCATION: 8, 10
<223> OTHER INFORMATION: Xaa = Any Amino Acid

<400> SEQUENCE: 49

Gly Tyr Thr Phe Thr Glu Tyr Xaa Met Xaa
1               5                   10

<210> SEQ ID NO 50
<211> LENGTH: 17
<212> TYPE: PRT
<213> ORGANISM: Artificial Sequence
<220> FEATURE:
<223> OTHER INFORMATION: consensus CDR2 of VH domain
<220> FEATURE:
<221> NAME/KEY: VARIANT
<222> LOCATION: 1, 2, 3, 5, 6, 9, 17
<223> OTHER INFORMATION: Xaa = Any Amino Acid

<400> SEQUENCE: 50

Xaa Xaa Xaa Pro Xaa Xaa Gly Gly Xaa Ser Tyr Asn Gln Lys Phe Lys
1               5                   10                  15

Xaa

<210> SEQ ID NO 51
<211> LENGTH: 13
<212> TYPE: PRT
<213> ORGANISM: Artificial Sequence
<220> FEATURE:
<223> OTHER INFORMATION: consensus CDR3 of VH domain

<400> SEQUENCE: 51

Asp Asp Gly Tyr Ser Thr Arg Tyr Trp Tyr Phe Asp Val
1               5                   10

<210> SEQ ID NO 52
<211> LENGTH: 11
<212> TYPE: PRT
<213> ORGANISM: Artificial Sequence
<220> FEATURE:
<223> OTHER INFORMATION: consensus CDR1 of VL domain

<400> SEQUENCE: 52

Gly Ala Ser Glu Asn Ile Tyr Gly Ala Leu Asn
1               5                   10

<210> SEQ ID NO 53
<211> LENGTH: 7
<212> TYPE: PRT
<213> ORGANISM: Artificial Sequence
<220> FEATURE:
<223> OTHER INFORMATION: consensus CDR2 of VL domain
<220> FEATURE:
<221> NAME/KEY: VARIANT
<222> LOCATION: 4
```

<223> OTHER INFORMATION: Xaa = Any Amino Acid

<400> SEQUENCE: 53

Gly Ala Thr Xaa Leu Ala Asp
1               5

<210> SEQ ID NO 54
<211> LENGTH: 9
<212> TYPE: PRT
<213> ORGANISM: Artificial Sequence
<220> FEATURE:
<223> OTHER INFORMATION: consensus CDR3 of VL domain

<400> SEQUENCE: 54

Gln Asn Val Leu Ser Thr Pro Tyr Thr
1               5

<210> SEQ ID NO 55
<211> LENGTH: 122
<212> TYPE: PRT
<213> ORGANISM: Artificial Sequence
<220> FEATURE:
<223> OTHER INFORMATION: antibody m3I13 VH domain

<400> SEQUENCE: 55

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Ser His Gly Lys Ser Leu Glu Trp Ile
            35                  40                  45

Gly Ser Phe Asn Pro Asp Ser Gly Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Ala Gly Thr Thr Val Thr Val Ser Ser
            115                 120

<210> SEQ ID NO 56
<211> LENGTH: 122
<212> TYPE: PRT
<213> ORGANISM: Artificial Sequence
<220> FEATURE:
<223> OTHER INFORMATION: antibody 3I13-HC-007-a VH domain

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Met
            35                  40                  45

Gly Ser Phe Asn Pro Asp Ser Gly Gly Thr Ser Tyr Asn Gln Lys Phe
        50                  55                  60

Lys Gly Arg Val Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 57
<211> LENGTH: 122
<212> TYPE: PRT
<213> ORGANISM: Artificial Sequence
<220> FEATURE:
<223> OTHER INFORMATION: antibody 3I13-HC-007-b VH domain

<400> SEQUENCE: 57

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Ser Phe Asn Pro Asp Ser Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 58
<211> LENGTH: 122
<212> TYPE: PRT
<213> ORGANISM: Artificial Sequence
<220> FEATURE:
<223> OTHER INFORMATION: antibody 3I13-HC-007-c VH domain

<400> SEQUENCE: 58

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Ser Phe Asn Pro Asp Ser Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 59
```

-continued

<211> LENGTH: 122
<212> TYPE: PRT
<213> ORGANISM: Artificial Sequence
<220> FEATURE:
<223> OTHER INFORMATION: antibody 3I13-HC-007-d VH domain

<400> SEQUENCE: 59

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Ser Phe Asn Pro Asp Ser Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 60
<211> LENGTH: 122
<212> TYPE: PRT
<213> ORGANISM: Artificial Sequence
<220> FEATURE:
<223> OTHER INFORMATION: antibody 3I13-HC-007-e VH domain

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala His Gly Gln Gly Leu Glu Trp Met
        35                  40                  45

Gly Ser Phe Asn Pro Asp Ser Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 61
<211> LENGTH: 122
<212> TYPE: PRT
<213> ORGANISM: Artificial Sequence
<220> FEATURE:
<223> OTHER INFORMATION: antibody 3I13-HC-007-f VH domain

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Lys Gly Leu Glu Trp Met
        35                  40                  45

Gly Ser Phe Asn Pro Asp Ser Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 62
<211> LENGTH: 122
<212> TYPE: PRT
<213> ORGANISM: Artificial Sequence
<220> FEATURE:
<223> OTHER INFORMATION: antibody 3I13-HC-007-g VH domain

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Ser Leu Glu Trp Met
        35                  40                  45

Gly Ser Phe Asn Pro Asp Ser Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 63
<211> LENGTH: 122
<212> TYPE: PRT
<213> ORGANISM: Artificial Sequence
<220> FEATURE:
<223> OTHER INFORMATION: antibody 3I13-HC-007-h VH domain

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Ile
        35                  40                  45

Gly Ser Phe Asn Pro Asp Ser Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 64
<211> LENGTH: 122
<212> TYPE: PRT
<213> ORGANISM: Artificial Sequence
<220> FEATURE:
<223> OTHER INFORMATION: antibody 3I13-HC-007-i VH domain

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Ser Phe Asn Pro Asp Ser Gly Gly Thr Ser Tyr Asn Gln Lys Phe
    50                  55                  60

Lys Gly Arg Ala Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 65
<211> LENGTH: 122
<212> TYPE: PRT
<213> ORGANISM: Artificial Sequence
<220> FEATURE:
<223> OTHER INFORMATION: antibody 3I13-HC-007-j VH domain

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Ser Phe Asn Pro Asp Ser Gly Gly Thr Ser Tyr Asn Gln Lys Phe
    50                  55                  60

Lys Gly Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 66
<211> LENGTH: 122
<212> TYPE: PRT
<213> ORGANISM: Artificial Sequence
<220> FEATURE:
<223> OTHER INFORMATION: antibody 3I13-HC-007-k VH domain

<400> SEQUENCE: 66

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Ser Phe Asn Pro Asp Ser Gly Gly Thr Ser Tyr Asn Gln Lys Phe
    50                  55                  60

Lys Gly Arg Val Thr Met Thr Val Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120
```

<210> SEQ ID NO 67
<211> LENGTH: 122
<212> TYPE: PRT
<213> ORGANISM: Artificial Sequence
<220> FEATURE:
<223> OTHER INFORMATION: antibody 3I13-HC-007-l VH domain

<400> SEQUENCE: 67

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Ser Phe Asn Pro Asp Ser Gly Gly Thr Ser Tyr Asn Gln Lys Phe
    50                  55                  60

Lys Gly Arg Val Thr Met Thr Arg Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120
```

<210> SEQ ID NO 68
<211> LENGTH: 122
<212> TYPE: PRT
<213> ORGANISM: Artificial Sequence
<220> FEATURE:
<223> OTHER INFORMATION: antibody 3I13-HC-007-m VH domain

<400> SEQUENCE: 68

```
Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
            35                  40                  45

Gly Ser Phe Asn Pro Asp Ser Gly Thr Ser Tyr Asn Gln Lys Phe
50                  55                  60

Lys Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
            115                 120

<210> SEQ ID NO 69
<211> LENGTH: 122
<212> TYPE: PRT
<213> ORGANISM: Artificial Sequence
<220> FEATURE:
<223> OTHER INFORMATION: antibody 3I13-HC-007-n VH domain

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Ile
            35                  40                  45

Gly Ser Phe Asn Pro Asp Ser Gly Thr Ser Tyr Asn Gln Lys Phe
50                  55                  60

Lys Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
            115                 120

<210> SEQ ID NO 70
<211> LENGTH: 122
<212> TYPE: PRT
<213> ORGANISM: Artificial Sequence
<220> FEATURE:
<223> OTHER INFORMATION: antibody 3I13-HC-007-o VH domain

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Ile
            35                  40                  45

Gly Ser Phe Asn Pro Asp Ser Gly Thr Ser Tyr Asn Gln Lys Phe
50                  55                  60

Lys Gly Arg Ala Thr Leu Thr Val Asp Lys Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 71
<211> LENGTH: 122
<212> TYPE: PRT
<213> ORGANISM: Artificial Sequence
<220> FEATURE:
<223> OTHER INFORMATION: antibody 3I13-HC-007-p VH domain

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala His Gly Lys Ser Leu Glu Trp Met
            35                  40                  45

Gly Ser Phe Asn Pro Asp Ser Gly Thr Ser Tyr Asn Gln Lys Phe
        50                  55                  60

Lys Gly Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 72
<211> LENGTH: 122
<212> TYPE: PRT
<213> ORGANISM: Artificial Sequence
<220> FEATURE:
<223> OTHER INFORMATION: antibody 3I13-HC-007-q VH domain

<400> SEQUENCE: 72

Gln Val Gln Leu Gln Gln Ser Gly Pro Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala His Gly Lys Ser Leu Glu Trp Ile
            35                  40                  45

Gly Ser Phe Asn Pro Asp Ser Gly Thr Ser Tyr Asn Gln Lys Phe
        50                  55                  60

Lys Gly Arg Val Thr Leu Thr Val Asp Thr Ser Thr Ser Thr Val Tyr
65                  70                  75                  80

Met Glu Leu Arg Ser Leu Arg Ser Glu Asp Thr Ala Val Tyr Tyr Cys
                    85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120
```

<210> SEQ ID NO 73
<211> LENGTH: 122
<212> TYPE: PRT
<213> ORGANISM: Artificial Sequence
<220> FEATURE:
<223> OTHER INFORMATION: antibody 3I13-HC-007-r VH domain

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Met
            35                  40                  45

Gly Ser Phe Asn Pro Asp Ser Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Arg Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 74
<211> LENGTH: 122
<212> TYPE: PRT
<213> ORGANISM: Artificial Sequence
<220> FEATURE:
<223> OTHER INFORMATION: antibody 3I13-HC-007-s VH domain

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Met
            35                  40                  45

Gly Ser Phe Asn Pro Asp Ser Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 75
<211> LENGTH: 122
<212> TYPE: PRT
<213> ORGANISM: Artificial Sequence
<220> FEATURE:
<223> OTHER INFORMATION: antibody 3I13-HC-007-t VH domain

<400> SEQUENCE: 75

Gln Val Gln Leu Val Gln Ser Gly Ala Glu Val Lys Lys Pro Gly Ala

-continued

```
                1               5                  10                 15
            Ser Val Lys Val Ser Cys Lys Ala Ser Gly Tyr Thr Phe Thr Glu Tyr
                        20                  25                 30

Thr Met His Trp Val Arg Gln Ala Pro Gly Lys Ser Leu Glu Trp Met
                        35                  40                 45

Gly Ser Phe Asn Pro Asp Ser Gly Gly Thr Ser Tyr Asn Gln Lys Phe
                        50                  55                 60

Lys Gly Arg Val Thr Met Thr Arg Asp Thr Ser Thr Ser Thr Val Tyr
             65                  70                  75                 80

Met Glu Leu Ser Ser Leu Arg Ser Glu Asp Thr Ala Val Tyr Tyr Cys
                        85                  90                 95

Ala Arg Asp Asp Gly Tyr Ser Thr Arg Tyr Trp Tyr Phe Asp Val Trp
                        100                 105                110

Gly Arg Gly Thr Leu Val Thr Val Ser Ser
                        115                 120
```

<210> SEQ ID NO 76
<211> LENGTH: 122
<212> TYPE: PRT
<213> ORGANISM: Artificial Sequence
<220> FEATURE:
<223> OTHER INFORMATION: antibody 3I13-HC-007-u VH domain

<400> SEQUENCE: 76

```
            Gln Val Gln Leu Val Gln Ser Gly Ala Glu Val Lys Lys Pro Gly Ala
             1               5                  10                 15

Ser Val Lys Val Ser Cys Lys Ala Ser Gly Tyr Thr Phe Thr Glu Tyr
                        20                  25                 30

Thr Met His Trp Val Arg Gln Ala Pro Gly Lys Ser Leu Glu Trp Met
                        35                  40                 45

Gly Ser Phe Asn Pro Asp Ser Gly Gly Thr Ser Tyr Asn Gln Lys Phe
                        50                  55                 60

Lys Gly Arg Val Thr Leu Thr Arg Asp Thr Ser Thr Ser Thr Val Tyr
             65                  70                  75                 80

Met Glu Leu Ser Ser Leu Arg Ser Glu Asp Thr Ala Val Tyr Tyr Cys
                        85                  90                 95

Ala Arg Asp Asp Gly Tyr Ser Thr Arg Tyr Trp Tyr Phe Asp Val Trp
                        100                 105                110

Gly Arg Gly Thr Leu Val Thr Val Ser Ser
                        115                 120
```

<210> SEQ ID NO 77
<211> LENGTH: 122
<212> TYPE: PRT
<213> ORGANISM: Artificial Sequence
<220> FEATURE:
<223> OTHER INFORMATION: antibody 3I13-HC-007-v VH domain

<400> SEQUENCE: 77

```
            Gln Val Gln Leu Val Gln Ser Gly Ala Glu Val Lys Lys Pro Gly Ala
             1               5                  10                 15

Ser Val Lys Val Ser Cys Lys Ala Ser Gly Tyr Thr Phe Thr Glu Tyr
                        20                  25                 30

Thr Met His Trp Val Arg Gln Ala Pro Gly Lys Ser Leu Glu Trp Ile
                        35                  40                 45

Gly Ser Phe Asn Pro Asp Ser Gly Gly Thr Ser Tyr Asn Gln Lys Phe
                        50                  55                 60
```

```
Lys Gly Arg Val Thr Met Thr Val Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 78
<211> LENGTH: 122
<212> TYPE: PRT
<213> ORGANISM: Artificial Sequence
<220> FEATURE:
<223> OTHER INFORMATION: antibody 3I13-HC-007-w VH domain

<400> SEQUENCE: 78

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Glu Tyr
                 20                  25                  30

Thr Met His Trp Val Arg Gln Ala Pro Gly Lys Ser Leu Glu Trp Ile
             35                  40                  45

Gly Ser Phe Asn Pro Asp Ser Gly Thr Ser Tyr Asn Gln Lys Phe
 50                  55                  60

Lys Gly Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 79
<211> LENGTH: 107
<212> TYPE: PRT
<213> ORGANISM: Artificial Sequence
<220> FEATURE:
<223> OTHER INFORMATION: antibody m3I13 VL domain

<400> SEQUENCE: 79

Asp Ile Gln Met Thr Gln Ser Pro Ala Ser Leu Ser Ala Ser Val Gly
  1               5                  10                  15

Glu Thr Val Thr Ile Thr Cys Gly Ala Ser Glu Asn Ile Tyr Gly Ala
                 20                  25                  30

Leu Asn Trp Phe Gln Arg Lys Gln Gly Lys Ser Pro Gln Leu Leu Ile
             35                  40                  45

Tyr Gly Ala Thr Ile Leu Ala Asp Gly Met Ser Ser Arg Phe Ser Gly
 50                  55                  60

Ser Gly Ser Gly Arg Gln Tyr Ser Leu Lys Ile Ser Ser Leu His Pro
 65                  70                  75                  80

Asp Asp Val Ala Thr Tyr Tyr Cys Gln Asn Val Leu Ser Thr Pro Tyr
                 85                  90                  95

Thr Phe Gly Gly Gly Thr Lys Leu Glu Ile Lys
                100                 105

<210> SEQ ID NO 80
```

```
<211> LENGTH: 107
<212> TYPE: PRT
<213> ORGANISM: Artificial Sequence
<220> FEATURE:
<223> OTHER INFORMATION: antibody 3I13-LC-007-a VL domain

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Ile Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 81
<211> LENGTH: 107
<212> TYPE: PRT
<213> ORGANISM: Artificial Sequence
<220> FEATURE:
<223> OTHER INFORMATION: antibody 3I13-LC-007-b VL domain

<400> SEQUENCE: 81

Asp Ile Gln Met Thr Gln Ser Pro Ser Ser Leu Ser Ala Ser Val Gly
1               5                   10                  15

Asp Thr Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Ile Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 82
<211> LENGTH: 107
<212> TYPE: PRT
<213> ORGANISM: Artificial Sequence
<220> FEATURE:
<223> OTHER INFORMATION: antibody 3I13-LC-007-c VL domain

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Phe Gln Gln Lys Pro Gly Lys Ala Pro Lys Leu Leu Ile
        35                  40                  45
```

```
Tyr Gly Ala Thr Ile Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asn Val Leu Ser Thr Pro Tyr
                 85                  90                  95

Thr Phe Gly Gly Gly Thr Lys Val Glu Ile Lys
            100                 105
```

<210> SEQ ID NO 83
<211> LENGTH: 107
<212> TYPE: PRT
<213> ORGANISM: Artificial Sequence
<220> FEATURE:
<223> OTHER INFORMATION: antibody 3I13-LC-007-d VL domain

<400> SEQUENCE: 83

```
Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
                 20                  25                  30

Leu Asn Trp Tyr Gln Arg Lys Pro Gly Lys Ala Pro Lys Leu Leu Ile
             35                  40                  45

Tyr Gly Ala Thr Ile Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asn Val Leu Ser Thr Pro Tyr
                 85                  90                  95

Thr Phe Gly Gly Gly Thr Lys Val Glu Ile Lys
            100                 105
```

<210> SEQ ID NO 84
<211> LENGTH: 107
<212> TYPE: PRT
<213> ORGANISM: Artificial Sequence
<220> FEATURE:
<223> OTHER INFORMATION: antibody 3I13-LC-007-e VL domain

<400> SEQUENCE: 84

```
Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
                 20                  25                  30

Leu Asn Trp Tyr Gln Gln Lys Gln Gly Lys Ala Pro Lys Leu Leu Ile
             35                  40                  45

Tyr Gly Ala Thr Ile Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asn Val Leu Ser Thr Pro Tyr
                 85                  90                  95

Thr Phe Gly Gly Gly Thr Lys Val Glu Ile Lys
            100                 105
```

<210> SEQ ID NO 85
<211> LENGTH: 107
<212> TYPE: PRT
<213> ORGANISM: Artificial Sequence

```
<220> FEATURE:
<223> OTHER INFORMATION: antibody 3I13-LC-007-f VL domain

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ser Pro Lys Leu Leu Ile
        35                  40                  45

Tyr Gly Ala Thr Ile Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: antibody 3I13-LC-007-g VL domain

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Gln Leu Leu Ile
        35                  40                  45

Tyr Gly Ala Thr Ile Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 87
<211> LENGTH: 107
<212> TYPE: PRT
<213> ORGANISM: Artificial Sequence
<220> FEATURE:
<223> OTHER INFORMATION: antibody 3I13-LC-007-h VL domain

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Ile Leu Ala Asp Gly Met Pro Ser Arg Phe Ser Gly
    50                  55                  60
```

-continued

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: antibody 3I13-LC-007-i VL domain

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Ile Leu Ala Asp Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: antibody 3I13-LC-007-j VL domain

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Ile Leu Ala Asp Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: antibody 3I13-LC-007-k VL domain

```
<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Ile Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 91
<211> LENGTH: 25
<212> TYPE: PRT
<213> ORGANISM: Artificial Sequence
<220> FEATURE:
<223> OTHER INFORMATION: Exemplary VH FR1 of Humanized Anti-Beta Klotho
      Antibodies

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 92
<211> LENGTH: 25
<212> TYPE: PRT
<213> ORGANISM: Artificial Sequence
<220> FEATURE:
<223> OTHER INFORMATION: Exemplary VH FR1 of Humanized Anti-Beta Klotho
      Antibodies

<400> SEQUENCE: 92

Gln Val Gln Leu Gln Gln Ser Gly Ala Glu Val Lys Lys Pro Gly Ala
1               5                   10                  15

Ser Val Lys Val Ser Cys Lys Ala Ser
            20                  25

<210> SEQ ID NO 93
<211> LENGTH: 25
<212> TYPE: PRT
<213> ORGANISM: Artificial Sequence
<220> FEATURE:
<223> OTHER INFORMATION: Exemplary VH FR1 of Humanized Anti-Beta Klotho
      Antibodies

<400> SEQUENCE: 93

Gln Val Gln Leu Val Gln Ser Gly Pro Glu Val Lys Lys Pro Gly Ala
1               5                   10                  15

Ser Val Lys Val Ser Cys Lys Ala Ser
            20                  25

<210> SEQ ID NO 94
<211> LENGTH: 25
<212> TYPE: PRT
<213> ORGANISM: Artificial Sequence
```

```
<220> FEATURE:
<223> OTHER INFORMATION: Exemplary VH FR1 of Humanized Anti-Beta Klotho
      Antibodies

<400> SEQUENCE: 94

Gln Val Gln Leu Val Gln Ser Gly Ala Glu Val Val Lys Pro Gly Ala
1               5                   10                  15

Ser Val Lys Val Ser Cys Lys Ala Ser
            20                  25

<210> SEQ ID NO 95
<211> LENGTH: 25
<212> TYPE: PRT
<213> ORGANISM: Artificial Sequence
<220> FEATURE:
<223> OTHER INFORMATION: Exemplary VH FR1 of Humanized Anti-Beta Klotho
      Antibodies

<400> SEQUENCE: 95

Gln Val Gln Leu Gln Gln Ser Gly Pro Glu Val Lys Lys Pro Gly Ala
1               5                   10                  15

Ser Val Lys Val Ser Cys Lys Ala Ser
            20                  25

<210> SEQ ID NO 96
<211> LENGTH: 6
<212> TYPE: PRT
<213> ORGANISM: Artificial Sequence
<220> FEATURE:
<223> OTHER INFORMATION: Antibody 2J21 VH CDR1 - Contact

<400> SEQUENCE: 96

Thr Glu Tyr Ile Met His
1               5

<210> SEQ ID NO 97
<211> LENGTH: 11
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 97

Trp Val Arg Gln Ala Pro Gly Gln Gly Leu Glu
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 98

Trp Val Arg Gln Ala His Gly Gln Gly Leu Glu
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies
```

```
<400> SEQUENCE: 99

Trp Val Arg Gln Ala Pro Gly Lys Gly Leu Glu
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 100

Trp Val Arg Gln Ala Pro Gly Gln Ser Leu Glu
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 101

Trp Val Arg Gln Ala Pro Gly Lys Ser Leu Glu
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 102

Trp Val Arg Gln Ala His Gly Lys Ser Leu Glu
1               5                   10

<210> SEQ ID NO 103
<211> LENGTH: 122
<212> TYPE: PRT
<213> ORGANISM: Artificial Sequence
<220> FEATURE:
<223> OTHER INFORMATION: VH domain of antibody 2J21

<400> SEQUENCE: 103

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Ile Met His Trp Val Lys Gln Ser His Gly Lys Ser Leu Glu Trp Ile
        35                  40                  45

Gly Asn Ile Asp Pro Asn Thr Gly Gly Thr Ser Tyr Asn Gln Lys Phe
    50                  55                  60

Lys Gly Lys Ala Thr Leu Thr Val Asp Lys Ser Ser Ile Thr Ala Phe
65                  70                  75                  80

Met Glu Leu Arg Ser Leu Thr Ser Glu Asp Ser Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Ala Gly Thr Thr Val Thr Val Ser Ser
        115                 120
```

-continued

```
            115                 120

<210> SEQ ID NO 104
<211> LENGTH: 122
<212> TYPE: PRT
<213> ORGANISM: Artificial Sequence
<220> FEATURE:
<223> OTHER INFORMATION: VH domain of antibody 4A2

<400> SEQUENCE: 104

Glu Val Gln Leu Gln Gln Ser Gly Pro Glu Leu Val Lys Pro Gly Thr
1               5                   10                  15

Ser Val Lys Ile Ser Cys Lys Thr Ser Gly Tyr Thr Phe Thr Glu Tyr
            20                  25                  30

Thr Met Tyr Trp Val Lys Gln Ser His Gly Lys Ser Leu Glu Trp Ile
        35                  40                  45

Gly Gly Phe Asn Pro Asn Tyr Gly Gly Ala Ser Tyr Asn Gln Lys Phe
    50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Ala Gly Thr Thr Val Thr Val Ser Ser
            115                 120

<210> SEQ ID NO 105
<211> LENGTH: 122
<212> TYPE: PRT
<213> ORGANISM: Artificial Sequence
<220> FEATURE:
<223> OTHER INFORMATION: VH domain of antibody 3I13

<400> SEQUENCE: 105

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Ser Phe Asn Pro Asp Ser Gly Gly Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Ala Gly Thr Thr Val Thr Val Ser Ser
            115                 120

<210> SEQ ID NO 106
<211> LENGTH: 14
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies
```

```
<400> SEQUENCE: 106

Trp Val Arg Gln Ala Pro Gly Gln Gly Leu Glu Trp Met Gly
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 107

Trp Val Arg Gln Ala His Gly Gln Gly Leu Glu Trp Met Gly
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 108

Trp Val Arg Gln Ala Pro Gly Lys Gly Leu Glu Trp Met Gly
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 109

Trp Val Arg Gln Ala Pro Gly Gln Ser Leu Glu Trp Met Gly
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 110

Trp Val Arg Gln Ala Pro Gly Gln Gly Leu Glu Trp Ile Gly
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 111

Trp Val Arg Gln Ala Pro Gly Lys Ser Leu Glu Trp Met Gly
1               5                   10

<210> SEQ ID NO 112
<211> LENGTH: 14
<212> TYPE: PRT
```

```
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 112

Trp Val Arg Gln Ala His Gly Lys Ser Leu Glu Trp Met Gly
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 113

Trp Val Arg Gln Ala His Gly Lys Ser Leu Glu Trp Ile Gly
1               5                   10

<210> SEQ ID NO 114
<211> LENGTH: 107
<212> TYPE: PRT
<213> ORGANISM: Artificial Sequence
<220> FEATURE:
<223> OTHER INFORMATION: VL domain of antibody 2J21

<400> SEQUENCE: 114

Asp Ile Gln Met Thr Gln Ser Pro Pro Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Tyr
                85                  90                  95

Thr Phe Gly Gly Gly Thr Lys Leu Glu Ile Lys
            100                 105

<210> SEQ ID NO 115
<211> LENGTH: 107
<212> TYPE: PRT
<213> ORGANISM: Artificial Sequence
<220> FEATURE:
<223> OTHER INFORMATION: VL domain of antibody 4A2

<400> SEQUENCE: 115

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80
```

```
Asp Asp Val Ala Thr Tyr Tyr Cys Gln Asn Val Leu Ser Thr Pro Tyr
                85                  90                  95

Thr Phe Gly Gly Gly Thr Lys Leu Glu Ile Lys
            100                 105

<210> SEQ ID NO 116
<211> LENGTH: 107
<212> TYPE: PRT
<213> ORGANISM: Artificial Sequence
<220> FEATURE:
<223> OTHER INFORMATION: VL domain of antibody 3I13

<400> SEQUENCE: 116

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Phe Gln Arg Lys Gln Gly Lys Ser Pro Gln Leu Leu Ile
        35                  40                  45

Tyr Gly Ala Thr Ile Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Tyr
                85                  90                  95

Thr Phe Gly Gly Gly Thr Lys Leu Glu Ile Lys
            100                 105

<210> SEQ ID NO 117
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 117

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 118
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 118

Arg Val Thr Leu Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
```

Antibodies

<400> SEQUENCE: 119

Arg Val Thr Met Thr Val Asp Thr Ser Thr Ser Val Tyr Met Glu
1               5                   10                  15

Leu Ser Ser Leu Arg Ser Glu Asp Thr Ala Val Tyr Tyr Cys
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 120

Arg Val Thr Met Thr Arg Asp Lys Ser Thr Ser Val Tyr Met Glu
1               5                   10                  15

Leu Ser Ser Leu Arg Ser Glu Asp Thr Ala Val Tyr Tyr Cys
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 121

Arg Val Thr Met Thr Arg Asp Thr Ser Thr Ser Val Tyr Met Glu
1               5                   10                  15

Leu Arg Ser Leu Arg Ser Glu Asp Thr Ala Val Tyr Tyr Cys
            20                  25                  30

<210> SEQ ID NO 122
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 122

Arg Val Thr Met Thr Arg Asp Thr Ser Thr Ser Val Tyr Met Glu
1               5                   10                  15

Leu Ser Ser Leu Thr Ser Glu Asp Thr Ala Val Tyr Tyr Cys
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 123

Arg Val Thr Leu Thr Val Asp Thr Ser Thr Ser Val Tyr Met Glu
1               5                   10                  15

Leu Arg Ser Leu Arg Ser Glu Asp Thr Ala Val Tyr Tyr Cys
            20                  25                  30

-continued

```
<210> SEQ ID NO 124
<211> LENGTH: 107
<212> TYPE: PRT
<213> ORGANISM: Artificial Sequence
<220> FEATURE:
<223> OTHER INFORMATION: antibody 3I13-LC-007-1 VL domain

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Ile Leu Ala Asp Gly Val Pro Ser Arg Phe Ser Gly
    50                  55                  60

Ser Gly Ser Gly Thr Asp Phe Thr Leu Lys Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 125
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 125

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 126

Arg Val Thr Leu Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 127
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 127

Arg Val Thr Met Thr Val Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
```

<210> SEQ ID NO 128
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 128

Arg Val Thr Met Thr Arg Asp Lys Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 129
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 129

Arg Val Thr Met Thr Arg Asp Thr Ser Thr Ser Thr Val Tyr Met Glu
1               5                   10                  15

Leu Arg Ser Leu Arg Ser Glu Asp Thr Ala Val Tyr Tyr Cys Ala Arg
            20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 130

Arg Val Thr Met Thr Arg Asp Thr Ser Thr Ser Thr Val Tyr Met Glu
1               5                   10                  15

Leu Ser Ser Leu Thr Ser Glu Asp Thr Ala Val Tyr Tyr Cys Ala Arg
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 131

Arg Val Thr Leu Thr Val Asp Thr Ser Thr Ser Thr Val Tyr Met Glu
1               5                   10                  15

Leu Arg Ser Leu Arg Ser Glu Asp Thr Ala Val Tyr Tyr Cys Ala Arg
            20                  25                  30

<210> SEQ ID NO 132
<211> LENGTH: 107
<212> TYPE: PRT
<213> ORGANISM: Artificial Sequence
<220> FEATURE:
<223> OTHER INFORMATION: antibody 3I13-LC-007-m VL domain

<400> SEQUENCE: 132

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
            35                  40                  45

Tyr Gly Ala Thr Ile Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Val Leu Ser Thr Pro Tyr
                85                  90                  95

Thr Phe Gly Gly Gly Thr Lys Val Glu Ile Lys
            100                 105
```

<210> SEQ ID NO 133
<211> LENGTH: 11
<212> TYPE: PRT
<213> ORGANISM: Artificial Sequence
<220> FEATURE:
<223> OTHER INFORMATION: Exemplary VH FR4 of Humanized Anti-Beta Klotho
      Antibodies

<400> SEQUENCE: 133

```
Trp Gly Arg Gly Thr Leu Val Thr Val Ser Ser
1               5                   10
```

<210> SEQ ID NO 134
<211> LENGTH: 107
<212> TYPE: PRT
<213> ORGANISM: Artificial Sequence
<220> FEATURE:
<223> OTHER INFORMATION: antibody 3I13-LC-007-n VL domain

<400> SEQUENCE: 134

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Phe Gln Gln Lys Pro Gly Lys Ala Pro Lys Leu Leu Ile
            35                  40                  45

Tyr Gly Ala Thr Ile Leu Ala Asp Gly Met Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105
```

<210> SEQ ID NO 135
<211> LENGTH: 23
<212> TYPE: PRT
<213> ORGANISM: Artificial Sequence
<220> FEATURE:
<223> OTHER INFORMATION: Exemplary VL FR1 of Humanized Anti-Beta Klotho
      Antibodies

<400> SEQUENCE: 135

Asp Ile Gln Met Thr Gln Ser Pro Ser Ser Leu Ser Ala Ser Val Gly

```
                1               5                  10                 15

Asp Arg Val Thr Ile Thr Cys
                20

<210> SEQ ID NO 136
<211> LENGTH: 23
<212> TYPE: PRT
<213> ORGANISM: Artificial Sequence
<220> FEATURE:
<223> OTHER INFORMATION: Exemplary VL FR1 of Humanized Anti-Beta Klotho
      Antibodies

<400> SEQUENCE: 136

Asp Ile Gln Met Thr Gln Ser Pro Ser Ser Leu Ser Ala Ser Val Gly
1               5                  10                 15

Asp Thr Val Thr Ile Thr Cys
                20

<210> SEQ ID NO 137
<211> LENGTH: 107
<212> TYPE: PRT
<213> ORGANISM: Artificial Sequence
<220> FEATURE:
<223> OTHER INFORMATION: antibody 3I13-LC-007-o VL domain

<400> SEQUENCE: 137

Asp Ile Gln Met Thr Gln Ser Pro Ser Ser Leu Ser Ala Ser Val Gly
1               5                  10                 15

Asp Arg Val Thr Ile Thr Cys Gly Ala Ser Glu Asn Ile Tyr Gly Ala
                20                  25                  30

Leu Asn Trp Phe Gln Gln Lys Pro Gly Lys Ala Pro Lys Leu Leu Ile
            35                  40                  45

Tyr Gly Ala Thr Ile Leu Ala Asp Gly Met Ser Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
                100                 105

<210> SEQ ID NO 138
<211> LENGTH: 11
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 138

Trp Tyr Gln Gln Lys Pro Gly Lys Ala Pro Lys
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 139

Trp Phe Gln Gln Lys Pro Gly Lys Ala Pro Lys
```

```
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 140

Trp Tyr Gln Arg Lys Pro Gly Lys Ala Pro Lys
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 141

Trp Tyr Gln Gln Lys Gln Gly Lys Ala Pro Lys
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 142

Trp Tyr Gln Gln Lys Pro Gly Lys Ser Pro Lys
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 143

Trp Tyr Gln Gln Lys Pro Gly Lys Ala Pro Gln
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 144

Trp Tyr Gln Gln Lys Gln Gly Lys Ser Pro Lys
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Exemplary VL FR2 of Humanized Anti-Beta Klotho
```

Antibodies

<400> SEQUENCE: 145

Trp Tyr Gln Gln Lys Gln Gly Lys Ser Pro Gln
1               5                   10

<210> SEQ ID NO 146
<211> LENGTH: 107
<212> TYPE: PRT
<213> ORGANISM: Artificial Sequence
<220> FEATURE:
<223> OTHER INFORMATION: antibody 3I13-LC-007-p VL domain

<400> SEQUENCE: 146

Asp Ile Gln Met Thr Gln Ser Pro Ser Ser Leu Ser Ala Ser Val Gly
1               5                   10                  15

Asp Thr Val Thr Ile Thr Cys Gly Ala Ser Glu Asn Ile Tyr Gly Ala
            20                  25                  30

Leu Asn Trp Tyr Gln Gln Lys Gln Gly Lys Ser Pro Lys Leu Leu Ile
        35                  40                  45

Tyr Gly Ala Thr Ile Leu Ala Asp Gly Met Pro Ser Arg Phe Ser Gly
    50                  55                  60

Ser Gly Ser Gly Arg Asp Phe Thr Leu Lys Ile Ser Ser Leu Gln Pro
65                  70                  75                  80

Glu Asp Val Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 147
<211> LENGTH: 15
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 147

Trp Phe Gln Gln Lys Pro Gly Lys Ala Pro Lys Leu Leu Ile Tyr
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 148

Trp Tyr Gln Arg Lys Pro Gly Lys Ala Pro Lys Leu Leu Ile Tyr
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 149

Trp Tyr Gln Gln Lys Gly Gly Lys Ala Pro Lys Leu Leu Ile Tyr
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 150

Trp Tyr Gln Gln Lys Pro Gly Lys Ser Pro Lys Leu Leu Ile Tyr
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 151

Trp Tyr Gln Gln Lys Pro Gly Lys Ala Pro Gln Leu Leu Ile Tyr
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 152

Trp Tyr Gln Gln Lys Gln Gly Lys Ser Pro Lys Leu Leu Ile Tyr
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 153

Trp Tyr Gln Gln Lys Gln Gly Lys Ser Pro Gln Leu Leu Val Tyr
1               5                   10                  15

<210> SEQ ID NO 154
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 154

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 155
<211> LENGTH: 32
<212> TYPE: PRT
<213> ORGANISM: Artificial Sequence

```
<220> FEATURE:
<223> OTHER INFORMATION: Exemplary VL FR3 of Humanized Anti-Beta Klotho
      Antibodies

<400> SEQUENCE: 155

Gly Met Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 156
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 156

Gly Val Ser Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 157

Gly Val Pro Ser Arg Phe Ser Gly Ser Gly Ser Gly Arg Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 158

Gly Val Pro Ser Arg Phe Ser Gly Ser Gly Ser Gly Thr Asp Phe Thr
1               5                   10                  15

Leu Lys Ile Ser Ser Leu Gln Pro Glu Asp Phe Ala Thr Tyr Tyr Cys
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 159

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30
```

<210> SEQ ID NO 160
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 160

Gly Met Pro Ser Arg Phe Ser Gly Ser Gly Ser Gly Arg Asp Phe Thr
1               5                   10                  15

Leu Lys Ile Ser Ser Leu Gln Pro Glu Asp Val Ala Thr Tyr Tyr Cys
            20                  25                  30

<210> SEQ ID NO 161
<211> LENGTH: 122
<212> TYPE: PRT
<213> ORGANISM: Artificial Sequence
<220> FEATURE:
<223> OTHER INFORMATION: antibody m2J21 VL domain

<400> SEQUENCE: 161

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Ile Met His Trp Val Lys Gln Ser His Gly Lys Ser Leu Glu Trp Ile
        35                  40                  45

Gly Asn Ile Asp Pro Asn Thr Gly Gly Thr Ser Tyr Asn Gln Lys Phe
    50                  55                  60

Lys Gly Lys Ala Thr Leu Thr Val Asp Lys Ser Ser Ile Thr Ala Phe
65                  70                  75                  80

Met Glu Leu Arg Ser Leu Thr Ser Glu Asp Ser Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Ala Gly Thr Thr Val Thr Val Ser Ser
        115                 120

<210> SEQ ID NO 162
<211> LENGTH: 122
<212> TYPE: PRT
<213> ORGANISM: Artificial Sequence
<220> FEATURE:
<223> OTHER INFORMATION: antibody m2J21-HC-336-a VH domain

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Asn Ile Asp Pro Asn Thr Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

```
Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 163
<211> LENGTH: 10
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 163

Phe Gly Gly Gly Thr Lys Leu Glu Ile Lys
1               5                   10

<210> SEQ ID NO 164
<211> LENGTH: 122
<212> TYPE: PRT
<213> ORGANISM: Artificial Sequence
<220> FEATURE:
<223> OTHER INFORMATION: antibody m2J21-HC-336-b VH domain

<400> SEQUENCE: 164

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Asn Ile Asp Pro Asn Thr Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 165
<211> LENGTH: 1044
<212> TYPE: PRT
<213> ORGANISM: Homo sapiens
<220> FEATURE:
<223> OTHER INFORMATION: human beta klotho sequence

<400> SEQUENCE: 165

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80
```

-continued

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
    370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
        435                 440                 445

Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

```
His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
        530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
        595                 600                 605

Thr Gly Asn Leu Ser Ala Val Asn Arg Gln Ala Leu Arg Tyr Tyr Arg
        610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
        690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
        770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
        850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
```

```
                915                 920                 925
Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
            995                 1000                1005

Val Leu Leu Leu Ser Ile Ala Ile Phe Gln Arg Gln Lys Arg Arg Lys
        1010                1015                1020

Phe Trp Lys Ala Lys Asn Leu Gln His Ile Pro Leu Lys Lys Gly Lys
1025                1030                1035                1040

Arg Val Val Ser

<210> SEQ ID NO 166
<211> LENGTH: 3132
<212> TYPE: DNA
<213> ORGANISM: Homo sapiens
<220> FEATURE:
<223> OTHER INFORMATION: human beta klotho

<400> SEQUENCE: 166
atgaagccag gctgtgcggc aggatctcca gggaatgaat ggatttttctt cagcactgat    60 gaaataacca cacgctatag gaatacaatg tccaacgggg gattgcaaag atctgtcatc   120
ctgtcagcac ttattctgct acgagctgtt actggattct ctggagatgg aagagctata   180
tggtctaaaa atcctaattt tactccggta aatgaaagtc agctgttttct ctatgacact   240 ttccctaaaa acttttttctg gggtattggg actggagcat gcaagtggaa agggagttgg   300
aagaaggatg gaaaaggacc ttctatatgg gatcatttca tccacacaca ccttaaaaat   360
gtcagcagca cgaatggttc cagtgacagt tatattttttc tggaaaaaga cttatcagcc   420
ctggatttta taggagtttc ttttttatcaa ttttcaattt cctggccaag gcttttcccc   480
gatggaatag taacagttgc caacgcaaaa ggtctgcagt actacagtac tcttctggac   540
gctctagtgc ttagaaacat tgaacctata gttactttat accactggga tttgcctttg   600
gcactacaag aaaaatatgg ggggtggaaa aatgatacca atagatat cttcaatgac   660 tatgccacat actgtttcca gatgtttggg gaccgtgtca atattggat tacaattcac   720 aacccatatc tagtggcttg gcatgggtat gggacaggta tgcatgcccc tggagagaag   780
ggaaatttag cagctgtcta cactgtggga cacaacttga tcaaggctca ctcgaaagtt   840
tggcataact acaacacaca tttccgccca catcagaagg ttggttatc gatcacgttg   900 ggatctcatt ggatcgagcc aaaccggtcg gaaaacacga tggatatatt caatgtcaa   960 caatccatgg tttctgtgct ggatggtttt gccaacccta tccatgggga tggcgactat  1020
ccagagggga tgagaaagaa gttgttctcc gttctaccca ttttctctga agcagagaag  1080
catgagatga gaggcacagc tgattttctt tgcctttctctt ttggacccaa caacttcaag  1140 ccccctaaaca ccatggctaa atgggacaa atgtttcac ttaatttaag agaagcgctg  1200
aactggatta aactggaata caacaaccct cgaatcttga ttgctgagaa tggctggttc  1260
acagacagtc gtgtgaaaac agaagacacc acggccatct acatgatgaa gaatttcctc  1320
```

| | |
|---|---|
| agccaggtgc ttcaagcaat aaggttagat gaaatacgag tgtttggtta tactgcctgg | 1380 |
| tctctcctgg atggctttga atggcaggat gcttacacca tccgccgagg attattttat | 1440 |
| gtggatttta acagtaaaca gaaagagcgg aaacctaagt cttcagcaca ctactacaaa | 1500 |
| cagatcatac gagaaaatgg ttttcttta aaagagtcca cgccagatgt gcagggccag | 1560 |
| tttcctgtg acttctcctg gggtgtcact gaatctgttc ttaagcccga gtctgtggct | 1620 |
| tcgtccccac agttcagcga tcctcatctg tacgtgtgga acgccactgg caacagactg | 1680 |
| ttgcaccgag tggaaggggt gaggctgaaa acacgacccg ctcaatgcac agattttgta | 1740 |
| aacatcaaaa aacaacttga gatgttggca agaatgaaag tcacccacta ccggtttgct | 1800 |
| ctggattggg cctcggtcct tcccactggc aacctgtccg cggtgaaccg acaggccctg | 1860 |
| aggtactaca ggtgcgtggt cagtgagggg ctgaagcttg gcatctccgc gatggtcacc | 1920 |
| ctgtattatc cgacccacgc ccacctaggc ctccccgagc ctctgttgca tgccgacggg | 1980 |
| tggctgaacc catcgacggc cgaggccttc caggcctacg ctgggctgtg cttccaggag | 2040 |
| ctgggggacc tggtgaagct ctggatcacc atcaacgagc ctaaccggct aagtgacatc | 2100 |
| tacaaccgct ctggcaacga cacctacggg gcggcgcaca acctgctggt ggcccacgcc | 2160 |
| ctggcctggc gcctctacga ccggcagttc aggccctcac agcgcgggc cgtgtcgctg | 2220 |
| tcgctgcacg cggactgggc ggaacccgcc aaccctatg ctgactcgca ctggagggcg | 2280 |
| gccgagcgct tcctgcagtt cgagatcgcc tggttcgccg agccgctctt caagaccggg | 2340 |
| gactaccccg cggccatgag ggaatacatt gcctccaagc accgacgggg gctttccagc | 2400 |
| tcggccctgc cgcgcctcac cgaggccgaa aggaggctgc tcaagggcac ggtcgacttc | 2460 |
| tgcgcgctca accacttcac cactaggttc gtgatgcacg agcagctggc cggcagccgc | 2520 |
| tacgactcgg acagggacat ccagtttctg caggacatca cccgcctgag ctcccccacg | 2580 |
| cgcctggctg tgattccctg gggggtgcgc aagctgctgc ggtgggtccg gaggaactac | 2640 |
| ggcgacatgg acatttacat caccgccagt ggcatcgacg accaggctct ggaggatgac | 2700 |
| cggctccgga gtactacct agggaagtac cttcaggagg tgctgaaagc atacctgatt | 2760 |
| gataaagtca gaatcaaagg ctattatgca ttcaaactgg ctgaagagaa atctaaaccc | 2820 |
| agatttggat tcttcacatc tgattttaaa gctaaatcct caatacaatt ttacaacaaa | 2880 |
| gtgatcagca gcaggggctt ccctttgag aacagtagtt ctagatgcag tcagacccaa | 2940 |
| gaaaatacag agtgcactgt ctgcttattc cttgtgcaga gaaaccact gatattcctg | 3000 |
| ggttgttgct tcttctccac cctggttcta ctcttatcaa ttgccatttt tcaaaggcag | 3060 |
| aagagaagaa agttttggaa agcaaaaaac ttacaacaca taccattaaa gaaaggcaag | 3120 |
| agagttgtta gc | 3132 |

<210> SEQ ID NO 167
<211> LENGTH: 1044
<212> TYPE: PRT
<213> ORGANISM: Macaca fascicularis (cynomolgus monkey)
<220> FEATURE:
<223> OTHER INFORMATION: cyno beta klotho

<400> SEQUENCE: 167

Met Lys Pro Gly Cys Ala Ala Gly Ser Pro Gly Asn Glu Trp Ile Phe
1               5                   10                  15

Phe Ser Thr Asp Glu Ile Thr Ile Arg Tyr Arg Asn Thr Met Ser Asn
                20                  25                  30

Gly Gly Leu Gln Arg Ser Val Ile Leu Ser Ala Leu Thr Leu Leu Arg

```
            35                  40                  45
Ala Val Thr Gly Phe Ser Gly Asp Gly Arg Ala Val Trp Ser Lys Asn
 50                  55                  60

Pro Asn Phe Thr Pro Val Asn Glu Ser Gln Leu Phe Leu Tyr Asp Thr
 65                  70                  75                  80

Phe Pro Lys Asn Phe Phe Trp Gly Val Gly Thr Gly Ala Leu Gln Val
                 85                  90                  95

Glu Gly Ser Trp Lys Lys Asp Gly Lys Gly Pro Ser Ile Trp Asp His
                100                 105                 110

Phe Val His Thr His Leu Lys Asn Val Ser Thr Asn Gly Ser Ser
                115                 120                 125

Asp Ser Tyr Ile Phe Leu Glu Lys Asp Leu Ser Ala Leu Asp Phe Ile
130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Asn
                165                 170                 175

Thr Leu Leu Asp Ser Leu Val Leu Arg Asn Ile Glu Pro Ile Val Thr
                180                 185                 190

Leu Tyr His Trp Asp Leu Pro Leu Ala Leu Gln Glu Lys Tyr Gly Gly
                195                 200                 205

Trp Lys Asn Asp Thr Ile Ile Asp Ile Phe Asn Asp Tyr Ala Thr Tyr
210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
                260                 265                 270

Leu Ile Lys Ala His Ser Lys Val Trp His Asn Tyr Asn Thr His Phe
                275                 280                 285

Arg Pro His Gln Lys Gly Trp Leu Ser Ile Thr Leu Gly Ser His Trp
290                 295                 300

Ile Glu Pro Asn Arg Ser Glu Asn Thr Met Asp Ile Leu Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Lys Lys Lys Leu Leu Ser Ile Leu
                340                 345                 350

Pro Leu Phe Ser Glu Ala Glu Lys Asn Glu Val Arg Gly Thr Ala Asp
                355                 360                 365

Phe Phe Ala Phe Ser Phe Gly Pro Asn Asn Phe Lys Pro Leu Asn Thr
                370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser His Val Lys Thr Glu Asp Thr Thr Ala
                420                 425                 430

Ile Tyr Met Met Lys Asn Phe Leu Ser Gln Val Leu Gln Ala Ile Arg
                435                 440                 445

Leu Asp Glu Ile Arg Val Phe Gly Tyr Thr Ala Trp Ser Leu Leu Asp
450                 455                 460
```

-continued

```
Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
            500                 505                 510

Ala Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
    530                 535                 540

Phe Ser Asp Pro Tyr Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
        595                 600                 605

Thr Gly Asn Leu Ser Ala Val Asn Arg Gln Ala Leu Arg Tyr Tyr Arg
    610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Gly Gly Trp Leu Asn Pro Ser Thr Val Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
    690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
    770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
    850                 855                 860

Ile Pro Trp Gly Val Arg Lys Leu Leu Arg Trp Val Arg Arg Asn Tyr
865                 870                 875                 880
```

| | | | | | | | | | | | |
|---|---|---|---|---|---|---|---|---|---|---|---|
|Gly|Asp|Met|Asp|Ile|Tyr|Ile|Thr|Ala|Ser|Gly|Ile|Asp|Asp|Gln|Ala|

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Glu Lys Tyr Leu Gln
        900                 905                 910

Glu Val Leu Lys Ala Tyr Leu Ile Asp Lys Val Arg Ile Lys Gly Tyr
            915                 920                 925

Tyr Ala Phe Lys Leu Ala Glu Glu Lys Ser Lys Pro Arg Phe Gly Phe
        930                 935                 940

Phe Thr Ser Asp Phe Lys Ala Lys Ser Ser Ile Gln Phe Tyr Asn Lys
945                 950                 955                 960

Met Ile Ser Ser Ser Gly Phe Pro Ser Glu Asn Ser Ser Ser Arg Cys
                965                 970                 975

Ser Gln Thr Gln Lys Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
        995                 1000                1005

Val Leu Leu Leu Ser Ile Thr Ile Phe His Arg Gln Lys Arg Arg Lys
    1010                1015                1020

Phe Trp Lys Ala Lys Asn Leu Gln His Ile Pro Leu Lys Lys Gly Lys
1025                1030                1035                1040

Arg Val Leu Ser

<210> SEQ ID NO 168
<211> LENGTH: 3135
<212> TYPE: DNA
<213> ORGANISM: Macaca fascicularis (cynomolgus monkey)
<220> FEATURE:
<223> OTHER INFORMATION: cyno beta klotho

<400> SEQUENCE: 168

```
atgaagcctg gatgtgccgc cggaagcccc ggcaacgagt ggatcttctt cagcaccgac     60
gagatcacca tccggtacag aaacaccatg agcaacggcg gcctgcagcg gagcgtgatc    120
ctgtctgctc tgaccctgct gagagccgtg accggcttca gcggagatgg cagagccgtg    180
tggtccaaga cccccaactt caccccccgtg aacgagagcc agctgttcct gtacgatacc    240
ttccccaaga acttcttctg gggcgtgggc acaggcgccc tgcaggtgga aggatcctgg    300
aagaaggacg gcaagggccc cagcatctgg gaccactttg cacacccca cctgaagaac    360
gtgtccagca ccaacggcag cagcgacagc tacatctttc tggaaaagga cctgagcgcc    420
ctggacttca tcgccgtgtc cttctaccag ttcagcatca gctggcccag actgttcccc    480
gacggcatcg tgacagtggc caatgccaag ggcctgcagt actacaacac cctgctggac    540
agcctggtgc tgcggaacat cgagcccatc gtgaccctgt accactggga cctgccactg    600
gctctgcagg agaaatacgg cggctggaag aacgacacca tcatcgacat cttcaacgac    660
tacgccacct actgcttcca gaccttcggc gacagagtga agtactggat cacaatccac    720
aaccccctac ctggtggcctg gcacggctat ggcaccggaa tgcatgcccc tggcgagaag    780
ggaaatctgg ccgccgtgta caccgtgggc cacaacctga tcaaggccca gcaaagtg    840
tggcacaact acaatatccca cttccggccc accagaagg gctggctgtc tatcacactg    900
ggcagccact ggatcgagcc taaccgcagc gagaacacca tggacatcct gaagtgccag    960
cagagcatgg tgtccgtgct gggatggttc gccaacccca ttcacggcga cggcgattac   1020
cccgagggca tgaagaagaa gctgctgagc atcctgcccc tgttcagcga ggccgagaag   1080
aacgaagtgc ggggcaccgc cgatttcttc gcctttagct tcggcccaa caacttcaag   1140
```

```
cccctgaata ccatggccaa gatgggccag aatgtgtccc tgaacctgag agaggccctg    1200
aactggatca agctggagta caacaacccc cggatcctga tcgccgagaa cggctggttc    1260
accgacagcc acgtgaaaac cgaggacacc accgccatct atatgatgaa gaacttcctg    1320
agccaggtgc tgcaggctat ccggctggat gagatccggg tgttcggcta caccgcctgg    1380
tcactgctgg acggcttcga atggcaggac gcctacacca tcagacgggg cctgttctac    1440
gtggacttca cagcaagca gaaagagcgg aagcccaaga gcagcgccca ctactacaag    1500
cagatcatca gagagaatgg cttcagcctg aaagaggcca ccccgacgt gcagggccag    1560 ttcccttgtg atttctcttg gggcgtgacc gagagcgtgc tgaagcctga agcgtggcc    1620 agcagccccc agttcagcga cccttacctg tacgtgtgga cgccaccgg caaccggctg    1680 ctgcatagag tggaaggcgt gcggctgaaa accagacccg cccagtgcac cgacttcgtg    1740
aacatcaaga acagctgga atgctggcc ggatgaaag tgacccacta cagattcgcc    1800
ctggactggg ccagcgtgct gcctaccgga atctgagcg ccgtgaacag acaggccctg    1860
cggtactaca gatgcgtggt gtccgagggc ctgaagctgg gcatcagcgc catggtcacc    1920
ctgtactacc ctacccacgc ccacctggga ctgcctgaac ctctgctgca tgctggcggc    1980
tggctgaacc ctagcaccgt ggaagccttt caggcctacg ccgggctgtg cttccaggaa    2040
ctgggcgacc tcgtgaagct gtggatcacc atcaacgagc caacagact gagcgacatc    2100 tacaacagaa gcggcaacga cacctacggc gctgcccaca atctgctggt ggctcatgcc    2160
ctggcttggc ggctgtacga cagacagttc cggccttctc agcggggagc cgtgtctctg    2220
tctctgcatg ccgattgggc cgagcccgcc aacccttacg ccgactctca ttggagagcc    2280
gccgagcggt tcctgcagtt cgagatcgct tggtttgccg agcccctgtt caagaccggc    2340
gattaccctg ccgccatgag agagtatatc gccagcaagc acagacgggg cctgagcagc    2400
tctgccctgc ctagactgac cgaggccgag cggagactgc tgaagggaac cgtggatttc    2460
tgcgccctga accacttcac caccagattc gtgatgcacg agcagctggc cggcagcaga    2520
tacgacagcg accggacat ccagtttctg caggacatca cccggctgag cagccctaca    2580
agactggccg tgatcccttg gggagtgcgg aagctgctga gatgggtgcg cagaaactac    2640
ggcgacatgg atatctacat caccgccagc ggcatcgacg accaggccct ggaagatgac    2700
cggctgcgga agtactacct ggaaaagtac ctgcaggaag tgctgaaggc ctacctgatc    2760
gacaaagtgc ggatcaaggg ctactacgcc ttcaagctgg ccgaggaaaa gagcaagccc    2820
agattcggct tcttcaccag cgacttcaag gccaagagca gcatccagtt ctacaacaag    2880
atgatcagca gcagcggctt ccccagcgag aacagcagct ccagatgcag ccagacccag    2940
aaaaacaccg agtgtaccgt gtgcctgttc ctggtgcaga agaagcccct gatcttcctg    3000
ggctgctgct tctttagcac cctggtgctg ctgctgtcca tcaccatctt ccaccggcag    3060
aagcggagaa agttctggaa ggccaaaaac ctgcagcaca tcccccctgaa gaaaggcaag    3120 cgggtgctga gctga                                                    3135
```

<210> SEQ ID NO 169
<211> LENGTH: 1043
<212> TYPE: PRT
<213> ORGANISM: Mus musculus
<220> FEATURE:
<223> OTHER INFORMATION: mouse beta klotho homolog

<400> SEQUENCE: 169

```
Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
            20                  25                  30

Arg Ala Leu Gln Arg Ser Ala Val Leu Ser Ala Phe Val Leu Leu Arg
            35                  40                  45

Ala Val Thr Gly Phe Ser Gly Asp Gly Lys Ala Ile Trp Asp Lys Lys
50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
            115                 120                 125

Asp Ser Tyr Ile Phe Leu Glu Lys Asp Leu Leu Ala Leu Asp Phe Leu
            130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
            165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
            195                 200                 205

Trp Lys Asn Ala Thr Met Ile Asp Leu Phe Asn Asp Tyr Ala Thr Tyr
            210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
            245                 250                 255

Pro Gly Glu Lys Gly Asn Leu Thr Ala Val Tyr Thr Val Gly His Asn
            260                 265                 270

Leu Ile Lys Ala His Ser Lys Val Trp His Asn Tyr Asp Lys Asn Phe
            275                 280                 285

Arg Pro His Gln Lys Gly Trp Leu Ser Ile Thr Leu Gly Ser His Trp
            290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
            325                 330                 335

Asp Gly Asp Tyr Pro Glu Phe Met Lys Thr Gly Ala Met Ile Pro Glu
            340                 345                 350

Phe Ser Glu Ala Glu Lys Glu Glu Val Arg Gly Thr Ala Asp Phe Phe
            355                 360                 365

Ala Phe Ser Phe Gly Pro Asn Asn Phe Arg Pro Ser Asn Thr Val Val
            370                 375                 380

Lys Met Gly Gln Asn Val Ser Leu Asn Leu Arg Gln Val Leu Asn Trp
385                 390                 395                 400

Ile Lys Leu Glu Tyr Asp Asp Pro Gln Ile Leu Ile Ser Glu Asn Gly
            405                 410                 415

Trp Phe Thr Asp Ser Tyr Ile Lys Thr Glu Asp Thr Thr Ala Ile Tyr
```

-continued

```
                420             425             430
    Met Met Lys Asn Phe Leu Asn Gln Val Leu Gln Ala Ile Lys Phe Asp
                    435             440             445

Glu Ile Arg Val Phe Gly Tyr Thr Ala Trp Thr Leu Leu Asp Gly Phe
                    450             455             460

Glu Trp Gln Asp Ala Tyr Thr Thr Arg Arg Gly Leu Phe Tyr Val Asp
    465             470             475             480

Phe Asn Ser Glu Gln Lys Glu Arg Lys Pro Lys Ser Ser Ala His Tyr
                    485             490             495

Tyr Lys Gln Ile Ile Gln Asp Asn Gly Phe Pro Leu Lys Glu Ser Thr
                    500             505             510

Pro Asp Met Lys Gly Arg Phe Pro Cys Asp Phe Ser Trp Gly Val Thr
                    515             520             525

Glu Ser Val Leu Lys Pro Glu Phe Thr Val Ser Ser Pro Gln Phe Thr
                    530             535             540

Asp Pro His Leu Tyr Val Trp Asn Val Thr Gly Asn Arg Leu Leu Tyr
    545             550             555             560

Arg Val Glu Gly Val Arg Leu Lys Thr Arg Pro Ser Gln Cys Thr Asp
                    565             570             575

Tyr Val Ser Ile Lys Lys Arg Val Glu Met Leu Ala Lys Met Lys Val
                    580             585             590

Thr His Tyr Gln Phe Ala Leu Asp Trp Thr Ser Ile Leu Pro Thr Gly
                    595             600             605

Asn Leu Ser Lys Val Asn Arg Gln Val Leu Arg Tyr Tyr Arg Cys Val
                    610             615             620

Val Ser Glu Gly Leu Lys Leu Gly Val Phe Pro Met Val Thr Leu Tyr
    625             630             635             640

His Pro Thr His Ser His Leu Gly Leu Pro Leu Pro Leu Leu Ser Ser
                    645             650             655

Gly Gly Trp Leu Asn Met Asn Thr Ala Lys Ala Phe Gln Asp Tyr Ala
                    660             665             670

Glu Leu Cys Phe Arg Glu Leu Gly Asp Leu Val Lys Leu Trp Ile Thr
                    675             680             685

Ile Asn Glu Pro Asn Arg Leu Ser Asp Met Tyr Asn Arg Thr Ser Asn
                    690             695             700

Asp Thr Tyr Arg Ala Ala His Asn Leu Met Ile Ala His Ala Gln Val
    705             710             715             720

Trp His Leu Tyr Asp Arg Gln Tyr Arg Pro Val Gln His Gly Ala Val
                    725             730             735

Ser Leu Ser Leu His Cys Asp Trp Ala Glu Pro Ala Asn Pro Phe Val
                    740             745             750

Asp Ser His Trp Lys Ala Ala Glu Arg Phe Leu Gln Phe Glu Ile Ala
                    755             760             765

Trp Phe Ala Asp Pro Leu Phe Lys Thr Gly Asp Tyr Pro Ser Val Met
                    770             775             780

Lys Glu Tyr Ile Ala Ser Lys Asn Gln Arg Gly Leu Ser Ser Ser Val
    785             790             795             800

Leu Pro Arg Phe Thr Ala Lys Glu Ser Arg Leu Val Lys Gly Thr Val
                    805             810             815

Asp Phe Tyr Ala Leu Asn His Phe Thr Thr Arg Phe Val Ile His Lys
                    820             825             830

Gln Leu Asn Thr Asn Arg Ser Val Ala Asp Arg Asp Val Gln Phe Leu
                    835             840             845
```

```
Gln Asp Ile Thr Arg Leu Ser Ser Pro Ser Arg Leu Ala Val Thr Pro
    850                 855                 860
Trp Gly Val Arg Lys Leu Leu Ala Trp Ile Arg Arg Asn Tyr Arg Asp
865                 870                 875                 880
Arg Asp Ile Tyr Ile Thr Ala Asn Gly Ile Asp Asp Leu Ala Leu Glu
                885                 890                 895
Asp Asp Gln Ile Arg Lys Tyr Tyr Leu Glu Lys Tyr Val Gln Glu Ala
            900                 905                 910
Leu Lys Ala Tyr Leu Ile Asp Lys Val Lys Ile Lys Gly Tyr Tyr Ala
        915                 920                 925
Phe Lys Leu Thr Glu Glu Lys Ser Lys Pro Arg Phe Gly Phe Phe Thr
    930                 935                 940
Ser Asp Phe Arg Ala Lys Ser Ser Val Gln Phe Tyr Ser Lys Leu Ile
945                 950                 955                 960
Ser Ser Ser Gly Leu Pro Ala Glu Asn Arg Ser Pro Ala Cys Gly Gln
                965                 970                 975
Pro Ala Glu Asp Thr Asp Cys Thr Ile Cys Ser Phe Leu Val Glu Lys
            980                 985                 990
Lys Pro Leu Ile Phe Phe Gly Cys Cys Phe Ile Ser Thr Leu Ala Val
        995                 1000                1005
Leu Leu Ser Ile Thr Val Phe His His Gln Lys Arg Arg Lys Phe Gln
    1010                1015                1020
Lys Ala Arg Asn Leu Gln Asn Ile Pro Leu Lys Lys Gly His Ser Arg
1025                1030                1035                1040
Val Phe Ser
```

<210> SEQ ID NO 170
<211> LENGTH: 3129
<212> TYPE: DNA
<213> ORGANISM: Mus musculus
<220> FEATURE:
<223> OTHER INFORMATION: mouse beta klotho homolog

<400> SEQUENCE: 170

| | | | | | |
|---|---|---|---|---|---|
| atgaagacag | gctgtgcagc | agggtctccg | gggaatgaat | ggattttctt | cagctctgat | 60 |
| gaaagaaaca | cacgctctag | gaaaacaatg | tccaacaggg | cactgcaaag | atctgccgtg | 120 |
| ctgtctgcgt | ttgttctgct | gcgagctgtt | accggcttct | ccggagacgg | aaagcaata | 180 |
| tgggataaaa | aacagtacgt | gagtccggta | aacccaagtc | agctgttcct | ctatgacact | 240 |
| ttccctaaaa | acttttcctg | gggcgttggg | accggagcat | tcaagtgga | agggagttgg | 300 |
| aagacagatg | gaagaggacc | ctcgatctgg | gatcggtacg | tctactcaca | cctgagaggt | 360 |
| gtcaacggca | cagacagatc | cactgacagt | tacatcttc | tggaaaaaga | cttgttggct | 420 |
| ctggattttt | taggagtttc | tttttatcag | ttctcaatct | cctggccacg | gttgtttccc | 480 |
| aatggaacag | tagcagcagt | gaatgcgcaa | ggtctccggt | actaccgtgc | acttctggac | 540 |
| tcgctggtac | ttaggaatat | cgagcccatt | gttaccttgt | accattggga | tttgcctctg | 600 |
| acgctccagg | aagaatatgg | gggctggaaa | aatgcaacta | tgatagatct | cttcaacgac | 660 |
| tatgccacat | actgcttcca | gacctttgga | gaccgtgtca | atattggat | tacaattcac | 720 |
| aacccttacc | ttgttgcttg | gcatgggttt | ggcacaggta | tgcatgcacc | aggagagaag | 780 |
| ggaaatttaa | cagctgtcta | cactgtggga | cacaacctga | tcaaggcaca | ttcgaaagtg | 840 |
| tggcataact | acgacaaaaa | cttccgccct | catcagaagg | gttggctctc | catcaccttg | 900 |

```
gggtcccatt ggatagagcc aaacagaaca gacaacatgg aggacgtgat caactgccag    960
cactccatgt cctctgtgct tggatggttc gccaacccca tccacgggga cggcgactac   1020
cctgagttca tgaagacggg cgccatgatc cccgagttct ctgaggcaga aaggaggag    1080 gtgaggggca cggctgattt cttttgcctt tccttcgggc caacaactt caggccctca    1140 aacaccgtgg tgaaaatggg acaaaatgta tcactcaact taaggcaggt gctgaactgg   1200
attaaactgg aatacgatga ccctcaaatc ttgatttcgg agaacggctg gttcacagat   1260
agctatataa agacagagga caccacggcc atctacatga tgaagaattt cctaaaccag   1320
gttcttcaag caataaaatt tgatgaaatc cgcgtgtttg ttatacggc ctggactctc    1380 ctggatggct ttgagtggca ggatgcctat acgacccgac gagggctgtt ttatgtggac   1440
tttaacagtg agcagaaaga gaggaaaccc aagtcctcgg ctcattacta caagcagatc   1500
atacaagaca acggcttccc tttgaaagag tccacgccag acatgaaggg tcggttcccc   1560
tgtgatttct cttggggagt cactgagtct gttcttaagc ccgagtttac ggtctcctcc   1620
ccgcagttta ccgatcctca cctgtatgtg tggaatgtca ctggcaacag attgctctac   1680
cgagtggaag gggtaaggct gaaaacaaga ccatcccagt gcacagatta tgtgagcatc   1740
aaaaaacgag ttgaaatgtt ggcaaaaatg aaagtcaccc actaccagtt tgctctggac   1800
tggacctcta tccttcccac tggcaatctg tccaaagtta acagacaagt gttaaggtac   1860
tataggtgtg tggtgagcga aggactgaag ctgggcgtct tccccatggt gacgttgtac   1920
cacccaaccc actcccatct cggcctcccc ctgccacttc tgagcagtgg ggggtggcta   1980
aacatgaaca cagccaaggc cttccaggac tacgctgagc tgtgcttccg ggagttgggg   2040
gacttggtga agctctggat caccatcaat gagcctaaca ggctgagtga catgtacaac   2100
cgcacgagta atgacaccta ccgtgcagcc cacaacctga tgatcgccca tgcccaggtc   2160
tggcacctct atgataggca gtataggccg gtccagcatg gggctgtgtc gctgtcctta   2220
cattgcgact gggcagaacc tgccaacccc tttgtggatt cacactggaa ggcagccgag   2280
cgcttcctcc agtttgagat cgcctggttt gcagatccgc tcttcaagac tggcgactat   2340
ccatcggtta tgaaggaata catcgcctcc aagaaccagc gagggctgtc tagctcagtc   2400
ctgccgcgct tcaccgcgaa ggagagcagg ctggtgaagg gtaccgtcga cttctacgca   2460
ctgaaccact tcactacgag gttcgtgata cacaagcagc tgaacaccaa ccgctcagtt   2520
gcagacaggg acgtccagtt cctgcaggac atcacccgcc taagctcgcc cagccgcctg   2580
gctgtaacac cctggggagt gcgcaagctc cttgcgtgga tccggaggaa ctacagagac   2640
agggatatct acatcacagc caatggcatc gatgacctgg ctctagagga tgatcagatc   2700
cgaaagtact acttggagaa gtatgtccag gaggctctga agcatatct cattgacaag   2760 gtcaaaatca aaggctacta tgcattcaaa ctgactgaag agaaatctaa gcctagattt   2820 ggattttca cctctgactt cagagctaag tcctctgtcc agttttacag caagctgatc   2880
agcagcagtg gcctccccgc tgagaacaga agtcctgcgt gtggtcagcc tgcggaagac   2940
acagactgca ccatttgctc atttctcgtg gagaagaaac cactcatctt cttcggttgc   3000
tgcttcatct ccactctggc tgtactgcta tccatcaccg tttttcatca tcaaaagaga   3060
agaaaattcc agaaagcaag gaacttacaa aatataccat tgaagaaagg ccacagcaga   3120
gttttcagc                                                           3129
```

<210> SEQ ID NO 171
<211> LENGTH: 1043

```
<212> TYPE: PRT
<213> ORGANISM: Rattus norvegicus
<220> FEATURE:
<223> OTHER INFORMATION: rat beta klotho

<400> SEQUENCE: 171

Met Lys Thr Gly Cys Ala Ala Gly Ser Pro Gly Asn Glu Trp Val Phe
1               5                   10                  15

Phe Ser Ser Asp Glu Arg Ser Thr Arg Ser Arg Lys Thr Met Ser Asn
                20                  25                  30

Gly Ala Leu Gln Arg Ser Ala Val Leu Ser Ala Leu Val Leu Leu Arg
            35                  40                  45

Ala Val Thr Gly Phe Ser Asp Gly Lys Ala Ile Trp Asp Lys Lys
    50                  55                  60

Gln Tyr Val Ser Pro Val Asn Pro Gly Gln Leu Phe Leu Tyr Asp Thr
65              70                  75                  80

Phe Pro Lys Asn Phe Ser Trp Gly Val Gly Thr Gly Ala Phe Gln Val
                85                  90                  95

Glu Gly Ser Trp Lys Ala Asp Gly Arg Gly Pro Ser Ile Trp Asp Arg
            100                 105                 110

Tyr Val Asp Ser His Leu Arg Gly Val Asn Ser Thr Ala Arg Ser Thr
        115                 120                 125

Asp Ser Tyr Val Phe Leu Glu Lys Asp Leu Leu Ala Leu Asp Phe Leu
130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Lys Gly Leu Gln Tyr Tyr Arg
                165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
        195                 200                 205

Trp Lys Asn Ala Thr Met Ile Asp Leu Phe Asn Asp Tyr Ala Thr Tyr
210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                245                 250                 255

Pro Gly Glu Lys Gly Asn Leu Thr Ala Val Tyr Thr Val Gly His Asn
            260                 265                 270

Leu Ile Lys Ala His Ser Lys Val Trp His Asn Tyr Asp Lys Asn Phe
        275                 280                 285

Arg Pro His Gln Lys Gly Trp Leu Ser Ile Thr Leu Gly Ser His Trp
290                 295                 300

Ile Glu Pro Asn Arg Thr Glu Asn Met Glu Asp Val Ile Asn Cys Gln
305                 310                 315                 320

His Ser Met Ser Ser Val Leu Gly Trp Phe Ala Asn Pro Ile His Gly
                325                 330                 335

Asp Gly Asp Tyr Pro Glu Phe Met Lys Thr Ser Ser Val Ile Pro Glu
            340                 345                 350

Phe Ser Glu Ala Glu Lys Glu Glu Val Arg Gly Thr Ala Asp Phe Phe
        355                 360                 365

Ala Phe Ser Phe Gly Pro Asn Asn Phe Arg Pro Ser Asn Thr Val Val
370                 375                 380
```

```
Lys Met Gly Gln Asn Val Ser Leu Asn Leu Arg Gln Val Leu Asn Trp
385                 390                 395                 400

Ile Lys Leu Glu Tyr Asp Asn Pro Arg Ile Leu Ile Ser Glu Asn Gly
            405                 410                 415

Trp Phe Thr Asp Ser Tyr Ile Lys Thr Glu Asp Thr Thr Ala Ile Tyr
            420                 425                 430

Met Met Lys Asn Phe Leu Asn Gln Val Leu Gln Ala Ile Lys Phe Asp
            435                 440                 445

Glu Ile Gln Val Phe Gly Tyr Thr Ala Trp Thr Leu Leu Asp Gly Phe
        450                 455                 460

Glu Trp Gln Asp Ala Tyr Thr Thr Arg Arg Gly Leu Phe Tyr Val Asp
465                 470                 475                 480

Phe Asn Ser Glu Gln Lys Glu Arg Lys Pro Lys Ser Ser Ala His Tyr
                485                 490                 495

Tyr Lys Gln Ile Ile Gln Asp Asn Gly Phe Pro Leu Gln Glu Ser Thr
            500                 505                 510

Pro Asp Met Lys Gly Gln Phe Pro Cys Asp Phe Ser Trp Gly Val Thr
            515                 520                 525

Glu Ser Val Leu Lys Pro Glu Phe Thr Val Ser Ser Pro Gln Phe Thr
530                 535                 540

Asp Pro His Leu Tyr Val Trp Asn Val Thr Gly Asn Arg Leu Leu Tyr
545                 550                 555                 560

Arg Val Glu Gly Val Arg Leu Lys Thr Arg Pro Ser Gln Cys Thr Asp
                565                 570                 575

Tyr Val Ser Ile Lys Lys Arg Val Glu Met Leu Ala Lys Met Lys Val
            580                 585                 590

Thr His Tyr Gln Phe Ala Leu Asp Trp Thr Ser Ile Leu Pro Thr Gly
        595                 600                 605

Asn Leu Ser Lys Ile Asn Arg Gln Val Leu Arg Tyr Tyr Arg Cys Val
610                 615                 620

Val Ser Glu Gly Leu Lys Leu Gly Ile Ser Pro Met Val Thr Leu Tyr
625                 630                 635                 640

His Pro Thr His Ser His Leu Gly Leu Pro Met Pro Leu Leu Ser Ser
                645                 650                 655

Gly Gly Trp Leu Asn Thr Asn Thr Ala Lys Ala Phe Gln Asp Tyr Ala
            660                 665                 670

Gly Leu Cys Phe Lys Glu Leu Gly Asp Leu Val Lys Leu Trp Ile Thr
        675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
                725                 730                 735

Ser Leu Ser Leu His Ser Asp Trp Ala Glu Pro Ala Asn Pro Tyr Val
            740                 745                 750

Glu Ser His Trp Lys Ala Ala Glu Arg Phe Leu Gln Phe Glu Ile Ala
            755                 760                 765

Trp Phe Ala Asp Pro Leu Phe Lys Thr Gly Asp Tyr Pro Leu Ala Met
        770                 775                 780

Lys Glu Tyr Ile Ala Ser Lys Gln Arg Gly Leu Ser Ser Ser Val
785                 790                 795                 800

Leu Pro Arg Phe Thr Leu Lys Glu Ser Arg Leu Val Lys Gly Thr Ile
```

|     |     |     | 805 |     |     |     | 810 |     |     |     | 815 |     |
| --- | --- | --- | --- | --- | --- | --- | --- | --- | --- | --- | --- | --- |
| Asp | Phe | Tyr | Ala | Leu | Asn | His | Phe | Thr | Thr | Arg | Phe | Val | Ile | His | Lys |
|     |     |     | 820 |     |     |     | 825 |     |     |     | 830 |     |

| Gln | Leu | Asn | Thr | Asn | Cys | Ser | Val | Ala | Asp | Arg | Asp | Val | Gln | Phe | Leu |
|     |     |     | 835 |     |     |     | 840 |     |     |     | 845 |     |

| Gln | Asp | Ile | Thr | Arg | Leu | Ser | Ser | Pro | Ser | Arg | Leu | Ala | Val | Thr | Pro |
|     |     |     | 850 |     |     |     | 855 |     |     |     | 860 |     |

| Trp | Gly | Met | Arg | Lys | Leu | Leu | Gly | Trp | Ile | Arg | Arg | Asn | Tyr | Arg | Asp |
| 865 |     |     |     | 870 |     |     |     | 875 |     |     |     | 880 |

| Met | Asp | Ile | Tyr | Val | Thr | Ala | Asn | Gly | Ile | Asp | Asp | Leu | Ala | Leu | Glu |
|     |     |     |     | 885 |     |     |     | 890 |     |     |     | 895 |

| Asp | Asp | Gln | Ile | Arg | Lys | Tyr | Tyr | Leu | Glu | Lys | Tyr | Val | Gln | Glu | Ala |
|     |     |     | 900 |     |     |     | 905 |     |     |     | 910 |     |

| Leu | Lys | Ala | Tyr | Leu | Ile | Asp | Lys | Val | Lys | Ile | Lys | Gly | Tyr | Tyr | Ala |
|     |     |     | 915 |     |     |     | 920 |     |     |     | 925 |     |

| Phe | Lys | Leu | Thr | Glu | Glu | Lys | Ser | Lys | Pro | Arg | Phe | Gly | Phe | Phe | Thr |
|     |     |     | 930 |     |     |     | 935 |     |     |     | 940 |     |

| Ser | Asp | Phe | Lys | Ala | Lys | Ser | Ser | Val | Gln | Phe | Tyr | Ser | Lys | Leu | Ile |
| 945 |     |     |     | 950 |     |     |     | 955 |     |     |     | 960 |

| Ser | Ser | Ser | Gly | Phe | Ser | Ser | Glu | Asn | Arg | Ser | Pro | Ala | Cys | Gly | Gln |
|     |     |     |     | 965 |     |     |     | 970 |     |     |     | 975 |

| Pro | Pro | Glu | Asp | Thr | Glu | Cys | Ala | Ile | Cys | Ser | Phe | Leu | Thr | Gln | Lys |
|     |     |     | 980 |     |     |     | 985 |     |     |     | 990 |     |

| Lys | Pro | Leu | Ile | Phe | Phe | Gly | Cys | Cys | Phe | Ile | Ser | Thr | Leu | Ala | Ala |
|     |     |     | 995 |     |     |     | 1000 |     |     |     | 1005 |     |

| Leu | Leu | Ser | Ile | Thr | Ile | Phe | His | His | Arg | Lys | Arg | Arg | Lys | Phe | Gln |
|     |     |     | 1010 |     |     |     | 1015 |     |     |     | 1020 |     |

| Lys | Ala | Arg | Asn | Leu | Gln | Asn | Ile | Pro | Leu | Lys | Lys | Gly | His | Ser | Arg |
| 1025 |     |     |     | 1030 |     |     |     | 1035 |     |     |     | 1040 |

Val Phe Ser

<210> SEQ ID NO 172
<211> LENGTH: 3132
<212> TYPE: DNA
<213> ORGANISM: Rattus norvegicus
<220> FEATURE:
<223> OTHER INFORMATION: rat beta klotho

<400> SEQUENCE: 172

| atgaagacag gctgtgcagc agggtctcca gggaatgaat gggttttctt cagctctgat | 60 |
| gaaagaagca cacgctctag gaaaacaatg tccaacggag cactgcaaag atctgccgtg | 120 |
| ctgtctgcat tggttctgct gcgagctgtt accggcttct ctggagacgg aaaagcaata | 180 |
| tgggataaaa acaatacgt gagtccggta aacccaggtc agctgttcct ctatgacact | 240 |
| ttccctaaaa actttttcctg gggcgttggg accggagcat tcaagtggaa agggagttgg | 300 |
| aaggcagatg gaagaggacc ctcgatctgg gaccgttatg tcgactcaca cctgagaggt | 360 |
| gtcaacagca cagacagatc cactgacagt tatgtctttc tggaaaagga cttgctggct | 420 |
| ctggattttt taggagtttc ttttttatcag ttctcaatct cctggccgcg gttgttcccc | 480 |
| aacggaacag tagcagctgt gaatgcaaaa ggtctccagt actacagagc acttctggac | 540 |
| tcgctggtac ttaggaatat cgaacccatt gttaccttat accattggga tttgcctttg | 600 |
| acgctacagg aagaatatgg gggctggaaa atgcaacta tgatagatct cttcaatgac | 660 |
| tatgccacat actgcttcca gacctttgga gaccgtgtca atattggat tacaattcac | 720 |

```
aacccttacc tcgttgcttg gcatgggttt ggcacaggta tgcatgcgcc aggagagaag      780
ggaaatttaa cagctgtcta cactgtggga cacaacctga tcaaggcgca ttcgaaagtg      840
tggcataact acgacaaaaa cttccgccct catcagaagg gttggctctc catcaccttg      900
gggtcccatt ggatagaacc aaacagaaca gaaaacatgg aggacgtgat caactgccag      960
cactccatgt cttctgtgct cggatggttt gccaaccccca tccacggaga cggcgactac     1020
cccgagttca tgaagacgag ctccgtaatc cctgagttct ctgaggcaga aaggaggag      1080
gtgcggggca ctgctgactt ctttgccttt tccttcgggc ccaacaattt caggccctcg     1140
aacaccgtgg taaaaatggg acaaaatgta tcactcaact taagacaggt gctgaactgg     1200
attaaactag aatatgacaa ccctcgaatc ttgatttcgg agaacggctg gttcacagat     1260
agttatataa agacggaaga taccacggcc atctacatga tgaagaattt cctcaaccag     1320
gttcttcaag caataaagtt tgatgaaata caagtgtttg ttatacggc ttggactctc     1380
ctggatggct ttgagtggca ggatgcctac acgacccgac gagggctgtt ttatgtggac     1440
tttaatagtg agcagaaaga gaggaaaccc aagtcctccg ctcattacta caaacagatt     1500
atacaagaca acgtttcccc tttgcaagaa tccacaccag acatgaaggg tcagtttccc     1560
tgtgacttct cctggggagt cactgagtct gttcttaagc cggagtttac ggtgtcctcc     1620
ccacagttta ctgatcctca cctgtatgtg tggaatgtca ctgcaacag attgctatac      1680
cgagtggaag gagtcaggct aaaaacaaga ccgtcccaat gcacagatta tgtgagcatc     1740
aaaaaacgag ttgaaatgtt ggccaaaatg aaagtcaccc actaccagtt tgctctggac     1800
tggacctcta tcctccctac cggaaaatctg tctaaaatta atagacaagt gttgaggtac     1860
tataggtgtg tggtgagcga aggactgaag ctgggcatct cccctatggt gacgttgtac     1920
caccccgaccc actcccatct aggcctcccc atgccacttc tgagcagtgg gggatggcta     1980
aacaccaaca cagccaaggc cttccaggac tacgcaggcc tgtgcttcaa ggagctgggg    2040
gacttggtaa agctctggat caccatcaat gaacccaata ggctgagtga catgtacaac    2100
cgcacgagta acgacaccta ccgtgcggcc cacaacctga tgatcgccca tgcccaggtc    2160
tggcacctct atgataggca gtataggccg gtccagcacg gggctgtgtc gctgtccta    2220
cattccgact gggcagaacc tgccaacccc tatgtggagt ctcactggaa ggcagccgag    2280
cgcttcctcc agtttgagat cgcctggttt gcggatccac tcttcaagac tggtgactac    2340
ccgctggcca tgaaggaata catcgcctcc aagaagcagc gagggctgtc tagctcagtc    2400
ctgccgcgct ttaccttgaa ggagagcagg ctggtgaagg gaccatcga cttttacgca    2460
ctgaaccact tcactactag attcgtgata cacaagcagt tgaataccaa ctgctcagtg    2520
gcagacaggg acgtccagtt cctgcaggac atcacccgcc tgagctcgcc cagtcgccta    2580
gccgtaacgc cctggggaat gcgcaagctc cttgggtgga tccggaggaa ctacagagac    2640
atggatatct acgtcacagc caatggcatt gatgatcttg ctctagagga cgatcagatt    2700
agaaagtact acttggagaa gtacgtccag gaggctctga agcatatct gattgacaag    2760
gtcaaaatca aaggctacta tgcattcaaa ctgactgaag agaaatctaa gcctagattt    2820
ggatttttca catctgactt caaagctaaa tcttctgtac agttttatag caagctgatc    2880
agcagcagcg gcttctcctc tgagaacaga agtcctgcct gtggtcagcc tccagaagac    2940
acagaatgcg ccatttgctc cttccttaca cagaagaaac cactcatctt ctttggttgt    3000
tgcttcatct ccactctggc tgcactgcta tcaatcacta ttttttcatca tcggaagaga    3060
```

-continued

```
agaaaattcc agaaagcaag gaacttacaa aatataccat tgaagaaagg gcacagcaga    3120
gtttttagct aa                                                        3132
```

<210> SEQ ID NO 173
<211> LENGTH: 1042
<212> TYPE: PRT
<213> ORGANISM: Cricetulus griseus
<220> FEATURE:
<223> OTHER INFORMATION: Hamster beta klotho

<400> SEQUENCE: 173

| Met | Lys | Ala | Gly | Cys | Ala | Ala | Gly | Ser | Pro | Gly | Asn | Glu | Trp | Ile | Phe |
|---|---|---|---|---|---|---|---|---|---|---|---|---|---|---|---|
| 1 | | | | 5 | | | | | 10 | | | | | 15 | |

| Leu | Ser | Ser | Tyr | Glu | Arg | Asn | Thr | Arg | Ser | Lys | Lys | Thr | Met | Ser | Asn |
|---|---|---|---|---|---|---|---|---|---|---|---|---|---|---|---|
| | | | 20 | | | | | 25 | | | | | 30 | | |

| Arg | Ala | Leu | Gln | Arg | Ser | Val | Val | Leu | Ser | Ala | Phe | Val | Leu | Leu | Arg |
|---|---|---|---|---|---|---|---|---|---|---|---|---|---|---|---|
| | | 35 | | | | | 40 | | | | | 45 | | | |

| Ala | Val | Thr | Gly | Leu | Ser | Gly | Asp | Gly | Lys | Ala | Ile | Trp | Asp | Lys | Lys |
|---|---|---|---|---|---|---|---|---|---|---|---|---|---|---|---|
| | 50 | | | | | 55 | | | | | 60 | | | | |

| Gln | Tyr | Val | Ser | Pro | Val | Asn | Ala | Ser | Gln | Leu | Phe | Leu | Tyr | Asp | Thr |
|---|---|---|---|---|---|---|---|---|---|---|---|---|---|---|---|
| 65 | | | | | 70 | | | | | 75 | | | | | 80 |

| Phe | Pro | Lys | Asn | Phe | Phe | Trp | Gly | Val | Gly | Thr | Gly | Ala | Phe | Gln | Val |
|---|---|---|---|---|---|---|---|---|---|---|---|---|---|---|---|
| | | | | 85 | | | | | 90 | | | | | 95 | |

| Glu | Gly | Asn | Trp | Gln | Ala | Asp | Gly | Arg | Gly | Pro | Ser | Ile | Trp | Asp | Arg |
|---|---|---|---|---|---|---|---|---|---|---|---|---|---|---|---|
| | | | 100 | | | | | 105 | | | | | 110 | | |

| Phe | Ile | Tyr | Thr | His | Leu | Arg | Asp | Val | Ser | Ile | Thr | Glu | Lys | Ser | Ala |
|---|---|---|---|---|---|---|---|---|---|---|---|---|---|---|---|
| | | | 115 | | | | | 120 | | | | | 125 | | |

| Asp | Ser | Tyr | Ile | Phe | Leu | Glu | Lys | Asp | Leu | Leu | Ala | Leu | Asp | Phe | Leu |
|---|---|---|---|---|---|---|---|---|---|---|---|---|---|---|---|
| | 130 | | | | | 135 | | | | | 140 | | | | |

| Gly | Val | Ser | Phe | Tyr | Gln | Phe | Ser | Ile | Ser | Trp | Pro | Arg | Leu | Phe | Pro |
|---|---|---|---|---|---|---|---|---|---|---|---|---|---|---|---|
| 145 | | | | | 150 | | | | | 155 | | | | | 160 |

| Asn | Gly | Thr | Val | Ala | Ser | Val | Asn | Ala | Lys | Gly | Leu | Gln | Tyr | Tyr | Asn |
|---|---|---|---|---|---|---|---|---|---|---|---|---|---|---|---|
| | | | | 165 | | | | | 170 | | | | | 175 | |

| Lys | Leu | Leu | Asp | Ser | Leu | Ile | Leu | Arg | Asn | Ile | Glu | Pro | Val | Val | Thr |
|---|---|---|---|---|---|---|---|---|---|---|---|---|---|---|---|
| | | | 180 | | | | | 185 | | | | | 190 | | |

| Leu | Tyr | His | Trp | Asp | Leu | Pro | Leu | Ala | Leu | Gln | Glu | Asp | Tyr | Gly | Gly |
|---|---|---|---|---|---|---|---|---|---|---|---|---|---|---|---|
| | | 195 | | | | | 200 | | | | | 205 | | | |

| Trp | Lys | Asn | Ala | Thr | Met | Ile | Asp | Leu | Phe | Asn | Asp | Tyr | Ala | Thr | Tyr |
|---|---|---|---|---|---|---|---|---|---|---|---|---|---|---|---|
| | 210 | | | | | 215 | | | | | 220 | | | | |

| Cys | Phe | Gln | Thr | Phe | Gly | Asp | Arg | Val | Lys | Tyr | Trp | Ile | Thr | Ile | His |
|---|---|---|---|---|---|---|---|---|---|---|---|---|---|---|---|
| 225 | | | | | 230 | | | | | 235 | | | | | 240 |

| Asn | Pro | Tyr | Leu | Val | Ala | Trp | His | Gly | Phe | Ala | Thr | Gly | Met | His | Ala |
|---|---|---|---|---|---|---|---|---|---|---|---|---|---|---|---|
| | | | | 245 | | | | | 250 | | | | | 255 | |

| Pro | Gly | Glu | Thr | Gly | Asn | Leu | Thr | Ala | Val | Tyr | Ile | Val | Gly | His | Asn |
|---|---|---|---|---|---|---|---|---|---|---|---|---|---|---|---|
| | | | 260 | | | | | 265 | | | | | 270 | | |

| Leu | Ile | Lys | Ala | His | Ser | Lys | Val | Trp | His | Asn | Tyr | Asp | Lys | Asn | Phe |
|---|---|---|---|---|---|---|---|---|---|---|---|---|---|---|---|
| | | | 275 | | | | | 280 | | | | | 285 | | |

| Arg | Pro | His | Gln | Lys | Gly | Leu | Leu | Ser | Ile | Thr | Leu | Gly | Ser | His | Trp |
|---|---|---|---|---|---|---|---|---|---|---|---|---|---|---|---|
| | | 290 | | | | | 295 | | | | | 300 | | | |

| Ile | Glu | Pro | Asn | Lys | Thr | Glu | Asn | Met | Ala | Asp | Thr | Ile | Ser | Cys | Gln |
|---|---|---|---|---|---|---|---|---|---|---|---|---|---|---|---|
| 305 | | | | | 310 | | | | | 315 | | | | | 320 |

| His | Ser | Met | Ala | Phe | Val | Leu | Gly | Trp | Phe | Ala | Asn | Pro | Ile | His | Ala |
|---|---|---|---|---|---|---|---|---|---|---|---|---|---|---|---|
| | | | | 325 | | | | | 330 | | | | | 335 | |

| Asp | Gly | Asp | Tyr | Pro | Glu | Phe | Met | Lys | Thr | Leu | Ser | Met | Pro | Arg | Val |
|---|---|---|---|---|---|---|---|---|---|---|---|---|---|---|---|
| | | | 340 | | | | | 345 | | | | | 350 | | |

```
Phe Ser Glu Ala Glu Lys Glu Val Arg Gly Thr Ala Asp Phe Phe
        355                 360                 365

Ala Phe Ser Phe Gly Pro Asn Asn Phe Arg Pro Ser Asn Thr Val Val
370             375                 380

Lys Met Gly Gln Asn Val Ser Leu Asn Leu Arg Gln Val Leu Asn Trp
385                 390                 395                 400

Ile Lys Leu Glu Tyr Asp Asn Pro Arg Ile Leu Ile Ser Glu Asn Gly
                405                 410                 415

Trp Phe Thr Asp Ser Asp Ile Lys Thr Glu Asp Thr Thr Ala Ile Tyr
            420                 425                 430

Met Met Lys His Phe Leu Asn Gln Val Leu Gln Ala Ile Gln Phe Asp
                435                 440                 445

Glu Ile Arg Val Phe Gly Tyr Thr Ala Trp Ser Leu Leu Asp Gly Phe
        450                 455                 460

Glu Trp Gln Tyr Ala Tyr Thr Ser Arg Arg Gly Leu Phe Tyr Val Asp
465                 470                 475                 480

Phe Asn Ser Glu Gln Lys Glu Arg Lys Pro Lys Thr Ser Ala His Tyr
                485                 490                 495

Tyr Lys Gln Ile Ile Gln Glu Asn Gly Phe Pro Leu Lys Glu Ser Thr
            500                 505                 510

Pro Asp Met Gln Gly Gln Phe Pro Cys Asp Phe Ser Trp Gly Val Thr
            515                 520                 525

Glu Ser Val Leu Lys Pro Glu Phe Met Val Ser Ser Pro Gln Phe Thr
530                 535                 540

Asp Pro His Leu Tyr Val Trp Asn Ala Thr Gly Asn Arg Leu Leu Gln
545                 550                 555                 560

Arg Val Glu Gly Val Arg Leu Lys Thr Lys Pro Ser His Cys Thr Asp
                565                 570                 575

Tyr Val Ser Ile Lys Lys Arg Val Glu Met Leu Ala Lys Met Lys Val
            580                 585                 590

Thr His Tyr Gln Phe Ala Leu Asp Trp Ala Thr Ile Leu Pro Thr Gly
        595                 600                 605

Asn Leu Ser Glu Val Asn Arg Gln Val Leu Arg Tyr Tyr Arg Cys Val
    610                 615                 620

Val Ser Glu Gly Leu Lys Leu Gly Val Ser Pro Met Val Thr Leu Tyr
625                 630                 635                 640

His Pro Thr His Ser His Leu Gly Leu Pro Glu Pro Leu Leu Asn Ser
                645                 650                 655

Gly Gly Trp Leu Asn Thr Tyr Thr Ala Lys Ala Phe Gln Asp Tyr Ala
            660                 665                 670

Gly Leu Cys Phe Gln Glu Leu Gly Asp Leu Val Lys Leu Trp Ile Thr
            675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp Arg Leu Tyr Asp Arg Gln Tyr Arg Pro Val Gln His Gly Ala Val
                725                 730                 735

Ser Leu Ser Leu His Ser Asp Trp Val Glu Pro Ala Asn Pro Tyr Val
            740                 745                 750

Asp Ser His Trp Lys Ala Ala Glu Arg Phe Leu Leu Phe Glu Ile Ala
            755                 760                 765
```

Trp Phe Ala Asp Pro Leu Phe Lys Thr Gly Asp Tyr Pro Leu Ala Met
770                 775                 780

Lys Glu Tyr Ile Ala Ser Lys Asn Gln Gln Gly Leu Ser Arg Ser Val
785                 790                 795                 800

Leu Pro Arg Phe Thr Pro Glu Glu Ser Arg Leu Val Lys Gly Thr Ile
        805                 810                 815

Asp Phe Tyr Ala Leu Asn His Phe Thr Thr Arg Phe Val Ile His Lys
        820                 825                 830

Gln Leu Asn Ser Ser Arg Ser Met Ala Asp Arg Asp Val Gln Phe Leu
        835                 840                 845

Gln Asp Ile Thr Arg Leu Ser Ser Pro Ser Arg Leu Ala Val Met Pro
850                 855                 860

Trp Gly Ala Arg Lys Leu Leu Gly Trp Ile Gln Arg Asn Tyr Gly Asp
865                 870                 875                 880

Met Asp Ile Tyr Ile Thr Ala Asn Gly Ile Asp Asp Leu Ala Leu Glu
                885                 890                 895

Asn Asp Gly Ile Arg Lys Tyr Tyr Leu Glu Lys Tyr Ile Gln Glu Ala
            900                 905                 910

Leu Lys Ala Tyr Leu Ile Asp Lys Val Lys Ile Lys Gly Tyr Tyr Ala
        915                 920                 925

Phe Lys Leu Thr Glu Glu Lys Ser Lys Pro Arg Phe Gly Phe Phe Thr
930                 935                 940

Ser Asp Phe Lys Ala Lys Ser Ser Val Glu Phe Tyr Ser Lys Leu Ile
945                 950                 955                 960

Ser Arg Ser Gly Phe Pro Ser Glu Thr Ser Asn Pro Ala Cys Gly Gln
                965                 970                 975

Pro Pro Glu Asp Thr Asp Cys Thr Ile Cys Ser Phe Phe Thr Gln Lys
            980                 985                 990

Lys Ser Leu Ile Phe Phe Gly Cys Cys Phe Ile Ser Thr Leu Ala Val
        995                 1000                1005

Leu Leu Ser Ile Thr Ile Phe His His Arg Lys Arg Arg Phe His Lys
    1010                1015                1020

Ser Lys Asn Leu Glu Asn Ile Pro Leu Lys Glu Gly His Ser Arg Val
1025                1030                1035                1040

Leu Ser

<210> SEQ ID NO 174
<211> LENGTH: 3042
<212> TYPE: DNA
<213> ORGANISM: Cricetulus griseus
<220> FEATURE:
<223> OTHER INFORMATION: Hamster beta klotho

<400> SEQUENCE: 174
atgtccaaca gggcactgca agatctgtc gtgctgtcag cgtttgttct gctgcgagct      60
gttaccggat tgtctggaga cgggaaagcg atatgggata aaaaacagta cgtgagtccg    120
gtgaatgcaa gtcagctgtt tctctatgac actttcccta aaaacttttt ctggggtgtt    180
ggaactggag catttcaagt ggaagggaat tggcaggcag acggaagagg accctcgatt    240
tgggatcgtt tcatctacac acacctgaga gatgtcagca tcacagagaa tccgccgac    300 agttacattt ttctggaaaa agatttgttg gctctggatt ttttaggagt ttcttttttat    360 cagttctcaa tctcctggcc acggttgttc cccaatggaa cagtagcatc cgtgaatgca    420
aaaggtctcc aatactacaa caaacttctg gactcgctga tacttaggaa tattgagccc    480

```
gttgttacct tataccattg ggatttgcct ttggcgctac aggaagacta tgggggttgg      540
aaaaatgcaa ctatgataga tctcttcaat gactatgcca catactgctt ccagaccttt      600
ggagaccgtg tcaagtattg gattacaatt cacaacccct acctggttgc ttggcatggg      660
tttgccacag gtatgcatgc gccaggagag acgggaaatt taacagctgt ctacattgtg      720
ggacacaacc tgatcaaggc tcattcgaaa gtgtggcata actacgacaa aaacttccgc      780
ccccatcaga agggtttgct gtccattacc ttggggtccc actggataga accaaacaaa      840
acagaaaaca tggccgatac aatcagctgc cagcactcta tggcttttgt gcttgggtgg      900
tttgccaacc ccatccatgc agacggcgac taccctgagt tcatgaaaac attgtccacc      960
atgccagtgt tctctgaggc agagaaggag gaggtgaggg gcacagctga cttctttgcc     1020
tttttccttt g ggcccaacaa tttcaggccc tcgaacactg tagtgaaaat gggacaaaat     1080
gtatcactca acttaagaca ggtgctgaac tggattaaat tagaatatga caaccctcga     1140
atcttgattt cggagaatgg ctggttcaca gatagtgaca taaagacaga ggacaccaca     1200
gccatctaca tgatgaagca tttcctcaac caggttcttc aagcaataca gtttgatgaa     1260
atacgagtgt ttggttacac ggcctggtct ctcctggatg gctttgaatg gcagtatgcc     1320
tacacgtctc gccgaggact gttttatgtg gactttaata gtgaacagaa agaaaggaaa     1380
cccaagacct cggcacatta ctacaaacag atcatacaag aaaatggttt ccctttgaaa     1440
gagtccacgc cagacatgca gggtcagttt ccctgtgact ctcctgggg g ggtcaccgag     1500 tctgttctta agccggagtt tatggttttcc tccccacagt ttaccgaccc tcacctgtat     1560
gtgtggaatg ccactggcaa cagattgcta cagcgagtag aaggagtaag gctaaaaaca     1620
aaaccatccc actgcacaga ctatgttagc atcaaaaaac gagttgagat gttggccaaa     1680
atgaaagtca cccactacca gtttgctctg gactgggcca ccatccttcc cactggcaat     1740
ctgtctgaag ttaatagaca agtactaagg tactataggt gtgtggtgag cgaaggactg     1800
aagctgggcg tctctcccat ggtgacgttg taccaccca cccactccca tctaggcctc     1860
cctgagccgc ttcttaacag tggggatgg ctaaacactt acaccgccaa ggccttccag     1920
gactacgcag gactgtgctt ccaggaacta ggggacttgg tgaagctctg gatcaccatc     1980
aatgagccta ataggctgag tgacatgtac aaccgcacga gtaatgacac ctaccgtgca     2040
gcccataacc tgatgattgc ccatgcccag gtctggcgtc tctacgacag gcagtatagg     2100
ccagtccagc atggagctgt gtcgctgtcc ctacattctg actgggtgga acctgccaac     2160
ccctatgtgg actcacactg gaaggcagcg gagcgcttcc tcctgtttga gatcgcctgg     2220
ttcgctgatc cgctcttcaa gactggcgac tatccactgg ccatgaagga gtacatcgcc     2280
tccaagaacc agcaagggct gtcccgctca gtcctgccgc gcttcacccc agaggagagc     2340
aggctggtga agggcaccat cgacttctac gcactgaacc acttcactac taggttcgtg     2400
atacacaaac agctcaacag cagccgctct atgcagacaa gggacgtcca gttcctgcag     2460
gacatcaccc gcctgagctc gcccagccgc ctggctgtta tgccctgggg agcacgcaag     2520
ctgcttgggt ggatccagag gaactatggg gacatggaca tctacatcac agccaatggc     2580
atcgatgatc tggctctgga gaatgatggg atccgaaagt actacttgga gaagtacatc     2640
caggaggctc tgaaagcata cctcattgac aaagtcaaaa tcaaaggcta ttatgcattc     2700
aaactgactg aagagaaatc taagcctaga tttggatttt tcacatctga cttcaaagct     2760
aagtcatctg tagagtttta tagcaagttg atcagcagaa gtggcttccc ctctgagact     2820
agcaatcccg catgtggtca gcctccagaa gacacagact gcaccatctg ctcattttc      2880
```

-continued

```
actcagaaga aatctctgat cttctttggt tgttgcttca tctccactct ggctgtactg    2940
ctgtcaatca ccattttca tcatcgaaag agaagatttc ataaatcaaa gaacttagaa     3000
aatataccat tgaaggaagg ccacagtaga gttcttagct aa                       3042
```

<210> SEQ ID NO 175
<211> LENGTH: 1044
<212> TYPE: PRT
<213> ORGANISM: Oryctolagus cuniculus
<220> FEATURE:
<223> OTHER INFORMATION: rabbit beta klotho

<400> SEQUENCE: 175

```
Met Lys Pro Gly Cys Ala Ala Gly Ser Pro Gly Asn Glu Trp Val Ser
1               5                   10                  15

Phe Cys Thr Asp Glu Arg Asn Arg Arg Cys Arg Glu Thr Met Ser Ser
            20                  25                  30

Gly Arg Leu Arg Arg Ser Val Met Leu Ser Ala Phe Ile Leu Leu Arg
        35                  40                  45

Ala Val Thr Gly Phe Pro Gly Asp Gly Arg Ala Val Trp Ser Gln Asn
    50                  55                  60

Pro Asn Leu Ser Pro Val Asn Glu Ser Gln Leu Phe Leu Tyr Asp Thr
65                  70                  75                  80

Phe Pro Lys Asn Phe Phe Trp Gly Val Gly Thr Gly Ala Phe Gln Val
                85                  90                  95

Glu Gly Ser Trp Lys Lys Asp Gly Lys Gly Leu Ser Val Trp Asp His
            100                 105                 110

Phe Ile Ala Thr His Leu Asn Val Ser Ser Arg Asp Gly Ser Ser Asp
        115                 120                 125

Ser Tyr Ile Phe Leu Glu Lys Asp Leu Ser Ala Leu Asp Phe Leu Gly
    130                 135                 140

Val Ser Phe Tyr Gln Phe Ser Ile Ser Trp Pro Arg Leu Phe Pro Asp
145                 150                 155                 160

Gly Thr Val Ala Val Ala Asn Ala Lys Gly Leu Gln Tyr Tyr Asn Arg
                165                 170                 175

Leu Leu Asp Ser Leu Leu Arg Asn Ile Glu Pro Val Val Thr Leu
            180                 185                 190

Tyr His Trp Asp Leu Pro Trp Ala Leu Gln Glu Lys Tyr Gly Gly Trp
        195                 200                 205

Lys Asn Glu Thr Leu Ile Asp Leu Phe Asn Asp Tyr Ala Thr Tyr Cys
    210                 215                 220

Phe Gln Thr Phe Gly Asp Arg Val Lys Tyr Trp Ile Thr Ile His Asn
225                 230                 235                 240

Pro Tyr Leu Val Ala Trp His Gly Tyr Gly Thr Gly Leu His Ala Pro
                245                 250                 255

Gly Glu Lys Gly Asn Val Ala Ala Val Tyr Thr Val Gly His Asn Leu
            260                 265                 270

Leu Lys Ala His Ser Lys Val Trp His Asn Tyr Asn Arg Asn Phe Arg
        275                 280                 285

Pro His Gln Lys Gly Trp Leu Ser Ile Thr Leu Gly Ser His Trp Ile
    290                 295                 300

Glu Pro Asn Arg Ala Glu Ser Ile Val Asp Ile Leu Lys Cys Gln Gln
305                 310                 315                 320

Ser Met Val Ser Val Leu Gly Trp Phe Ala Asn Pro Ile His Gly Asp
                325                 330                 335
```

```
Gly Asp Tyr Pro Glu Val Met Thr Lys Lys Leu Leu Ser Val Leu Pro
            340                 345                 350

Ala Phe Ser Glu Ala Glu Lys Asn Glu Val Arg Gly Thr Ala Asp Phe
                355                 360                 365

Phe Ala Phe Ser Phe Gly Pro Asn Asn Phe Lys Pro Leu Asn Thr Met
370                 375                 380

Ala Lys Met Gly Gln Asn Val Ser Leu Asn Leu Arg Gln Val Leu Asn
385                 390                 395                 400

Trp Ile Lys Leu Glu Tyr Gly Asn Pro Arg Ile Leu Ile Ala Glu Asn
                405                 410                 415

Gly Trp Phe Thr Asp Ser Tyr Val Gln Thr Glu Asp Thr Ala Ile
                420                 425                 430

Tyr Met Met Lys Asn Phe Leu Asn Gln Val Leu Gln Ala Ile Arg Leu
            435                 440                 445

Asp Gly Val Arg Val Phe Gly Tyr Thr Ala Trp Ser Leu Leu Asp Gly
            450                 455                 460

Phe Glu Trp Gln Asp Ala Tyr Asn Thr Arg Arg Gly Leu Phe Tyr Val
465                 470                 475                 480

Asp Phe Asn Ser Glu Gln Arg Glu Arg Pro Lys Ser Ser Ala His
                485                 490                 495

Tyr Tyr Lys Gln Val Ile Gly Glu Asn Gly Phe Thr Leu Arg Glu Ala
            500                 505                 510

Thr Pro Asp Leu Gln Gly Gln Phe Pro Cys Asp Phe Ser Trp Gly Val
            515                 520                 525

Thr Glu Ser Val Leu Lys Pro Glu Ser Val Ala Ser Ser Pro Gln Phe
            530                 535                 540

Ser Asp Pro His Leu Tyr Val Trp Asn Ala Thr Gly Asn Arg Met Leu
545                 550                 555                 560

His Arg Val Glu Gly Val Arg Leu Lys Thr Arg Pro Ala Gln Cys Thr
                565                 570                 575

Asp Phe Ile Thr Ile Lys Lys Gln Leu Glu Met Leu Ala Arg Met Lys
            580                 585                 590

Val Thr His Phe Arg Phe Ala Leu Asp Trp Ala Ser Val Leu Pro Thr
            595                 600                 605

Gly Asn Leu Ser Glu Val Asn Arg Gln Ala Leu Arg Tyr Tyr Arg Cys
            610                 615                 620

Val Val Thr Glu Gly Leu Lys Leu Asn Ile Ser Pro Met Val Thr Leu
625                 630                 635                 640

Tyr Tyr Pro Thr His Ala His Leu Gly Leu Pro Ala Pro Leu Leu His
                645                 650                 655

Ser Gly Gly Trp Leu Asp Pro Ser Thr Ala Lys Ala Phe Arg Asp Tyr
                660                 665                 670

Ala Gly Leu Cys Phe Arg Glu Leu Gly Asp Leu Val Lys Leu Trp Ile
            675                 680                 685

Thr Ile Asn Glu Pro Asn Arg Leu Ser Asp Val Tyr Asn Arg Thr Ser
            690                 695                 700

Asn Asp Thr Tyr Gln Ala Ala His Asn Leu Leu Ile Ala His Ala Leu
705                 710                 715                 720

Val Trp His Leu Tyr Asp Arg Gln Tyr Arg Pro Ser Gln Arg Gly Ala
                725                 730                 735

Leu Ser Leu Ser Leu His Ser Asp Trp Ala Glu Pro Ala Asn Pro Tyr
            740                 745                 750
```

-continued

| | | | | | | | | | | | | |
|---|---|---|---|---|---|---|---|---|---|---|---|---|
|Val|Ala|Ser|His|Trp|Gln|Ala|Glu|Arg|Phe|Leu|Gln|Phe|Glu|Ile|
| | |755| | | |760| | | |765| | |

Ala Trp Phe Ala Glu Pro Leu Phe Lys Thr Gly Asp Tyr Pro Val Ala
770                 775                 780

Met Arg Glu Tyr Ile Ala Ser Lys Thr Arg Arg Gly Leu Ser Ser Ser
785                 790                 795                 800

Val Leu Pro Arg Phe Ser Asp Ala Glu Arg Arg Leu Val Lys Gly Ala
                805                 810                 815

Ala Asp Phe Tyr Ala Leu Asn His Phe Thr Thr Arg Phe Val Met His
            820                 825                 830

Glu Gln Gln Asn Gly Ser Arg Tyr Asp Ser Arg Asp Val Gln Phe
        835                 840                 845

Leu Gln Asp Ile Thr Arg Leu Ala Ser Pro Ser Arg Leu Ala Val Met
850                 855                 860

Pro Trp Gly Glu Gly Lys Leu Leu Arg Trp Met Arg Asn Asn Tyr Gly
865                 870                 875                 880

Asp Leu Asp Val Tyr Ile Thr Ala Asn Gly Ile Asp Asp Gln Ala Leu
                885                 890                 895

Gln Asn Asp Gln Leu Arg Gln Tyr Tyr Leu Glu Lys Tyr Val Gln Glu
            900                 905                 910

Ala Leu Lys Ala Tyr Leu Ile Asp Lys Ile Lys Ile Lys Gly Tyr Tyr
        915                 920                 925

Ala Phe Lys Leu Thr Glu Glu Lys Ser Lys Pro Arg Phe Gly Phe Phe
    930                 935                 940

Thr Ser Asp Phe Lys Ala Lys Ser Ser Ile Gln Phe Tyr Asn Lys Leu
945                 950                 955                 960

Ile Thr Ser Asn Gly Phe Pro Ser Glu Asn Gly Gly Pro Arg Cys Asn
                965                 970                 975

Gln Thr Gln Gly Asn Pro Glu Cys Thr Val Cys Leu Leu Leu Gln
            980                 985                 990

Lys Lys Pro Leu Ile Phe Phe Ser Cys Cys Phe Phe Cys Thr Leu Val
        995                 1000                1005

Leu Leu Ser Ser Ile Thr Ile Phe His Arg Arg Lys Arg Arg Lys Phe
    1010                1015                1020

Trp Lys Ala Lys Asp Leu Gln His Ile Pro Leu Lys Lys Gly His Lys
1025                1030                1035                1040

Arg Val Leu Ser

<210> SEQ ID NO 176
<211> LENGTH: 5737
<212> TYPE: DNA
<213> ORGANISM: Oryctolagus cuniculus
<220> FEATURE:
<223> OTHER INFORMATION: rabbit beta klotho

<400> SEQUENCE: 176
tgaagccgtg ataagacggt cccgcagttc gtggcaaatg aagccaggct gtgcggcagg    60
atctccaggg aatgaatggg tttccttctg caccgatgaa agaaacagac gctgtaggga   120
aacgatgtcc agcggacgcc tgcggagatc tgtcatgctg tcagccttca tcctgctgcg   180
agccgtgact gggttccccg agacggaag agctgtatgg tcgcaaaatc ctaatttgag    240
tccggtaaac gaaagtcagc tgtttctcta tgacactttc ccaaaaaact ttttctgggg   300
tgtggggact ggagccttcc aagtggaagg gagttggaag aaggatggga aaggactctc   360
tgtatgggat catttcatcg ctacacacct gaacgtcagc agccgcgatg gctccagtga   420

```
cagctacatt tttttggaga aagacttatc ggcgctggat tttttaggag tctctttttta    480 tcagttttca atttcctggc caagactgtt cccggatggc acagtagcag tcgccaatgc    540
aaaaggtctc cagtactata atcggctcct ggactctctg ctacttagaa acattgaacc    600
tgtagtcact ttataccatt gggatctgcc ttgggcgcta caagaaaaat acggggggtg    660
gaaaaacgag acgttgattg atttattcaa tgactatgcc acctactgtt ccagacgtt     720 tggggaccgt gtcaaatact ggatcaccat tcacaatccc tatctggtgg cttggcatgg    780
ctacgggaca ggtctgcatg ctccgggaga aagggaaat gtggcagctg tctacactgt     840
gggacacaac ctgcttaagg ctcattcaaa agtctggcac aactacaaca ggaatttccg    900
cccgcatcag aaaggctggc tgtcgatcac gctgggatcc cactggattg agccaaacag    960
agcggaaagc atcgtggaca tactcaagtg ccagcagtcc atggtctcgg tgctgggctg   1020
gtttgccaac ccgatccacg gggacgggga ctacccagag gtgatgacaa agaagctgct   1080
ctccgtcctg cccgctttct cagaagcaga aagaacgag gtacgaggca ccgcagactt    1140
cttTgccttt tcgtttggac ccaacaactt caagcccta aacaccatgg ctaaaatggg   1200
gcagaatgtg tcactcaatc taagacaggt gctgaactgg attaaactgg aatatggcaa   1260
ccctcgaatc ctgatcgctg agaacggctg gttcacagac agttacgtgc aaacagaaga   1320
caccacagcc atctacatga tgaagaattt cctcaaccag gttcttcaag caataaggtt   1380
ggatggagtc cgagtgtttg ctacactgc ctggtctctc ctggatggct tcgaatggca    1440
ggacgcttac aacacccgcc gtggactgtt ttatgtggac ttcaacgcg aacagagaga    1500 aagaaggccc aagtcctcgg cgcattacta taaacaggtc ataggagaaa acggcttcac   1560
gctcagagag gccaccccgg atctgcaggg gcagtttccc tgtgacttct cctggggcgt   1620
caccgagtct gttcttaagc ccgagtcggt ggcttcctcg ccacagttca gcgaccctca   1680
cctctacgtg tggaacgcca ctggcaaccg aatgcttcac cggtggaag gggtgaggct    1740 gaaaacacgg cccgctcagt gcacagattt catcaccatc aagaaacaac tcgagatgtt   1800
ggcaagaatg aaagtcaccc acttccggtt tgctctggac tgggcctcgg tccttcccac   1860
gggcaacctg tccgaggtga accgacaagc cctgaggtac tacaggtgtg tggtcaccga   1920
ggggctgaag ctcaacatct cgcccatggt caccttgtac taccgaccc atgcccacct    1980 gggcctgccc gcgccgctgc tgcacagcgg ggggtggctg acccatcca cggccaaggc    2040 cttccgcgac tacgcagggc tgtgcttccg ggagctgggg gacctggtga agctctggat   2100
caccatcaac gagcccaacc ggctgagcga cgtctacaac cgcaccagca acgacaccta   2160
ccaggccgcc cacaacctgc tgatcgcgca cgcgctcgtg tggcacctgt acgaccgcca   2220
gtaccggccg tcgcagcgcg gggcgctgtc gctgtccctg cactcggact gggccgagcc   2280
cgccaacccc tacgtggcct cgcactggca ggcggccgag cgcttcctgc agttcgagat   2340
tgcgtggttc gccgagcccc tgttcaagac cggggactac ccggtggcca tgagggagta   2400
catcgcctcc aagacccggc gcgggctctc cagctccgtg ctgccccgct tcagcgacgc   2460
cgagcggcgg ctggtcaagg gcgccgccga cttctacgcc ctcaaccact tcaccaccag   2520
gttcgtgatg cacgagcagc agaacggcag ccgctacgac tcggacaggg acgtgcagtt   2580
cctgcaggac atcacccgcc tggcctcacc cagccgcctg gccgtgatgc cctggggcga   2640
gggcaagctg ctgcggtgga tgcggaacaa ctacggagac ctggacgtct acatcacggc   2700
caatggcatc gacgaccagg ccctgcagaa cgaccagctt cgccagtact acctgggaaa   2760
```

-continued

```
gtacgtccag gaggctctga agcatatct gatagataaa ataaaaatca aaggctatta    2820
tgcattcaaa ctgactgaag aaaaatctaa acccaggttt ggattcttca cctctgattt    2880
caaagccaag tcttcaatac agttttacaa caaactaatt accagcaacg cttcccgtc    2940
tgagaacggc ggtcctagat gcaatcagac tcaaggaaat cccgagtgca ccgtctgctt    3000
actcctcctg cagaagaagc cgctgatatt ctttagctgc tgcttcttct gcaccctggt    3060
tctactctca tcaattacca tcttttcacag acggaagaga agaaaatttt ggaaagcaaa   3120
ggacttacaa cacataccat taaagaaagg ccacaagaga gtccttagct aaagtgaact    3180
tatttctctc tgaagagttt agaaattcac tccagttcca tatgctggta acacaaaaga   3240
catacccgta ttgtacacag agtatttgag atactgtgct aaccaaggcg atgacaatca    3300
aaacctctgc catgtggttg aatgcatttt cccttaagcg gtgacaatca gcgaactcag    3360
ttcttggttc taaggaggc ttcgcactgc cactaggcta tgagtattac ctgacgcatt     3420
gctttgtcaa gtttgatgag ctgtttcgca tcattctcta gctttcttta gataccaata    3480
gctactatgg taaaagttgt ttttaaaagt caaactctgt aaggcttcac agcagattta    3540
aaactattct ttacactgga tctgtgattt tgtcactcgt agcaaggtgc tttccccttt    3600
tggtcctagt ggctctcaaa tagaaagcaa acacatctta gggtaatcta cttatctata    3660
gccaatcaca gcactgaccc acaactacac aaatccgtta gctcttctcc ataaaacacc    3720
taattttgtg atcttttaag taatctgaaa tgtaaaagta tgacttccgt aacccatctc    3780
atggaaagat cgactaagga gagccatacc cagctgtgag gacaatttag tcactaatct    3840
caccgtactg caacttcctc ctttagagca ggcattcctt accattttg taagatgaca    3900
tgatttagca tctagaaccc ctatctgcag tttcttttcta tggcttacct acatttcaag   3960
aatattgaac ggaaaatttc agaaagattt ccaagtttta aattgtgtac tagcattagt    4020
gcatgatgaa atctcatttt ctttgctcca tcctgcacag gatgtgaaac atccctctgt    4080
ccagcaagtc caagctacct atattactca cttgatagtc accatggtta tccagctgtt    4140
attacttgct catacccagg taaccctttt ttattttaat atagctccaa agtataagac    4200
tagtgatgaa aaggaggtaa gtcatcaaat atggaaggac agattaactc tggcactaag    4260
tgggaatgct gcaggtttta caggaaaaca aaattcagtc agtggtttaa agcatcctct    4320
gaggtacctg gggcacaatc tccacagata aggggaaaga gcactgacaa agactaaaca    4380
tcctaaaaag acgcaatgtt ctacttactg gccatcagaa taatggccaa aggaccctat    4440
acttgcttgc tctctagcca agtttcgctg cacataggtg tagaatgcag cgactgaccc    4500
tggatgcgat tcagaatgct gatctgagtg aactagtttt ttatacagca cttttttaaag   4560
cctagaattc ttccatctga acttgggagt tttgacttt ttgaaattaa ttgtgcttaa     4620
gatttattca gtgattctaa acactggagg tagaaaactg tatacccatt atgcctatta    4680
atttttcttg attagccaac atttaaataa ccacaaagtg gccagtcgtt gtctttccct    4740
ttcaggaatt taagtcaaag gatgctgctg cctgcgatgc tggcacttca tagggggtgac   4800
agtttgtgtc cctgcggttc cacttcctat ccagctccct gctaatggct gggagagcc     4860
ctgcacccac atgggagacc caaaagcaga tcctgctgct ttcagcctgc tcggccact     4920
tggagtatga accagtggat ggaagatcaa tgtctctccc aacaattctt tgaataaatt    4980
ttttcaaaag tcaaaataaa attctccagc tcaaaaagct ttagtagaaa acgatcctac    5040
attaaggcgg ttgtgattgt atcccaagtg catctacgtt acaaaccaaa ttgagtatgc    5100
aattcagtat gctactagac tataaggaga aaacagccaa ttcaaacaaa ataccaaagt    5160
```

```
cacgtgcagt taatttgctt tctggttggc caaatgtttt ttttctcttc ttgccaccac    5220
tgttttacat gtactttaga agaaattttg acttttttgct tcctttgaga aatcactatt    5280
atcaaaggca attcataatt acaagtggtc cattgtctta agagctcaag attatagccc    5340
ttcaaacttg ccaaactcct caaatagtga agctcctaac gaagggttta caacatcctg    5400
ttccttaggg gttatatttt taagtgactg taatttacct aacaaattta atctggctat    5460
ctattggtaa tacatgtaat attcaggttt atcataaacc cacttaaaaa ctaaaggtta    5520
agtggaagtt gctgcttttc aaagtaacag gcttctcagg ggaaaatatc accttagcgt    5580
ccacctggta ctacatctcg tgtattcact gtaacccatc tttccgaaca tgtctgatat    5640
atatggaaac aacactagtg cttagcctct ggaaatgagg ccaggatttt gtgattaaat    5700
gtctaattta ttccaaataa actgatttac gccaata                              5737
```

<210> SEQ ID NO 177
<211> LENGTH: 1045
<212> TYPE: PRT
<213> ORGANISM: Canis lupus familiaris
<220> FEATURE:
<223> OTHER INFORMATION: dog beta klotho

<400> SEQUENCE: 177

```
Met Lys Pro Gly Cys Ala Ala Gly Ser Pro Gly Asn Glu Trp Ile Phe
1               5                   10                  15

Leu Ser Thr Asp Glu Ser Asn Thr His Tyr Arg Lys Thr Met Cys Asn
            20                  25                  30

His Gly Leu Gln Arg Ser Val Ile Leu Ser Ala Phe Ile Leu Leu Gly
        35                  40                  45

Ala Val Pro Gly Phe Ser Gly Asp Gly Arg Ala Ile Trp Ser Lys Asn
    50                  55                  60

Pro His Phe Ser Pro Val Asn Glu Ser Gln Leu Phe Leu Tyr Asp Thr
65                  70                  75                  80

Phe Pro Lys Asn Phe Phe Trp Gly Val Gly Thr Gly Ala Phe Gln Val
                85                  90                  95

Glu Gly Asn Trp Lys Thr Asp Gly Lys Gly Pro Ser Ile Trp Asp His
            100                 105                 110

Phe Ile His Thr His Leu Lys Asn Val Asn Ser Met Asn Ser Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Ala Ala Val Ala Asn Ala Lys Gly Leu Gln Tyr Tyr Asn
                165                 170                 175

Ser Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Glu Thr Ile Thr Asp Ile Phe Asn Asp Tyr Ala Thr Tyr
    210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255
```

```
Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr Asn Phe
        275                 280                 285

Arg Pro Tyr Gln Lys Gly Leu Leu Ser Ile Thr Leu Gly Ser His Trp
    290                 295                 300

Ile Glu Pro Asn Arg Ser Glu Asn Met Met Asp Ile Leu Lys Cys Gln
305                 310                 315                 320

Gln Ser Met Val Ser Val Leu Gly Trp Phe Ala Asn Pro Ile His Gly
                325                 330                 335

Asn Gly Asp Tyr Pro Glu Val Met Lys Lys Leu Leu Ser Thr Leu
            340                 345                 350

Pro Leu Phe Ser Glu Ala Glu Lys Asn Glu Val Arg Gly Thr Ala Asp
        355                 360                 365

Phe Phe Ala Phe Ser Phe Gly Pro Asn Asn Phe Lys Pro Gln Asn Thr
370                 375                 380

Met Ala Lys Met Gly Gln Asn Val Ser Leu Asn Leu Arg Glu Val Leu
385                 390                 395                 400

Asn Trp Ile Lys Leu Glu Tyr Gly Asn Pro Arg Ile Leu Ile Ala Glu
                405                 410                 415

Asn Gly Trp Phe Thr Asp Ser His Val Lys Thr Glu Asp Thr Thr Ala
            420                 425                 430

Ile Tyr Met Met Lys Asn Phe Leu Asn Gln Val Leu Gln Ala Ile Arg
        435                 440                 445

Phe Asp Glu Ile Gln Val Phe Gly Tyr Thr Ala Trp Ser Leu Leu Asp
    450                 455                 460

Gly Phe Glu Trp Gln Asp Ala Tyr Ser Thr Arg Arg Gly Leu Phe Tyr
465                 470                 475                 480

Val Asp Phe Asn Ser Lys Gln Lys Glu Arg Lys Pro Lys Ser Ser Ala
                485                 490                 495

Tyr Tyr Tyr Lys Gln Ile Ile Gln Glu Asn Gly Phe Thr Phe Lys Glu
            500                 505                 510

Ser Thr Pro Asp Val Gln Gly Gln Phe Pro Cys Asp Phe Ser Trp Gly
        515                 520                 525

Val Thr Glu Ser Val Leu Lys Pro Lys Val Val Ala Ser Ser Pro Gln
    530                 535                 540

Phe Ser Asp Pro His Leu Tyr Val Trp Asn Val Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Ser Ile Lys Arg Gln Leu Glu Met Leu Ala Arg Met
            580                 585                 590

Asn Val Thr His Tyr Arg Phe Ala Leu Asp Trp Pro Ser Ile Leu Pro
        595                 600                 605

Thr Gly Asn Leu Ser Thr Val Asn Arg Gln Ala Leu Arg Tyr Tyr Arg
    610                 615                 620

Cys Val Val Ser Glu Ser Leu Lys Leu Ser Ile Ser Pro Met Val Thr
625                 630                 635                 640

Leu Tyr Tyr Pro Thr His Ala His Leu Gly Leu Pro Ser Pro Leu Leu
                645                 650                 655

His Ser Gly Gly Trp Leu Asn Ala Ser Thr Ala Arg Ala Phe Gln Asp
            660                 665                 670

Tyr Ala Gly Leu Cys Phe Gln Glu Leu Gly Asp Leu Val Lys Leu Trp
```

```
                    675                 680                 685

Ile Thr Ile Asn Glu Pro Asn Arg Leu Ser Asp Val Tyr Ser His Thr
            690                 695                 700

Ser Ser Asp Thr Tyr Arg Ala Ala His Asn Leu Leu Ile Ala His Ala
705                 710                 715                 720

Leu Val Trp His Leu Tyr Asp Arg Arg Tyr Arg Pro Ala Gln Arg Gly
                725                 730                 735

Ala Val Ser Leu Ser Leu His Ser Asp Trp Ala Glu Pro Ala Asn Pro
            740                 745                 750

Tyr Ala Asp Ser His Trp Lys Ala Ala Glu Arg Phe Leu Gln Phe Glu
        755                 760                 765

Ile Ala Trp Phe Ala Glu Pro Leu Phe Lys Thr Gly Asp Tyr Pro Pro
770                 775                 780

Ala Met Arg Glu Tyr Ile Ala Ser Lys Asn Arg Gln Gly Leu Ser Arg
785                 790                 795                 800

Ser Thr Leu Pro Arg Phe Thr Asp Glu Glu Arg Arg Leu Val Lys Gly
                805                 810                 815

Ala Ala Asp Phe Tyr Ala Leu Asn His Phe Thr Thr Arg Phe Val Met
            820                 825                 830

His Ala Arg Gln Asn Gly Ser Arg Tyr Asp Ala Asp Arg Asp Val Gln
        835                 840                 845

Phe Leu Gln Asp Ile Thr Cys Leu Ser Ser Pro Ser Arg Leu Ala Val
850                 855                 860

Leu Pro Trp Gly Glu Arg Lys Val Leu Arg Trp Ile Gln Lys Asn Tyr
865                 870                 875                 880

Gly Asp Val Asp Val Tyr Ile Thr Ala Ser Gly Ile Asp Asp Gln Ser
                885                 890                 895

Leu Glu Asn Asp Glu Leu Arg Lys Tyr Tyr Leu Glu Lys Tyr Ile Gln
            900                 905                 910

Glu Ala Leu Lys Ala His Leu Ile Asp Lys Val Lys Val Lys Gly Tyr
        915                 920                 925

Tyr Ala Phe Lys Leu Thr Glu Glu Lys Ser Lys Pro Arg Phe Gly Phe
930                 935                 940

Phe Thr Ser Glu Phe Lys Ala Lys Ser Ser Val Gln Leu Tyr Asn Lys
945                 950                 955                 960

Leu Ile Ser Asn Ser Gly Phe Pro Ser Glu Asn Arg Ser Pro Arg Cys
                965                 970                 975

Ser Glu Thr Gln Arg Asn Thr Glu Cys Met Val Cys Leu Phe Leu Val
            980                 985                 990

Gln Lys Lys Pro Leu Ile Phe Phe Ser Cys Cys Phe Phe Ser Thr Leu
        995                 1000                1005

Val Leu Leu Ser Ser Ile Thr Ile Leu His Lys Arg Lys Arg Arg Lys
1010                1015                1020

Ile Trp Lys Ala Lys Asn Leu Gln His Ile Pro Leu Lys Lys Ser Lys
1025                1030                1035                1040

Asn Ser Leu Gln Ser
                1045

<210> SEQ ID NO 178
<211> LENGTH: 4350
<212> TYPE: DNA
<213> ORGANISM: Canis lupus familiaris
<220> FEATURE:
<223> OTHER INFORMATION: dog beta klotho
```

<400> SEQUENCE: 178

```
acaatcacaa gctttctactg aagcgttgat aagacaggcg agcagttagt ggcaaatgaa      60
gccaggctgt gcggctggat ctccagggaa tgaatggatt ttcctcagca ccgatgaaag     120
caacacacac tataggaaaa caatgtgcaa ccacgggcta cagagatctg tcatcctgtc     180
agcatttatt ctcctaggag ctgttcctgg attctctgga gacggaagag ctatatggtc     240
taaaaatcct cattttagtc cggtaaatga aagtcagctg tttctctatg acacttttcc     300
taaaaacttt ttttggggcg ttgggactgg agcatttcaa gtggaaggga attggaagac     360
agatggaaaa ggaccctcta tatgggatca tttcatccac acacaccta aaaatgtcaa      420
cagcatgaat agttccagtg acagttacat ttttctggaa aaagacctat cagccctgga     480
ttttatcgga gttctttttt atcaattttc aatttcctgg ccaaggcttt tccccgatgg     540
aatagcagca gttgccaacg caaaaggtct ccagtactac aattctcttc tcgatgctct     600
agtacttagg aacattgaac ctatagttac tttataccat tgggatttgc ctttggcact     660
acaagaaaaa tatgggggt ggaaaatga aaccataacg atatcttca atgactatgc         720
cacctactgt ttccagacgt tcggggatcg tgtcaaatac tggattacaa ttcacaatcc     780
atatctagtt gcttggcatg ggtatgggac aggtatgcac gcgcctggag agaagggaaa     840
cttagcagct gtctacactg tgggacacaa cctaatcaag gctcattcga agtttggca      900
taactacaac acaaatttcc gcccatatca gaagggtttg ttatcaatca cgttgggatc     960
ccattggatt gaaccaaaca gatcagaaaa catgatggat atactcaaat gtcaacaatc    1020
catggtttca gtgctcgggt ggtttgccaa ccccatccat gggaatggag actatccaga    1080
agtgatgaaa aagaagttgc tctccactct accccttttc tctgaagcag agaagaatga    1140
agtgaggggc acagctgact tctttgcctt ttcctttgga cccaacaatt tcaagcccca    1200
gaacaccatg gctaaaatgg acaaaatgt gtcactcaat ttaagagaag tgctgaattg     1260
gattaaactg gaatatggca accccgaat cttgattgct gagaatggct ggttcacaga    1320
cagtcatgtg aaaacagaag ataccacagc catttacatg atgaagaatt tcctcaacca    1380
ggttcttcaa gcaataaggt ttgacgaaat acaagtgttt ggctacactg cttggtctct    1440
cctggatggc tttgaatggc aggatgctta ctccactcgc cgaggattat tttatgtgga    1500
ttttaatagt aaacaaaag aaagaaagcc caagtcttcg gcatattact ataaacagat     1560
catacaagaa aatggtttta ctttcaaaga gtccaccca gatgtgcagg gtcagtttcc      1620
ctgtgacttc tcatggggtg tcaccgaatc tgtccttaag cccaaagtcg tggcttcctc    1680
cccacagttc agcgacccctc acctgtacgt gtggaatgtg acaggcaaca gactgttgca    1740
ccgagtggaa ggggtgaggc tgaagacacg gccggctcaa tgcacagatt ttgtcagcat    1800
caaaagacaa cttgagatgt tggcgaggat gaacgtcact cactacaggt ttgctctgga    1860
ctggccctcc atccttccca ccggcaacct gtccacggtt aaccgacaag ccctgaggta    1920
ctacaggtgt gtggtcagcg agtcgctgaa gctcagcatc tccccgatgg tcacgctgta    1980
ctacccgacc cacgcccacc tgggcctccc ctcgccgctg ctgcacagcg ggggctggct    2040
gaacgcgtcc accgcccgcg ccttccagga ctatgccggg ctgtgcttcc aggagctggg    2100
ggacctggtg aagctctgga tcaccatcaa tgagcccaac cggctgagtg acgtctacag    2160
ccacaccagc agcgacacct accgggcagc gcacaacctg ctgatcgccc acgccctggt    2220
gtggcacctg tacgaccggc ggtaccggcc ggcgcagcgc gggccgtgt cgctgtccct     2280
gcactcggac tgggcggagc ccgccaaccc ctacgccgac tcgcactgga aggcggccga    2340
```

```
gcgcttcctg cagttcgaaa tcgcctggtt cgccgagccg ctcttcaaga ccggggacta    2400
cccgccggcc atgagggagt acatcgcctc caagaacagg caggggctct cgcgctccac    2460
cctgccccgc ttcaccgacg aggagaggag gctggtcaag ggcgccgccg acttctacgc    2520
gctgaaccac ttcaccacca ggttcgtgat gcacgcgcgc cagaacggca gccgctacga    2580
cgcggaccgc gacgtccagt cctgcaggca catcacctgc ctgagctccc ccagccgcct    2640
ggccgtcctg ccctgggggg agcgcaaggt gctcaggtgg atccagaaga actacggaga    2700
cgtggacgtg tacatcacgg ccagtggcat cgatgaccag tctctggaaa atgatgagct    2760
cagaaaatac tacttggaga aatacatcca ggaggctctg aaagcacacc taattgataa    2820
agtcaaagtc aaaggctatt atgcattcaa actgactgaa gaaaatctaa acccagatt    2880 tggattcttc acgtctgaat tcaaagctaa atcctcagtt cagctttaca acaaactgat    2940
cagcaacagt ggcttcccctt ctgagaacag gagtcctaga tgcagtgaga ctcaaagaaa    3000
cacagagtgc atggtctgct tatttcttgt gcaaaagaaa ccactgatat tctttagttg    3060
ttgcttcttc tctaccctgg ttctactttc atcgattacc attcttcata agcgaaagag    3120
aagaaaaatt tggaaagcaa agaacttaca acatatacca ttaaagtgag gccacagaaa    3180
gttcttagtg aaactgatcc tatttctgtc tgcatgatag aaagtctaaa aattcactcc    3240
agtcccaaat actggtaaca tagaagacaa tttgaaacac tagtagtaac caaggtgatg    3300
acaatcaagg tctctgctgt gtggtccaaa tgaattttcc attaggtgtt gacatcactg    3360
aatacagttt ttagatctga agactaagat ctagagagta agctaggatt atctgataca    3420
atgcttcatt aagtttaata agctgttatc catcattctt ctctggcttc cttctagaaa    3480
taccaatagc taattatagc aacttagaaa aaagtgcaac ttttgctaga ctccatagca    3540
gaaatctaaa actcttaaca ctggatattc agtgattatt ctatcacttc taacaaggtg    3600 ctttcccct ttagaagata tacaataggg taaatagtgc tcctttatca tccattccag    3660
cacttttttt ttccagcata gactcttaaa cacattgatc ctagttttc tcaatagaaa    3720 taaaaaatca tttagaaaac atggaatttt gtgaggtctc tccttgcatt agatctgagt    3780 ttttttttaaa aaaaagactt aacttccata acccatctca tgggaagatc acaggactaa    3840
gattaaggag agttagaccc atcaactgcc tgaggagaca gcactcaacc tcacagtaca    3900
gcaaattcct tgggacaaac tgacagcaat cttccgcact tggattgttg aggcagcaca    3960
caagatctta acatacttag gaaagttaaa tattctaaaa agatgtaaag ttttattttt    4020
attatcaagt cttcaaagga ccatattatt ccataagact tgctctctcc tgagttccac    4080
tcttctgaca ctatgtgtat atggggacac tcaaactgca ccttgacatt gcaactttgg    4140
atacaattca gaatgtaaat gtttgaagga cttaaaactt tctccactgc accttttgaa    4200
gctgggatta agtaaatacg aactgggagt ttgactttt tgaactctgt gcttgattta    4260
ttcactgtat tctaaatttt aaggaaaacc tgaatgtaaa cccattcata cccttttcttt    4320 gggttagtaa acatttaacc acccatttca                                     4350
```

<210> SEQ ID NO 179
<211> LENGTH: 1045
<212> TYPE: PRT
<213> ORGANISM: Artificial Sequence
<220> FEATURE:
<223> OTHER INFORMATION: human/mouse beta klotho chimeric protein
      (human KLB (M1-F508)-mouse KLB (P507-S1043)

<400> SEQUENCE: 179

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
            35                  40                  45

Ala Val Thr Gly Phe Ser Gly Asp Gly Arg Ala Ile Trp Ser Lys Asn
50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
                100                 105                 110

Phe Ile His Thr His Leu Lys Asn Val Ser Thr Asn Gly Ser Ser
                115                 120                 125

Asp Ser Tyr Ile Phe Leu Glu Lys Asp Leu Ser Ala Leu Asp Phe Ile
            130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
            195                 200                 205

Trp Lys Asn Asp Thr Ile Ile Asp Ile Phe Asn Asp Tyr Ala Thr Tyr
210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
            245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
            275                 280                 285

Arg Pro His Gln Lys Gly Trp Leu Ser Ile Thr Leu Gly Ser His Trp
            290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
            355                 360                 365

Phe Phe Ala Phe Ser Phe Gly Pro Asn Asn Phe Lys Pro Leu Asn Thr
370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415
```

```
Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
        435                 440                 445

Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Pro Leu Lys Glu
            500                 505                 510

Ser Thr Pro Asp Met Lys Gly Arg Phe Pro Cys Asp Phe Ser Trp Gly
        515                 520                 525

Val Thr Glu Ser Val Leu Lys Pro Glu Phe Thr Val Ser Ser Pro Gln
    530                 535                 540

Phe Thr Asp Pro His Leu Tyr Val Trp Asn Val Thr Gly Asn Arg Leu
545                 550                 555                 560

Leu Tyr Arg Val Glu Gly Val Arg Leu Lys Thr Arg Pro Ser Gln Cys
                565                 570                 575

Thr Asp Tyr Val Ser Ile Lys Lys Arg Val Glu Met Leu Ala Lys Met
            580                 585                 590

Lys Val Thr His Tyr Gln Phe Ala Leu Asp Trp Thr Ser Ile Leu Pro
        595                 600                 605

Thr Gly Asn Leu Ser Lys Val Asn Arg Gln Val Leu Arg Tyr Tyr Arg
    610                 615                 620

Cys Val Val Ser Glu Gly Leu Lys Leu Gly Val Phe Pro Met Val Thr
625                 630                 635                 640

Leu Tyr His Pro Thr His Ser His Leu Gly Leu Pro Leu Pro Leu Leu
                645                 650                 655

Ser Ser Gly Gly Trp Leu Asn Met Asn Thr Ala Lys Ala Phe Gln Asp
            660                 665                 670

Tyr Ala Glu Leu Cys Phe Arg Glu Leu Gly Asp Leu Val Lys Leu Trp
        675                 680                 685

Ile Thr Ile Asn Glu Pro Asn Arg Leu Ser Asp Met Tyr Asn Arg Thr
    690                 695                 700

Ser Asn Asp Thr Tyr Arg Ala Ala His Asn Leu Met Ile Ala His Ala
705                 710                 715                 720

Gln Val Trp His Leu Tyr Asp Arg Gln Tyr Arg Pro Val Gln His Gly
                725                 730                 735

Ala Val Ser Leu Ser Leu His Cys Asp Trp Ala Glu Pro Ala Asn Pro
            740                 745                 750

Phe Val Asp Ser His Trp Lys Ala Ala Glu Arg Phe Leu Gln Phe Glu
        755                 760                 765

Ile Ala Trp Phe Ala Asp Pro Leu Phe Lys Thr Gly Asp Tyr Pro Ser
    770                 775                 780

Val Met Lys Glu Tyr Ile Ala Ser Lys Asn Gln Arg Gly Leu Ser Ser
785                 790                 795                 800

Ser Val Leu Pro Arg Phe Thr Ala Lys Glu Ser Arg Leu Val Lys Gly
                805                 810                 815

Thr Val Asp Phe Tyr Ala Leu Asn His Phe Thr Thr Arg Phe Val Ile
            820                 825                 830

His Lys Gln Leu Asn Thr Asn Arg Ser Val Ala Asp Arg Asp Val Gln
```

```
                835                 840                 845
Phe Leu Gln Asp Ile Thr Arg Leu Ser Ser Pro Ser Arg Leu Ala Val
        850                 855                 860
Thr Pro Trp Gly Val Arg Lys Leu Leu Ala Trp Ile Arg Arg Asn Tyr
865                 870                 875                 880
Arg Asp Arg Asp Ile Tyr Ile Thr Ala Asn Gly Ile Asp Asp Leu Ala
                885                 890                 895
Leu Glu Asp Asp Gln Ile Arg Lys Tyr Tyr Leu Glu Lys Tyr Val Gln
            900                 905                 910
Glu Ala Leu Lys Ala Tyr Leu Ile Asp Lys Val Lys Ile Lys Gly Tyr
        915                 920                 925
Tyr Ala Phe Lys Leu Thr Glu Glu Lys Ser Lys Pro Arg Phe Gly Phe
    930                 935                 940
Phe Thr Ser Asp Phe Arg Ala Lys Ser Ser Val Gln Phe Tyr Ser Lys
945                 950                 955                 960
Leu Ile Ser Ser Ser Gly Leu Pro Ala Glu Asn Arg Ser Pro Ala Cys
                965                 970                 975
Gly Gln Pro Ala Glu Asp Thr Asp Cys Thr Ile Cys Ser Phe Leu Val
            980                 985                 990
Glu Lys Lys Pro Leu Ile Phe Phe Gly Cys Cys Phe Ile Ser Thr Leu
        995                 1000                1005
Ala Val Leu Leu Ser Ile Thr Val Phe His His Gln Lys Arg Arg Lys
        1010                1015                1020
Phe Gln Lys Ala Arg Asn Leu Gln Asn Ile Pro Leu Lys Lys Gly His
1025                1030                1035                1040
Ser Arg Val Phe Ser
                1045

<210> SEQ ID NO 180
<211> LENGTH: 3138
<212> TYPE: DNA
<213> ORGANISM: Artificial Sequence
<220> FEATURE:
<223> OTHER INFORMATION: human/mouse beta klotho chimeric protein

<400> SEQUENCE: 180
atgaagccag gctgtgcggc aggatctcca gggaatgaat ggatttttct cagcactgat      60
gaaataacca cacgctatag gaatacaatg tccaacgggg gattgcaaag atctgtcatc     120
ctgtcagcac ttattctgct acgagctgtt actggattct ctggagatgg aagagctata     180
tggtctaaaa atcctaattt tactccggta aatgaaagtc agctgtttct ctatgacact     240
ttccctaaaa acttttttct gggtattggg actggagcat gcaagtggag agggagttgg     300
aagaaggatg gaaaaggacc ttctatatgg gatcatttca tccacacaca ccttaaaaat     360
gtcagcagca cgaatggttc cagtgacagt tatatttttc tggaaaaaga cttatcagcc     420 ctggattta taggagtttc tttttatcaa ttttcaattt cctggccaag cttttcccc      480 gatggaatag taacagttgc caacgcaaaa ggtctgcagt actacagtac tcttctggac     540
gctctagtgc ttagaaacat tgaacctata gttactttat accactggga tttgcctttg     600
gcactacaag aaaaatatgg ggggtggaaa atgatacca taatagatat cttcaatgac     660
tatgccacat actgtttcca gatgtttggg accgtgtca atattggat tacaattcac     720 aacccatatc tagtggcttg gcatgggtat gggacaggta tgcatgcccc tggagagaag     780
ggaaatttag cagctgtcta cactgtggga cacaacttga tcaaggctca ctcgaaagtt     840
```

| | |
|---|---:|
| tggcataact acaacacaca tttccgccca catcagaagg gttggttatc gatcacgttg | 900 |
| ggatctcatt ggatcgagcc aaaccggtcg gaaaacacga tggatatatt caaatgtcaa | 960 |
| caatccatgg tttctgtgct tggatggttt gccaaccctca tccatgggga tggcgactat | 1020 |
| ccagagggga tgagaaagaa gttgttctcc gttctaccca ttttctctga agcagagaag | 1080 |
| catgagatga gaggcacagc tgatttcttt gccttttctt ttggacccaa caacttcaag | 1140 |
| cccctaaaca ccatggctaa aatgggacaa aatgtttcac ttaatttaag agaagcgctg | 1200 |
| aactggatta aactggaata caacaaccct cgaatcttga ttgctgagaa tggctggttc | 1260 |
| acagacagtc gtgtgaaaac agaagacacc acggccatct acatgatgaa gaatttcctc | 1320 |
| agccaggtgc ttcaagcaat aaggttagat gaaatacgag tgtttggtta tactgcctgg | 1380 |
| tctctcctgg atggctttga atggcaggat gcttacacca tccgccgagg attattttat | 1440 |
| gtggatttta acagtaaaca gaaagagcgg aaacctaagt cttcagcaca ctactacaaa | 1500 |
| cagatcatac gagaaaatgg ttttccttg aaagagtcca cgccagacat gaagggtcgg | 1560 |
| ttcccctgtg atttctcttg gggagtcact gagtctgttc ttaagcccga gtttacggtc | 1620 |
| tcctccccgc agtttaccga tcctcacctg tatgtgtgga atgtcactgg caacagattg | 1680 |
| ctctaccgag tggaaggggt aaggctgaaa acaagaccat cccagtgcac agattatgtg | 1740 |
| agcatcaaaa aacgagttga aatgttggca aaaatgaaag tcacccacta ccagtttgct | 1800 |
| ctggactgga cctctatcct tcccactggc aatctgtcca agttaacag acaagtgtta | 1860 |
| aggtactata ggtgtgtggt gagcgaagga ctgaagctgg gcgtcttccc catggtgacg | 1920 |
| ttgtaccacc caacccactc ccatctcggc ctcccctgc cacttctgag cagtgggggg | 1980 |
| tggctaaaca tgaacacagc caaggccttc caggactacg ctgagctgtg cttccgggag | 2040 |
| ttgggggact tggtgaagct ctggatcacc atcaatgagc ctaacaggct gagtgacatg | 2100 |
| tacaaccgca cgagtaatga cacctaccgt gcagcccaca acctgatgat cgcccatgcc | 2160 |
| caggtctggc acctctatga taggcagtat aggccggtcc agcatggggc tgtgtcgctg | 2220 |
| tccttacatt gcgactgggc agaacctgcc aaccccttg tggattcaca ctggaaggca | 2280 |
| gccgagcgct tcctccagtt tgagatcgcc tggtttgcag atccgctctt caagactggc | 2340 |
| gactatccat cggttatgaa ggaatacatc gcctccaaga accagcgagg gctgtctagc | 2400 |
| tcagtcctgc cgcgcttcac cgcgaaggag agcaggctgg tgaagggtac cgtcgacttc | 2460 |
| tacgcactga accacttcac tacgaggttc gtgatacaca agcagctgaa caccaaccgc | 2520 |
| tcagttgcag acagggacgt ccagttcctg caggacatca cccgcctaag ctcgcccagc | 2580 |
| cgcctggctg taacaccctg gggagtgcgc aagctccttg cgtggatccg gaggaactac | 2640 |
| agagacaggg atatctacat cacagccaat ggcatcgatg acctggctct agaggatgat | 2700 |
| cagatccgaa agtactactt ggagaagtat gtccaggagg ctctgaaagc atatctcatt | 2760 |
| gacaaggtca aaatcaaagg ctactatgca ttcaaactga ctgaagagaa atctaagcct | 2820 |
| agatttggat ttttcacctc tgacttcaga gctaagtcct ctgtccagtt ttacagcaag | 2880 |
| ctgatcagca gcagtggcct ccccgctgag aacagaagtc ctgcgtgtgg tcagcctgcg | 2940 |
| gaagacacag actgcaccat ttgctcattt ctcgtggaga gaaaccact catcttcttc | 3000 |
| ggttgctgct tcatctccac tctggctgta ctgctatcca tcaccgtttt tcatcatcaa | 3060 |
| aagagaagaa aattccagaa agcaaggaac ttacaaaata taccattgaa gaaaggccac | 3120 |
| agcagagttt tcagctga | 3138 |

<210> SEQ ID NO 181
<211> LENGTH: 1042
<212> TYPE: PRT
<213> ORGANISM: Artificial Sequence
<220> FEATURE:
<223> OTHER INFORMATION: mouse/human beta klotho chimeric protein
(mouse KLB (M1-F506) - human KLB(S509-S1044))

<400> SEQUENCE: 181

```
Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
                20                  25                  30

Arg Ala Leu Gln Arg Ser Ala Val Leu Ser Ala Phe Val Leu Leu Arg
            35                  40                  45

Ala Val Thr Gly Phe Ser Gly Asp Gly Lys Ala Ile Trp Asp Lys Lys
        50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
        115                 120                 125

Asp Ser Tyr Ile Phe Leu Glu Lys Asp Leu Leu Ala Leu Asp Phe Leu
130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
                165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
        195                 200                 205

Trp Lys Asn Ala Thr Met Ile Asp Leu Phe Asn Asp Tyr Ala Thr Tyr
210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                245                 250                 255

Pro Gly Glu Lys Gly Asn Leu Thr Ala Val Tyr Thr Val Gly His Asn
            260                 265                 270

Leu Ile Lys Ala His Ser Lys Val Trp His Asn Tyr Asp Lys Asn Phe
        275                 280                 285

Arg Pro His Gln Lys Gly Trp Leu Ser Ile Thr Leu Gly Ser His Trp
290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
                325                 330                 335

Asp Gly Asp Tyr Pro Glu Phe Met Lys Thr Gly Ala Met Ile Pro Glu
            340                 345                 350

Phe Ser Glu Ala Glu Lys Glu Glu Val Arg Gly Thr Ala Asp Phe Phe
        355                 360                 365
```

-continued

```
Ala Phe Ser Phe Gly Pro Asn Asn Phe Arg Pro Ser Asn Thr Val Val
370                 375                 380

Lys Met Gly Gln Asn Val Ser Leu Asn Leu Arg Gln Val Leu Asn Trp
385                 390                 395                 400

Ile Lys Leu Glu Tyr Asp Asp Pro Gln Ile Leu Ile Ser Glu Asn Gly
            405                 410                 415

Trp Phe Thr Asp Ser Tyr Ile Lys Thr Glu Asp Thr Thr Ala Ile Tyr
            420                 425                 430

Met Met Lys Asn Phe Leu Asn Gln Val Leu Gln Ala Ile Lys Phe Asp
            435                 440                 445

Glu Ile Arg Val Phe Gly Tyr Thr Ala Trp Thr Leu Leu Asp Gly Phe
450                 455                 460

Glu Trp Gln Asp Ala Tyr Thr Thr Arg Gly Leu Phe Tyr Val Asp
465                 470                 475                 480

Phe Asn Ser Glu Gln Lys Glu Arg Lys Pro Lys Ser Ser Ala His Tyr
            485                 490                 495

Tyr Lys Gln Ile Ile Gln Asp Asn Gly Phe Ser Leu Lys Glu Ser Thr
            500                 505                 510

Pro Asp Val Gln Gly Gln Phe Pro Cys Asp Phe Ser Trp Gly Val Thr
            515                 520                 525

Glu Ser Val Leu Lys Pro Glu Ser Val Ala Ser Ser Pro Gln Phe Ser
530                 535                 540

Asp Pro His Leu Tyr Val Trp Asn Ala Thr Gly Asn Arg Leu Leu His
545                 550                 555                 560

Arg Val Glu Gly Val Arg Leu Lys Thr Arg Pro Ala Gln Cys Thr Asp
            565                 570                 575

Phe Val Asn Ile Lys Lys Gln Leu Glu Met Leu Ala Arg Met Lys Val
            580                 585                 590

Thr His Tyr Arg Phe Ala Leu Asp Trp Ala Ser Val Leu Pro Thr Gly
            595                 600                 605

Asn Leu Ser Ala Val Asn Arg Gln Ala Leu Arg Tyr Tyr Arg Cys Val
            610                 615                 620

Val Ser Glu Gly Leu Lys Leu Gly Ile Ser Ala Met Val Thr Leu Tyr
625                 630                 635                 640

Tyr Pro Thr His Ala His Leu Gly Leu Pro Glu Pro Leu Leu His Ala
            645                 650                 655

Asp Gly Trp Leu Asn Pro Ser Thr Ala Glu Ala Phe Gln Ala Tyr Ala
            660                 665                 670

Gly Leu Cys Phe Gln Glu Leu Gly Asp Leu Val Lys Leu Trp Ile Thr
            675                 680                 685

Ile Asn Glu Pro Asn Arg Leu Ser Asp Ile Tyr Asn Arg Ser Gly Asn
690                 695                 700

Asp Thr Tyr Gly Ala Ala His Asn Leu Leu Val Ala His Ala Leu Ala
705                 710                 715                 720

Trp Arg Leu Tyr Asp Arg Gln Phe Arg Pro Ser Gln Arg Gly Ala Val
            725                 730                 735

Ser Leu Ser Leu His Ala Asp Trp Ala Glu Pro Ala Asn Pro Tyr Ala
            740                 745                 750

Asp Ser His Trp Arg Ala Ala Glu Arg Phe Leu Gln Phe Glu Ile Ala
            755                 760                 765

Trp Phe Ala Glu Pro Leu Phe Lys Thr Gly Asp Tyr Pro Ala Ala Met
770                 775                 780

Arg Glu Tyr Ile Ala Ser Lys His Arg Arg Gly Leu Ser Ser Ser Ala
```

```
                785                 790                 795                 800
Leu Pro Arg Leu Thr Glu Ala Glu Arg Arg Leu Leu Lys Gly Thr Val
                805                 810                 815
Asp Phe Cys Ala Leu Asn His Phe Thr Thr Arg Phe Val Met His Glu
                820                 825                 830
Gln Leu Ala Gly Ser Arg Tyr Asp Ser Asp Arg Asp Ile Gln Phe Leu
                835                 840                 845
Gln Asp Ile Thr Arg Leu Ser Ser Pro Thr Arg Leu Ala Val Ile Pro
        850                 855                 860
Trp Gly Val Arg Lys Leu Leu Arg Trp Val Arg Arg Asn Tyr Gly Asp
865                 870                 875                 880
Met Asp Ile Tyr Ile Thr Ala Ser Gly Ile Asp Asp Gln Ala Leu Glu
                885                 890                 895
Asp Asp Arg Leu Arg Lys Tyr Tyr Leu Gly Lys Tyr Leu Gln Glu Val
                900                 905                 910
Leu Lys Ala Tyr Leu Ile Asp Lys Val Arg Ile Lys Gly Tyr Tyr Ala
                915                 920                 925
Phe Lys Leu Ala Glu Glu Lys Ser Lys Pro Arg Phe Gly Phe Phe Thr
        930                 935                 940
Ser Asp Phe Lys Ala Lys Ser Ser Ile Gln Phe Tyr Asn Lys Val Ile
945                 950                 955                 960
Ser Ser Arg Gly Phe Pro Phe Glu Asn Ser Ser Ser Arg Cys Ser Gln
                965                 970                 975
Thr Gln Glu Asn Thr Glu Cys Thr Val Cys Leu Phe Leu Val Gln Lys
                980                 985                 990
Lys Pro Leu Ile Phe Leu Gly Cys Cys Phe Phe Ser Thr Leu Val Leu
        995                 1000                1005
Leu Leu Ser Ile Ala Ile Phe Gln Arg Gln Lys Arg Arg Lys Phe Trp
        1010                1015                1020
Lys Ala Lys Asn Leu Gln His Ile Pro Leu Lys Lys Gly Lys Arg Val
1025                1030                1035                1040
Val Ser

<210> SEQ ID NO 182
<211> LENGTH: 3129
<212> TYPE: DNA
<213> ORGANISM: Artificial Sequence
<220> FEATURE:
<223> OTHER INFORMATION: encoding sequence of mouse/human beta klotho
      chimeric protein

<400> SEQUENCE: 182
atgaagacag gctgtgcagc agggtctccg gggaatgaat ggattttctt cagctctgat        60
gaaagaaaca cacgctctag gaaaacaatg tccaacaggg cactgcaaag atctgccgtg       120
ctgtctgcgt tgttctgct gcagctgtt accggcttct ccggagacgg gaaagcaata       180
tgggataaaa acagtacgt gagtccggta acccaagtc agctgttcct ctatgacact       240
ttccctaaaa acttttcctg gggcgttggg accggagcat tcaagtgga agggagttgg       300 aagacagatg gaaggaggacc ctcgatctgg gatcggtacg tctactcaca cctgagaggt       360
gtcaacggca cagacagatc cactgacagt tacatctttc tggaaaaaga cttgttggct       420
ctggattttt taggagtttc tttttatcag ttctcaatct cctggccacg gttgtttccc       480
aatgaaacag tagcagcagt gaatgcgcaa ggtctccggt actaccgtgc acttctggac       540
tcgctggtac ttaggaatat cgagcccatt gttaccttgt accattggga tttgcctctg       600
```

```
acgctccagg aagaatatgg gggctggaaa aatgcaacta tgatagatct cttcaacgac    660
tatgccacat actgcttcca gacctttgga gaccgtgtca atattggat  tacaattcac    720
aacccttacc ttgttgcttg gcatgggttt ggcacaggta tgcatgcacc aggagagaag    780
ggaaatttaa cagctgtcta cactgtggga cacaacctga tcaaggcaca ttcgaaagtg    840
tggcataact acgacaaaaa cttccgccct catcagaagg gttggctctc catcaccttg    900
gggtcccatt ggatagagcc aaacagaaca gacaacatgg aggacgtgat caactgccag    960
cactccatgt cctctgtgct tggatggttc gccaaccca  tccacgggga cggcgactac   1020
cctgagttca tgaagacggg cgccatgatc cccgagttct ctgaggcaga aaggaggag    1080
gtgaggggca cggctgattt ctttgccttt tccttcgggc ccaacaactt caggccctca   1140
aacaccgtgg tgaaaatggg acaaaatgta tcactcaact taaggcaggt gctgaactgg   1200
attaaactgg aatacgatga ccctcaaatc ttgatttcgg agaacggctg gttcacagat   1260
agctatataa agacagagga caccacggcc atctacatga tgaagaattt cctaaaccag   1320
gttcttcaag caataaaatt tgatgaaatc cgcgtgtttg gttatacggc ctggactctc   1380
ctggatggct ttgagtggca ggatgcctat acgacccgac gagggctgtt ttatgtggac   1440
tttaacagtg agcagaaaga gaggaaaccc aagtcctcgg ctcattacta caagcagatc   1500
atacaagaca acgcttctc  tttaaaagag tccacgccag atgtgcaggg ccagtttccc   1560
tgtgacttct cctggggtgt cactgaatct gttcttaagc ccgagtctgt ggcttcgtcc   1620
ccacagttca gcgatcctca tctgtacgtg tggaacgcca ctggcaacag actgttgcac   1680
cgagtggaag gggtgaggct gaaaacacga cccgctcaat gcacagattt tgtaaacatc   1740
aaaaaacaac ttgagatgtt ggcaagaatg aaagtcaccc actaccggtt tgctctggat   1800
tgggcctcgg tccttcccac tggcaacctg tccgcggtga accgacaggc cctgaggtac   1860
tacaggtgcg tggtcagtga ggggctgaag cttggcatct ccgcgatggt caccctgtat   1920
tatccgaccc acgccacct  aggcctcccc gagcctctgt tgcatgccga cgggtggctg   1980
aacccatcga cggccgaggc cttccaggcc tacgctgggc tgtgcttcca ggagctgggg   2040
gacctggtga agctctggat caccatcaac gagcctaacc ggctaagtga catctacaac   2100
cgctctggca acgacaccta cggggcggcg cacaacctgc tggtggccca cgccctggcc   2160
tggcgcctct acgaccggca gttcaggccc tcacagcgcg gggccgtgtc gctgtcgctg   2220
cacgcggact gggcggaacc cgccaacccc tatgctgact cgcactggag ggcggccgag   2280
cgcttcctgc agttcgagat cgcctggttc gccgagccgc tcttcaagac cggggactac   2340
cccgcggcca tgagggaata cattgcctcc aagcaccgac gggggctttc cagctcggcc   2400
ctgccgcgcc tcaccgaggc cgaaaggagg ctgctcaagg gcacggtcga cttctgcgcg   2460
ctcaaccact tcaccactag gttcgtgatg cacgagcagc tggccggcag ccgctacgac   2520
tcggacaggg acatccagtt tctgcaggac atcacccgcc tgagctcccc cacgcgcctg   2580
gctgtgattc cctgggggt  gcgcaagctg ctgcggtggg tccggaggaa ctacggcgac   2640
atggacattt acatcaccgc cagtggcatc gacgaccagg ctctggagga tgaccggctc   2700
cggaagtact acctagggaa gtaccttcag gaggtgctga agcatacct  gattgataaa   2760
gtcagaatca aaggctatta tgcattcaaa ctggctgaag agaaatctaa acccagattt   2820
ggattcttca catctgattt taagctaaa  tcctcaatac aattttacaa caaagtgatc   2880
agcagcaggg gcttccctt  tgagaacagt agttctagat gcagtcagac ccaagaaaat   2940
```

```
acagagtgca ctgtctgctt attccttgtg cagaagaaac cactgatatt cctgggttgt      3000
tgcttcttct ccaccctggt tctactctta tcaattgcca ttttttcaaag gcagaagaga     3060 agaaagtttt ggaaagcaaa aaacttacaa cacataccat taaagaaagg caagagagtt     3120
gttagctag                                                              3129

<210> SEQ ID NO 183
<211> LENGTH: 209
<212> TYPE: PRT
<213> ORGANISM: Artificial Sequence
<220> FEATURE:
<223> OTHER INFORMATION: full length mature form FGF21

<400> SEQUENCE: 183

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 184
<211> LENGTH: 630
<212> TYPE: DNA
<213> ORGANISM: Artificial Sequence
<220> FEATURE:
<223> OTHER INFORMATION: full length mature form FGF21

<400> SEQUENCE: 184
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg ggcgctgctg accagagccc cgaaagtctc     240
ctgcagctga agccttgaa gccgggagtt attcaaatct gggagtcaa gacatccagg       300
```

-continued

```
ttcctgtgcc agcggccaga tggggccctg tatggatcgc tccactttga ccctgaggcc    360
tgcagcttcc gggagctgct tcttgaggac ggatacaatg tttaccagtc cgaagcccac    420
ggcctcccgc tgcacctgcc aggaacaag tccccacacc gggaccctgc accccgagga    480
ccagctcgct tcctgccact accaggcctg ccccccgcac cccggagcc acccggaatc    540 ctggccccc agccccccga tgtgggctcc tcggacccctc tgagcatggt gggaccttcc    600
cagggccgaa gccccagcta cgcttcctga                                    630
```

<210> SEQ ID NO 185
<211> LENGTH: 209
<212> TYPE: PRT
<213> ORGANISM: Artificial Sequence
<220> FEATURE:
<223> OTHER INFORMATION: full length mature form FGF21

<400> SEQUENCE: 185

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 186
<211> LENGTH: 630
<212> TYPE: DNA
<213> ORGANISM: Artificial Sequence
<220> FEATURE:
<223> OTHER INFORMATION: full length mature form FGF21

<400> SEQUENCE: 186

```
atggactcgg acgagaccgg gttcgagcac tcaggactgt gggtttctgt gctggctggt    60
cttctgctgg gagcctgcca ggcacacccc atccctgact ccagtcctct cctgcaattc    120
gggggccaag tccggcagcg gtacctctac acagatgatg cccagcagac agaagcccac    180
```

```
ctggagatca gggaggatgg gacggtgggg ggcgctgctg accagagccc cgaaagtctc    240
ctgcagctga aagccttgaa gccgggagtt attcaaatct tgggagtcaa gacatccagg    300
ttcctgtgcc agcggccaga tggggccctg tatggatcgc tccactttga ccctgaggcc    360
tgcagcttcc gggagctgct tcttgaggac ggatacaatg tttaccagtc cgaagcccac    420
ggcctcccgc tgcacctgcc agggaacaag tccccacacc gggaccctgc accccgagga    480
ccagctcgct tcctgccact accaggcctg cccccgcac tcccgagcc acccggaatc     540 ctggcccccc agcccccga tgtgggctcc tcggaccctc tgagcatggt gggaccttcc    600
cagggccgaa gccccagcta cgcttcctga                                    630
```

<210> SEQ ID NO 187
<211> LENGTH: 651
<212> TYPE: DNA
<213> ORGANISM: Artificial Sequence
<220> FEATURE:
<223> OTHER INFORMATION: full length mature form of FGF19

<400> SEQUENCE: 187

```
atgcggagcg ggtgtgtggt ggtccacgta tggatcctgg ccggcctctg gctggccgtg     60
gccgggcgcc ccctcgcctt ctcggacgcg gggccccacg tgcactacgg ctggggcgac    120
cccatccgcc tgcggcacct gtacaccctc gggcccacg gctctccag ctgcttcctg     180 cgcatccgtg ccgacggcgt cgtggactgc gcgcggggcc agagcgcgca cagtttgctg    240
gagatcaagg cagtcgctct gcggaccgtg gccatcaagg gcgtgcacag cgtgcggtac    300
ctctgcatgg gcgccgacgg caagatgcag ggctgcttc agtactcgga ggaagactgt    360
gctttcgagg aggagatccg cccagatggc tacaatgtgt accgatccga aagcaccgc    420 ctcccggtct ccctgagcag tgccaaacag cggcagctgt acaagaacag aggctttctt    480
ccactctctc atttcctgcc catgctgccc atggtcccag aggagcctga ggacctcagg    540
ggccacttgg aatctgacat gttctcttcg cccctggaga ccgacagcat ggacccattt    600
gggcttgtca ccggactgga ggccgtgagg agtcccagct ttgagaagta a            651
```

<210> SEQ ID NO 188
<211> LENGTH: 216
<212> TYPE: PRT
<213> ORGANISM: Artificial Sequence
<220> FEATURE:
<223> OTHER INFORMATION: full length mature form of FGF19

<400> SEQUENCE: 188

```
Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110
```

```
Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
        130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
            195                 200                 205

Val Arg Ser Pro Ser Phe Glu Lys
            210                 215

<210> SEQ ID NO 189
<211> LENGTH: 2469
<212> TYPE: DNA
<213> ORGANISM: Homo sapiens
<220> FEATURE:
<223> OTHER INFORMATION: human FGFR1c (GenBank Accession Number NM
      023110; also designated FGFR-alpha IIIc)

<400> SEQUENCE: 189
atgtggagct ggaagtgcct cctcttctgg gctgtgctgg tcacagccac actctgcacc      60
gctaggccgt ccccgacctt gcctgaacaa gcccagccct ggggagcccc tgtggaagtg     120
gagtccttcc tggtccaccc cggtgacctg ctgcagcttc gctgtcggct gcgggacgat     180
gtgcagagca tcaactggct gcgggacggg gtgcagctgg cggaaagcaa ccgcacccgc     240
atcacagggg aggaggtgga ggtgcaggac tccgtgcccg cagactccgg cctctatgct     300
tgcgtaacca gcagcccctc gggcagtgac accacctact tctccgtcaa tgtttcagat     360
gctctcccct cctcggagga tgatgatgat gatgatgact cctcttcaga ggagaaagaa     420
acagataaca ccaaaccaaa ccgtatgccc gtagctccat attggacatc accagaaaag     480
atggaaaaga aattgcatgc agtgccggct gccaagacag tgaagttcaa atgcccttcc     540
agtgggacac caaacccaac actgcgctgg ttgaaaaatg caagaattc aaacctgac      600 cacagaattg aggctacaa ggtccgttat gccacctgga gcatcataat ggactctgtg     660
gtgccctctg acaagggcaa ctacacctgc attgtggaga tgagtacgg cagcatcaac     720 cacacatacc agctggatgt cgtggagcgg tcccctcacc ggcccatcct gcaagcaggg     780
ttgcccgcca acaaaacagt ggccctgggt agcaacgtgg agttcatgtg taaggtgtac     840
agtgacccgc agccgcacat ccagtggcta aagcacatcg aggtaatgg agcaagatt      900 ggcccagaca acctgcctta tgtccagatc ttgaagactg ctggagttaa taccaccgac     960
aaagagatgg aggtgcttca cttaagaaat gtctcctttg aggacgcagg ggagtatacg    1020
tgcttggcgg gtaactctat cggactctcc catcactctg catggttgac cgttctggaa    1080
gccctggaag agaggccggc agtgatgacc tcgcccctgt acctggagat catcatctat    1140
tgcacagggg ccttcctcat ctcctgcatg gtgggtcgg tcatcgtcta caagatgaag    1200
agtggtacca agaagagtga cttccacagc cagatggctg tgcacaagct ggccaagagc    1260
atccctctgc gcagacaggt aacagtgtct gctgactcca gtgcatccat gaactctggg    1320
gttcttctgg ttcggccatc acggctctcc tccagtggga ctcccatgct agcagggtc    1380 tctgagtatg agcttcccga agaccctcgc tgggagctgc ctcgggacag actggtctta    1440
```

-continued

```
ggcaaacccc tgggagaggg ctgctttggg caggtggtgt tggcagaggc tatcgggctg    1500
gacaaggaca aacccaaccg tgtgaccaaa gtggctgtga agatgttgaa gtcggacgca    1560
acagagaaag acttgtcaga cctgatctca gaaatggaga tgatgaagat gatcgggaag    1620
cataagaata tcatcaacct gctggggggcc tgcacgcagg atggtccctt gtatgtcatc    1680
gtggagtatg cctccaaggg caacctgcgg gagtacctgc aggcccggag gccccaggg     1740 ctggaatact gctacaaccc cagccacaac ccagaggagc agctctcctc caaggacctg    1800
gtgtcctgcg cctaccaggt ggcccgaggc atggagtatc tggcctccaa gaagtgcata    1860
caccgagacc tggcagccag gaatgtcctg gtgacagagg acaatgtgat gaagatagca    1920
gactttggcc tcgcacggga cattcaccac atcgactact ataaaaagac aaccaacggc    1980
cgactgcctg tgaagtggat ggcacccgag gcattatttg accggatcta cacccaccag    2040
agtgatgtgt ggtctttcgg ggtgctcctg tgggagatct tcactctggg cggctcccca    2100
taccccggtg tgcctgtgga ggaacttttc aagctgctga aggagggtca ccgcatggac    2160
aagcccagta actgcaccaa cgagctgtac atgatgatgc gggactgctg gcatgcagtg    2220
ccctcacaga gacccacctt caagcagctg gtggaagacc tggaccgcat cgtggccttg    2280
acctccaacc aggagtacct ggacctgtcc atgcccctgg accagtactc ccccagcttt    2340
cccgacaccc ggagctctac gtgctcctca ggggaggatt ccgtcttctc tcatgagccg    2400
ctgcccgagg agccctgcct gccccgacac ccagcccagc ttgccaatgg cggactcaaa    2460
cgccgctga                                                            2469
```

<210> SEQ ID NO 190
<211> LENGTH: 822
<212> TYPE: PRT
<213> ORGANISM: Homo sapiens
<220> FEATURE:
<223> OTHER INFORMATION: human FGFR1c (GenBank Accession Number NM 023110; also designated FGFR-alpha IIIc)

<400> SEQUENCE: 190

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
```

-continued

```
                165                 170                 175
Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
            245                 250                 255

Leu Gln Ala Gly Leu Pro Ala Asn Lys Thr Val Ala Leu Gly Ser Asn
        260                 265                 270

Val Glu Phe Met Cys Lys Val Tyr Ser Asp Pro Gln Pro His Ile Gln
    275                 280                 285

Trp Leu Lys His Ile Glu Val Asn Gly Ser Lys Ile Gly Pro Asp Asn
            290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
            325                 330                 335

Gly Glu Tyr Thr Cys Leu Ala Gly Asn Ser Ile Gly Leu Ser His His
        340                 345                 350

Ser Ala Trp Leu Thr Val Leu Glu Ala Leu Glu Glu Arg Pro Ala Val
    355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Thr Val Ser Ala Asp
        420                 425                 430

Ser Ser Ala Ser Met Asn Ser Gly Val Leu Leu Val Arg Pro Ser Arg
    435                 440                 445

Leu Ser Ser Ser Gly Thr Pro Met Leu Ala Gly Val Ser Glu Tyr Glu
    450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
            485                 490                 495

Ala Ile Gly Leu Asp Lys Asp Lys Pro Asn Arg Val Thr Lys Val Ala
        500                 505                 510

Val Lys Met Leu Lys Ser Asp Ala Thr Glu Lys Asp Leu Ser Asp Leu
    515                 520                 525

Ile Ser Glu Met Glu Met Met Lys Met Ile Gly Lys His Lys Asn Ile
    530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
            565                 570                 575

Arg Pro Pro Gly Leu Glu Tyr Cys Tyr Asn Pro Ser His Asn Pro Glu
        580                 585                 590
```

```
Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
            645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
            690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
            725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
            770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
            805                 810                 815

Gly Gly Leu Lys Arg Arg
            820

<210> SEQ ID NO 191
<211> LENGTH: 374
<212> TYPE: PRT
<213> ORGANISM: Artificial Sequence
<220> FEATURE:
<223> OTHER INFORMATION: example of an extracellular region of FGFR1c

<400> SEQUENCE: 191

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
            50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
            85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
            115                 120                 125
```

```
Asp Asp Asp Asp Asp Ser Ser Glu Glu Lys Glu Thr Asp Asn Thr
            130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
                180                 185                 190

Asn Gly Lys Glu Phe Lys Pro Asp His Arg Ile Gly Gly Tyr Lys Val
                195                 200                 205

Arg Tyr Ala Thr Trp Ser Ile Ile Met Asp Ser Val Val Pro Ser Asp
210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
                260                 265                 270

Val Glu Phe Met Cys Lys Val Tyr Ser Asp Pro Gln Pro His Ile Gln
                275                 280                 285

Trp Leu Lys His Ile Glu Val Asn Gly Ser Lys Ile Gly Pro Asp Asn
290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
                340                 345                 350

Ser Ala Trp Leu Thr Val Leu Glu Ala Leu Glu Glu Arg Pro Ala Val
                355                 360                 365

Met Thr Ser Pro Leu Tyr
    370

<210> SEQ ID NO 192
<211> LENGTH: 354
<212> TYPE: PRT
<213> ORGANISM: Artificial Sequence
<220> FEATURE:
<223> OTHER INFORMATION: example of an extracellular region of FGFR1c
      (alpha-IIIc)

<400> SEQUENCE: 192

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
                20                  25                  30

Arg Cys Arg Leu Arg Asp Asp Val Gln Ser Ile Asn Trp Leu Arg Asp
                35                  40                  45

Gly Val Gln Leu Ala Glu Ser Asn Arg Thr Arg Ile Thr Gly Glu Glu
            50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp
```

```
              100                 105                 110
Ser Ser Ser Glu Glu Lys Glu Thr Asp Asn Thr Lys Pro Asn Arg Met
            115                 120                 125

Pro Val Ala Pro Tyr Trp Thr Ser Pro Glu Lys Met Glu Lys Lys Leu
        130                 135                 140

His Ala Val Pro Ala Ala Lys Thr Val Lys Phe Lys Cys Pro Ser Ser
145                 150                 155                 160

Gly Thr Pro Asn Pro Thr Leu Arg Trp Leu Lys Asn Gly Lys Glu Phe
                165                 170                 175

Lys Pro Asp His Arg Ile Gly Gly Tyr Lys Val Arg Tyr Ala Thr Trp
            180                 185                 190

Ser Ile Ile Met Asp Ser Val Val Pro Ser Asp Lys Gly Asn Tyr Thr
        195                 200                 205

Cys Ile Val Glu Asn Glu Tyr Gly Ser Ile Asn His Thr Tyr Gln Leu
    210                 215                 220

Asp Val Val Glu Arg Ser Pro His Arg Pro Ile Leu Gln Ala Gly Leu
225                 230                 235                 240

Pro Ala Asn Lys Thr Val Ala Leu Gly Ser Asn Val Glu Phe Met Cys
                245                 250                 255

Lys Val Tyr Ser Asp Pro Gln Pro His Ile Gln Trp Leu Lys His Ile
            260                 265                 270

Glu Val Asn Gly Ser Lys Ile Gly Pro Asp Asn Leu Pro Tyr Val Gln
        275                 280                 285

Ile Leu Lys Thr Ala Gly Val Asn Thr Thr Asp Lys Glu Met Glu Val
    290                 295                 300

Leu His Leu Arg Asn Val Ser Phe Glu Asp Ala Gly Glu Tyr Thr Cys
305                 310                 315                 320

Leu Ala Gly Asn Ser Ile Gly Leu Ser His His Ser Ala Trp Leu Thr
                325                 330                 335

Val Leu Glu Ala Leu Glu Glu Arg Pro Ala Val Met Thr Ser Pro Leu
            340                 345                 350

Tyr Glu

<210> SEQ ID NO 193
<211> LENGTH: 264
<212> TYPE: PRT
<213> ORGANISM: Artificial Sequence
<220> FEATURE:
<223> OTHER INFORMATION: example of an extracellular region of FGFR1c
      (beta IIIc)

<400> SEQUENCE: 193

Arg Pro Ser Pro Thr Leu Pro Glu Gln Asp Ala Leu Pro Ser Ser Glu
1               5                   10                  15

Asp Asp Asp Asp Asp Asp Ser Ser Ser Glu Glu Lys Glu Thr Asp
            20                  25                  30

Asn Thr Lys Pro Asn Pro Val Ala Pro Tyr Trp Thr Ser Pro Glu Lys
            35                  40                  45

Met Glu Lys Lys Leu His Ala Val Pro Ala Ala Lys Thr Val Lys Phe
        50                  55                  60

Lys Cys Pro Ser Ser Gly Thr Pro Asn Pro Thr Leu Arg Trp Leu Lys
65                  70                  75                  80

Asn Gly Lys Glu Phe Lys Pro Asp His Arg Ile Gly Gly Tyr Lys Val
                85                  90                  95

Arg Tyr Ala Thr Trp Ser Ile Ile Met Asp Ser Val Val Pro Ser Asp
```

```
                100             105             110
Lys Gly Asn Tyr Thr Cys Ile Val Glu Asn Glu Tyr Gly Ser Ile Asn
            115                 120                 125

His Thr Tyr Gln Leu Asp Val Val Glu Arg Ser Pro His Arg Pro Ile
        130                 135                 140

Leu Gln Ala Gly Leu Pro Ala Asn Lys Thr Val Ala Leu Gly Ser Asn
145                 150                 155                 160

Val Glu Phe Met Cys Lys Val Tyr Ser Asp Pro Gln Pro His Ile Gln
                165                 170                 175

Trp Leu Lys His Ile Glu Val Asn Gly Ser Lys Ile Gly Pro Asp Asn
            180                 185                 190

Leu Pro Tyr Val Gln Ile Leu Lys Thr Ala Gly Val Asn Thr Thr Asp
        195                 200                 205

Lys Glu Met Glu Val Leu His Leu Arg Asn Val Ser Phe Glu Asp Ala
210                 215                 220

Gly Glu Tyr Thr Cys Leu Ala Gly Asn Ser Ile Gly Leu Ser His His
225                 230                 235                 240

Ser Ala Trp Leu Thr Val Leu Glu Ala Leu Glu Glu Arg Pro Ala Val
                245                 250                 255

Met Thr Ser Pro Leu Tyr Leu Glu
            260

<210> SEQ ID NO 194
<211> LENGTH: 2466
<212> TYPE: DNA
<213> ORGANISM: Homo sapiens
<220> FEATURE:
<223> OTHER INFORMATION: human FGFR2c

<400> SEQUENCE: 194
atggtcagct ggggtcgttt catctgcctg gtcgtggtca ccatggcaac cttgtccctg     60
gcccggccct ccttcagttt agttgaggat accacattag agccagaaga gccaccaacc    120
aaataccaaa tctctcaacc agaagtgtac gtggctgcgc aggggagtc gctagaggtg    180
cgctgcctgt tgaaagatgc cgccgtgatc agttggacta aggatgggt gcacttgggg    240
cccaacaata ggacagtgct tattggggag tacttgcaga taagggcgc cacgcctaga    300
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac atactgac caacacagaa    480
aagatggaaa agcggctcca tgctgtgcct gcggccaaca ctgtcaagtt cgctgccca    540
gccggggga acccaatgcc aaccatgcgg tggctgaaaa acgggaagga gtttaagcag    600
gagcatcgca ttggaggcta caaggtacga acccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggccat cctccaagcc    780
ggactgccgg caaatgccct cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg ccgccggtgt aacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
```

```
tactgcatag gggtcttctt aatcgcctgt atggtggtaa cagtcatcct gtgccgaatg    1200
aagaacacga ccaagaagcc agacttcagc agccagccgg ctgtgcacaa gctgaccaaa    1260
cgtatccccc tgcggagaca ggtaacagtt tcggctgagt ccagctcctc catgaactcc    1320 aacacccgc tggtgaggat aacaacacgc ctctcttcaa cggcagacac ccccatgctg     1380 gcagggtct ccgagtatga acttccagag acccaaaat gggagtttcc aagagataag      1440
ctgacactgg gcaagcccct gggagaaggt tgctttgggc aagtggtcat ggcggaagca    1500
gtgggaattg acaaagacaa gcccaaggag gcggtcaccg tggccgtgaa gatgttgaaa    1560
gatgatgcca cagagaaaga cctttctgat ctggtgtcag agatggagat gatgaagatg    1620
attgggaaac acaagaatat cataaatctt cttggagcct gcacacagga tgggcctctc    1680
tatgtcatag ttgagtatgc ctctaaaggc aacctccgag aatacctccg agcccggagg    1740
ccacccggga tggagtactc ctatgacatt aaccgtgttc ctgaggagca gatgaccttc    1800
aaggacttgg tgtcatgcac ctaccagctg gccagaggca tggagtactt ggcttcccaa    1860
aaatgtattc atcgagattt agcagccaga atgttttgg taacagaaaa caatgtgatg     1920
aaaatagcag acttggact cgccagagat atcaacaata tagactatta caaaaagacc     1980
accaatgggc ggcttccagt caagtggatg gctccagaag ccctgtttga tagagtatac    2040
actcatcaga gtgatgtctg gtccttcggg gtgttaatgt gggagatctt cactttaggg    2100
ggctcgccct acccagggat tcccgtggag gaacttttta gctgctgaa ggaaggacac     2160 agaatggata gccagccaa ctgcaccaac gaactgtaca tgatgatgag ggactgttgg     2220
catgcagtgc cctcccagag accaacgttc aagcagttgg tagaagactt ggatcgaatt    2280
ctcactctca caaccaatga ggaatacttg gacctcagcc aacctctcga acagtattca    2340
cctagttacc ctgacacaag aagttcttgt tcttcaggag atgattctgt ttttctcca    2400 gaccccatgc cttacgaacc atgccttcct cagtatccac acataaacgg cagtgttaaa    2460
acatga                                                               2466
```

<210> SEQ ID NO 195
<211> LENGTH: 821
<212> TYPE: PRT
<213> ORGANISM: Homo sapiens
<220> FEATURE:
<223> OTHER INFORMATION: human FGFR2c

<400> SEQUENCE: 195

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
```

-continued

```
            115                 120                 125
Ser Ser Gly Asp Asp Glu Asp Thr Asp Gly Ala Glu Asp Phe Val
        130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
            180                 185                 190
Lys Asn Gly Lys Glu Phe Lys Gln Glu His Arg Ile Gly Gly Tyr Lys
            195                 200                 205
Val Arg Asn Gln His Trp Ser Leu Ile Met Glu Ser Val Val Pro Ser
210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
Ile Leu Gln Ala Gly Leu Pro Ala Asn Ala Ser Thr Val Val Gly Gly
            260                 265                 270
Asp Val Glu Phe Val Cys Lys Val Tyr Ser Asp Ala Gln Pro His Ile
            275                 280                 285
Gln Trp Ile Lys His Val Glu Lys Asn Gly Ser Lys Tyr Gly Pro Asp
290                 295                 300
Gly Leu Pro Tyr Leu Lys Val Leu Lys Ala Ala Gly Val Asn Thr Thr
305                 310                 315                 320
Asp Lys Glu Ile Glu Val Leu Tyr Ile Arg Asn Val Thr Phe Glu Asp
                325                 330                 335
Ala Gly Glu Tyr Thr Cys Leu Ala Gly Asn Ser Ile Gly Ile Ser Phe
            340                 345                 350
His Ser Ala Trp Leu Thr Val Leu Pro Ala Pro Gly Arg Glu Lys Glu
            355                 360                 365
Ile Thr Ala Ser Pro Asp Tyr Leu Glu Ile Ala Ile Tyr Cys Ile Gly
370                 375                 380
Val Phe Leu Ile Ala Cys Met Val Val Thr Val Ile Leu Cys Arg Met
385                 390                 395                 400
Lys Asn Thr Thr Lys Lys Pro Asp Phe Ser Ser Gln Pro Ala Val His
                405                 410                 415
Lys Leu Thr Lys Arg Ile Pro Leu Arg Arg Gln Val Thr Val Ser Ala
            420                 425                 430
Glu Ser Ser Ser Ser Met Asn Ser Asn Thr Pro Leu Val Arg Ile Thr
            435                 440                 445
Thr Arg Leu Ser Ser Thr Ala Asp Thr Pro Met Leu Ala Gly Val Ser
    450                 455                 460
Glu Tyr Glu Leu Pro Glu Asp Pro Lys Trp Glu Phe Pro Arg Asp Lys
465                 470                 475                 480
Leu Thr Leu Gly Lys Pro Leu Gly Glu Gly Cys Phe Gly Gln Val Val
                485                 490                 495
Met Ala Glu Ala Val Gly Ile Asp Lys Asp Lys Pro Lys Glu Ala Val
            500                 505                 510
Thr Val Ala Val Lys Met Leu Lys Asp Asp Ala Thr Glu Lys Asp Leu
            515                 520                 525
Ser Asp Leu Val Ser Glu Met Glu Met Met Lys Met Ile Gly Lys His
    530                 535                 540
```

```
Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
            565                 570                 575

Arg Ala Arg Arg Pro Pro Gly Met Glu Tyr Ser Tyr Asp Ile Asn Arg
        580                 585                 590

Val Pro Glu Glu Gln Met Thr Phe Lys Asp Leu Val Ser Cys Thr Tyr
    595                 600                 605

Gln Leu Ala Arg Gly Met Glu Tyr Leu Ala Ser Gln Lys Cys Ile His
610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
    770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 196
<211> LENGTH: 2421
<212> TYPE: DNA
<213> ORGANISM: Homo sapiens
<220> FEATURE:
<223> OTHER INFORMATION: human FGFR3c (GenBank Accession Number NP
      000133)

<400> SEQUENCE: 196
atgggcgccc ctgcctgcgc cctcgcgctc tgcgtggccg tggccatcgt ggccggcgcc      60
tcctcggagt ccttggggac ggagcagcgc gtcgtgggc gagcggcaga agtcccgggc      120
ccagagcccg ccagcagga gcagttggtc ttcggcagcg gggatgctgt ggagctgagc      180
tgtcccccgc ccgggggtgg tcccatgggg cccactgtct gggtcaagga tggcacaggg      240
ctggtgccct cggagcgtgt cctggtgggg ccccagcggc tgcaggtgct gaatgcctcc      300
cacgaggact ccgggcccta cagctgccgg cagcggctca cgcagcgcgt actgtgccac      360
ttcagtgtgc gggtgacaga cgctccatcc tcgggagatg acgaagacgg ggaggacgag      420
```

```
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga gcgctccccg caccggccca cctgcaggc ggggctgccg     780 gccaaccaga cggcggtgct gggcagcgac gtggagttcc actgcaaggt gtacagtgac     840
gcacagcccc acatccagtg gctcaagcac gtggaggtga atggcagcaa ggtgggcccg     900
gacggcacac cctacgttac cgtgctcaag acggcgggcg ctaacaccac cgacaaggag     960
ctagaggttc tctccttgca caacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200
ccccccaaga aaggcctggg ctcccccacc gtgcacaaga tctcccgctt ccgctcaag    1260 cgacaggtgt ccctggagtc caacgcgtcc atgagctcca acacaccact ggtgcgcatc    1320
gcaaggctgt cctcagggga gggcccacg ctggccaatg tctccgagct cgagctgcct    1380
gccgacccca atgggagct gtctcgggcc cggctgaccc tgggcaagcc ccttgggag     1440 ggctgcttcg gccaggtggt catggcgag gccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga acacaaaaaa catcatcaac    1620
ctgctgggcg cctgcacgca gggcgggccc ctgtacgtgc tggtggagta cgcggccaag    1680
ggtaacctgc gggagtttct gcgggcgcgg cggccccgg gcctggacta ctccttcgac    1740
acctgcaagc cgcccgagga gcagctcacc ttcaaggacc tggtgtcctg tgcctaccag    1800
gtggcccggg gcatggagta cttggcctcc agaagtgca tccacagga cctggctgcc    1860 cgcaatgtgc tggtgaccga ggacaacgtg atgaagatcg cagacttcgg gctggcccgg    1920
gacgtgcaca acctcgacta ctacaagaag acaaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg gggggctccc cgtaccccgg catccctgtg    2100
gaggagctct tcaagctgct gaaggagggc caccgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccgggtg gccaggacac ccccagctcc    2340
agctcctcag gggacgactc cgtgtttgcc cacgacctgc tgcccccggc cccacccagc    2400
agtgggggct cgcggacgtg a                                              2421
```

<210> SEQ ID NO 197
<211> LENGTH: 806
<212> TYPE: PRT
<213> ORGANISM: Homo sapiens
<220> FEATURE:
<223> OTHER INFORMATION: human FGFR3c

<400> SEQUENCE: 197

-continued

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65              70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
```

```
                  420              425              430
Ser Asn Thr Pro Leu Val Arg Ile Ala Arg Leu Ser Ser Gly Glu Gly
        435                  440                  445

Pro Thr Leu Ala Asn Val Ser Glu Leu Glu Leu Pro Ala Asp Pro Lys
450                  455                  460

Trp Glu Leu Ser Arg Ala Arg Leu Thr Leu Gly Lys Pro Leu Gly Glu
465                  470                  475                  480

Gly Cys Phe Gly Gln Val Val Met Ala Glu Ala Ile Gly Ile Asp Lys
                485                  490                  495

Asp Arg Ala Ala Lys Pro Val Thr Val Ala Val Lys Met Leu Lys Asp
            500                  505                  510

Asp Ala Thr Asp Lys Asp Leu Ser Asp Leu Val Ser Glu Met Glu Met
        515                  520                  525

Met Lys Met Ile Gly Lys His Lys Asn Ile Ile Asn Leu Leu Gly Ala
    530                  535                  540

Cys Thr Gln Gly Gly Pro Leu Tyr Val Leu Val Glu Tyr Ala Ala Lys
545                  550                  555                  560

Gly Asn Leu Arg Glu Phe Leu Arg Ala Arg Arg Pro Pro Gly Leu Asp
                565                  570                  575

Tyr Ser Phe Asp Thr Cys Lys Pro Pro Glu Glu Gln Leu Thr Phe Lys
            580                  585                  590

Asp Leu Val Ser Cys Ala Tyr Gln Val Ala Arg Gly Met Glu Tyr Leu
        595                  600                  605

Ala Ser Gln Lys Cys Ile His Arg Asp Leu Ala Ala Arg Asn Val Leu
    610                  615                  620

Val Thr Glu Asp Asn Val Met Lys Ile Ala Asp Phe Gly Leu Ala Arg
625                  630                  635                  640

Asp Val His Asn Leu Asp Tyr Tyr Lys Lys Thr Thr Asn Gly Arg Leu
                645                  650                  655

Pro Val Lys Trp Met Ala Pro Glu Ala Leu Phe Asp Arg Val Tyr Thr
            660                  665                  670

His Gln Ser Asp Val Trp Ser Phe Gly Val Leu Leu Trp Glu Ile Phe
        675                  680                  685

Thr Leu Gly Gly Ser Pro Tyr Pro Gly Ile Pro Val Glu Glu Leu Phe
    690                  695                  700

Lys Leu Leu Lys Glu Gly His Arg Met Asp Lys Pro Ala Asn Cys Thr
705                  710                  715                  720

His Asp Leu Tyr Met Ile Met Arg Glu Cys Trp His Ala Ala Pro Ser
                725                  730                  735

Gln Arg Pro Thr Phe Lys Gln Leu Val Glu Asp Leu Asp Arg Val Leu
            740                  745                  750

Thr Val Thr Ser Thr Asp Glu Tyr Leu Asp Leu Ser Ala Pro Phe Glu
        755                  760                  765

Gln Tyr Ser Pro Gly Gly Gln Asp Thr Pro Ser Ser Ser Ser Ser Gly
    770                  775                  780

Asp Asp Ser Val Phe Ala His Asp Leu Leu Pro Pro Ala Pro Pro Ser
785                  790                  795                  800

Ser Gly Gly Ser Arg Thr
                805

<210> SEQ ID NO 198
<211> LENGTH: 2409
<212> TYPE: DNA
<213> ORGANISM: Homo sapiens
```

<220> FEATURE:
<223> OTHER INFORMATION: human FGFR4c

<400> SEQUENCE: 198

```
atgcggctgc tgctggccct gttgggggtc ctgctgagtg tgcctgggcc tccagtcttg      60
tccctggagg cctctgagga gtggagctt gagccctgcc tggctcccag cctggagcag      120
caagagcagg agctgacagt agcccttggg cagcctgtgc gtctgtgctg tgggcgggct      180
gagcgtggtg gccactggta caaggagggc agtcgcctgg cacctgctgg ccgtgtacgg      240
ggctggaggg gccgcctaga gattgccagc ttcctacctg aggatgctgg ccgctacctc      300
tgcctggcac gaggctccat gatcgtcctg cagaatctca ccttgattac aggtgactcc      360
ttgacctcca gcaacgatga tgaggacccc aagtcccata gggacccctc gaataggcac      420
agttacccc agcaagcacc ctactggaca caccccagc gcatggagaa gaaactgcat       480
gcagtacctg cggggaacac cgtcaagttc cgctgtccag ctgcaggcaa ccccacgccc      540
accatccgct ggcttaagga tggacaggcc tttcatgggg agaaccgcat tggaggcatt      600
cggctgcgcc atcagcactg gagtctcgtg atggagagcg tggtgccctc ggaccgcggc      660
acatacacct gcctggtaga gaacgctgtg ggcagcatcc gctataacta cctgctagat      720
gtgctggagc ggtccccgca ccggcccatc ctgcaggccg gctcccggc caacaccaca      780
gccgtggtgg cagcgacgt ggagctgctg tgcaaggtgt acagcgatgc ccagccccac      840
atccagtggc tgaagcacat cgtcatcaac ggcagcagct tcggagccga cggtttcccc      900
tatgtgcaag tcctaaagac tgcagacatc aatagctcag aggtggaggt cctgtacctg      960
cggaacgtgt cagccgagga cgcaggcgag tacacctgcc tcgcaggcaa ttccatcggc     1020
ctctcctacc agtctgcctg gctcacggtg ctgccagagg aggacccac atggaccgca      1080
gcagcgcccg aggccaggta tacggacatc atcctgtacg cgtcgggctc cctggccttg     1140
gctgtgctcc tgctgctggc cgggctgtat cgagggcagg cgctccacgg ccggcacccc     1200
cgccccgccg ccactgtgca gaagctctcc cgcttccctc tggcccgaca gttctccctg     1260
gagtcaggct cttccggcaa gtcaagctca tccctggtac gaggcgtgcg tctctcctcc     1320
agcggccccg ccttgctcgc cggcctcgtg agtctagatc tacctctcga cccactatgg     1380
gagttcccc gggacaggct ggtgcttggg aagcccctag gcgagggctg ctttggccag     1440
gtagtacgtg cagaggcctt tggcatggac cctgccccgg ctgaccaagc cagcactgtg     1500
gccgtcaaga tgctcaaaga caacgcctct gacaaggacc tggccgacct ggtctcggag     1560
atggaggtga tgaagctgat cggccgacac aagaacatca tcaacctgct ggtgtctgc       1620
acccaggaag ggccctgta cgtgatcgtg gagtgcgccg ccaagggaaa cctgcgggag     1680
ttcctgcggg cccggcgcc cccaggcccc gacctcagcc ccgacggtcc tcggagcagt     1740
gaggggccgc tctccttccc agtcctggtc tcctgcgcct accaggtggc ccgaggcatg     1800
cagtatctgg agtcccggaa gtgtatccac cgggacctgg ctgcccgcaa tgtgctggtg     1860
actgaggaca atgtgatgaa gattgctgac tttgggctgg cccgcggcgt ccaccacatt     1920
gactactata agaaaaccag caacggccgc ctgcctgtga gtggatggc gcccgaggcc     1980
ttgtttgacc gggtgtacac acaccagagt gacgtgtggt cttttgggat cctgctatgg     2040
gagatcttca ccctcggggg ctccccgtat cctggcatcc cggtggagga gctgttctcg     2100
ctgctgcggg agggacatcg gatggaccga cccccacact gcccccaga gctgtacggg     2160
ctgatgcgtg agtgctggca cgcagcgccc tcccagagc ctacctttca gcagctggtg     2220
```

-continued

```
gaggcgctgg acaaggtcct gctggccgtc tctgaggagt acctcgacct ccgcctgacc      2280
ttcggaccct attccccctc tggtggggac gccagcagca cctgctcctc cagcgattct      2340
gtcttcagcc acgaccccct gccattggga tccagctcct tcccttcgg gtctggggtg       2400 cagacatga                                                              2409

<210> SEQ ID NO 199
<211> LENGTH: 802
<212> TYPE: PRT
<213> ORGANISM: Homo sapiens
<220> FEATURE:
<223> OTHER INFORMATION: human FGFR4 (GenBank Accession Number NP.
      002002.3)

<400> SEQUENCE: 199

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
                20                  25                  30

Cys Leu Ala Pro Ser Leu Glu Gln Gln Glu Gln Glu Leu Thr Val Ala
            35                  40                  45

Leu Gly Gln Pro Val Arg Leu Cys Cys Gly Arg Ala Glu Arg Gly Gly
        50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320
```

```
Arg Asn Val Ser Ala Glu Asp Ala Gly Glu Tyr Thr Cys Leu Ala Gly
            325                 330                 335

Asn Ser Ile Gly Leu Ser Tyr Gln Ser Ala Trp Leu Thr Val Leu Pro
        340                 345                 350

Glu Glu Asp Pro Thr Trp Thr Ala Ala Pro Glu Ala Arg Tyr Thr
        355                 360                 365

Asp Ile Ile Leu Tyr Ala Ser Gly Ser Leu Ala Leu Ala Val Leu Leu
    370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
            420                 425                 430

Val Arg Gly Val Arg Leu Ser Ser Ser Gly Pro Ala Leu Leu Ala Gly
        435                 440                 445

Leu Val Ser Leu Asp Leu Pro Leu Asp Pro Leu Trp Glu Phe Pro Arg
    450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
        515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
```

```
              740                 745                 750
Glu Tyr Leu Asp Leu Arg Leu Thr Phe Gly Pro Tyr Ser Pro Ser Gly
            755                 760                 765

Gly Asp Ala Ser Ser Thr Cys Ser Ser Ser Asp Ser Val Phe Ser His
        770                 775                 780

Asp Pro Leu Pro Leu Gly Ser Ser Ser Phe Pro Phe Gly Ser Gly Val
785                 790                 795                 800

Gln Thr

<210> SEQ ID NO 200
<211> LENGTH: 330
<212> TYPE: PRT
<213> ORGANISM: Artificial Sequence
<220> FEATURE:
<223> OTHER INFORMATION: modified human IgG1 Fc sequence

<400> SEQUENCE: 200

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 201
<211> LENGTH: 9
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 201

Gln Gln Lys Pro Gly Lys Ala Pro Lys
1               5

<210> SEQ ID NO 202
<211> LENGTH: 9
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 202

Gln Arg Lys Pro Gly Lys Ala Pro Lys
1               5

<210> SEQ ID NO 203
<211> LENGTH: 9
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 203

Gln Gln Lys Gln Gly Lys Ala Pro Lys
1               5

<210> SEQ ID NO 204
<211> LENGTH: 9
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 204

Gln Gln Lys Pro Gly Lys Ser Pro Lys
1               5

<210> SEQ ID NO 205
<211> LENGTH: 9
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 205

Gln Gln Lys Pro Gly Lys Ala Pro Gln
1               5

<210> SEQ ID NO 206
```

```
<211> LENGTH: 9
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 206

Gln Gln Lys Gln Gly Lys Ser Pro Lys
1               5

<210> SEQ ID NO 207
<211> LENGTH: 122
<212> TYPE: PRT
<213> ORGANISM: Artificial Sequence
<220> FEATURE:
<223> OTHER INFORMATION: antibody m2J21-HC-336-c VH domain

<400> SEQUENCE: 207

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Met
            35                  40                  45

Gly Asn Ile Asp Pro Asn Thr Gly Gly Thr Ser Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 208
<211> LENGTH: 13
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 208

Gln Gln Lys Pro Gly Lys Ala Pro Lys Leu Leu Ile Tyr
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Exemplary VL FR2 of Humanized Anti-Beta Klotho
      Antibodies

<400> SEQUENCE: 209

Gln Arg Lys Pro Gly Lys Ala Pro Lys Leu Leu Ile Tyr
1               5                   10

<210> SEQ ID NO 210
<211> LENGTH: 13
<212> TYPE: PRT
<213> ORGANISM: Artificial Sequence
```

<220> FEATURE:
<223> OTHER INFORMATION: Exemplary VL FR2 of Humanized Anti-Beta Klotho
     Antibodies

<400> SEQUENCE: 210

Gln Gln Lys Gln Gly Lys Ala Pro Lys Leu Leu Ile Tyr
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Exemplary VL FR2 of Humanized Anti-Beta Klotho
     Antibodies

<400> SEQUENCE: 211

Gln Gln Lys Pro Gly Lys Ser Pro Lys Leu Leu Ile Tyr
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Exemplary VL FR2 of Humanized Anti-Beta Klotho
     Antibodies

<400> SEQUENCE: 212

Gln Gln Lys Pro Gly Lys Ala Pro Gln Leu Leu Ile Tyr
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Exemplary VL FR2 of Humanized Anti-Beta Klotho
     Antibodies

<400> SEQUENCE: 213

Gln Gln Lys Gln Gly Lys Ser Pro Lys Leu Leu Ile Tyr
1               5                   10

<210> SEQ ID NO 214
<211> LENGTH: 122
<212> TYPE: PRT
<213> ORGANISM: Artificial Sequence
<220> FEATURE:
<223> OTHER INFORMATION: antibody m2J21-HC-336-d VH domain

<400> SEQUENCE: 214

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Asn Ile Asp Pro Asn Thr Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

```
Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 215
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 215

Arg Val Thr Met Thr Arg Asp Thr Ser Thr Ile Thr Val Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 216
<211> LENGTH: 122
<212> TYPE: PRT
<213> ORGANISM: Artificial Sequence
<220> FEATURE:
<223> OTHER INFORMATION: antibody m2J21-HC-336-e VH domain

<400> SEQUENCE: 216

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala His Gly Gln Gly Leu Glu Trp Met
            35                  40                  45

Gly Asn Ile Asp Pro Asn Thr Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 217
<211> LENGTH: 14
<212> TYPE: PRT
<213> ORGANISM: Artificial Sequence
<220> FEATURE:
<223> OTHER INFORMATION: Exemplary VH FR2 of Humanized Anti-Beta Klotho
      Antibodies

<400> SEQUENCE: 217

Trp Val Arg Gln Ala Pro Gly Lys Ser Leu Glu Trp Ile Gly
1               5                   10

<210> SEQ ID NO 218
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies
```

<400> SEQUENCE: 218

Arg Ala Thr Met Thr Arg Asp Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 219
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 219

Arg Ala Thr Met Thr Arg Asp Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 220
<211> LENGTH: 122
<212> TYPE: PRT
<213> ORGANISM: Artificial Sequence
<220> FEATURE:
<223> OTHER INFORMATION: antibody m2J21-HC-336-f VH domain

<400> SEQUENCE: 220

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Lys Gly Leu Glu Trp Met
        35                  40                  45

Gly Asn Ile Asp Pro Asn Thr Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Tyr Trp Tyr Phe Asp Val Trp
            100                 105                 110

Gly Arg Gly Thr Leu Val Thr Val Ser Ser
        115                 120

<210> SEQ ID NO 221
<211> LENGTH: 122
<212> TYPE: PRT
<213> ORGANISM: Artificial Sequence
<220> FEATURE:
<223> OTHER INFORMATION: antibody m2J21-HC-336-g VH domain

<400> SEQUENCE: 221

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Ser Leu Glu Trp Met
        35                  40                  45

```
Gly Asn Ile Asp Pro Asn Thr Gly Gly Thr Ser Tyr Asn Gln Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 222
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 222

Arg Val Thr Met Thr Arg Asp Thr Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 223
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 223

Arg Val Thr Met Thr Arg Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 224
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 224

Arg Val Thr Met Thr Val Asp Lys Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 225
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 225

Arg Val Thr Met Thr Val Asp Lys Ser Thr Ser Thr Val Tyr Met Glu
1               5                   10                  15
```

Leu Ser Ser Leu Arg Ser Glu Asp Thr Ala Val Tyr Tyr Cys Ala Arg
            20                  25                  30

<210> SEQ ID NO 226
<211> LENGTH: 30
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 226

Arg Ala Thr Leu Thr Val Asp Lys Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 227
<211> LENGTH: 32
<212> TYPE: PRT
<213> ORGANISM: Artificial Sequence
<220> FEATURE:
<223> OTHER INFORMATION: Exemplary VH FR3 of Humanized Anti-Beta Klotho
      Antibodies

<400> SEQUENCE: 227

Arg Ala Thr Leu Thr Val Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 228
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 228

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 229
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 229

Gly Met Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 230
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

```
                        Antibodies

<400> SEQUENCE: 230

Gly Met Ser Ser Arg Phe Ser Gly Ser Gly Ser Gly Arg Asp Tyr Thr
1               5                   10                  15

Leu Thr Ile Ser Ser Leu Gln Pro Glu Asp Val Ala Thr Tyr Tyr Cys
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 231

Gly Met Ser Ser Arg Phe Ser Gly Ser Gly Ser Gly Arg Asp Tyr Thr
1               5                   10                  15

Leu Lys Ile Ser Ser Leu Gln Pro Glu Asp Val Ala Thr Tyr Tyr Cys
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: Exemplary VL FR3 of Humanized Anti-Beta Klotho
      Antibodies

<400> SEQUENCE: 232

Gly Met Ser Ser Arg Phe Ser Gly Ser Gly Ser Gly Arg Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 233
<211> LENGTH: 122
<212> TYPE: PRT
<213> ORGANISM: Artificial Sequence
<220> FEATURE:
<223> OTHER INFORMATION: antibody m2J21-HC-336-h VH domain

<400> SEQUENCE: 233

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Ile
        35                  40                  45

Gly Asn Ile Asp Pro Asn Thr Gly Gly Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120
```

```
<210> SEQ ID NO 234
<211> LENGTH: 122
<212> TYPE: PRT
<213> ORGANISM: Artificial Sequence
<220> FEATURE:
<223> OTHER INFORMATION: antibody m2J21-HC-336-i VH domain

<400> SEQUENCE: 234

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Met
            35                  40                  45

Gly Asn Ile Asp Pro Asn Thr Gly Gly Thr Ser Tyr Asn Gln Lys Phe
    50                  55                  60

Lys Gly Arg Ala Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
        115                 120

<210> SEQ ID NO 235
<211> LENGTH: 122
<212> TYPE: PRT
<213> ORGANISM: Artificial Sequence
<220> FEATURE:
<223> OTHER INFORMATION: antibody m2J21-HC-336-j VH domain

<400> SEQUENCE: 235

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Met
            35                  40                  45

Gly Asn Ile Asp Pro Asn Thr Gly Gly Thr Ser Tyr Asn Gln Lys Phe
    50                  55                  60

Lys Gly Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
        115                 120

<210> SEQ ID NO 236
<211> LENGTH: 122
<212> TYPE: PRT
<213> ORGANISM: Artificial Sequence
<220> FEATURE:
<223> OTHER INFORMATION: antibody m2J21-HC-336-k VH domain

<400> SEQUENCE: 236

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
            35                  40                  45

Gly Asn Ile Asp Pro Asn Thr Gly Gly Thr Ser Tyr Asn Gln Lys Phe
        50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
            115                 120

<210> SEQ ID NO 237
<211> LENGTH: 122
<212> TYPE: PRT
<213> ORGANISM: Artificial Sequence
<220> FEATURE:
<223> OTHER INFORMATION: antibody m2J21-HC-336-l VH domain

<400> SEQUENCE: 237

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
            35                  40                  45

Gly Asn Ile Asp Pro Asn Thr Gly Gly Thr Ser Tyr Asn Gln Lys Phe
        50                  55                  60

Lys Gly Arg Val Thr Met Thr Arg Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
            115                 120

<210> SEQ ID NO 238
<211> LENGTH: 122
<212> TYPE: PRT
<213> ORGANISM: Artificial Sequence
<220> FEATURE:
<223> OTHER INFORMATION: antibody m2J21-HC-336-m VH domain

<400> SEQUENCE: 238

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
            35                  40                  45

Gly Asn Ile Asp Pro Asn Thr Gly Gly Thr Ser Tyr Asn Gln Lys Phe
        50                  55                  60

Lys Gly Arg Val Thr Met Thr Arg Asp Thr Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
                115                 120

<210> SEQ ID NO 239
<211> LENGTH: 122
<212> TYPE: PRT
<213> ORGANISM: Artificial Sequence
<220> FEATURE:
<223> OTHER INFORMATION: antibody m2J21-HC-336-n VH domain

<400> SEQUENCE: 239

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Ile
            35                  40                  45

Gly Ser Phe Asn Pro Asp Ser Gly Thr Ser Tyr Asn Gln Lys Phe
        50                  55                  60

Lys Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
                115                 120

<210> SEQ ID NO 240
<211> LENGTH: 122
<212> TYPE: PRT
<213> ORGANISM: Artificial Sequence
<220> FEATURE:
<223> OTHER INFORMATION: antibody m2J21-HC-336-o VH domain

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Gly Leu Glu Trp Ile
            35                  40                  45

Gly Asn Ile Asp Pro Asn Thr Gly Gly Thr Ser Tyr Asn Gln Lys Phe
        50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
                115                 120
```

<210> SEQ ID NO 241
<211> LENGTH: 122
<212> TYPE: PRT
<213> ORGANISM: Artificial Sequence
<220> FEATURE:
<223> OTHER INFORMATION: antibody m2J21-HC-336-p VH domain

<400> SEQUENCE: 241

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Glu Tyr
            20                  25                  30
Thr Met His Trp Val Arg Gln Ala Pro Gly Lys Ser Leu Glu Trp Met
        35                  40                  45
Gly Asn Ile Asp Pro Asn Thr Gly Gly Thr Ser Tyr Asn Gln Lys Phe
    50                  55                  60
Lys Gly Arg Val Thr Leu Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Asp Gly Tyr Ser Thr Arg Tyr Trp Tyr Phe Asp Val Trp
            100                 105                 110
Gly Arg Gly Thr Leu Val Thr Val Ser Ser
        115                 120
```

<210> SEQ ID NO 242
<211> LENGTH: 122
<212> TYPE: PRT
<213> ORGANISM: Artificial Sequence
<220> FEATURE:
<223> OTHER INFORMATION: antibody m2J21-HC-336-q VH domain

<400> SEQUENCE: 242

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Glu Tyr
            20                  25                  30
Thr Met His Trp Val Arg Gln Ala His Gly Lys Ser Leu Glu Trp Met
        35                  40                  45
Gly Asn Ile Asp Pro Asn Thr Gly Gly Thr Ser Tyr Asn Gln Lys Phe
    50                  55                  60
Lys Gly Arg Val Thr Leu Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Asp Gly Tyr Ser Thr Arg Tyr Trp Tyr Phe Asp Val Trp
            100                 105                 110
Gly Arg Gly Thr Leu Val Thr Val Ser Ser
        115                 120
```

<210> SEQ ID NO 243
<211> LENGTH: 122
<212> TYPE: PRT
<213> ORGANISM: Artificial Sequence
<220> FEATURE:
<223> OTHER INFORMATION: antibody m2J21-HC-336-r VH domain

<400> SEQUENCE: 243

```
Gln Val Gln Leu Gln Gln Ser Gly Pro Glu Val Lys Lys Pro Gly Ala
```

-continued

```
1               5                   10                  15
Ser Val Lys Val Ser Cys Lys Ala Ser Gly Tyr Thr Phe Thr Glu Tyr
            20                  25                  30

Thr Met His Trp Val Arg Gln Ala His Gly Lys Ser Leu Glu Trp Ile
        35                  40                  45

Gly Asn Ile Asp Pro Asn Thr Gly Gly Thr Ser Tyr Asn Gln Lys Phe
    50                  55                  60

Lys Gly Arg Val Thr Leu Thr Val Asp Thr Ser Thr Ser Thr Val Tyr
65                  70                  75                  80

Met Glu Leu Arg Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
                115                 120
```

<210> SEQ ID NO 244
<211> LENGTH: 122
<212> TYPE: PRT
<213> ORGANISM: Artificial Sequence
<220> FEATURE:
<223> OTHER INFORMATION: antibody m2J21-HC-336-s VH domain

<400> SEQUENCE: 244

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Asn Ile Asp Pro Asn Thr Gly Gly Thr Ser Tyr Asn Gln Lys Phe
    50                  55                  60

Lys Gly Arg Val Thr Met Thr Arg Asp Thr Ser Thr Ile Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
                115                 120
```

<210> SEQ ID NO 245
<211> LENGTH: 122
<212> TYPE: PRT
<213> ORGANISM: Artificial Sequence
<220> FEATURE:
<223> OTHER INFORMATION: antibody m2J21-HC-336-t VH domain

<400> SEQUENCE: 245

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Asn Ile Asp Pro Asn Thr Gly Gly Thr Ser Tyr Asn Gln Lys Phe
    50                  55                  60
```

```
Lys Gly Arg Val Thr Met Thr Arg Asp Thr Ser Thr Thr Val Tyr
 65                  70                  75                  80

Met Glu Leu Arg Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 246
<211> LENGTH: 122
<212> TYPE: PRT
<213> ORGANISM: Artificial Sequence
<220> FEATURE:
<223> OTHER INFORMATION: antibody m2J21-HC-336-u VH domain

<400> SEQUENCE: 246

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Asn Ile Asp Pro Asn Thr Gly Thr Ser Tyr Asn Gln Lys Phe
    50                  55                  60

Lys Gly Arg Val Thr Met Thr Arg Asp Thr Ser Thr Ser Thr Val Tyr
 65                  70                  75                  80

Met Glu Leu Ser Ser Leu Thr Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 247
<211> LENGTH: 122
<212> TYPE: PRT
<213> ORGANISM: Artificial Sequence
<220> FEATURE:
<223> OTHER INFORMATION: antibody m2J21-HC-336-v VH domain

<400> SEQUENCE: 247

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Lys Ser Leu Glu Trp Met
        35                  40                  45

Gly Ser Phe Asn Pro Asp Ser Gly Thr Ser Tyr Asn Gln Lys Phe
    50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120
```

<210> SEQ ID NO 248
<211> LENGTH: 122
<212> TYPE: PRT
<213> ORGANISM: Artificial Sequence
<220> FEATURE:
<223> OTHER INFORMATION: antibody m2J21-HC-336-w VH domain

<400> SEQUENCE: 248

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Lys Ser Leu Glu Trp Ile
        35                  40                  45

Gly Ser Phe Asn Pro Asp Ser Gly Gly Thr Ser Tyr Asn Gln Lys Phe
    50                  55                  60

Lys Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 249
<211> LENGTH: 122
<212> TYPE: PRT
<213> ORGANISM: Artificial Sequence
<220> FEATURE:
<223> OTHER INFORMATION: antibody m2J21-HC-336-x VH domain

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Lys Ser Leu Glu Trp Met
        35                  40                  45

Gly Asn Ile Asp Pro Asn Thr Gly Gly Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 250
<211> LENGTH: 107
<212> TYPE: PRT
<213> ORGANISM: Artificial Sequence
<220> FEATURE:
<223> OTHER INFORMATION: antibody m2J21 VL domain

<400> SEQUENCE: 250

```
Asp Ile Gln Met Thr Gln Ser Pro Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
            35                  40                  45

Tyr Gly Ala Thr Asn Leu Ala Asp Gly Met Ser Ser Arg Phe Ser Gly
        50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Tyr
                85                  90                  95

Thr Phe Gly Gly Gly Thr Lys Leu Glu Ile Lys
                100                 105
```

<210> SEQ ID NO 251
<211> LENGTH: 107
<212> TYPE: PRT
<213> ORGANISM: Artificial Sequence
<220> FEATURE:
<223> OTHER INFORMATION: antibody m2J21-LC-336-a VL domain

<400> SEQUENCE: 251

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
                100                 105
```

<210> SEQ ID NO 252
<211> LENGTH: 107
<212> TYPE: PRT
<213> ORGANISM: Artificial Sequence
<220> FEATURE:
<223> OTHER INFORMATION: antibody m2J21-LC-336-b VL domain

<400> SEQUENCE: 252

```
Asp Ile Gln Met Thr Gln Ser Pro Ser Ser Leu Ser Ala Ser Val Gly
1               5                   10                  15

Asp Thr Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95
```

```
Thr Phe Gly Gly Gly Thr Lys Val Glu Ile Lys
            100                 105

<210> SEQ ID NO 253
<211> LENGTH: 107
<212> TYPE: PRT
<213> ORGANISM: Artificial Sequence
<220> FEATURE:
<223> OTHER INFORMATION: antibody m2J21-LC-336-c VL domain

<400> SEQUENCE: 253

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 254
<211> LENGTH: 107
<212> TYPE: PRT
<213> ORGANISM: Artificial Sequence
<220> FEATURE:
<223> OTHER INFORMATION: antibody m2J21-LC-336-d VL domain

<400> SEQUENCE: 254

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Gln Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 255
<211> LENGTH: 107
<212> TYPE: PRT
<213> ORGANISM: Artificial Sequence
<220> FEATURE:
<223> OTHER INFORMATION: antibody m2J21-LC-336-e VL domain

<400> SEQUENCE: 255

Asp Ile Gln Met Thr Gln Ser Pro Ser Ser Leu Ser Ala Ser Val Gly
1               5                   10                  15
```

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ser Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 256
<211> LENGTH: 107
<212> TYPE: PRT
<213> ORGANISM: Artificial Sequence
<220> FEATURE:
<223> OTHER INFORMATION: antibody m2J21-LC-336-f VL domain

<400> SEQUENCE: 256

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Gln Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 257
<211> LENGTH: 107
<212> TYPE: PRT
<213> ORGANISM: Artificial Sequence
<220> FEATURE:
<223> OTHER INFORMATION: antibody m2J21-LC-336-g VL domain

<400> SEQUENCE: 257

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 258
<211> LENGTH: 107
<212> TYPE: PRT
<213> ORGANISM: Artificial Sequence
<220> FEATURE:
<223> OTHER INFORMATION: antibody m2J21-LC-336-h VL domain

<400> SEQUENCE: 258

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105
```

<210> SEQ ID NO 259
<211> LENGTH: 107
<212> TYPE: PRT
<213> ORGANISM: Artificial Sequence
<220> FEATURE:
<223> OTHER INFORMATION: antibody m2J21-LC-336-i VL domain

<400> SEQUENCE: 259

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105
```

<210> SEQ ID NO 260
<211> LENGTH: 107
<212> TYPE: PRT
<213> ORGANISM: Artificial Sequence
<220> FEATURE:
<223> OTHER INFORMATION: antibody m2J21-LC-336-j VL domain

<400> SEQUENCE: 260

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30
```

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Asn Val Leu Ser Thr Pro Tyr
                 85                  90                  95

Thr Phe Gly Gly Gly Thr Lys Val Glu Ile Lys
            100                 105

<210> SEQ ID NO 261
<211> LENGTH: 107
<212> TYPE: PRT
<213> ORGANISM: Artificial Sequence
<220> FEATURE:
<223> OTHER INFORMATION: antibody m2J21-LC-336-k VL domain

<400> SEQUENCE: 261

Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
 50                  55                  60

Ser Gly Ser Gly Thr Asp Phe Thr Leu Lys Ile Ser Ser Leu Gln Pro
 65                  70                  75                  80

Glu Asp Phe Ala Thr Tyr Tyr Cys Gln Asn Val Leu Ser Thr Pro Tyr
                 85                  90                  95

Thr Phe Gly Gly Gly Thr Lys Val Glu Ile Lys
            100                 105

<210> SEQ ID NO 262
<211> LENGTH: 107
<212> TYPE: PRT
<213> ORGANISM: Artificial Sequence
<220> FEATURE:
<223> OTHER INFORMATION: antibody m2J21-LC-336-l VL domain

<400> SEQUENCE: 262

Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Asn Val Leu Ser Thr Pro Tyr
                 85                  90                  95

Thr Phe Gly Gly Gly Thr Lys Val Glu Ile Lys
            100                 105

<210> SEQ ID NO 263

```
<211> LENGTH: 107
<212> TYPE: PRT
<213> ORGANISM: Artificial Sequence
<220> FEATURE:
<223> OTHER INFORMATION: antibody m2J21-LC-336-m VL domain

<400> SEQUENCE: 263

Asp Ile Gln Met Thr Gln Ser Pro Ser Ser Leu Ser Ala Ser Val Gly
1               5                   10                  15

Asp Thr Val Thr Ile Thr Cys Gly Ala Ser Glu Asn Ile Tyr Gly Ala
            20                  25                  30

Leu Asn Trp Tyr Gln Gln Lys Gln Gly Lys Ser Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Arg Asp Phe Thr Leu Lys Ile Ser Ser Leu Gln Pro
65                  70                  75                  80

Glu Asp Val Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 264
<211> LENGTH: 107
<212> TYPE: PRT
<213> ORGANISM: Artificial Sequence
<220> FEATURE:
<223> OTHER INFORMATION: antibody m2J21-LC-336-n VL domain

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 265
<211> LENGTH: 107
<212> TYPE: PRT
<213> ORGANISM: Artificial Sequence
<220> FEATURE:
<223> OTHER INFORMATION: antibody m2J21-LC-336-o VL domain

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45
```

```
Tyr Gly Ala Thr Asn Leu Ala Asp Gly Met Ser Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Val Ala Thr Tyr Tyr Cys Gln Asn Val Leu Ser Thr Pro Tyr
                85                  90                  95

Thr Phe Gly Gly Gly Thr Lys Val Glu Ile Lys
            100                 105
```

<210> SEQ ID NO 266
<211> LENGTH: 107
<212> TYPE: PRT
<213> ORGANISM: Artificial Sequence
<220> FEATURE:
<223> OTHER INFORMATION: antibody m2J21-LC-336-p VL domain

<400> SEQUENCE: 266

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Gln Gly Lys Ser Pro Lys Leu Leu Ile
            35                  40                  45

Tyr Gly Ala Thr Asn Leu Ala Asp Gly Met Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105
```

<210> SEQ ID NO 267
<211> LENGTH: 107
<212> TYPE: PRT
<213> ORGANISM: Artificial Sequence
<220> FEATURE:
<223> OTHER INFORMATION: antibody m2J21-LC-336-q VL domain

<400> SEQUENCE: 267

```
Asp Ile Gln Met Thr Gln Ser Pro Ser Ser Leu Ser Ala Ser Val Gly
1               5                   10                  15

Asp Thr Val Thr Ile Thr Cys Gly Ala Ser Glu Asn Ile Tyr Gly Ala
                20                  25                  30

Leu Asn Trp Tyr Gln Gln Lys Gln Gly Lys Ser Pro Lys Leu Leu Ile
            35                  40                  45

Tyr Gly Ala Thr Asn Leu Ala Asp Gly Met Ser Ser Arg Phe Ser Gly
    50                  55                  60

Ser Gly Ser Gly Arg Asp Tyr Thr Leu Lys Ile Ser Ser Leu Gln Pro
65                  70                  75                  80

Glu Asp Val Ala Thr Tyr Tyr Cys Gln Asn Val Leu Ser Thr Pro Tyr
                85                  90                  95

Thr Phe Gly Gly Gly Thr Lys Val Glu Ile Lys
            100                 105
```

<210> SEQ ID NO 268
<211> LENGTH: 122
<212> TYPE: PRT
<213> ORGANISM: Artificial Sequence
<220> FEATURE:
<223> OTHER INFORMATION: antibody m4A2 VH domain

<400> SEQUENCE: 268

Glu Val Gln Leu Gln Gln Ser Gly Pro Glu Leu Val Lys Pro Gly Thr
1               5                   10                  15

Ser Val Lys Ile Ser Cys Lys Thr Ser Gly Tyr Thr Phe Thr Glu Tyr
            20                  25                  30

Thr Met Tyr Trp Val Lys Gln Ser His Gly Lys Ser Leu Glu Trp Ile
        35                  40                  45

Gly Gly Phe Asn Pro Asn Tyr Gly Gly Ala Ser Tyr Asn Gln Lys Phe
    50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
            85                  90                  95

Ala Arg Asp Asp Gly Tyr Ser Thr Arg Tyr Trp Tyr Phe Asp Val Trp
            100                 105                 110

Gly Ala Gly Thr Thr Val Thr Val Ser Ser
        115                 120

<210> SEQ ID NO 269
<211> LENGTH: 122
<212> TYPE: PRT
<213> ORGANISM: Artificial Sequence
<220> FEATURE:
<223> OTHER INFORMATION: antibody m4A2-LC-337-a VH domain

<400> SEQUENCE: 269

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Gln Gly Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 270
<211> LENGTH: 122
<212> TYPE: PRT
<213> ORGANISM: Artificial Sequence
<220> FEATURE:
<223> OTHER INFORMATION: antibody m4A2-LC-337-b VH domain

<400> SEQUENCE: 270

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

```
Thr Met Tyr Trp Val Arg Gln Ala Pro Gly Gln Gly Leu Glu Trp Met
        35                  40                  45

Gly Gly Phe Asn Pro Asn Tyr Gly Gly Ala Ser Tyr Asn Gln Lys Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
             115                 120
```

<210> SEQ ID NO 271
<211> LENGTH: 122
<212> TYPE: PRT
<213> ORGANISM: Artificial Sequence
<220> FEATURE:
<223> OTHER INFORMATION: antibody m4A2-LC-337-c VH domain

<400> SEQUENCE: 271

```
Gln Val Gln Leu Val Gln Ser Gly Pro Glu Val Lys Lys Pro Gly Ala
  1               5                  10                  15

Ser Val Lys Val Ser Cys Lys Ala Ser Gly Tyr Thr Phe Thr Glu Tyr
                 20                  25                  30

Thr Met Tyr Trp Val Arg Gln Ala Pro Gly Gln Gly Leu Glu Trp Met
             35                  40                  45

Gly Gly Phe Asn Pro Asn Tyr Gly Gly Ala Ser Tyr Asn Gln Lys Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
             115                 120
```

<210> SEQ ID NO 272
<211> LENGTH: 122
<212> TYPE: PRT
<213> ORGANISM: Artificial Sequence
<220> FEATURE:
<223> OTHER INFORMATION: antibody m4A2-LC-337-d VH domain

<400> SEQUENCE: 272

```
Gln Val Gln Leu Val Gln Ser Gly Ala Glu Val Val Lys Pro Gly Ala
  1               5                  10                  15

Ser Val Lys Val Ser Cys Lys Ala Ser Gly Tyr Thr Phe Thr Glu Tyr
                 20                  25                  30

Thr Met Tyr Trp Val Arg Gln Ala Pro Gly Gln Gly Leu Glu Trp Met
             35                  40                  45

Gly Gly Phe Asn Pro Asn Tyr Gly Gly Ala Ser Tyr Asn Gln Lys Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95
```

```
Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 273
<211> LENGTH: 122
<212> TYPE: PRT
<213> ORGANISM: Artificial Sequence
<220> FEATURE:
<223> OTHER INFORMATION: antibody m4A2-LC-337-e VH domain

<400> SEQUENCE: 273

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala His Gly Gln Gly Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 274
<211> LENGTH: 122
<212> TYPE: PRT
<213> ORGANISM: Artificial Sequence
<220> FEATURE:
<223> OTHER INFORMATION: antibody m4A2-LC-337-f VH domain

<400> SEQUENCE: 274

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Lys Gly Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 275
<211> LENGTH: 122
<212> TYPE: PRT
```

```
<213> ORGANISM: Artificial Sequence
<220> FEATURE:
<223> OTHER INFORMATION: antibody m4A2-LC-337-g VH domain

<400> SEQUENCE: 275

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Gln Ser Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 276
<211> LENGTH: 122
<212> TYPE: PRT
<213> ORGANISM: Artificial Sequence
<220> FEATURE:
<223> OTHER INFORMATION: antibody m4A2-LC-337-h VH domain

<400> SEQUENCE: 276

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Gln Gly Leu Glu Trp Ile
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 277
<211> LENGTH: 122
<212> TYPE: PRT
<213> ORGANISM: Artificial Sequence
<220> FEATURE:
<223> OTHER INFORMATION: antibody m4A2-LC-337-i VH domain

<400> SEQUENCE: 277

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30
```

```
Thr Met Tyr Trp Val Arg Gln Ala Pro Gly Gln Gly Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Ala Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
                115                 120

<210> SEQ ID NO 278
<211> LENGTH: 122
<212> TYPE: PRT
<213> ORGANISM: Artificial Sequence
<220> FEATURE:
<223> OTHER INFORMATION: antibody m4A2-LC-337-j VH domain

<400> SEQUENCE: 278

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met Tyr Trp Val Arg Gln Ala Pro Gly Gln Gly Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
                115                 120

<210> SEQ ID NO 279
<211> LENGTH: 122
<212> TYPE: PRT
<213> ORGANISM: Artificial Sequence
<220> FEATURE:
<223> OTHER INFORMATION: antibody m4A2-LC-337-k VH domain

<400> SEQUENCE: 279

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met Tyr Trp Val Arg Gln Ala Pro Gly Gln Gly Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                    85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 280
<211> LENGTH: 122
<212> TYPE: PRT
<213> ORGANISM: Artificial Sequence
<220> FEATURE:
<223> OTHER INFORMATION: antibody m4A2-LC-337-l VH domain

<400> SEQUENCE: 280

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met Tyr Trp Val Arg Gln Ala Pro Gly Gln Gly Leu Glu Trp Met
            35                  40                  45

Gly Gly Phe Asn Pro Asn Tyr Gly Gly Ala Ser Tyr Asn Gln Lys Phe
        50                  55                  60

Lys Asp Arg Val Thr Met Thr Arg Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 281
<211> LENGTH: 122
<212> TYPE: PRT
<213> ORGANISM: Artificial Sequence
<220> FEATURE:
<223> OTHER INFORMATION: antibody m4A2-LC-337-m VH domain

<400> SEQUENCE: 281

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met Tyr Trp Val Arg Gln Ala Pro Gly Gln Gly Leu Glu Trp Met
            35                  40                  45

Gly Gly Phe Asn Pro Asn Tyr Gly Gly Ala Ser Tyr Asn Gln Lys Phe
        50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 282
<211> LENGTH: 122
```

```
<212> TYPE: PRT
<213> ORGANISM: Artificial Sequence
<220> FEATURE:
<223> OTHER INFORMATION: antibody m4A2-LC-337-n VH domain

<400> SEQUENCE: 282

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Gln Gly Leu Glu Trp Ile
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 283
<211> LENGTH: 122
<212> TYPE: PRT
<213> ORGANISM: Artificial Sequence
<220> FEATURE:
<223> OTHER INFORMATION: antibody m4A2-LC-337-o VH domain

<400> SEQUENCE: 283

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Gln Gly Leu Glu Trp Ile
        35                  40                  45

Gly Gly Phe Asn Pro Asn Tyr Gly Gly Ala Ser Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 284
<211> LENGTH: 122
<212> TYPE: PRT
<213> ORGANISM: Artificial Sequence
<220> FEATURE:
<223> OTHER INFORMATION: antibody m4A2-LC-337-p VH domain

<400> SEQUENCE: 284

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
```

```
            20                  25                  30
Thr Met Tyr Trp Val Arg Gln Ala His Gly Lys Ser Leu Glu Trp Met
                35                  40                  45

Gly Gly Phe Asn Pro Asn Tyr Gly Gly Ala Ser Tyr Asn Gln Lys Phe
         50                  55                  60

Lys Asp Arg Val Thr Leu Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
            115                 120

<210> SEQ ID NO 285
<211> LENGTH: 122
<212> TYPE: PRT
<213> ORGANISM: Artificial Sequence
<220> FEATURE:
<223> OTHER INFORMATION: antibody m4A2-LC-337-q VH domain

<400> SEQUENCE: 285

Gln Val Gln Leu Gln Gln Ser Gly Pro Glu Val Lys Lys Pro Gly Ala
 1               5                  10                  15

Ser Val Lys Val Ser Cys Lys Ala Ser Gly Tyr Thr Phe Thr Glu Tyr
            20                  25                  30

Thr Met Tyr Trp Val Arg Gln Ala His Gly Lys Ser Leu Glu Trp Ile
                35                  40                  45

Gly Gly Phe Asn Pro Asn Tyr Gly Gly Ala Ser Tyr Asn Gln Lys Phe
         50                  55                  60

Lys Asp Arg Val Thr Leu Thr Val Asp Thr Ser Thr Ser Thr Val Tyr
 65                  70                  75                  80

Met Glu Leu Arg Ser Leu Arg Ser Glu Asp Thr Ala Val Tyr Tyr Cys
                 85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
            115                 120

<210> SEQ ID NO 286
<211> LENGTH: 474
<212> TYPE: PRT
<213> ORGANISM: Artificial Sequence
<220> FEATURE:
<223> OTHER INFORMATION: modified 3I13-hIgG1(E233A)(L235A)

<400> SEQUENCE: 286

Met Asp Met Arg Val Pro Ala Gln Leu Leu Gly Leu Leu Leu Leu Trp
 1               5                  10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
            35                  40                  45

Tyr Thr Phe Thr Glu Tyr Thr Met His Trp Val Arg Gln Ala Pro Gly
         50                  55                  60

Gln Gly Leu Glu Trp Met Gly Ser Phe Asn Pro Asp Ser Gly Gly Thr
 65                  70                  75                  80
```

Ser Tyr Asn Gln Lys Phe Lys Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Asp Asp Gly Tyr Ser Thr Arg Tyr
        115                 120                 125

Trp Tyr Phe Asp Val Trp Gly Arg Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Ala Leu Ala Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 287
<211> LENGTH: 236
<212> TYPE: PRT

-continued

```
<213> ORGANISM: Artificial Sequence
<220> FEATURE:
<223> OTHER INFORMATION: chimeric construct of antibody 3I13

<400> SEQUENCE: 287

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ala Ser
            20                  25                  30

Leu Ser Ala Ser Val Gly Glu Thr Val Thr Ile Thr Cys Gly Ala Ser
        35                  40                  45

Glu Asn Ile Tyr Gly Ala Leu Asn Trp Phe Gln Arg Lys Gln Gly Lys
50                  55                  60

Ser Pro Gln Leu Leu Ile Tyr Gly Ala Thr Ile Leu Ala Asp Gly Met
65                  70                  75                  80

Ser Ser Arg Phe Ser Gly Ser Gly Ser Gly Arg Gln Tyr Ser Leu Lys
                85                  90                  95

Ile Ser Ser Leu His Pro Asp Asp Val Ala Thr Tyr Tyr Cys Gln Asn
            100                 105                 110

Val Leu Ser Thr Pro Tyr Thr Phe Gly Gly Gly Thr Lys Leu Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 288
<211> LENGTH: 122
<212> TYPE: PRT
<213> ORGANISM: Artificial Sequence
<220> FEATURE:
<223> OTHER INFORMATION: antibody m4A2-LC-337-r VH domain

<400> SEQUENCE: 288

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Gln Gly Leu Glu Trp Met
        35                  40                  45

Gly Gly Phe Asn Pro Asn Tyr Gly Gly Ala Ser Tyr Asn Gln Lys Phe
50                  55                  60

Lys Asp Arg Val Thr Met Thr Arg Asp Thr Ser Thr Ser Thr Val Tyr
65                  70                  75                  80

Met Glu Leu Arg Ser Leu Arg Ser Glu Asp Thr Ala Val Tyr Tyr Cys
                85                  90                  95
```

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
            115                 120

<210> SEQ ID NO 289
<211> LENGTH: 122
<212> TYPE: PRT
<213> ORGANISM: Artificial Sequence
<220> FEATURE:
<223> OTHER INFORMATION: antibody m4A2-LC-337-s VH domain

<400> SEQUENCE: 289

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Gln Gly Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
            115                 120

<210> SEQ ID NO 290
<211> LENGTH: 122
<212> TYPE: PRT
<213> ORGANISM: Artificial Sequence
<220> FEATURE:
<223> OTHER INFORMATION: antibody m4A2-LC-337-t VH domain

<400> SEQUENCE: 290

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Lys Ser Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
            115                 120

<210> SEQ ID NO 291
<211> LENGTH: 122
<212> TYPE: PRT
<213> ORGANISM: Artificial Sequence

```
<220> FEATURE:
<223> OTHER INFORMATION: antibody m4A2-LC-337-u VH domain

<400> SEQUENCE: 291

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Lys Ser Leu Glu Trp Met
        35                  40                  45

Gly Gly Phe Asn Pro Asn Tyr Gly Gly Ala Ser Tyr Asn Gln Lys Phe
    50                  55                  60

Lys Asp Arg Val Thr Leu Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 292
<211> LENGTH: 122
<212> TYPE: PRT
<213> ORGANISM: Artificial Sequence
<220> FEATURE:
<223> OTHER INFORMATION: antibody m4A2-LC-337-v VH domain

<400> SEQUENCE: 292

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met Tyr Trp Val Arg Gln Ala Pro Gly Lys Ser Leu Glu Trp Ile
        35                  40                  45

Gly Gly Phe Asn Pro Asn Tyr Gly Gly Ala Ser Tyr Asn Gln Lys Phe
    50                  55                  60

Lys Asp Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
            100                 105                 110

Gly Arg Gly Thr Leu Val Thr Val Ser Ser
        115                 120

<210> SEQ ID NO 293
<211> LENGTH: 122
<212> TYPE: PRT
<213> ORGANISM: Artificial Sequence
<220> FEATURE:
<223> OTHER INFORMATION: antibody m4A2-LC-337-w VH domain

<400> SEQUENCE: 293

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30
```

Thr Met Tyr Trp Val Arg Gln Ala Pro Gly Lys Ser Leu Glu Trp Ile
                35                  40                  45

Gly Gly Phe Asn Pro Asn Tyr Gly Gly Ala Ser Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Ser Thr Arg Tyr Trp Tyr Phe Asp Val Trp
                100                 105                 110

Gly Arg Gly Thr Leu Val Thr Val Ser Ser
            115                 120

<210> SEQ ID NO 294
<211> LENGTH: 107
<212> TYPE: PRT
<213> ORGANISM: Artificial Sequence
<220> FEATURE:
<223> OTHER INFORMATION: antibody m4A2 VL domain

<400> SEQUENCE: 294

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
                20                  25                  30

Leu Asn Trp Tyr Gln Arg Lys Gln Gly Lys Ser Pro Gln Leu Leu Ile
                35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Tyr
                85                  90                  95

Thr Phe Gly Gly Gly Thr Lys Leu Glu Ile Lys
                100                 105

<210> SEQ ID NO 295
<211> LENGTH: 107
<212> TYPE: PRT
<213> ORGANISM: Artificial Sequence
<220> FEATURE:
<223> OTHER INFORMATION: antibody m4A2-LC-337-a VL domain

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Pro Gly Lys Ala Pro Lys Leu Leu Ile
                35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
                100                 105

<210> SEQ ID NO 296
<211> LENGTH: 107
<212> TYPE: PRT
<213> ORGANISM: Artificial Sequence
<220> FEATURE:
<223> OTHER INFORMATION: antibody m4A2-LC-337-b VL domain

<400> SEQUENCE: 296

Asp Ile Gln Met Thr Gln Ser Pro Ser Ser Leu Ser Ala Ser Val Gly
1               5                   10                  15

Asp Thr Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 297
<211> LENGTH: 107
<212> TYPE: PRT
<213> ORGANISM: Artificial Sequence
<220> FEATURE:
<223> OTHER INFORMATION: antibody m4A2-LC-337-c VL domain

<400> SEQUENCE: 297

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 298
<211> LENGTH: 107
<212> TYPE: PRT
<213> ORGANISM: Artificial Sequence
<220> FEATURE:
<223> OTHER INFORMATION: antibody m4A2-LC-337-d VL domain

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

-continued

Leu Asn Trp Tyr Gln Gln Lys Gln Gly Lys Ala Pro Lys Leu Leu Ile
            35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 299
<211> LENGTH: 107
<212> TYPE: PRT
<213> ORGANISM: Artificial Sequence
<220> FEATURE:
<223> OTHER INFORMATION: antibody m4A2-LC-337-e VL domain

<400> SEQUENCE: 299

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ser Pro Lys Leu Leu Ile
            35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 300
<211> LENGTH: 107
<212> TYPE: PRT
<213> ORGANISM: Artificial Sequence
<220> FEATURE:
<223> OTHER INFORMATION: exemplary kappa constant region

<400> SEQUENCE: 300

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 301

```
<211> LENGTH: 107
<212> TYPE: PRT
<213> ORGANISM: Artificial Sequence
<220> FEATURE:
<223> OTHER INFORMATION: antibody m4A2-LC-337-f VL domain

<400> SEQUENCE: 301

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Gln Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 302
<211> LENGTH: 107
<212> TYPE: PRT
<213> ORGANISM: Artificial Sequence
<220> FEATURE:
<223> OTHER INFORMATION: antibody m4A2-LC-337-g VL domain

<400> SEQUENCE: 302

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 303
<211> LENGTH: 107
<212> TYPE: PRT
<213> ORGANISM: Artificial Sequence
<220> FEATURE:
<223> OTHER INFORMATION: antibody m4A2-LC-337-h VL domain

<400> SEQUENCE: 303

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45
```

Tyr Gly Ala Thr Asn Leu Ala Asp Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 304
<211> LENGTH: 107
<212> TYPE: PRT
<213> ORGANISM: Artificial Sequence
<220> FEATURE:
<223> OTHER INFORMATION: antibody m4A2-LC-337-i VL domain

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 305
<211> LENGTH: 107
<212> TYPE: PRT
<213> ORGANISM: Artificial Sequence
<220> FEATURE:
<223> OTHER INFORMATION: antibody m4A2-LC-337-j VL domain

<400> SEQUENCE: 305

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 306
<211> LENGTH: 107
<212> TYPE: PRT
<213> ORGANISM: Artificial Sequence
<220> FEATURE:
<223> OTHER INFORMATION: antibody m4A2-LC-337-k VL domain

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Lys Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 307
<211> LENGTH: 107
<212> TYPE: PRT
<213> ORGANISM: Artificial Sequence
<220> FEATURE:
<223> OTHER INFORMATION: antibody m4A2-LC-337-l VL domain

<400> SEQUENCE: 307

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 308
<211> LENGTH: 107
<212> TYPE: PRT
<213> ORGANISM: Artificial Sequence
<220> FEATURE:
<223> OTHER INFORMATION: antibody m4A2-LC-337-m VL domain

<400> SEQUENCE: 308

Asp Ile Gln Met Thr Gln Ser Pro Ser Ser Leu Ser Ala Ser Val Gly
1               5                   10                  15

Asp Thr Val Thr Ile Thr Cys Gly Ala Ser Glu Asn Ile Tyr Gly Ala
            20                  25                  30

Leu Asn Trp Tyr Gln Gln Lys Gln Gly Lys Ser Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Arg Asp Phe Thr Leu Lys Ile Ser Ser Leu Gln Pro
65                  70                  75                  80

Glu Asp Val Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 309
<211> LENGTH: 107
<212> TYPE: PRT
<213> ORGANISM: Artificial Sequence
<220> FEATURE:
<223> OTHER INFORMATION: antibody m4A2-LC-337-n VL domain

<400> SEQUENCE: 309

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 310
<211> LENGTH: 107
<212> TYPE: PRT
<213> ORGANISM: Artificial Sequence
<220> FEATURE:
<223> OTHER INFORMATION: antibody m4A2-LC-337-o VL domain

<400> SEQUENCE: 310

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Asp Tyr Thr Leu Lys Ile Ser Ser Leu Gln Pro
65                  70                  75                  80

Glu Asp Val Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 311
<211> LENGTH: 107
<212> TYPE: PRT
<213> ORGANISM: Artificial Sequence
<220> FEATURE:
<223> OTHER INFORMATION: antibody m4A2-LC-337-p VL domain

```
<400> SEQUENCE: 311

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Gln Gly Lys Ser Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 312
<211> LENGTH: 107
<212> TYPE: PRT
<213> ORGANISM: Artificial Sequence
<220> FEATURE:
<223> OTHER INFORMATION: antibody m4A2-LC-337-q VL domain

<400> SEQUENCE: 312

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Gln Gly Lys Ser Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gly Gly Thr Lys Val Glu Ile Lys
            100                 105

<210> SEQ ID NO 313
<211> LENGTH: 107
<212> TYPE: PRT
<213> ORGANISM: Artificial Sequence
<220> FEATURE:
<223> OTHER INFORMATION: antibody m4A2-LC-337-r VL domain

<400> SEQUENCE: 313

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Gln Gly Lys Ser Pro Lys Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Asp Tyr Thr Leu Lys Ile Ser Ser Leu Gln Pro
65                  70                  75                  80
```

```
-continued

Glu Asp Val Ala Thr Tyr Tyr Cys Gln Asn Val Leu Ser Thr Pro Tyr
                85                  90                  95

Thr Phe Gly Gly Gly Thr Lys Val Glu Ile Lys
            100                 105
```